(12) United States Patent
Hauser

(10) Patent No.: US 10,731,157 B2
(45) Date of Patent: Aug. 4, 2020

(54) POLYNUCLEOTIDE NANOPARTICLES FOR THE MODULATION OF GENE EXPRESSION AND USES THEREOF

(71) Applicant: HALO-BIO RNAI THERAPEUTICS, INC., Seattle, WA (US)

(72) Inventor: Todd M. Hauser, Seattle, WA (US)

(73) Assignee: HALO-BIO RNAI THERAPEUTICS, INC., Seattle, WA (US)

( * ) Notice: Subject to any disclaimer, the term of this patent is extended or adjusted under 35 U.S.C. 154(b) by 6 days.

(21) Appl. No.: 15/904,224

(22) Filed: Feb. 23, 2018

(65) Prior Publication Data

US 2019/0055555 A1 Feb. 21, 2019

Related U.S. Application Data

(63) Continuation of application No. PCT/US2016/048492, filed on Aug. 24, 2016.

(60) Provisional application No. 62/209,278, filed on Aug. 24, 2015.

(51) Int. Cl.
| | |
|---|---|
| *C12N 15/113* | (2010.01) |
| *A61K 9/14* | (2006.01) |
| *C12N 15/11* | (2006.01) |
| *C12N 15/82* | (2006.01) |
| *A61P 35/00* | (2006.01) |

(52) U.S. Cl.
CPC .............. *C12N 15/113* (2013.01); *A61K 9/14* (2013.01); *A61P 35/00* (2018.01); *C12N 15/111* (2013.01); *C12N 15/82* (2013.01); *C12N 2310/14* (2013.01); *C12N 2310/16* (2013.01); *C12N 2310/351* (2013.01); *C12N 2310/51* (2013.01); *C12N 2310/52* (2013.01)

(58) Field of Classification Search
CPC .................................................... C12N 15/113
See application file for complete search history.

(56) References Cited

U.S. PATENT DOCUMENTS

| | | | |
|---|---|---|---|
| 4,737,323 A | 4/1988 | Martin et al. | |
| 5,023,179 A | 6/1991 | Lam et al. | |
| 5,034,506 A | 7/1991 | Summerton et al. | |
| 5,110,732 A | 5/1992 | Benfey et al. | |
| 5,142,047 A | 8/1992 | Summerton et al. | |
| 5,166,315 A | 11/1992 | Summerton et al. | |
| 5,208,036 A | 5/1993 | Eppstein et al. | |
| 5,217,866 A | 6/1993 | Summerton et al. | |
| 5,264,618 A | 11/1993 | Felgner et al. | |
| 5,268,463 A | 12/1993 | Jefferson | |
| 5,279,833 A | 1/1994 | Rose | |
| 5,283,185 A | 2/1994 | Epand et al. | |
| 5,399,680 A | 3/1995 | Zhu et al. | |
| 5,401,836 A | 3/1995 | Baszczynski et al. | |
| 5,428,148 A | 6/1995 | Reddy et al. | |
| 5,445,934 A | 8/1995 | Fodor et al. | |
| 5,459,252 A | 10/1995 | Conkling et al. | |
| 5,466,785 A | 11/1995 | de Framond | |
| 5,506,337 A | 4/1996 | Summerton et al. | |
| 5,521,063 A | 5/1996 | Summerton et al. | |
| 5,539,082 A | 7/1996 | Nielsen et al. | |
| 5,569,597 A | 10/1996 | Grimsley et al. | |
| 5,604,121 A | 2/1997 | Hilder et al. | |
| 5,608,142 A | 3/1997 | Barton et al. | |
| 5,608,144 A | 3/1997 | Baden et al. | |
| 5,608,149 A | 3/1997 | Barry et al. | |
| 5,633,363 A | 5/1997 | Colbert et al. | |
| 5,650,298 A | 7/1997 | Bujard et al. | |
| 5,659,026 A | 8/1997 | Baszczynski et al. | |
| 5,698,685 A | 12/1997 | Summerton et al. | |
| 5,705,385 A | 1/1998 | Bally et al. | |
| 5,714,331 A | 2/1998 | Buchardt et al. | |
| 5,719,262 A | 2/1998 | Buchardt et al. | |
| 5,750,386 A | 5/1998 | Conkling et al. | |
| 5,753,613 A | 5/1998 | Ansell et al. | |
| 5,785,992 A | 7/1998 | Ansell et al. | |
| 5,789,156 A | 8/1998 | Bujard et al. | |
| 5,814,618 A | 9/1998 | Bujard et al. | |
| 5,837,876 A | 11/1998 | Conkling et al. | |
| 5,856,174 A | 1/1999 | Lipshutz et al. | |
| 5,874,554 A | 2/1999 | Gamble et al. | |
| 5,885,613 A | 3/1999 | Holland et al. | |
| 5,898,031 A | 4/1999 | Crooke | |
| 5,922,927 A | 7/1999 | Bujard et al. | |
| 5,976,567 A | 11/1999 | Wheeler et al. | |
| 5,981,501 A | 11/1999 | Wheeler et al. | |
| 6,013,516 A | 1/2000 | Verma et al. | |
| 6,072,050 A | 6/2000 | Bowen et al. | |
| 6,107,094 A | 8/2000 | Crooke | |
| 6,110,745 A | 8/2000 | Zhang et al. | |

(Continued)

FOREIGN PATENT DOCUMENTS

| | | |
|---|---|---|
| AU | 2004263830 B2 | 12/2008 |
| AU | 2002326410 B2 | 8/2012 |

(Continued)

OTHER PUBLICATIONS

Shu et al. (RNA (2013), 19:767-777). (Year: 2013).*
Li et al. (Nano Today (2015) 10: 631-655 [available online Oct. 26, 2015]), (Year: 2015).*
Adolph et al., "Studies on the Assembly of a Spherical Plant Virus", J. Mol. Biol., vol. 109, 1977, pp. 345-357.
Afonin et al., "Design and self-assembly of siRNA-functionalized RNA nanoparticles for use in automated nanomedicine", Nat Protoc., vol. 6 (12), Dec. 1, 2011, pp. 2022-2034.

(Continued)

*Primary Examiner* — Scott Long
(74) *Attorney, Agent, or Firm* — Leber IP Law; Narendra K. Vaish

(57) ABSTRACT

The present invention is directed to novel self-forming polynucleotide nanoparticles, and the use of such nanoparticles and compositions comprising the same for gene modulation in a variety of organisms.

21 Claims, 27 Drawing Sheets
Specification includes a Sequence Listing.

(56) References Cited

U.S. PATENT DOCUMENTS

| | | |
|---|---|---|
| 6,177,611 B1 | 1/2001 | Rice |
| 6,218,181 B1 | 4/2001 | Verma et al. |
| 6,225,529 B1 | 5/2001 | Lappegard et al. |
| 6,271,348 B1 | 8/2001 | Bujard et al. |
| 6,320,017 B1 | 11/2001 | Ansell |
| 6,506,559 B1 | 1/2003 | Fire et al. |
| 6,534,484 B1 | 3/2003 | Wheeler et al. |
| 6,586,410 B1 | 7/2003 | Wheeler et al. |
| 6,586,559 B2 | 7/2003 | Ansell |
| 6,670,461 B1 | 12/2003 | Wengel et al. |
| 6,770,750 B2 | 8/2004 | Oh et al. |
| 6,774,180 B2 | 8/2004 | Kozlowski et al. |
| 6,794,499 B2 | 9/2004 | Wengel et al. |
| 6,797,859 B2 | 9/2004 | Abbitt et al. |
| 6,852,334 B1 | 2/2005 | Cullis et al. |
| 6,911,577 B2 | 6/2005 | Simmons et al. |
| 6,969,766 B2 | 11/2005 | Kim et al. |
| 7,022,851 B2 | 4/2006 | Kim et al. |
| 7,034,133 B2 | 4/2006 | Wengel et al. |
| 7,053,150 B2 | 5/2006 | Kozlowski et al. |
| 7,053,207 B2 | 5/2006 | Wengel |
| 7,056,704 B2 | 6/2006 | Tuschl et al. |
| 7,060,809 B2 | 6/2006 | Wengel et al. |
| 7,078,196 B2 | 7/2006 | Kim et al. |
| 7,084,125 B2 | 8/2006 | Wengel |
| 7,125,994 B2 | 10/2006 | Kim et al. |
| 7,145,006 B2 | 12/2006 | Kim et al. |
| 7,179,896 B2 | 2/2007 | Kim et al. |
| 7,196,187 B2 | 3/2007 | Frenken et al. |
| 7,211,668 B2 | 5/2007 | Kim et al. |
| 7,320,965 B2 | 1/2008 | Sah et al. |
| 7,348,314 B2 | 3/2008 | John et al. |
| 7,361,752 B2 | 4/2008 | Heidenreich et al. |
| 7,404,969 B2 | 7/2008 | Chen et al. |
| 7,423,142 B2 | 9/2008 | Vornlocher |
| 7,432,250 B2 | 10/2008 | Crooke |
| 7,473,525 B2 | 1/2009 | Kreutzer et al. |
| 7,507,809 B2 | 3/2009 | Meyers |
| 7,517,865 B2 | 4/2009 | Meyers |
| 7,528,118 B2 | 5/2009 | Soutschek et al. |
| 7,569,575 B2 | 8/2009 | Sorenson et al. |
| 7,572,582 B2 | 8/2009 | Wengel et al. |
| 7,579,451 B2 | 8/2009 | Manoharan et al. |
| 7,582,744 B2 | 9/2009 | Manoharan et al. |
| 7,595,306 B2 | 9/2009 | Bumerot |
| 7,615,618 B2 | 11/2009 | Manoharan et al. |
| 7,626,014 B2 | 12/2009 | Manoharan et al. |
| 7,629,321 B2 | 12/2009 | Crooke |
| 7,632,932 B2 | 12/2009 | Manoharan et al. |
| 7,674,778 B2 | 3/2010 | Manoharan et al. |
| 7,674,779 B2 | 3/2010 | Heidenreich et al. |
| 7,695,902 B2 | 4/2010 | Crooke |
| 7,745,651 B2 | 6/2010 | Reyes et al. |
| 7,799,565 B2 | 9/2010 | Maclachlan et al. |
| 7,901,708 B2 | 3/2011 | Maclachlan et al. |
| 8,058,069 B2 | 11/2011 | Yaworski et al. |
| 9,200,276 B2 | 12/2015 | Hauser |
| 2002/0072121 A1 | 6/2002 | Lam et al. |
| 2002/0086356 A1 | 7/2002 | Tuschl et al. |
| 2003/0027783 A1 | 2/2003 | Zernicka-Goetz et al. |
| 2003/0077829 A1 | 4/2003 | Maclachlan |
| 2003/0106097 A1 | 6/2003 | Haigler et al. |
| 2003/0108923 A1 | 6/2003 | Tuschl et al. |
| 2003/0139363 A1 | 7/2003 | Kay et al. |
| 2003/0153519 A1 | 8/2003 | Kay et al. |
| 2004/0072779 A1 | 4/2004 | Kreutzer et al. |
| 2004/0053875 A1 | 5/2004 | Kreutzer et al. |
| 2004/0102408 A1 | 5/2004 | Kreutzer et al. |
| 2004/0142025 A1 | 7/2004 | Maclachlan et al. |
| 2004/0171031 A1 | 9/2004 | Baker et al. |
| 2004/0259247 A1 | 12/2004 | Tuschl et al. |
| 2005/0008689 A1 | 1/2005 | Semple et al. |
| 2005/0026278 A1 | 2/2005 | Tuschl et al. |
| 2005/0100907 A1 | 5/2005 | Kreutzer et al. |
| 2005/0107325 A1 | 5/2005 | Manoharan et al. |
| 2005/0142114 A1 | 6/2005 | Gieseler et al. |
| 2005/0153337 A1 | 7/2005 | Manoharan |
| 2005/0164235 A1 | 7/2005 | Manoharan et al. |
| 2005/0176667 A1 | 8/2005 | Vomlocher |
| 2005/0191618 A1 | 9/2005 | McSwiggen et al. |
| 2005/0196781 A1 | 9/2005 | Robin et al. |
| 2005/0233342 A1 | 10/2005 | Manoharan et al. |
| 2005/0234006 A1 | 10/2005 | Tuschl et al. |
| 2005/0234007 A1 | 10/2005 | Tuschl et al. |
| 2006/0083780 A1 | 4/2006 | Heyes et al. |
| 2006/0094678 A1 | 5/2006 | Vomlocher et al. |
| 2006/0166913 A1 | 7/2006 | Suzuki |
| 2006/0166922 A1 | 7/2006 | Eichler et al. |
| 2006/0240554 A1 | 10/2006 | Chen et al. |
| 2007/0003960 A1 | 1/2007 | Tuschl et al. |
| 2007/0003961 A1 | 1/2007 | Tuschl et al. |
| 2007/0003962 A1 | 1/2007 | Tuschl et al. |
| 2007/0003963 A1 | 1/2007 | Tuschl et al. |
| 2007/0042031 A1 | 2/2007 | Maclachlan et al. |
| 2007/0093445 A1 | 4/2007 | Tuschl et al. |
| 2007/0123482 A1 | 5/2007 | Stoffel et al. |
| 2007/0141610 A1 | 6/2007 | Spier |
| 2007/0148246 A1 | 6/2007 | Luo et al. |
| 2007/0155686 A1 | 7/2007 | Akinc et al. |
| 2007/0173473 A1 | 7/2007 | McSwiggen et al. |
| 2007/0179100 A1 | 8/2007 | Manoharan |
| 2007/0185050 A1 | 8/2007 | Heidenreich et al. |
| 2007/0197460 A1 | 8/2007 | Fougerolles et al. |
| 2007/0213292 A1 | 9/2007 | Stoffel et al. |
| 2007/0238676 A1 | 10/2007 | Mohapatra et al. |
| 2007/0264265 A1 | 11/2007 | Goldenberg et al. |
| 2007/0270579 A1 | 11/2007 | Jadhav et al. |
| 2007/0275465 A1 | 11/2007 | Woppmann et al. |
| 2007/0275914 A1 | 11/2007 | Manoharan et al. |
| 2008/0009457 A1 | 1/2008 | Gould-Fogerite et al. |
| 2008/0039415 A1 | 2/2008 | Stewart et al. |
| 2008/0132461 A1 | 6/2008 | Tuschl et al. |
| 2008/0166800 A1 | 7/2008 | Kreutzer et al. |
| 2008/0171861 A1 | 7/2008 | Kreutzer et al. |
| 2008/0171862 A1 | 7/2008 | Kreutzer et al. |
| 2008/0182981 A1 | 7/2008 | Kreutzer et al. |
| 2008/0194512 A1 | 8/2008 | John et al. |
| 2008/0213891 A1 | 9/2008 | Manoharan et al. |
| 2008/0221054 A1 | 9/2008 | Zernicka-Goetz et al. |
| 2008/0221055 A1 | 9/2008 | Sah et al. |
| 2008/0233651 A1 | 9/2008 | Kreutzer et al. |
| 2008/0242628 A1 | 10/2008 | Zernicka-Goetz et al. |
| 2008/0255345 A1 | 10/2008 | Manoharan et al. |
| 2008/0261303 A1 | 10/2008 | Kreutzer et al. |
| 2008/0269147 A1 | 10/2008 | Tuschl et al. |
| 2008/0311630 A1 | 12/2008 | Schroff et al. |
| 2009/0005549 A1 | 1/2009 | Manoharan et al. |
| 2009/0023673 A1 | 1/2009 | Manoharan et al. |
| 2009/0143323 A1 | 6/2009 | Bavari et al. |
| 2010/0016405 A1 | 1/2010 | Bumcrot et al. |
| 2010/0069461 A1 | 3/2010 | Vornlocher et al. |
| 2010/0136614 A1 | 6/2010 | Luo et al. |
| 2010/0209487 A1 | 8/2010 | Quay et al. |
| 2010/0240730 A1 | 9/2010 | Beigelman et al. |
| 2011/0159586 A1 | 6/2011 | Hauser |
| 2012/0016007 A1 | 1/2012 | Lee et al. |
| 2014/0179758 A1 | 6/2014 | Guo |
| 2017/0121708 A1 | 5/2017 | Shapiro et al. |

FOREIGN PATENT DOCUMENTS

| | | |
|---|---|---|
| EP | 1144623 B1 | 8/2002 |
| EP | 0928290 B1 | 3/2005 |
| EP | 1214945 B1 | 6/2005 |
| EP | 1230375 B1 | 7/2005 |
| EP | 1600506 A2 | 11/2005 |
| EP | 1621545 A2 | 2/2006 |
| EP | 1407044 B1 | 9/2007 |
| EP | 1849868 A3 | 2/2008 |
| EP | 1550719 B1 | 12/2008 |
| EP | 1309726 B1 | 12/2009 |
| EP | 1605978 B1 | 9/2010 |
| EP | 1873259 B1 | 1/2012 |
| EP | 1409506 B1 | 5/2012 |

(56) References Cited

FOREIGN PATENT DOCUMENTS

| | | |
|---|---|---|
| EP | 1633770 B1 | 4/2015 |
| JP | 2004261002 A | 9/2004 |
| JP | 4095895 B2 | 3/2008 |
| WO | 9610390 A1 | 4/1996 |
| WO | 9640964 A2 | 12/1996 |
| WO | 9746570 A1 | 12/1997 |
| WO | 9943819 A1 | 9/1999 |
| WO | 9943838 A1 | 9/1999 |
| WO | 0012733 A1 | 3/2000 |
| WO | 0062813 A2 | 10/2000 |
| WO | 2002044321 A2 | 6/2002 |
| WO | 2004030634 A2 | 4/2004 |
| WO | 2004035765 A2 | 4/2004 |
| WO | 2004064737 A2 | 8/2004 |
| WO | 2004080406 A2 | 9/2004 |
| WO | 2004090108 A2 | 10/2004 |
| WO | 2004091515 A2 | 10/2004 |
| WO | 2004094345 A2 | 11/2004 |
| WO | 2004094595 A2 | 11/2004 |
| WO | 2005004794 A2 | 1/2005 |
| WO | 2005/014782 A2 | 2/2005 |
| WO | 2005026372 A2 | 3/2005 |
| WO | 2005089224 A2 | 9/2005 |
| WO | 2005097817 A2 | 10/2005 |
| WO | 2005115471 A2 | 12/2005 |
| WO | 2006020768 A2 | 2/2006 |
| WO | 2006032041 A2 | 3/2006 |
| WO | 2006036916 A2 | 4/2006 |
| WO | 2006063252 A2 | 6/2006 |
| WO | 2006066158 A2 | 6/2006 |
| WO | 2006073458 A2 | 7/2006 |
| WO | 2006073602 A2 | 7/2006 |
| WO | 2006073727 A2 | 7/2006 |
| WO | 2006074346 A2 | 7/2006 |
| WO | 2006078278 A2 | 7/2006 |
| WO | 2006081192 A2 | 8/2006 |
| WO | 2006084209 A2 | 8/2006 |
| WO | 2006088490 A2 | 8/2006 |
| WO | 2006093526 A2 | 9/2006 |
| WO | 2006112872 A2 | 10/2006 |
| WO | 2007002718 A2 | 1/2007 |
| WO | 2007014077 A2 | 2/2007 |
| WO | 2007021896 A2 | 2/2007 |
| WO | 2007022470 A2 | 2/2007 |
| WO | 2007051045 A2 | 5/2007 |
| WO | 2007053696 A2 | 5/2007 |
| WO | 2007056326 A2 | 5/2007 |
| WO | 2007056331 A2 | 5/2007 |
| WO | 2007056859 A1 | 5/2007 |
| WO | 2007059760 A1 | 5/2007 |
| WO | 2007091269 A2 | 8/2007 |
| WO | 2007109097 A2 | 9/2007 |
| WO | 2007115168 A2 | 10/2007 |
| WO | 2007127919 A2 | 11/2007 |
| WO | 2007134161 A2 | 11/2007 |
| WO | 2007137156 A2 | 11/2007 |
| WO | 2007137220 A2 | 11/2007 |
| WO | 2007137239 A2 | 11/2007 |
| WO | 2008008719 A2 | 1/2008 |
| WO | 2008021157 A1 | 2/2008 |
| WO | 2008036127 A2 | 3/2008 |
| WO | 2008036638 A2 | 3/2008 |
| WO | 2008036929 A2 | 3/2008 |
| WO | 2008036933 A2 | 3/2008 |
| WO | 2008042973 A2 | 4/2008 |
| WO | 2008091703 A2 | 7/2008 |
| WO | 2008121604 A2 | 10/2008 |
| WO | 2008131419 A2 | 10/2008 |
| WO | 2009018332 A1 | 2/2009 |
| WO | 2009020771 A2 | 2/2009 |
| WO | 2009064471 A1 | 5/2009 |
| WO | 2009073809 A2 | 6/2009 |
| WO | 2009086558 A1 | 7/2009 |
| WO | 2009127060 A1 | 10/2009 |
| WO | 2010006282 A2 | 1/2010 |
| WO | 2010042877 A1 | 4/2010 |
| WO | 2010078516 A2 | 7/2010 |
| WO | 2010090452 A2 | 8/2010 |
| WO | 2010135716 A1 | 11/2010 |
| WO | 2010141511 A2 | 12/2010 |
| WO | 2011000106 A1 | 1/2011 |
| WO | 2011066651 A1 | 6/2011 |
| WO | 2017035278 A1 | 3/2017 |
| WO | 2014059022 A1 | 4/2017 |

OTHER PUBLICATIONS

Allison et al., "Infectious In Vitro Transcripts from Cowpea Chlorotic Mottle Virus cDNA Clones and Exchange of Individual RNA Components with Brome Mosaic Virus", Journal of Virology, Oct. 1988, vol. 62, No. 10, pp. 3581-3588.

Annamalai et al., "Dispensability of 3' tRNA-like sequence for packaging cowpea chlorotic mottle virus genomic RNAs", Virology, vol. 332, available online Jan. 8, 2005, pp. 650-658.

Annamalai et al., "Packaging of Brome Mosaid Virus Subgenomic RNA Is Functionally Coupled to Replication-Dependent Transcription and Translation of Coat Protein", Journal of Virology, vol. 80, No. 20, Oct. 2006, pp. 10096-10108.

Annamalai et al., "Replication-Coupled Packaging Mechanism in Positive-Strand RNA Viruses: Synchronized Coexpression of Functional Multigenome RNA Components of an Animal and a Plant Virus in Nicotiana benthamiana Cells by Agroinfiltration", Journal of Virology, vol. 82, No. 3, Feb. 2008, pp. 1484-1490.

Bamunusinghe et al., "Subcellular Localization and Rearrangement of Endoplasmic Reticulum by Brome Mosaic Virus Capsid Protein", Journal of Virology, Mar. 2011, vol. 85, No. 6, pp. 2953-2963.

Basnak et al., "Viral Genomic Single-Stranded RNA Directs the Pathway Toward a T=3 Capsid", J. Mol. Biol., vol. 395, 2010, pp. 924-936.

Bernstein et al., "Role for a bidentate ribonuclease in the initiation step of RNA interference," Nature, vol. 409, Jan. 18, 2001, pp. 363-366.

Bindewald et al., "RNAJunction: a database of RNA junctions and kissing loops for three-dimensional structural analysis and nanodesign", Nucleic Acids Research, vol. 36, 2008, published online Oct. 18, 2007, pp. D392-D397.

Brummelkamp et al., "A system for stable expression of short interfering RNAs in mammalian cells," Science, vol. 296, Apr. 19, 2002, pp. 550-553.

Brummelkamp et al., "Stable suppression of tumorigenicity by virus-mediated RNA interference", Cancer Cell, vol. 2 (3), Sep. 2002, pp. 243-247.

Chang et al., "Characterization of a "kissing" hairpin complex derived from the human immunodeficiency virus genome", Proc. Natl. Acad. Sci. USA, vol. 91, Aug. 1994, pp. 8705-8709.

Choi et al., "Molecular Studies on Bromovirus Capsid Protein: VII. Selective Packaging of BMV RNA4 by Specific N-Terminal Arginine Residues", Virology, 275, Sep. 2000, pp. 207-217.

Clever et al., "Requirements for Kissing-Loop-Mediated Dimerization of Human Immunodeficiency Virus RNA", Journal of Virology, Sep. 1996, vol. 70, No. 9, pp. 5902-5908.

Denli et al., "Processing of primary microRNAs by the Microprocessor complex", Nature, vol. 432, Nov. 11, 2004, pp. 231-235.

Ding et al., "In vivo genome-wide profiling of RNA secondary structure reveals novel regulatory features", Nature, vol. 505, Jan. 30, 2014, 17 pages.

Elrad et al., "Encapsulation of a polymer by an icosahedral virus", Phys. Biol., vol. 7 (4), 2010, pp. 1-29.

Filippov et al., "A novel type of RNase III family proteins in eukaryotes", Gene, vol. 245, 2000, pp. 213-221.

Grabow et al., "Self-assembling RNA nanorings based on RNAI/II inverse kissing complexes", Nano Lett, Feb. 9, 2011, vol. 11 (2), pp. 878-887.

Guo et al., "Inter-RNA Interaction of Phase phi29 pRNA to Form a Hexameric Complex for Viral DNA Transportation", Molecular Cell, vol. 2, Jul. 1998, pp. 149-155.

(56) References Cited

OTHER PUBLICATIONS

Haque et al., "Ultrastable synergistic tetravalent RNA nanoparticles for targeting to cancers", Nano Today, Aug. 2012, vol. 7 (4), pp. 245-257.
Lee et al., "Self-assembled RNA interference microsponges for efficient siRNA delivery", Nat. Mater, vol. 11 (4), Feb. 26, 2012, pp. 316-322.
Han et al., "Molecular Basis for the Recognition of Primary microRNAs by the Drosha-DGCR8 Complex", Cell, vol. 125, Jun. 2, 2006, pp. 887-901.
Fraenkel-Conrat et al., "Reconstituion of Active Tobacco Mosaic Virus From Its Inactive Protein and Nucliec Acid Components", Biochemistry, vol. 41, Jun. 17, 1955, pp. 690-698.
Jaeger et al., "TectoRNA: modular assembly units for the constructions of RNA nano-objects", Nucleic Acids Research, vol. 29, No. 2, Jan. 15, 2001, pp. 455-463.
Jaronczyk et al., "Exploring the functions of RNA interference pathway proteins: some functions are more RISCy than others?", Biochem. J., 387(Pt 3), 2005, pp. 561-571.
Jensen et al., "Spherical Nucleic Acid Nanoparticle Conjugates as an RNAi-Based Therapy for Glioblastoma", Sci. Transl. Med., Oct. 30, 2013, vol. 5 (209), pp. 1-22.
Kim et al., "Strategies for silencing human disease using RNA interference", Nat. Rev. Genet., vol. 8(3), Mar. 2007, pp. 173-184.
Lamontagne et al., "Evaluation of the RNA Determinants for Bacterial and Yeast RNase III Binding and Cleavage", J. Biol. Chem., vol. 279 (3), Jan. 16, 2004, pp. 2231-2241.
Lilley, "Structures of helical junctions in nucleic acids", Quarterly Reviews of Biophysics, vol. 33(2), 2000, pp. 109-159.
Logan et al., "Adenovirus tripartite leader sequence enhances translation of mRNAs late after infection", Proc. Natl. Acad. Sci. USA; vol. 81(12), Jun. 1984, pp. 3655-3659.
Macrae et al., "Structural basis for double-stranded RNA processing by Dicer", Science, Jan. 13, 2006, vol. 311 (5758), pp. 195-198.
Ares, Jr., et al., "A handful of intron-containing genes produces the lion's share of yeast mRNA", RNA, Sep. 1999, vol. 5, pp. 1138-1139.
Mujeeb, "Structure of the dimer initiation complex of HIV-1 genomic RNA", Nature Structural Biology, vol. 5, No. 6, Jun. 1998, pp. 432-436.
Ohno et al., "A human RNA helicase-like protein, HRH1, facilitates nuclear export of spliced mRNA by releasing the RNA from the spliceosome", Genes and Development, vol. 10, 1996, pp. 997-1007.
Perriman et al., "Circular mRNA can direct translation of extremely long repeating-sequence proteins in vivo", RNA, www.majounral.cshlp.org, 1998, vol. 4, pp. 1047-1054.
Porterfield et al., "Full-Length Hepatitis B Virus Core Protein Packages Viral and Heterologous RNA with Similarly High Levels of Cooperativity", Journal of Virology, Jul. 2010, vol. 84, No. 14, pp. 7174-7184.
Prats et al., "cis Elements and trans-Acting Factors Involved in Dimer Formation of Murine Leukemia Virus RNA", Journal of Virology, Feb. 1990, vol. 64 (2), pp. 774-783.
Prinsen, et al., "Multishell Structures of Virus Coat Proteins", J. Phys. Chem. B., vol. 114, 2010, pp. 5522-5533.
Rao et al., "Genome Packaging by Spherical Plant RNA Viruses", Annu. Rev. Phytopathol, vol. 44, 2006, first published online on Feb. 15, 2006, pp. 61-87.
Schroeder et al., "A Cholesterol-Binding Viral Proteins in Virus Entry and Morphogenesis", Chapter 3, Cholesterol Binding and Cholesterol Transport Proteins, Subcellular Biochemistry, 2010, vol. 51, pp. 77-108.
Shu et al., "Bottom-up Assembly of RNA Arrays and Superstructures as Potential Parts in Nanotechnology", Nano Lett., Sep. 2004, vol. 4 (9), pp. 1717-1723.
Shu et al., "Counting of six pRNAs of phi29 DNA-packaging motor with customized single-molecule dual-view system", The EMBO Journal, vol. 26, Jan. 24, 2007, pp. 527-537.
Shu et al., "Thermodynamically Stable RNA three-way junctions as platform for constructing multi-functional nanoparticles for delivery of therapeutics", Nat. Nanotechnol, Apr. 1, 2012, vol. 6 (10), pp. 658-667.
Song et al., "Sustained Small Interfering RNA-Mediated Human Immunodeficiency Virus Type 1 Inhibition in Primary Macrophages", Journal of Virology, Jul. 2003, vol. 77, No. 13, pp. 7174-7181.
Sun et al., "Core-controlled polymorphism in virus-like particles", PNAS, Jan. 23, 2007, vol. 104, No. 4, pp. 1354-1359.
Turner et al., "RNA interference in the light brown apple moth, Epiphyas postvittana (Walker) induced by double-stranded RNA feeding", Insect Molecular Biology, vol. 15, No. 3, 2006, pp. 383-391.
Venter et al., "Capsid Protein Synthesis from Replicating RNA Directs Specific Packaging of the Genome of a Mulipartite, Positive-Strand RNA Virus", Journal of Virology, vol. 79, No. 10, May 2005, pp. 6239-6248.
Wagner et al., "Mechanism of Dimerization of Bicoid mRNA", The Journal of Biological Chemistry, vol. 279, No. 6, Feb. 6, 2004, first published Nov. 7, 2003, pp. 4560-4569.
Shapiro et al., "Bridging the gap in RNA structure prediction", Current Opinion in Structural Biology, 2007, vol. 17, pp. 157-165., Curr Opin Struct Biol.; 17(2):157-65 (2007).
Yoffe et al., "Predicting the sizes of large RNA molecules", PNAS, Oct. 21, 2008, vol. 105, No. 42. pp. 16153-16158.
Zandi et al., "Size Regulation of ss-RNA Viruses", Biophysical Journal, vol. 96, Jan. 2009, pp. 9-20.
Zhang et al., "Structure of the Maize Streak Virus Geminate Particle", Virology, vol. 279, Jan. 2001, pp. 471-477.
Zheng et al., "Topical delivery of siRNA-based spherical nucleic acid nanoparticle conjugates for gene regulation", PNAS, vol. 109, No. 30, Jul. 24, 2012, pp. 11975-11980.
Zhou et al., "RNA-based mechanisms regulating host-virus interactions", Immunol. Rev., May 2013, vol. 253 (1), pp. 97-111.
Zlotnick et al., "Mechanism of Capsid Assembly for an Icosahedral Plant Virus", Virology, vol. 277, 2000, pp. 450-456.
European Patent Application No. 16840069.5, Extended European Search Report dated Jul. 11, 2019, 8 pages.
International Patent Application No. PCT/US2018/042356, International Search Report dated Nov. 5, 2018, 4 pages.
International Patent Application No. PCT/US2013/020109, International Search Report dated Mar. 14, 2013, 2 pages.
International Patent Application No. PCT/US2016/048492, International Search Report and Written Opinion dated Jan. 24, 2017, 10 pages.
Schroeder et al., "A structural database for k-turn motifs in RNA", Subcell Biochem., vol. 51, 2010, pp. 77-108.
Shu et al., "Dengue Virus serotyping based on Envelope and Membrane and Nonstructural Protein NS1 Serotype-Specific Capture Immunoglobulin M Enzyme-Linked Immunosorbent Assays", Journal of Clinical Microbiology, Jun. 2004, vol. 42, No. 6, pp. 2489-2494.
Shu et al., "Structural basis of viral RNA-dependent RNA polymerase catalysis and translocation" PNAS, published online Jun. 23, 2016, pp. E4005-E4014.
Perlmutter et al., "Mechanisms of Virus Assembly", Annu Rev Phys Chem, Apr. 2015, vol. 66, pp. 217-239.
Choi et al., "Packaging of Tobacco Mosaic Virus Subgenomic RNAs by Brome Mosaic Virus Coat Protein Exhibits RNA Controlled Polymorphism", Virology, 2000, vol. 275, pp. 249-257.
Raghupathi et al., "Utilizing Inverse Emulsion Polymerization to Generate Responsive Nanogels for Cytosolic Protein Delivery", Molecular Pharmaceutics, 2017, vol. 14, 4515-4524.
Zhou et al., "Cell-Type-Specific, Aptamer-Functionalized Agents for Targeted Disease Therapy," Mol. Ther. Nucl. Acids, 2014, vol. 3:e169, pp. 1-17.

* cited by examiner

Fig. 1

SINGLE-STRANDED MV-RNA NANOPARTICLES SHOWING INCREASING PLURALITY OF MV-RNA COMPOSITION

Fig. 3A

~40 nm Diameter

PLURALITY OF SINGLE MV-RNA INTO ~40nm SPHERE. CORE STEM-TO-SURFACE RATIO OF 1 TO 2

Fig. 3B

~100 nm Diameter

PLURALITY OF STACKED MV-RNA INTO ~100nm SPHERE. CORE STEM-TO-SURFACE RATIO OF 1 TO 4

SINGLE-STRANDED
TRI MV-RNA NANOPARTICLE

EXPANDING WITH MANY MV-RNA

1: EXAMPLE OF LINEAR RNA TRANSCRIPT OF MV-RNA BASED NANOPARTICLE

2. EXAMPLE OF CIRCULARIZED MV-RNA BASED NANOPARTICLE FROM TRANSCRIPTION

12-unit w/dsRNA tail 16-unit CryoEM

SINGLE-STRANDED POLYNUCLEOTIDE
NANOPARTICLE

THREE 3-STRANDED
POLYNUCLEOTIDE COMPLEXES

SINGLE STRANDED EXPANDED TRANSCRIPT VIEW

SINGLE STRANDED EXPANDED TRANSCRIPT VIEW

ACTUAL TRANSCRIPT STRUCTURE

SINGLE STRANDED EXPANDED
TRANSCRIPT VIEW

ACTUAL TRANSCRIPT
STRUCTURE

SINGLE STRANDED EXPANDED
TRANSCRIPT VIEW

ACTUAL TRANSCRIPT
STRUCTURE

Fig. 14

SINGLE-STRANDED MV-RNA NANOPARTICLES WITH LONG dsRNA UPTAKE SIGNAL

SINGLE-STRANDED POLYNUCLEOTIDE
MOLECULE

RESULTING THREE-STRANDED
POLYNUCLEOTIDE COMPLEX

Fig. 18

40 nm Self-forming Nanoparticle Encapsulated by Viral Coat Protein

1. INDIVIDUAL MV-RNA GUIDE STRAND ORIENTATIONS WITHIN THE MV-RNA SEQUENCE

Single MV-RNA in P/S/K Orientation      Single MV-RNA in P/S/K, S/K/P, K/P/S Orientation

2. INDIVIDUAL MV-RNA GUIDE STRAND ORIENTATIONS IN PLURALITY WITHIN THE TRANSCRIPT SEQUENCE

Expanded to show MV-RNA guide strand orientations within the polynucleotide nanoparticle transcript.

WCR FOREGUT(20x) ISH:

WCR FOREGUT (40x) ISH:

PHYTOENE DESATURASE: PDS-1 NANOPARTICLE

| 1 | 2 | 3 |
| NANOPARTICLE TREATED | TREATMENT ALONE | UNTREATED |

SIMPLIFIED VIEW OF
POLYNUCLEOTIDE NANOPARTICLE
IN NATIVE TRANSCRIPTIONAL
STRUCTURE

SIMPLIFIED VIEW OF
POLYNUCLEOTIDE NANOPARTICLE
IN pH EXPANDED ph 6.0-8.0    ~ph 5.5

POLYNUCLEOTIDE NANOPARTICLES FOR THE MODULATION OF GENE EXPRESSION AND USES THEREOF

PRIORITY CLAIM

This application is a continuation of International Application No. PCT/US2016/048492, filed Aug. 24, 2016, which claims priority to U.S. Provisional Application No. 62/209,278, filed Aug. 24, 2015, both of which are incorporated herein by reference in their entirety, including drawings.

BACKGROUND OF THE INVENTION

Double-stranded RNA based interference (dsRNAi) has become an important tool for reverse functional genomics (Fire 1998). RNAi is a naturally occurring defense mechanism that is highly conserved among eukaryotes. RNAi protects the genome against invention by mobile genetic elements, such as transposons, viruses, and other highly repetitive genomic sequences, and also to control the function of developmental programs in eukaryotic organisms (Sidahmed 2010).

RNAi involves the cleavage of double-stranded RNA (dsRNA) by an RNaseIII-type enzyme called Dicer into small interfering RNAs (siRNA), which then direct sequence-specific, homology-dependent, post-transcriptional gene silencing by binding to their complementary RNA sequences and triggering their elimination through degradation or by inducing translational inhibition (Fire 1998; Meister 2004).

Multivalent RNA (MV-RNA) represents a junction-class RNA molecule that is not canonical dsRNA, but which has a similar mode of action to dsRNA-based RNAi molecules described above. Uniquely, MV-RNA exhibits the ability to cleave multiple sites on the same or different genes simultaneously as well as utilize different pre-processing pathway than dsRNAi (U.S. Patent Publication No. 2011/0159586 and PCT Publication No. WO2012/014155) (FIG. 15).

RNAi molecules such as siRNA, shRNA, miRNA or MV-RNA interact with Ago, PAZ, and PIWI domains as initial steps in loading into the RNA Induced Silencing Complex (RISC). Thus, controlling the accessibility of the 5' and 3' ends of the RNAi molecule by the silencing complex (i.e. RISC) or even Dicer would enhance specificity. Additionally, the production of multiple siRNA molecules from the biogenesis of longer dsRNA by Dicer is a means of producing multiple siRNA molecules from a single transcript. Cleavage of dsRNA RNAi pre-cursors by Dicer or Drosha endonucleases is common in plants, animals, and humans. However, long dsRNA is a poor RNAi trigger in mammals due to the negative immunological response, is rapidly degraded in nearly all uses, and does support the precise production of multiple short RNAi molecules, such as MV-RNA, from a single transcript.

RNA nanotechnology itself has been around since 1998. Many efforts have been made over the years to overcome the susceptibility of RNA to nuclease degradation, structural flexibility, serum instability, and RNase sensitivity and the challenges remain for most commercial uses when building concrete shapes with RNA. Several nucleic acid self-assembly methods, including the use of structural DNA scaffolds, have been employed to generate siRNA-containing nano-structures for in vivo delivery.

Utilizing the intermolecular interactions of RNA, diverse RNA assemblies of nanoparticles have been tried. The pRNA dimer, trimer, and hexamer formations (Guo 1987, 1988; Shu 2004, 2007, 2011, Haque 2012) have also been well studied. The pRNA molecules contain the bacteriophage phi29 at their core, and one to many active modulating molecules at each end of the 3-way junction. In vitro and in vivo results have shown that the pRNA substrate can be directed by RNA, DNA aptamer or Peptide ligand and be gene modulating by appended siRNA, shRNA, ribozyme, peptide, or antibody. RNA nanorings based on RNAI/II inverse kissing complexes (Yingling and Shapiro 2007; Afonin et al. 2011; Grabow et al. 2011); kissing loops of HIV RNA (Chang and Tinoco 1994; Bindewald et al. 2008) and the hand-in-arm interactions of Drosophila bicoid mRNA (Wagner et al. 2004); (2) palindrome sequence-mediated formation of pRNA dimers, tetramers, and arrays (Shu et al. 2004); (3) RNA motifs as LEGO pieces to build quaternary structures via non-templated assemblies including tecto-RNA, two-way junctions (2WJs), 3WJs, and four-way junctions (4WJs), and self-assembly by colE1 kissing loop interactions (Prats et al. 1990; Clever et al. 1996; Mujeeb et al. 1998; Jaeger and Leontis 2000; Lilley 2000; Shu et al. 2011a; Haque et al. 2012); (4) extension of arms of thermodynamically stable core to carry multiple therapeutic small RNAs (Shu et al. 2011a; Haque et al. 2012); (5) use of RNA binding proteins to serve as scaffolds for the formation of nanostructures, such as equilateral triangle constructs, where three proteins are bound to an RNA scaffold containing a kink-turn motif for protein binding (Schroeder et al. 2010; Ohno et al. 2011).

Despite nearly 30 years of study, each RNA nanoparticle is handicapped by features making commercial use difficult. Nanorings are dependent on non-covalent kissing loop interactions that can denature easily in temperature gradients; are not able to be formed efficiently in vivo; and the rational assembly can be variable. The pRNA overcomes the stability issues of Nanorings, but lack the molarity by being limited to three active molecules and also lack a rational control of nuclease degradation. In fact, nearly all nanoparticles above are either limited by non-covalent bonding, molarity limits, or by the lack of nuclease control.

It was previously shown that RNA Microsponge particles could be made by in vitro Rolling Circle Transcription and even used in RNAi with little or no toxicity (Hammond 2012). By utilizing a canonical shRNA structure expressed repetitively as a single stranded concatamer, spherical particles of 2 µM are formed and then later condensed by PEI treatment to ~200 nanometers. Hammond illustrated that the transcription of hundreds of thousands of shRNA form sheets that eventually collapse into spherical form—referred to as "microsponges." Such microsponges are also shown to be active RNAi triggers. However in 2014, Hammond proved that such spherical formation was unrelated to the RNA itself and was the result of the RNA binding to nanocrystalline magnesium pyrophosphate during the T7 transcription reaction. While such RNA microsponges can be formed and even used in RNAi, there lacks the ability to produce smaller sizes of a programmed composition as well as the ability to do so in vivo.

Spherical Nucleic Acid (SNA) nanoparticle conjugates have also been published recently (Zheng 2012, 2013; Zhou 2013, Jensen 2013, Ding 2014) showing conjugated siRNA arranged spherically around a gold particle. Gold nanoparticles offer both covalent and non-covalent attachment of the active nucleic acid molecule. The arrangement is stacked around the gold particle center. While the approach has proven to be active due to the spherical arrangement of the nucleic acids and cellular penetration, it remains a synthetic (inorganic) delivery vector.

Viral coat proteins or capsid proteins function in the transportation and protection of nucleic acids. It was shown half a century ago that infective virus particles of helical symmetry self-assemble upon mixing aqueous solutions of the coat protein and RNA (H. Fraenkel-Conrat, 1955). In most cases, this protective layer is due to the presence of multiple copies of a coat protein that self-assemble into what is typically rod or sphere-like shapes surrounding the nucleic acid. While many of the details surrounding the spontaneous self-assembly process remain obscure, recent data (see citations 'Coat Protein References') suggests that at least the protein-protein interactions and the nucleic acids characteristics dictate the structural outcome. In the case of Cowpea Chlorotic Mottle Virus (CCMV), evidence suggests that the diameter is controlled by nucleotide length. Researchers determined that a length of less than 3000 nt resulted in a ~24-26 nm Coat Protein (CP) diameter, and that a length greater than 4,500 nt resulted in a ~30 nm Coat Protein (CP) diameter when combined with a protein/RNA mass ratio of 6:1. While the use of CP in vitro and in vivo has been demonstrated to encapsulate nucleic acids, this RNA length to CP dependency is inefficient for long dsRNA uses and not possible for short RNAi triggers without pre-packaging (i.e., lipids).

There remains a need for methods and compositions that allow for self-forming polynucleotide nanoparticles for gene modulation with programmable diameters, nuclease stability, molarity, cell-specificity, uptake, and reliable nuclease biogenesis of the active trigger—that is useful for both transgenic and exogenic uses. The present invention addresses this need, and can be applied in humans, animals, plants, insects, and fungi.

BRIEF SUMMARY OF THE INVENTION

The present invention relates generally to compositions and methods for self-forming polynucleotide based RNA interference (RNAi) nanoparticles. More specifically, the invention presents methods and compositions for utilizing a plurality of MV-RNA molecules within a single-stranded polynucleotide that is self-forming into a compact spherical, discus-like, or rod-like nanoparticle. The resulting nanoparticle exhibits unique properties of cellular uptake and nuclease stability, and delivers highly molar RNAi triggers.

The polynucleotide nanoparticles disclosed herein provide novel compositions and methods useful in specifically regulating gene expression of one or more genes simultaneously, in one or more organisms simultaneously with a nanoparticle of programmable diameter, cellular delivery and uptake, and precise trigger release by endonuclease digestion. Such self-forming polynucleotide nanoparticles of this invention exhibit high trigger molarity, in vitro and in vivo production, nuclease resistance, and multi-organism use.

The nanoparticles provided herein are distinguished by a general ratio of RNA stems that are approximately twice as frequent near the surface of the nanoparticle than at the core of the nanoparticle.

Provided herein are isolated polynucleotide nanoparticles comprising two or more connected MV-RNA molecules, each MV-RNA molecule separated by at least one linkage nucleotide that is cleavable by an endonuclease, wherein upon cleavage by the endonuclease the two or more connected MV-RNA molecules are separated, exposing at least one biologically active RNAi molecule.

In certain embodiments, the nanoparticle is composed of 2, 3, 6, 9, 12, 15, 27, or more than 27 separate MV-RNA molecules joined by linkage nucleotides into a single-stranded self-forming polynucleotide disc-like or sphere-like nanoparticle structure.

In still other embodiments, the nanoparticle is composed of 27 or more separate MV-RNA molecules joined by connecting molecules into a single-stranded self-forming polynucleotide sphere-like nanoparticle structure.

In certain embodiments, the isolated polynucleotide nanoparticle has a plurality of MV-RNA in a general structure set forth in any one of FIGS. 1-3A-B.

In certain embodiments, the first MV-RNA in the nanoparticle closes the nanoparticle by containing both the 5' and the 3' of the polynucleotide nanoparticle sequence. In more specific embodiments, the first guide strand of MV-RNA represents the 5' end to the polynucleotide nanoparticle and the second and third guide strands portion represent the 3' end of the polynucleotide nanoparticle. In even more specific embodiments, the first and second guide strand of MV-RNA with it's joining loop represent the 5' end of the polynucleotide nanoparticle and only the third guide strand represents the 3' end of the polynucleotide nanoparticle.

In certain embodiments, a first strand of a linear oligonucleotide represent as the 5' end to the polynucleotide nanoparticle and a reverse compliment to the first oligonucleotide represents the 3' end of the polynucleotide nanoparticle, closing the group of MV-RNA upon hybridization of the two linear oligonucleotide forming a stem.

In other embodiments, the polynucleotide nanoparticle is not closed by complementary sequences. Such embodiments rely on transcription of the antiparallel secondary structure to create a sphere by rolling transcription of single MV-RNA (FIG. 3A) or stack MV-RNA (FIG. 3B).

In still other embodiments, upon cleavage of the linkage nucleotides by the endonuclease the two or more connected MV-RNA molecules are released as separate entities, wherein the separate MV-RNA guide strands are substrates for the RNA-induced silencing complex (RISC). In specific embodiments, cleavage of the linkage nucleotides by the endonuclease controls the accessibility of the separate MV-RNA sequences to the RNA-induced silencing complex (RISC). In other specific embodiments, cleavage linkage nucleotide(s) provides a 5' terminus and a 3' terminus of each MV-RNA guide strand that are substrates for the RNA-induced silencing complex (RISC).

In yet other embodiments, upon cleavage of the linkage nucleotides by the endonuclease the two or more connected MV-RNA molecules are released as separate entities, wherein the separate MV-RNA guide strands are substrates for the microRNA-induced silencing complex (miRISC). In specific embodiments, cleavage of the linkage nucleotides by the endonuclease controls the accessibility of the separate MV-RNA sequences to the microRNA-induced silencing complex (miRISC). In other specific embodiments, cleavage linkage nucleotide(s) provides a 5' terminus and a 3' terminus of each MV-RNA guide strand that are substrates for the microRNA-induced silencing complex (miRISC).

The two or more MV-RNA molecules can be the same or different and can be selected, for example, from group MV-RNA molecules containing aptamers, ligands, linkage nucleotides, loops, ssRNA ends, or a combination thereof.

The linkage nucleotides, in certain embodiments are 1, 2, 3, or more nucleotides.

In certain other embodiments, the linkage nucleotides form a stem-loop that denatures or re-anneal at specific pH ranges causing the polynucleotide nanoparticle change diameter.

In other specific embodiments, the isolated polynucleotide nanoparticle is expressed within a host cell selected from a human cell or animal cell or plant cell or yeast cell or insect cell or bacterial cell, or by in vitro transcription.

In other specific embodiments, the isolated polynucleotide nanoparticle determines the diameter of a coat protein surrounding the invention (FIG. 18).

In other specific embodiments, the isolated polynucleotide nanoparticle targets genes in organisms other than those of the host. Organism specificity can be determined by complementarity of the MV-RNA to the target genes and cellular uptake signals such as aptamers, ligands, linkage nucleotides, loops, long dsRNA, ssRNA ends, or a combination thereof.

In certain specific embodiments, the isolated polynucleotide nanoparticle is produced by in-planta transcription by a promoter (transgenic) or applied topically to plants (exogenic) following in vitro transcription in a general structure set forth in any one of FIGS. 1-3A-B, 8-10, and 18.

In certain embodiments, the isolated polynucleotide nanoparticle targets genes of insects, or virus, or fungus, or animals, or humans, or the host plant (FIG. 24), other plants, or any combination thereof by using a general structure set forth in any one of FIGS. 1-3A-B, 8-10, and 18.

In still other specific embodiments, the isolated polynucleotide nanoparticle is a single polynucleotide nanoparticle circularized with the cleavable ribozyme (FIGS. 5 and 13).

In still other specific embodiments, the polynucleotide nanoparticle comprises natural or synthetic RNA or DNA.

In still other specific embodiments, the polynucleotide nanoparticle comprises natural or synthetic RNA or DNA, 2' modified nucleotides, locked or unlocked nucleotides.

According to another aspect of the invention provides composition comprising one or more isolated polynucleotide nanoparticles, as described in any of the embodiments herein, in combination with a physiologically acceptable excipient.

According to still another aspect of the invention provides methods for delivering two or more RNA molecules to a target cell comprising contacting the target cell with an isolated polynucleotide nanoparticle or composition described herein.

According to still yet another aspect of the invention, as described in any of the embodiments herein, the ratio or surface to core stems scales proportionately with the nanoparticles' diameter by either increasing end-to-end plurality of each MV-RNA or by end-to-end arrangements of stacked MV-RNA, closed by 5' complementarity to 3', or not.

BRIEF DESCRIPTION OF THE DRAWINGS

FIG. 1: Example of self-forming, self-delivering 40 nm MV-RNAi nanoparticles with increasing MV-RNA plurality.

FIGS. 3A-B: (FIG. 3A) 40 nm and (FIG. 3B) 100 nm polynucleotide nanoparticle structures indicating (1) the core stem area and (2) the surface stem area. Core stem to surface ratio for 40 nm and 100 nm sphere is 1:2 and 1:4, respectively.

FIG. 6A shows a single-stranded polynucleotide nanoparticle according to one embodiment. FIG. 6B shows atomic Force Microscopy (AFM) of the nanoparticle with a plurality of three MV-RNA, open and closed in the manner described herein, and resulting in a 40 nm nanoparticle having the predicted structure. FIG. 6C shows the AFM of a tailed 12-unit nanoparticle is provided and indicates the same diameter, despite the higher number of MV-RNA's in the composition and longer RNA transcript. FIG. 6D shows a 16-unit MV-RNA observed in solution via CryoEM.

FIG. 14: Self-forming ~40 nm MV-RNAi nanoparticles with dsRBD signal.

FIG. 18: Coat protein encapsulation of MV-RNA nanoparticle. (1): Coat or capsid protein.

FIG. 21A shows the gene silencing effect of a Phytoene Desaturate (PDS) target gene in Palmer Amaranth nine days after the topical application of the PDS-1 polynucleotide nanoparticle provided herein compared to topical treatment lacking the nanoparticle and to untreated plants. FIG. 21B shown the effect on not-treated leaves seven-days following treatment to the meristem. FIG. 21C shows a five-day time course on a treated leaf showing photobleaching of some cells.

DETAILED DESCRIPTION OF THE INVENTION

As described in detail below, a novel set of self-forming polynucleotide nanoparticles has been constructed and found to be unexpectedly effective at reducing target gene expression of one or more genes. These polynucleotide nanoparticles possess optimal characteristics for a variety of uses, including but not limited to medicinal, bioherbicide, and biopesticide uses. As such, provided herein are polynucleotide nanoparticles, compositions and formulations comprising these polynucleotide nanoparticles, and methods of using these polynucleotide nanoparticles.

The polynucleotide nanoparticles disclosed herein provide significant advantages over previously described RNAi techniques, including superior size/molarity, size/charge, and size/nuclease resistance ratios, high trigger molarity, simple in vivo and in vitro production, nuclease resistance, the ability to regulate expression of multiple genes simultaneously, and the ability to regulate expression across multiple organisms. The disclosed polynucleotide nanoparticles are also superior to traditional dsRNA molecules used for RNAi because they substantially eliminate off-target suppression associated with dsRNA molecules and offer self-forming nanoparticles for transgenic uses. The design of the polynucleotide nanoparticles provided herein allows for nanoparticles having programmable diameter, cellular delivery and uptake, and precise trigger release by endonuclease digestion.

In certain embodiments, the polynucleotide nanoparticles disclosed herein can be used to regulate expression of multiple genes or pathways simultaneously. These multiple genes or pathways may all be associated with a particular phenotype or with multiple phenotypes. In certain embodiments, the polynucleotide nanoparticles disclosed herein may be used to treat a condition associated with aberrant expression (i.e., over- or under-expression) of one or more genes or aberrant activity of one or more pathways. For example, the polynucleotide nanoparticles disclosed herein can be used to treat cancer by regulating the expression of one or more genes associated with the cancer.

Figure 11:
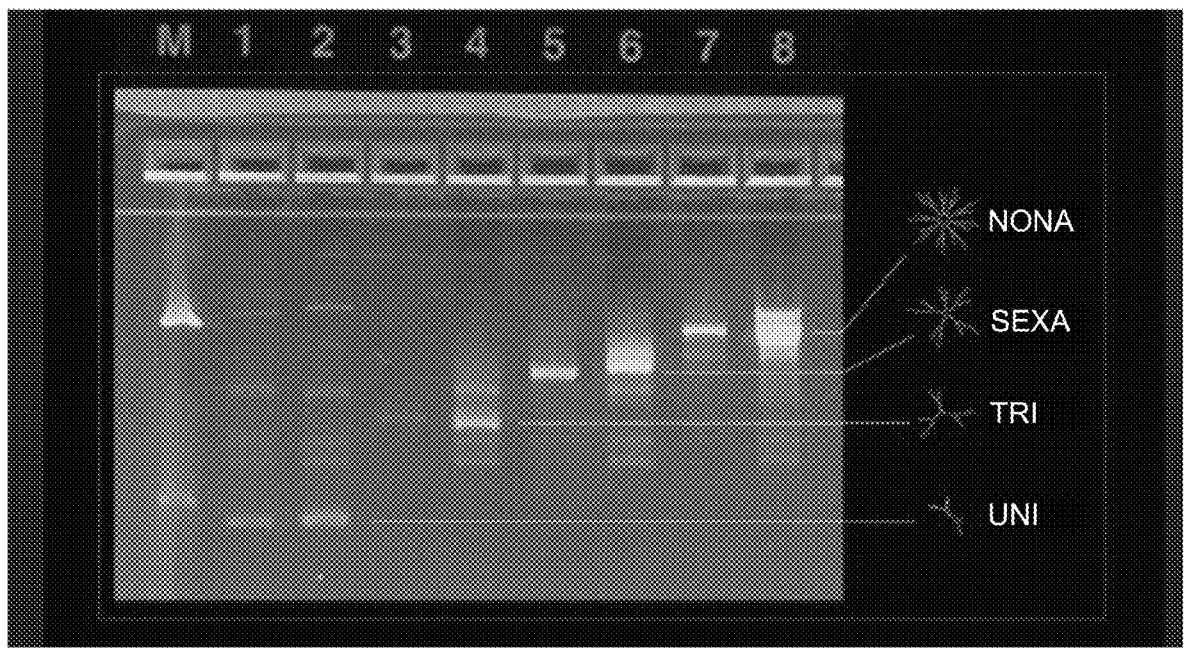
FIG. 11: Size comparison of nanoparticle transcripts. 2% agarose gel electrophoresis of example nanoparticles with increasing plurality: (1, 2) circularized 'UNI', (3) linear 'TRI', (4) circularized 'TRI', (5) linear 'SEXA', (6) circularized 'SEXA', (7) linear 'NONA', and (8) circularized 'NONA'.

The polynucleotide nanoparticles provided herein are distinguishable from prior art molecules by general ratio of RNA stems that are approximately twice as frequent near the surface of the nanoparticle than at the core of the nanoparticle. This fundamental size/stem-loop ratio results in a compact and nuclease degradation resistant nanoparticle containing a high molarity of active triggers without the use of chemicals to further compact the RNA. In fact, the self-forming nanoparticles of this invention are small enough for pinocytosis and/or endocytosis (a range of 40-100 nanometers), and large enough for effective in vivo circulation (greater than 20 nanometers) directly after transcription alone (see FIG. 11).

The polynucleotide nanoparticles provided herein comprise two or more connected MV-RNA, each separated by one or more nucleotides, resulting in at least one biologically active MV-RNA molecule after endonuclease biogenesis. Each MV-RNA removed from the nanoparticle by Dicer or Dicer-like nuclease cleavage is able to load into downstream silencing complexes, including but not limited to RNA Induced Silencing Complex (RISC) and miRNA-Induced Silencing Complex (miRISC). The removed MV-RNAs may also function in downstream immune-stimulatory events. The possibility for both gene suppression and immune-stimulant characteristics within a single nanoparticle offers the ability to suppress antagonists to immune surveillance in certain cancers while simultaneously stimulating the immune response to that particular cell. In this manner, the polynucleotide nanoparticles provided herein act as a unique single-stranded and purely RNA nanoparticle precursor for RNA Interference, miRNA Interference, or immunotherapy—one that can contain a highly-scalable active trigger molarity.

In certain embodiments, the polynucleotide nanoparticles provided herein comprise 2, 3, 6, 9, 12, 15, 16, 27, or more than 27 separate MV-RNA molecules joined by linkage nucleotides into a single-stranded self-forming polynucleotide nanoparticle. In other embodiments, the polynucleotide nanoparticles are composed of 27 or more separate MV-RNA molecules joined by connecting molecules into a single-stranded self-forming polynucleotide nanoparticle. In certain embodiments, the polynucleotide nanoparticles provided herein have a plurality of MV-RNA in a general structure set forth in any one of FIGS. 1-3A-B. In certain embodiments, the plurality of MV-RNA within a single polynucleotide nanoparticle are all different. In other embodiments, two or more of the MV-RNA within a single polynucleotide nanoparticle may be the same. In these embodiments, MV-RNAs that are repeated within a polynucleotide nanoparticle may be in the same or different orientations.

In certain embodiments, the first MV-RNA in the nanoparticle closes the nanoparticle by containing both the 5' and the 3' of the polynucleotide nanoparticle sequence. In more specific embodiments, the first guide strand of MV-RNA represents the 5' end to the polynucleotide nanoparticle and the second and third guide strands portion represent the 3' end of the polynucleotide nanoparticle. In even more specific embodiments, the first and second guide strand of MV-RNA with it's joining loop represent the 5' end of the polynucleotide nanoparticle and only the third guide strand represents the 3' end of the polynucleotide nanoparticle.

In certain embodiments, a first strand of a linear oligonucleotide represents the 5' end of the polynucleotide nanoparticle and a reverse complement to the first oligonucleotide represents the 3' end of the polynucleotide nanoparticle, closing the group of MV-RNA upon hybridization of the two linear oligonucleotide forming a stem.

In other embodiments, the polynucleotide nanoparticle is not closed by complementary sequences. Such embodiments rely on transcription of the antiparallel secondary structure to create a sphere by rolling transcription of single MV-RNA (FIG. 3A) or stack MV-RNA (FIG. 3B).

In still other embodiments, upon cleavage of the linkage nucleotides by the endonuclease the two or more connected MV-RNA molecules are released as separate entities, wherein the separate MV-RNA guide strands are substrates for the RNA-induced silencing complex (RISC). In specific embodiments, cleavage of the linkage nucleotides by the endonuclease controls the accessibility of the separate MV-RNA sequences to the RNA-induced silencing complex (RISC). In other specific embodiments, cleavage linkage nucleotide(s) provides a 5' terminus and a 3' terminus of each MV-RNA guide strand that are substrates for the RNA-induced silencing complex (RISC).

In yet other embodiments, upon cleavage of the linkage nucleotides by the endonuclease the two or more connected MV-RNA molecules are released as separate entities, wherein the separate MV-RNA guide strands are substrates for the microRNA-induced silencing complex (miRISC). In specific embodiments, cleavage of the linkage nucleotides by the endonuclease controls the accessibility of the separate MV-RNA sequences to the microRNA-induced silencing complex (miRISC). In other specific embodiments, cleavage linkage nucleotide(s) provides a 5' terminus and a 3' terminus of each MV-RNA guide strand that are substrates for the microRNA-induced silencing complex (miRISC).

The two or more MV-RNA molecules can be the same or different and can be selected, for example, from group MV-RNA molecules containing aptamers, ligands, linkage nucleotides, loops, ssRNA ends, or a combination thereof.

The linkage nucleotides in the polynucleotide nanoparticles disclosed herein may comprise 1, 2, 3, or more than 3 nucleotides. In certain embodiments, the linkage nucleotides are 3-12 nucleotides and form a stem-loop that denature or re-nature at specific pH ranges causing the polynucleotide nanoparticle change diameter.

In certain embodiments, the polynucleotide nanoparticles provided herein are expressed within a host cell selected from a human, non-human animal, plant, yeast, insect, or bacterial cell, or by in vitro transcription.

In certain, the polynucleotide nanoparticles determine the diameter of a coat protein surrounding the invention (FIG. 18).

The polynucleotide nanoparticles provided herein may contain single or multiple RNA sequences represented on the surface (aptamers, long dsRNA, ssRNA), enabling a highly molar cellular uptake and/or cellular specificity from a single RNA nanoparticle without compromising the general RNAi activity.

In other specific embodiments, the isolated polynucleotide nanoparticle targets genes in organisms other than those of the host. Organism specificity can be determined by complementarity of the MV-RNA to the target genes and cellular uptake signals such as aptamers, ligands, linkage nucleotides, loops, long dsRNA, ssRNA ends, or a combination thereof.

The polynucleotide nanoparticles provided herein naturally fold via Watson-Crick base pairing into stable secondary structures of 40, 80, 100, or 130 nanometers by in vivo or in vitro expression under typical ionic conditions for transcription (see, e.g., FIGS. 6A-D).

Figure 17:
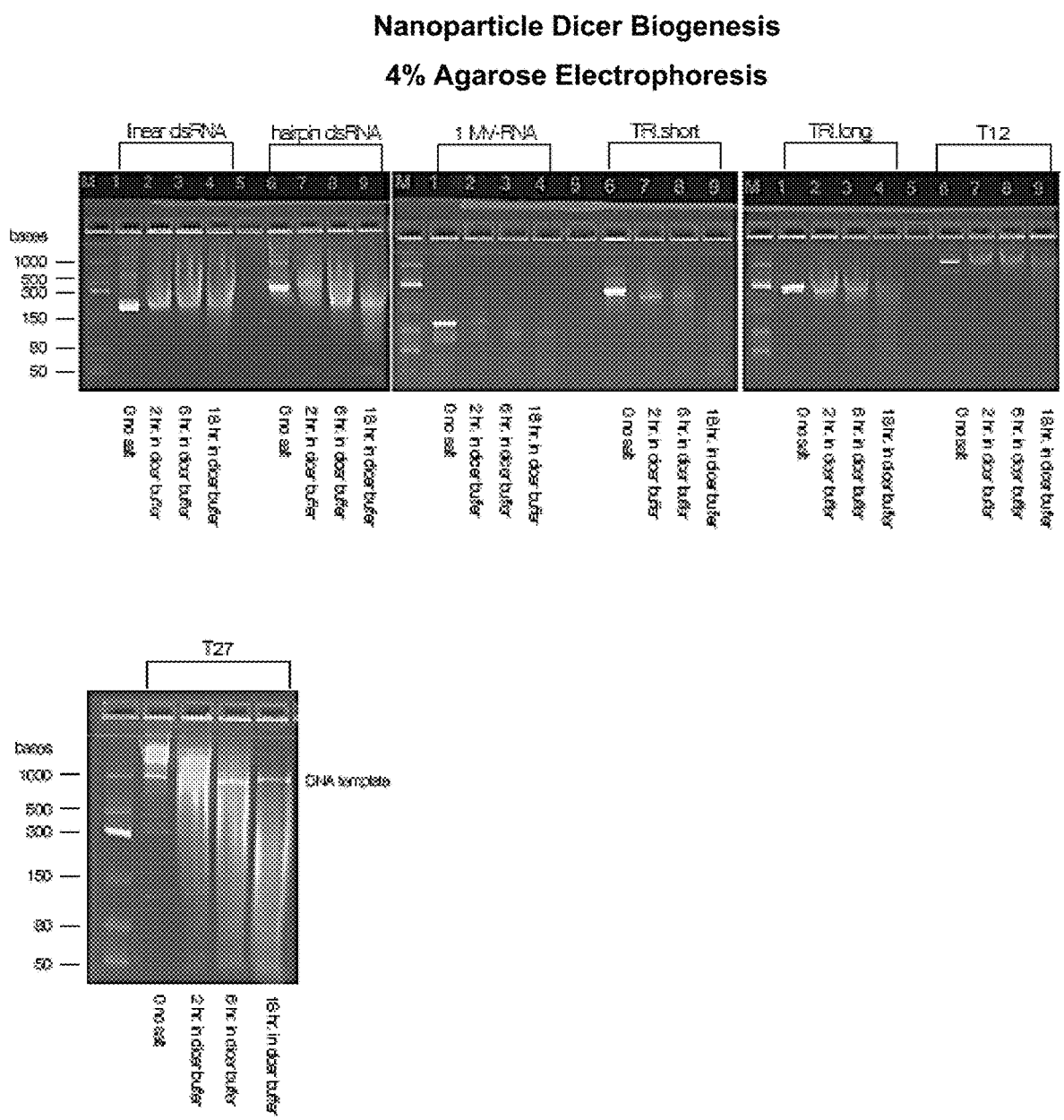
FIG. 17: Dicer biogenesis time-course of each polynucleotide nanoparticle in a growing plurality compared to long dsRNA.
Figure 23:
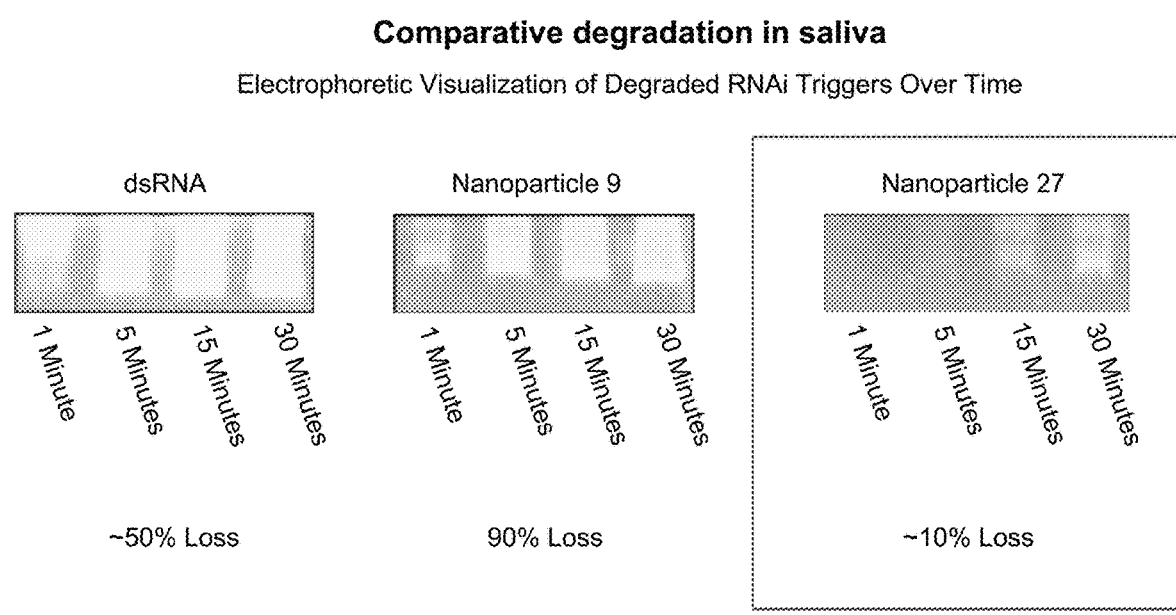
FIG. 23: Endo-nucleic degradation rate in saliva. Electrophoresis shows degradation products of RNA at 1-30 minutes. The short degradation product produced by long dsRNA is compared to the short degradation products produced by two different nanoparticles provided herein, each with increasing plurality.
Figure 24:
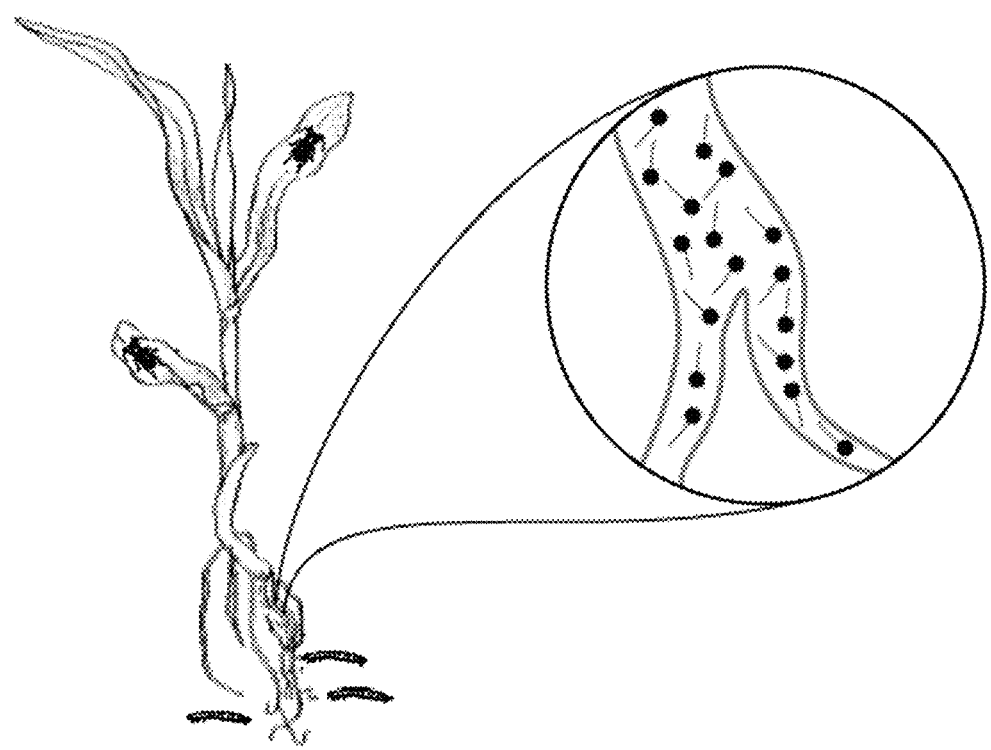
FIG. 24: In planta transcription of nanoparticles targeting pests. Nanoparticle is stably expressed in the plant.
Figure 25:
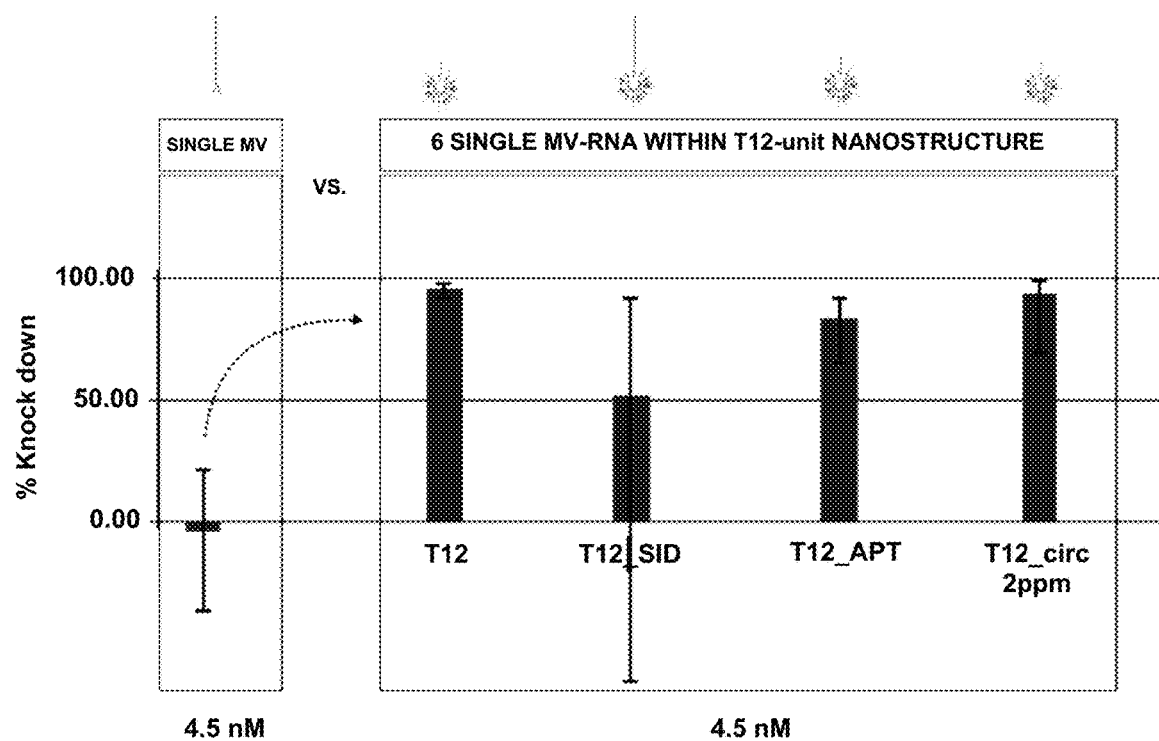
FIG. 25: shows a qRT-PCR graph of the equimolar potency benefit of MV-RNA Nanostructures composed of 6 repetitive MV-RNA vs. a single MV-RNA of the same target site.

Such self-forming single-stranded nanoparticles produced by transgene expression provide advantages over linear dsRNA based RNAi methods in matters of degradation resistance, potency, Dicer biogenesis specificity, trigger molarity, host-related competition of endogenous gene regulation mechanisms, and trans-kingdom applications. (see, e.g., FIGS. 17, 23, 25)

These single-stranded polynucleotide nanoparticles produced by transcription provide a simpler process and greatly reduced costs in comparison to other RNAi nanoparticle composition methods requiring chemical modifications by synthesis or lipid-style encapsulation for stability and delivery.

Such self-forming nanoparticles can be combined with organic compounds, inorganic compounds, peptides or capsid proteins, resulting in a broad spectrum of exogenic uses from agriculture to human therapeutics.

Figure 7:
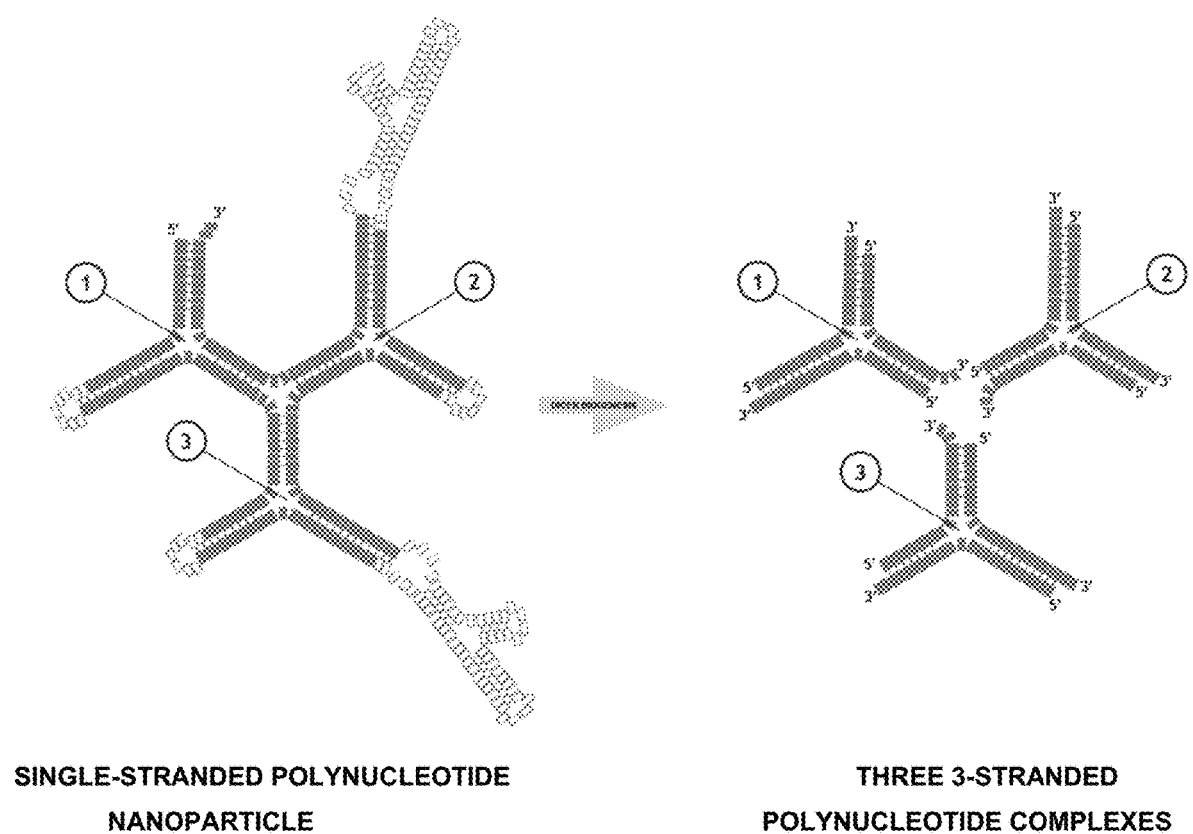
FIG. 7: Single-stranded nanoparticle biogenesis. Single-stranded nanoparticle containing multiple end-to-end MV-RNAs ((1), (2), and (3)) and targeting aptamers results in multiple MV-RNAs following Dicer or Dicer-like biogenesis.
Figure 8:
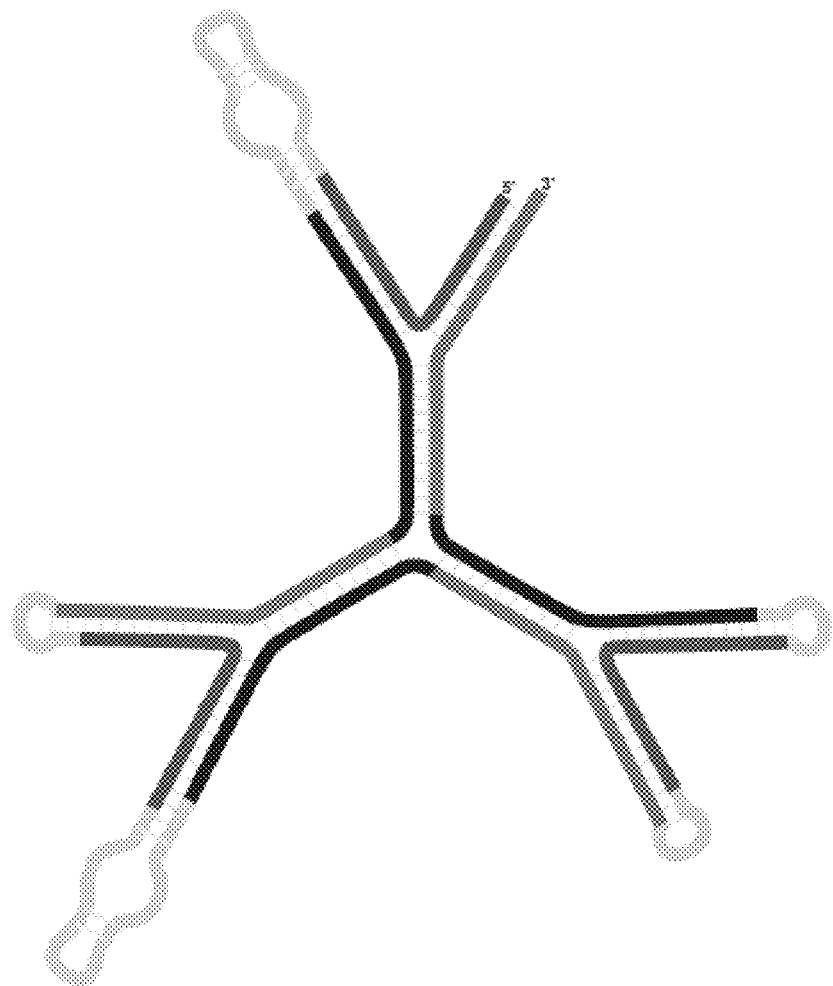
FIG. 8: TRI plurality nanoparticle.
Figure 9:
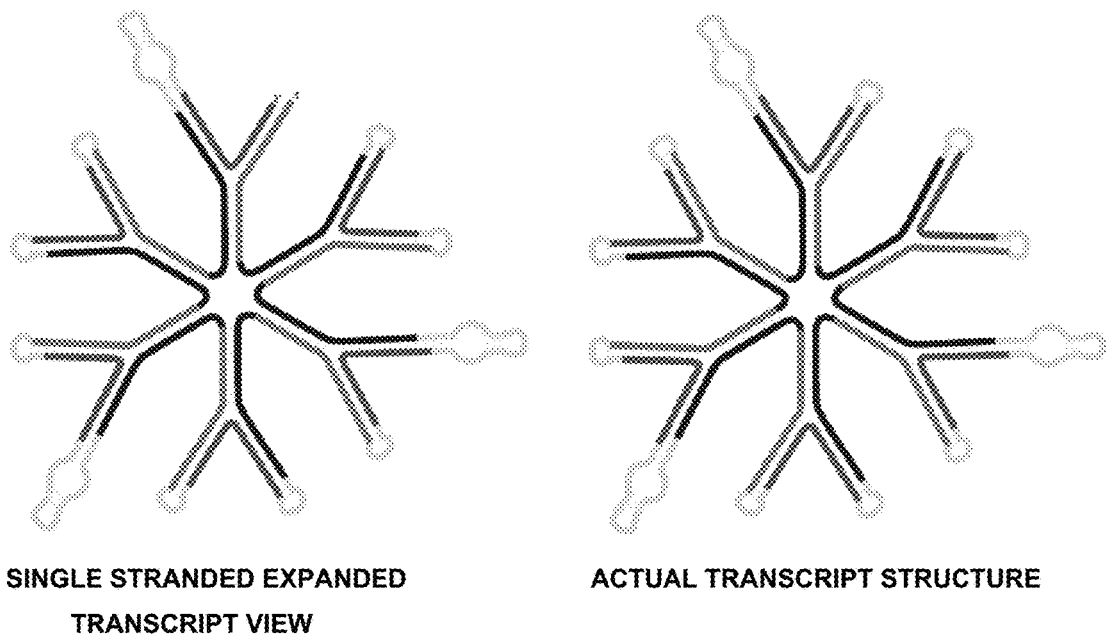
FIG. 9: SEXA plurality nanoparticle.
Figure 10:
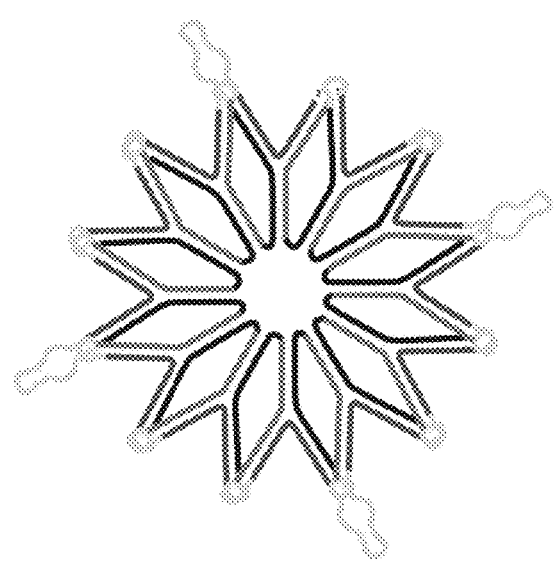
FIG. 10: Dodecahedron and higher plurality nanoparticles.
Figure 10:
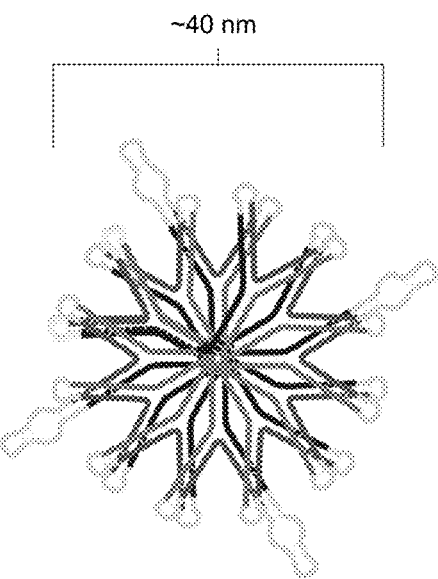
Figure 10:
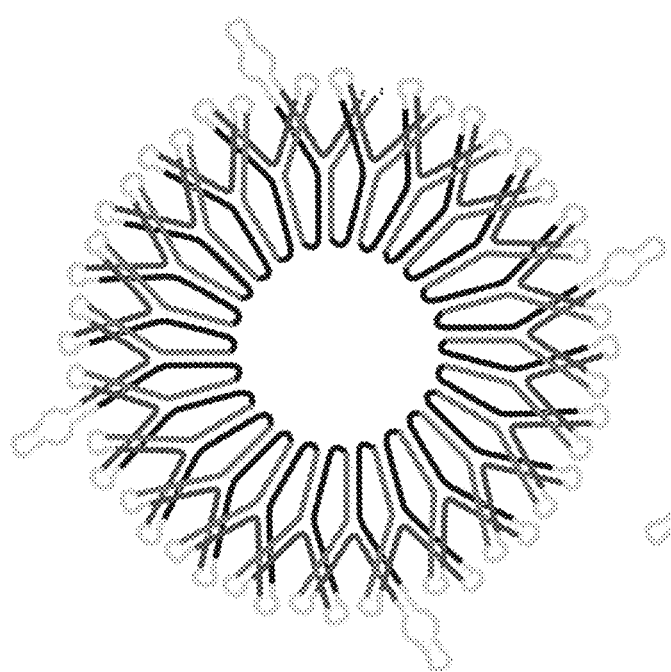
Figure 10:
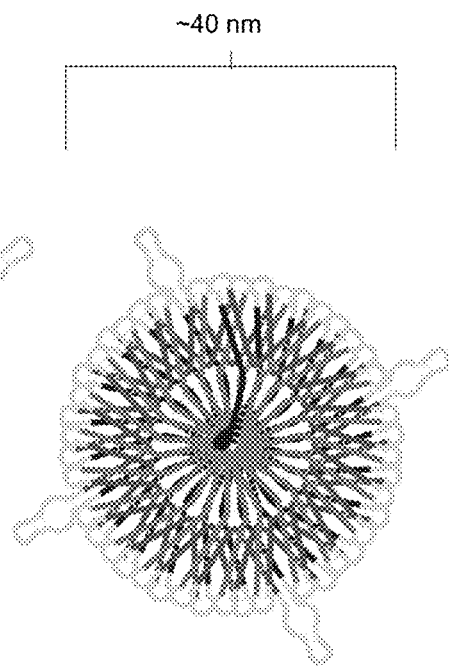
Figure 16:
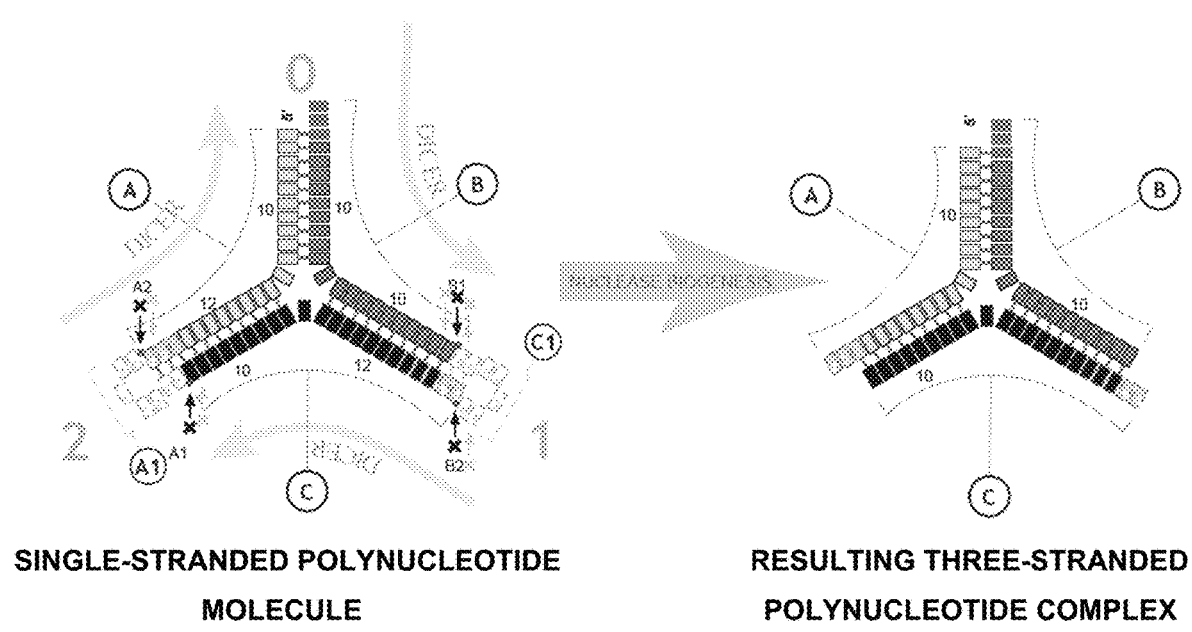
FIG. 16: Dicer biogenesis of single-stranded polynucleotide module. (A1), (A2), (B1), (B2): Dicer cleavage sites.

Provided herein in certain embodiments are compositions and methods relating to the in situ production of multiple, or repetitive, MV-RNA by the controlled endonuclease-mediated biogenesis of a precisely structured single transcript. Also provided are precisely structured transcripts that allow for the controlled biogenesis of the transcript in a specific and selective manner. The endonuclease biogenesis of a structured nanoparticle transcript can control the accessibility of RNA Induced Silencing Complex (RISC) by exposing the preferred 5' and 3' ends of an RNAi molecule. Therefore, in certain embodiments, the present disclosure provides single-stranded self-forming polynucleotide nanoparticle molecules containing multiple RNAi sequences, or MV-RNA precursor sequences, which, following in situ endonuclease cleavage, are released as multiple biologically active RNA molecules, allowing for the targeted inhibition of gene expression at multiple sites within the same gene and/or at one or more sites on different target genes simultaneously. Non-limiting examples of these embodiments are shown in FIGS. 7 and 16.

In certain embodiments, an isolated polynucleotide nanoparticle provided herein comprises a self-forming polynucleotide nanoparticle.

The polynucleotide nanoparticles provided herein offer a number of important advantages, including nuclease resistance, enhanced molarity, enhanced spectrum, charge distribution, production of multiple novel MV-RNA triggers from a single transcript, optimal Size Activity Relationship (SAR) for ingestion, and allows small RNA molecule in-Planta expression despite long transcript requirements of plant promoters, and support for enzymatically produced molecules not possible with linear dsRNA. Furthermore, it is advantageous to have the ability to stabilize a precursor molecule, and then make available in a controlled fashion a plurality of active RNAi molecules in situ in single or multivalent highly molar forms.

In certain embodiments, the polynucleotide nanoparticles provided herein are produced by in planta transcription by a promoter (transgenic) or applied topically to plants (exogenic) following in vitro transcription, in a general structure set forth in any one of FIGS. 1-3A-B, 8-10, and 18.

In certain embodiments, the polynucleotide nanoparticles provided herein target genes of insects or virus or fungus or the host plant in a cis-kingdom or trans-kingdom manner, or any combination thereof within a general structure set forth in any one of FIGS. 1-3A-B, 8-10, and 18.

Figure 2:
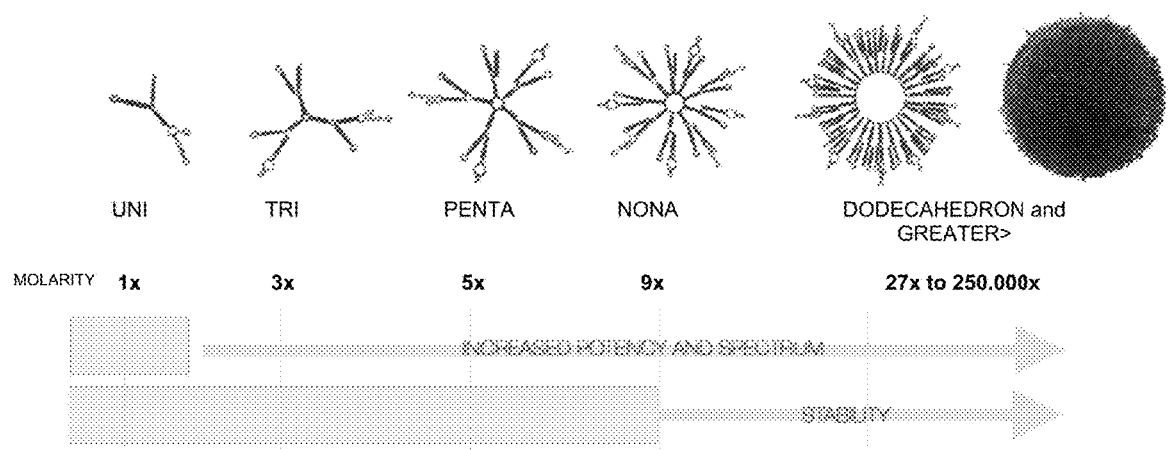
FIG. 2: RNAfold secondary structures of the family of polynucleotide nanoparticles with increasing MV-RNA plurality of SEQ ID NOs:39-52, and a chart indicating effect of increasing plurality on trigger molarity (i.e., potency), spectrum, and nuclease stability.
Figure 4:
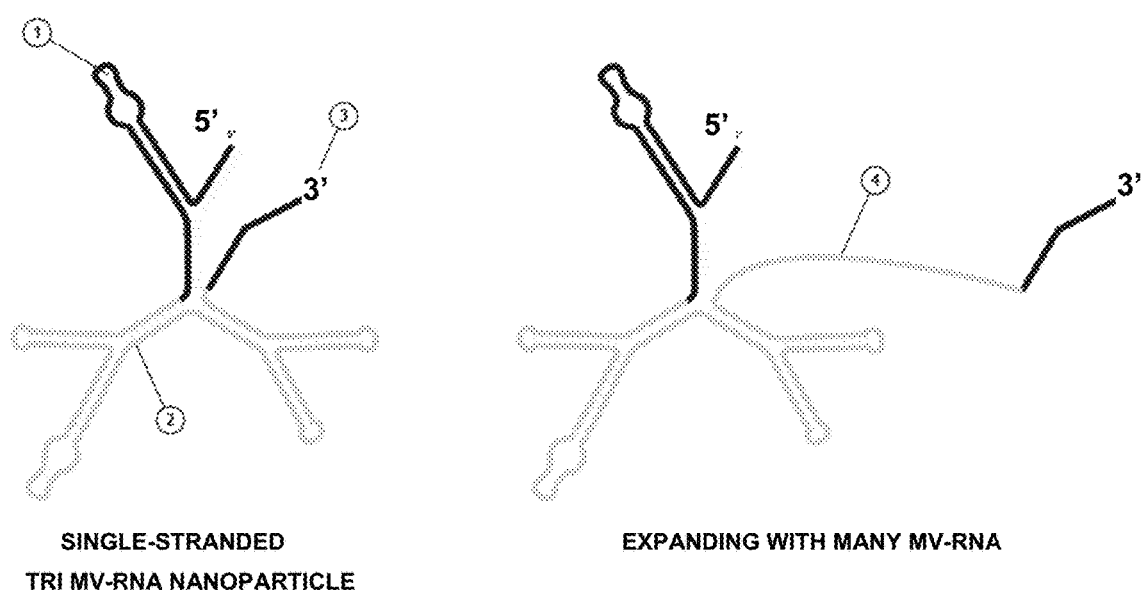
FIG. 4: Rational assembly of polynucleotide nanoparticle using Opening/Closing MV-RNA. (1) Closing MV-RNA 5' leader sequence (black), (2) example region of one or more end-to-end MV-RNA (light grey), (3) 3' end of the Closing MV-RNA (black), and (4) additional example region of highly plural end-to-end MV-RNA (light grey).
Figure 5:
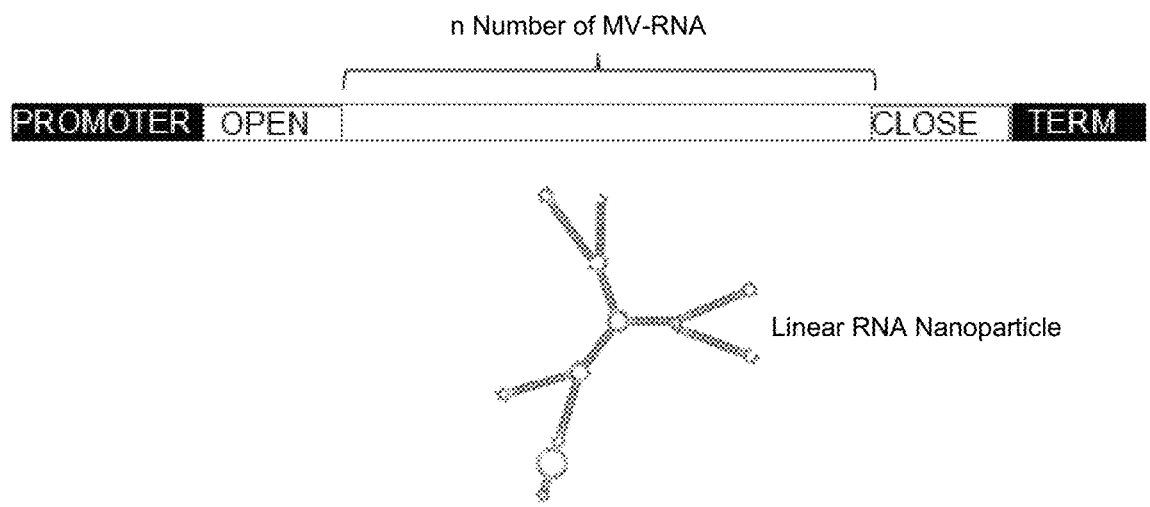
FIG. 5: Self-assembling nanoparticles by transcription. The entire nanoparticle can be transcribed from DNA using promoters in either (1) linear or (2) circularized by ribozyme formats.
Figure 5:
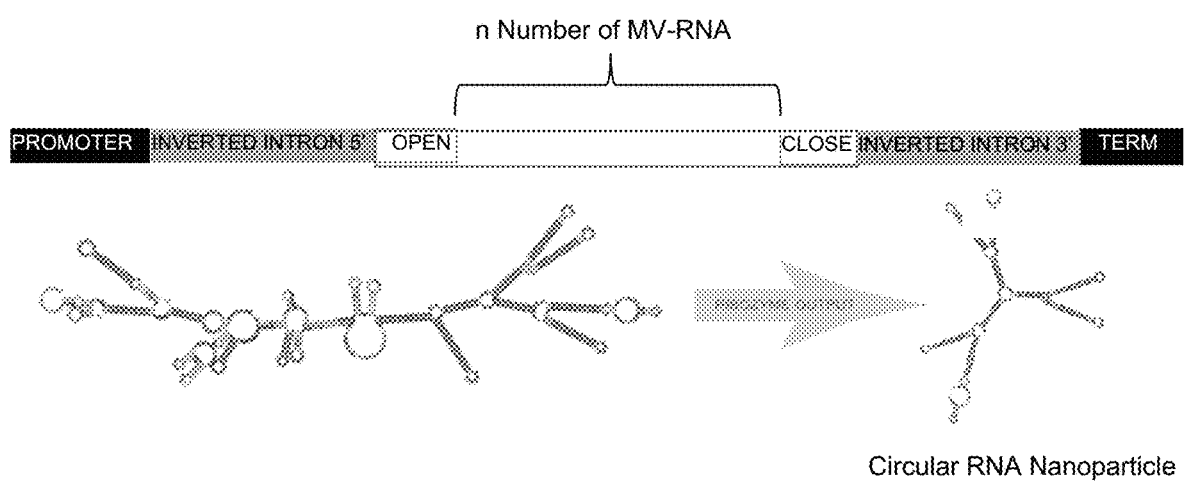
Figure 6A:
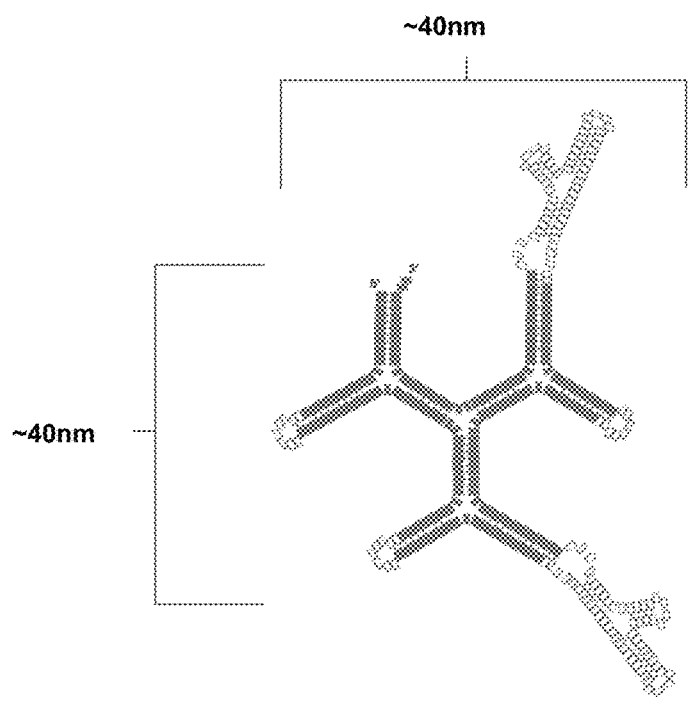
FIGS. 6A-D: MV-RNA nanoparticles form rational structure and size.
Figure 6B:
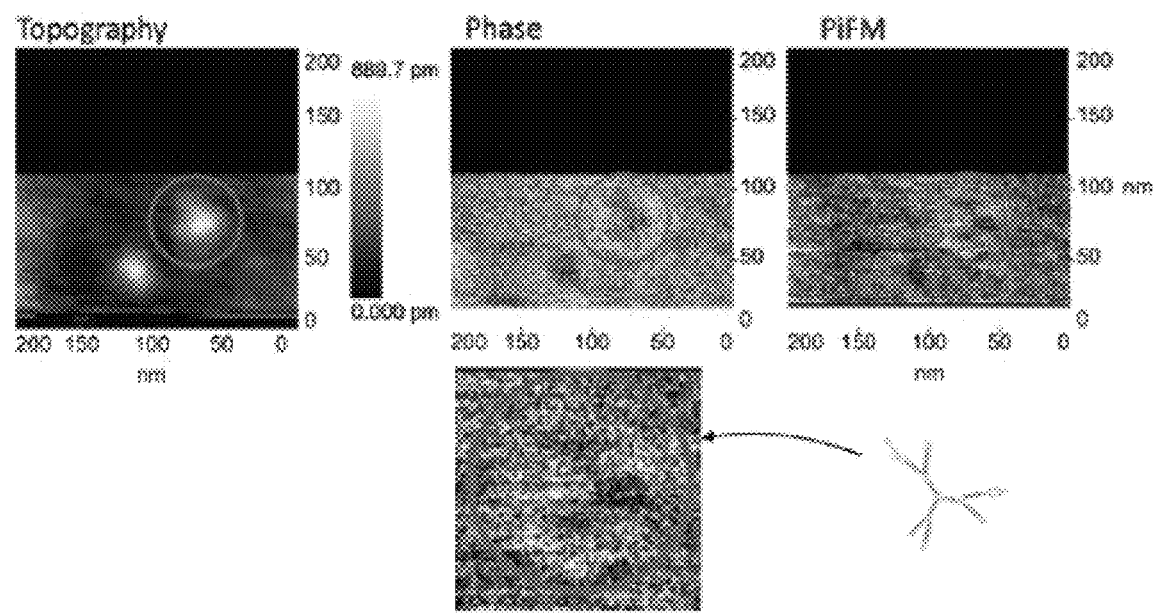
Figure 6C:
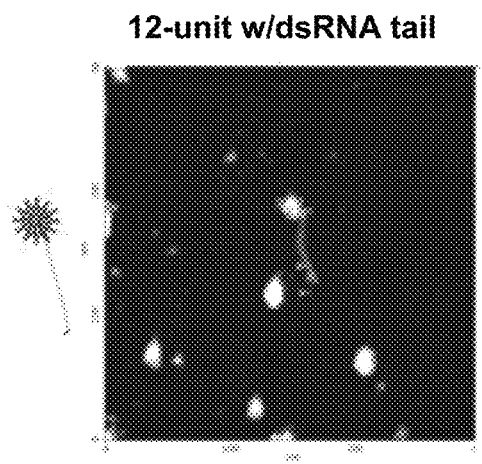
Figure 6D:
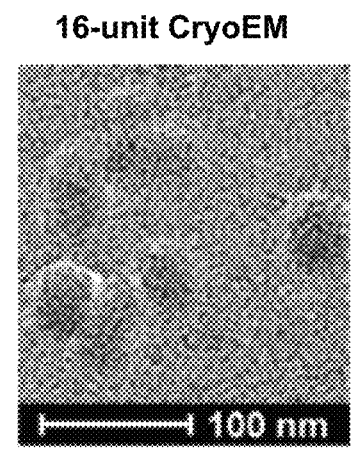
Figure 13:
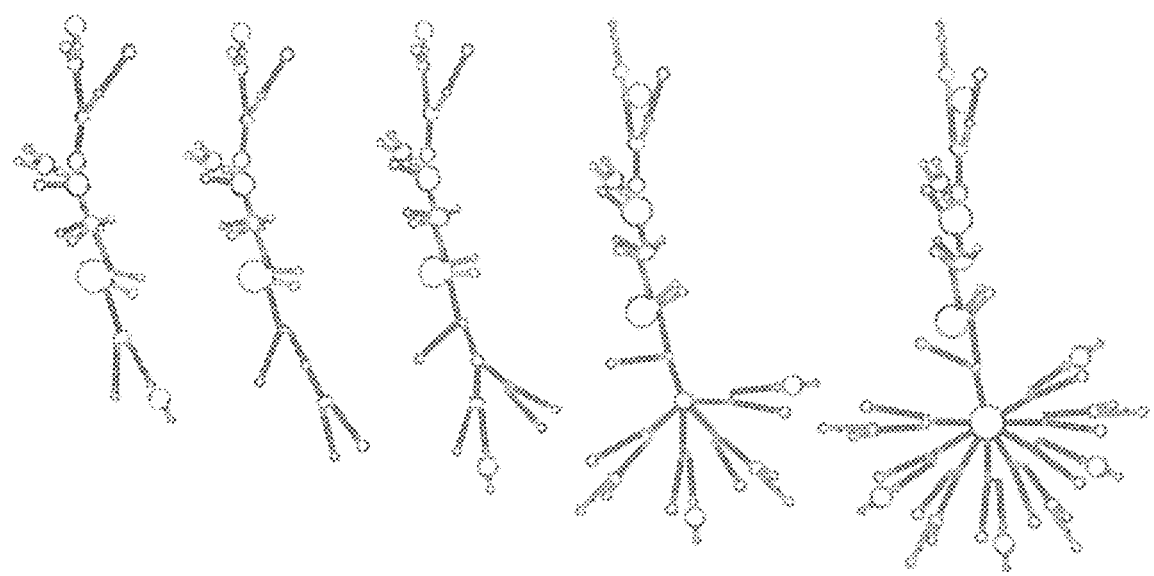
FIG. 13: Example RNAfolds of circularization transcripts, each with increasing plurality.
Figure 15:
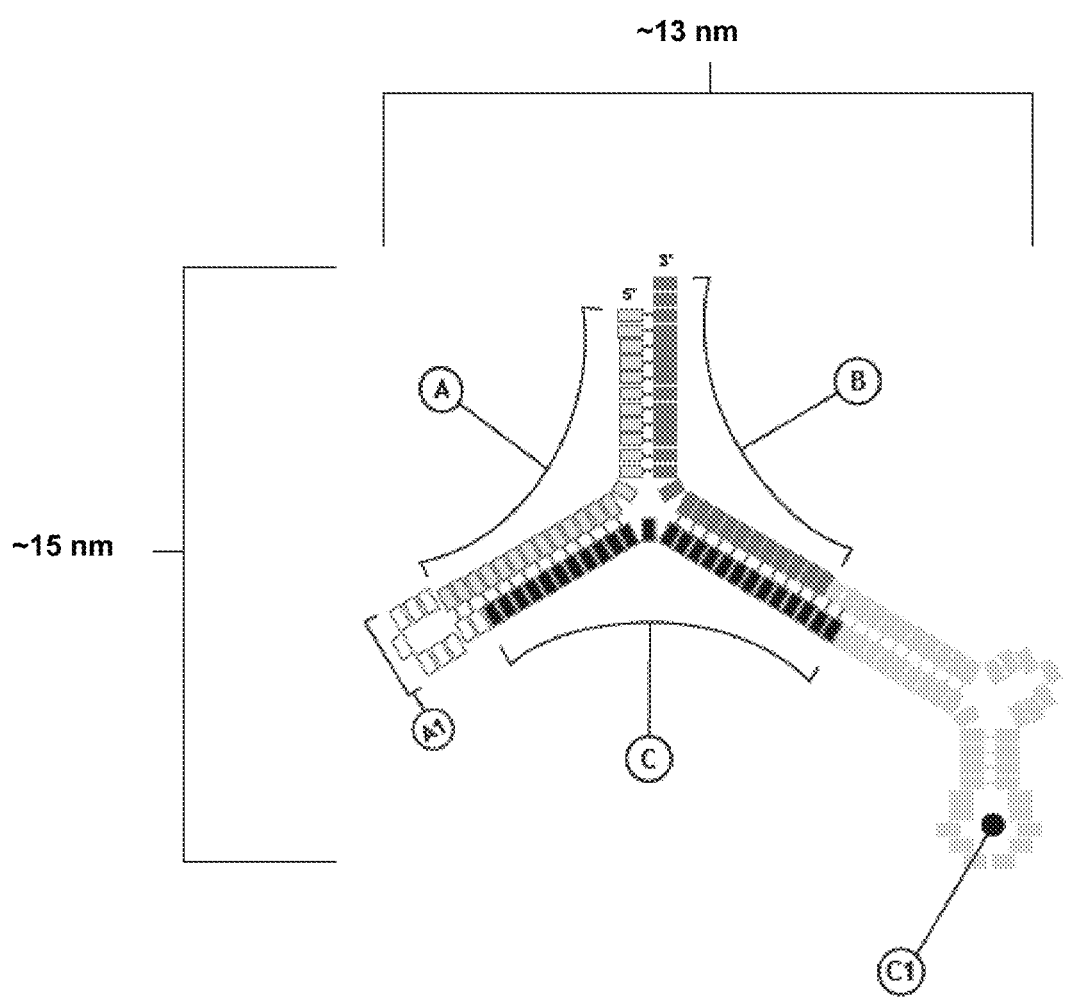
FIG. 15: Overview of a single MV-RNA module (U.S. Patent Publication No. 2011/0159586 and PCT Publication No. WO2012/014155, which is incorporated by reference). (A), (B), (C) correspond to three guide strands within an MV-RNA.

In still other specific embodiments, the polynucleotide nanoparticles provided herein are single polynucleotide nanoparticles circularized by a cleavable ribozyme resulting in a nanoparticle without a 5' phosphate end or 3' hydroxyl terminus (FIGS. 5 and 13).

The design features and production technology for RNAi molecules are generally known and established. Accordingly, in light of the present disclosure, one will understand how to produce isolated polynucleotide nanoparticles containing multiple MV-RNA precursor sequences separated by linkage nucleotides, as described herein, such that upon endonuclease cleavage a desired plurality of biologically active RNAi molecules are released in situ from the original single polynucleotide nanoparticle transcript.

As noted above, in the embodiments, the two or more RNAi sequences that are present in an isolated polynucleotide nanoparticle of the invention are MV-RNA precursors. Such precursors contained within the isolated polynucleotide nanoparticle of the invention are either monovalent, bivalent and/or multivalent, as described, e.g., in U.S. Patent Publication No. 2011/0159586 and PCT Publication No. WO2012/014155, the contents of which are incorporated herein by reference in their entireties.

The linkage nucleotides or stem-loop linkage elements used to separate MV-RNA sequences in an isolated polynucleotide nanoparticle of the invention generally comprise (i) 1, 2, 3 nucleotides, or (ii) 3-12 nucleotide stem-loops (Example 1b).

The cell-specific aptamers (FIG. 1) or long dsRNA elements (FIG. 10) contained within individual MV-RNA in an isolated polynucleotide nanoparticle can contribute to cell specificity or cellular uptake.

Figure 26:
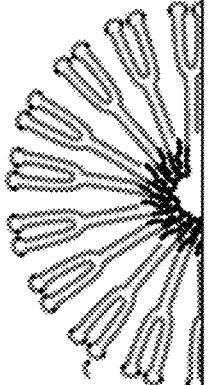
FIG. 26: Polynucleotide nanoparticles with pH-responsive linkages. pH responsive linkage (1) and kissing loops (2) in native state at pH 6-8 (left) and expanded state at a lower pH (right & (3)).
Figure 26:
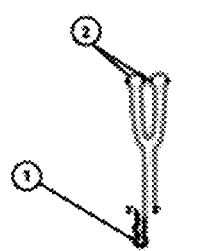
Figure 26:
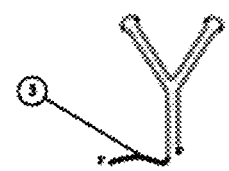

After entry into a target cell, escape from the endosome may also be facilitated by aptamers (Example 1a, 2, 3), or physical changes to the nanoparticle elicited by the pH gradient during endosome aging (Example 1b.). In certain embodiments, the nanoparticle of this invention enlarges diameter within the endosome as the pH becomes more acidic (see, e.g., FIG. 26). In certain other embodiments, the nanoparticle of this invention changes conformation thus contributing to endosome membrane disruption features of the capsid protein in which it is encased.

RNase III endoribonucleases typically fall into one of four classes (see, e.g., Lamontagne 2004). Class I RNases III are largely found in bacteria and bacteriophage, and include all bacterial enzymes that possess both the classical nuclease domain and a dsRNA binding domain. Exemplary Class I RNase III endoribonucleases include mc from *E. coli*.

Class II enzymes are typically distinguished from Class I enzymes by the presence of an N-terminal extension. Examples of Class II endoribonucleases include PacI from *Saccharomyces pombe*, and Rnt1p from *S. cerevisiae*.

Class III enzymes typically possess two nuclease domains and include both plant and vertebrate enzymes. Examples of Class III enzymes include Drosha proteins (see, e.g., Filippov 2000). Drosha enzymes are typically responsible for initiating the processing of microRNA (miRNA), or short RNA molecules naturally expressed by the cell that regulate a wide variety of other genes by interacting with the RISC complex to induce cleavage of complementary mRNA. Drosha exists as part of a protein complex called the Microprocessor complex, which also contains the double-stranded RNA binding protein Pasha (also called DGCR8; see Denli 2004), which is essential for Drosha activity and is capable of binding single-stranded fragments of the pri-miRNA that are required for proper processing (Han 2006). Both Drosha and Pasha are localized to the cell nucleus, where processing of pri-miRNA to pre-miRNA occurs. This latter molecule is then further processed by the RNase DICER into mature miRNAs in the cell cytoplasm.

Class IV RNase III endoribonucleases include the DICER and DICER-like family of enzymes, which are known to function in RNA interference (RNAi). DICER is an endoribonuclease in the RNase III family that cleaves double-stranded RNA (dsRNA) and pre-microRNA (miRNA) into short double-stranded RNA fragments (Bernstein 2001). These short double-stranded RNA fragments are often referred to as small interfering RNA (siRNA), which are typically about 20-25 nucleotides long, and usually contain a two-base overhang on the 3' end. DICER enzymes contain dual RNase III domains/motifs and one PAZ domain (see Song 2003 for the structure of PAZ domains), and the distance between these two regions of the molecule is determined by the length and angle of the connector helix and determines the length of the siRNAs it produces (Macrae 2006). DICER catalyzes the first step in the RNA interference pathway, and initiates formation of the RISC, whose catalytic component argonaute is an endonuclease that is capable of degrading messenger RNA (mRNA) having a sequence that is complementary to that of the siRNA guide strand, or target gene sequence (Jaronczyk 2005).

In still other specific embodiments, the polynucleotide nanoparticle slows down the endonuclease degradation, including Class IV Dicer.

In still other specific embodiments, the polynucleotide nanoparticle comprises natural or synthetic RNA or DNA.

In still other specific embodiments, the polynucleotide nanoparticle comprises natural or synthetic RNA or DNA, 2' modified, locked or unlocked nucleotides.

According to another aspect of the invention, the polynucleotide nanoparticle provides composition comprising one or more isolated polynucleotide nanoparticles, as described in any of the embodiments herein, in combination with a physiologically acceptable excipient.

According to still another aspect of the invention, the polynucleotide nanoparticle provides methods for delivering two or more MV-RNA molecules, either the same or different, with a single target uptake cell event comprising contacting the target cell with an isolated polynucleotide nanoparticle or composition described herein.

According to still yet another aspect of the invention, as described in any of the embodiments herein, the ratio or surface to core stems scales proportionately with the nanoparticles' diameter by either increasing end-to-end plurality of each MV-RNA or by end-to-end arrangements of stacked MV-RNA, closed by 5' complementarity to 3', or not.

The polynucleotide nanoparticles of the present invention can comprise natural or synthetic RNA or DNA, or peptide nucleic acids, or a combination of any or all of these types of molecules. In addition, a polynucleotide nanoparticle may comprise modified nucleic acids, or derivatives or analogs of nucleic acids.

In preferred embodiments, the polynucleotide nanoparticles of this invention are comprised of naturally occurring RNA, DNA, 2' Fluor RNA, 2'-OMe RNA analogs, or other nucleotide moieties compatible with transcription.

In the context of the invention, the term isolated refers to a material that is at least partially free from components that normally accompany the material in the material's native state. Isolation connotes a degree of separation from an original source or surroundings. Isolated, as used herein, e.g., related to DNA, refers to a polynucleotide nanoparticle that is substantially away from other coding sequences, and that the nanoparticle does not contain large portions of unrelated RNA or DNA, such as large chromosomal fragments or other functional genes or polypeptide coding regions. Of course, this refers to the DNA molecule as originally isolated, and does not exclude genes or coding regions later added to the segment by the hand of man.

Examples of nucleic acid modifications that can be made to an isolated polynucleotide nanoparticle of the invention include, but are not limited to, biotin labeling, fluorescent labeling, amino modifiers introducing a primary amine into the polynucleotide nanoparticle, phosphate groups, deoxyuridine, halogenated nucleosides, phosphorothioates, 2'-OMe RNA analogs, chimeric RNA analogs, wobble groups, and deoxyinosine.

The term "analog" as used herein refers to a molecule, compound, or composition that retains the same structure and/or function (e.g., binding to a target) as a polynucleotide nanoparticle herein. Examples of analogs include peptidomimetics, peptide nucleic acids, and small and large organic or inorganic compounds.

The term "derivative" or "variant" as used herein refers to a sequence that differs from a naturally occurring sequence (e.g., target gene sequence) by one or more nucleic acid deletions, additions, substitutions or side-chain modifications. In certain embodiments, variants have at least 70%, at least 80% at least 90%, at least 95%, or at least 99% sequence identity to a region of a target gene sequence. Thus, for example, in certain embodiments, a nanoparticle of the invention may include a region that is complementary to a variant of a target gene sequence.

With respect to targeting sequences, the isolated polynucleotide nanoparticles of the invention generally contain sequence regions that are complementary, and more preferably, completely complementary to one or more regions of a target gene or polynucleotide nanoparticle sequence (or a variant thereof). In certain embodiments, selection of a sequence region complementary to a target gene (or mRNA) is based upon analysis of the chosen target sequence and determination of secondary structure, $T_m$, binding energy, and relative stability. Such sequences may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA, sequences that are substantially complementary to the coding region of the mRNA, or those sequences that are substantially complementary to 3' regions of the mRNA. These secondary structure analyses and target site selection considerations can be performed, for example, using v.4 of the OLIGO primer analysis software and/or the BLASTN 2.0.5 algorithm software (Altschul et al., Nucleic Acids Res. 1997, 25(17):3389-402) or Oligoengine Workstation 2.0.

In one embodiment, target sites are preferentially not located within the 5' and 3' untranslated regions (UTRs) or regions near the start codon (within approximately 75 bases), since proteins that bind regulatory regions may interfere with the binding of the polynucleotide nanoparticle. In addition, potential target sites may be compared to an appropriate genome database, such as BLASTN 2.0.5, available on the NCBI server at www.ncbi.nlm, and potential target sequences with significant homology to other coding sequences eliminated.

In another embodiment, the target sites are located within the 5' or 3' untranslated region (UTRs). In addition, the self-complementary of the self-forming polynucleotide nanoparticle may be composed of a particular sequence found in the mRNA of the target.

In yet another embodiment, one or more target sites are located on a non-coding gene or exogenously introduced RNA.

In another embodiment, complementarity to the target site contains preferable mismatches or wobbles to the target at the 3' end of the guide strand. In such embodiments, the production of secondary RNAi triggers from amplification processes may be controlled.

In another embodiment, the loop region may designed to form a kissing-loop interaction with a determined loop region found in the 5' or 3' untranslated region (UTRs) of the target gene or a secondary target gene to that of the self-forming polynucleotide nanoparticle.

The target gene or mRNA may be from an organism of any species, including, for example, plant, animal (e.g. mammalian), protozoan, viral, bacterial or fungal.

As noted above, the target gene sequence and the complementary region of the polynucleotide nanoparticle may be complete complements of each other, or they may be less than completely complementary, i.e., partially complementary, as long as the strands hybridize to each other under physiological conditions.

Methods of Regulating Gene Expression

A target gene may be a known gene target, or, alternatively, a target gene may be not known, i.e., a random sequence may be used. In certain embodiments, target mRNA levels of one or more, preferably two or more, target mRNAs are reduced at least 10%, at least 20%, at least 30%, at least 40%, at least 50%, at least 60%, at least 70%, at least 75%, at least 80%, at least 90%, or at least 95%.

In one embodiment of the invention, the level of inhibition of target gene expression (i.e., mRNA expression) is at least 90%, at least 95%, at least 98%, at least 99% or is almost 100%, and hence the cell or organism will in effect have the phenotype equivalent to a so-called "knock out" of a gene. However, in some embodiments, it may be preferred to achieve only partial inhibition so that the phenotype is equivalent to a so-called "knockdown" of the gene. This method of knocking down gene expression can be used therapeutically or for research (e.g., to generate models of disease states, to examine the function of a gene, to assess whether an agent acts on a gene, to validate targets for drug discovery).

The invention further provides arrays of self-forming polynucleotide nanoparticles of the invention, including microarrays. Microarrays are miniaturized devices typically with dimensions in the micrometer to millimeter range for performing chemical and biochemical reactions and are particularly suited for embodiments of the invention. Arrays may be constructed via microelectronic and/or microfabrication using essentially any and all techniques known and available in the semiconductor industry and/or in the biochemistry industry, provided only that such techniques are amenable to and compatible with the deposition and/or screening of polynucleotide nanoparticle sequences.

Microarrays of the invention are particularly desirable for high throughput analysis of multiple self-forming polynucleotide nanoparticles. A microarray typically is constructed with discrete region or spots that comprise self-forming polynucleotide nanoparticles of the present invention, each spot comprising one or more self-forming polynucleotide nanoparticle, preferably at position addressable locations on the array surface. Arrays of the invention may be prepared by any method available in the art. For example, the light-directed chemical synthesis process developed by Affymetrix (see, U.S. Pat. Nos. 5,445,934 and 5,856,174) may be used to synthesize biomolecules on chip surfaces by combining solid-phase photochemical synthesis with photolithographic fabrication techniques. The chemical deposition approach developed by Incyte Pharmaceutical uses pre-synthesized cDNA probes for directed deposition onto chip surfaces (see, e.g., U.S. Pat. No. 5,874,554).

In certain embodiments, a polynucleotide nanoparticle of the present invention is synthesized as self-forming polynucleotide nanoparticle, using techniques widely available in the art. In other embodiments, it is expressed in vitro or in vivo using appropriate and widely known techniques. Accordingly, in certain embodiments, the present invention includes in vitro and in vivo expression vectors or sequences comprising the sequence of a self-forming polynucleotide nanoparticle of the present invention. Methods well known to those skilled in the art may be used to construct expression vectors containing sequences encoding a self-forming polynucleotide nanoparticle, as well as appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

Expression vectors typically include regulatory sequences, which regulate expression of the self-forming polynucleotide nanoparticle. Regulatory sequences present in an expression vector include those non-translated regions of the vector, e.g., enhancers, promoters, 5' and 3' untranslated regions, which interact with host cellular proteins to carry out transcription and translation. Such elements may vary in their strength and specificity. Depending on the vector system and cell utilized, any number of suitable transcription and translation elements, including constitutive and inducible promoters, may be used. In addition, tissue- or-cell specific promoters may also be used.

For expression in mammalian cells, promoters from mammalian genes or from mammalian viruses are generally preferred. In addition, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus that is capable of expressing the polypeptide in infected host cells (Logan 1984). In addition, transcription enhancers, such as the Rous sarcoma virus (RSV) enhancer, may be used to increase expression in mammalian host cells.

In certain embodiments, the invention provides for the conditional expression of a self-forming polynucleotide nanoparticle. A variety of conditional expression systems are known and available in the art for use in both cells and animals, and the invention contemplates the use of any such conditional expression system to regulate the expression or activity of a self-forming polynucleotide nanoparticle. In one embodiment of the invention, for example, inducible expression is achieved using the REV-TET system. Components of this system and methods of using the system to control the expression of a gene are well documented in the literature, and vectors expressing the tetracycline-controlled transactivator (tTA) or the reverse tTA (rtTA) are commercially available (e.g., pTet-Off, pTet-On and ptTA-2/3/4 vectors, Clontech, Palo Alto, Calif.). Such systems are described, for example, in U.S. Pat. Nos. 5,650,298, 6,271,348, 5,922,927, and related patents, which are incorporated by reference in their entirety.

In one particular embodiment, polynucleotide nanoparticles are expressed using a vector system comprising a pSUPER vector backbone and additional sequences corresponding to the self-forming polynucleotide nanoparticle to be expressed. The pSUPER vectors system has been shown useful in expressing siRNA reagents and downregulating gene expression (Brummelkamp 2002a, Brummelkamp 2002b). PSUPER vectors are commercially available from OligoEngine, Seattle, Wash.

Polynucleotide nanoparticles of the invention may be used for a variety of purposes, all generally related to their ability to inhibit or reduce expression of a target gene. Accordingly, the invention provides methods of reducing expression of one or more target genes comprising introducing a self-forming polynucleotide nanoparticle of the invention into a cell that contains a target gene or a homolog, variant or ortholog thereof. In addition, self-forming polynucleotide nanoparticles may be used to reduce expression indirectly. For example, a self-forming polynucleotide nanoparticle may be used to reduce expression of a transactivator that drives expression of a second gene, thereby reducing expression of the second gene. Similarly, a self-forming polynucleotide nanoparticle may be used to increase expression indirectly. For example, a self-forming polynucleotide nanoparticle may be used to reduce expression of a transcriptional repressor that inhibits expression of a second gene, thereby increasing expression of the second gene.

In various embodiments, a target gene is a gene derived from the cell into which a self-forming polynucleotide nanoparticle is to be introduced, an endogenous gene, an exogenous gene, a transgene, or a gene of a pathogen that is present in the cell after transfection thereof. Depending on the particular target gene and the amount of the self-forming polynucleotide nanoparticle delivered into the cell, the method of this invention may cause partial or complete inhibition of the expression of the target gene. The cell containing the target gene may be derived from or contained in any organism (e.g., plant, animal, protozoan, virus, bacterium, or fungus).

Inhibition of the expression of the target gene can be verified by means including, but not limited to, observing or detecting an absence or observable decrease in the level of protein encoded by a target gene, and/or mRNA product from a target gene, and/or a phenotype associated with expression of the gene, using techniques known to a person skilled in the field of the present invention.

Examples of cell characteristics that may be examined to determine the effect caused by introduction of a self-forming polynucleotide nanoparticle of the invention include, cell growth, apoptosis, cell cycle characteristics, cellular differentiation, and morphology.

A self-forming polynucleotide nanoparticle may be directly introduced to the cell (i.e., intracellularly), or introduced extracellularly into a cavity, interstitial space, into the circulation of an organism, introduced orally, by ingestion of the expression host, by bathing an organism in a solution containing the self-forming polynucleotide nanoparticle, or by some other means sufficient to deliver the self-forming polynucleotide nanoparticle into the cell.

In addition, a vector engineered to express a self-forming polynucleotide nanoparticle may be introduced into a cell, wherein the vector expresses the self-forming polynucleotide nanoparticle, thereby introducing it into the cell.

Methods of transferring an expression vector into a cell are widely known and available in the art, including, e.g., transfection, lipofection, scrape loading, electroporation, microinjection, infection, gene gun, and retrotransposition. Generally, a suitable method of introducing a vector into a cell is readily determined by one of skill in the art based upon the type of vector and the type of cell, and teachings widely available in the art. Infective agents may be introduced by a variety of means readily available in the art, including, e.g., nasal inhalation.

Methods of inhibiting gene expression using self-forming polynucleotide nanoparticles of the invention may be combined with other knockdown and knockout methods, e.g., gene targeting, antisense RNA, ribozymes, double-stranded RNA (e.g., shRNA and siRNA) to further reduce expression of a target gene.

In different embodiments, target cells of the invention are primary cells, cell lines, immortalized cells, or transformed cells. A target cell may be a somatic cell or a germ cell. The target cell may be a non-dividing cell, such as a neuron, or it may be capable of proliferating in vitro in suitable cell culture conditions. Target cells may be normal cells, or they may be diseased cells, including those containing a known genetic mutation. Eukaryotic target cells of the invention include mammalian cells, such as, for example, a human cell, a murine cell, a rodent cell, and a primate cell. In one embodiment, a target cell of the invention is a stem cell, which includes, for example, an embryonic stem cell, such as a murine embryonic stem cell.

The self-forming polynucleotide nanoparticles and methods of the present invention may be used for regulating genes in plants, e.g., by providing RNA for systemic or non-systemic regulation of genes.

The self-forming polynucleotide nanoparticles and methods of the present invention are useful for regulating endogenous genes of a plant pest or pathogen.

The self-forming polynucleotide nanoparticles and methods of the present invention may be used to treat any of a wide variety of diseases or disorders, including, but not limited to, inflammatory diseases, cardiovascular diseases, nervous system diseases, tumors, demyelinating diseases, digestive system diseases, endocrine system diseases, reproductive system diseases, hemic and lymphatic diseases, immunological diseases, mental disorders, musculoskeletal diseases, neurological diseases, neuromuscular diseases, metabolic diseases, sexually transmitted diseases, skin and connective tissue diseases, urological diseases, and infections.

In certain embodiments, the methods are practiced on an animal, in particular embodiments, a mammal, and in certain embodiments, a human.

Accordingly, in one embodiment, the present invention includes methods of using a self-forming polynucleotide nanoparticles for the treatment or prevention of a disease associated with gene deregulation, overexpression, or mutation. For example, a self-forming polynucleotide nanoparticle may be introduced into a cancerous cell or tumor and thereby inhibit expression of a gene required for or associated with maintenance of the carcinogenic/tumorigenic phenotype. To prevent a disease or other pathology, a target gene may be selected that is, e.g., required for initiation or maintenance of a disease/pathology. Treatment may include amelioration of any symptom associated with the disease or clinical indication associated with the pathology.

In addition, self-forming polynucleotide nanoparticles of the present invention are used to treat diseases or disorders associated with gene mutation. In one embodiment, a self-forming polynucleotide nanoparticle is used to modulate expression of a mutated gene or allele. In such embodiments, the mutated gene is the target of the self-forming polynucleotide nanoparticle, which will comprise a region complementary to a region of the mutated gene. This region may include the mutation, but it is not required, as another region of the gene may also be targeted, resulting in decreased expression of the mutant gene or mRNA. In certain embodiments, this region comprises the mutation, and, in related embodiments, the resulting self-forming polynucleotide nanoparticles specifically inhibits expression of the mutant mRNA or gene but not the wild type mRNA or gene. Such a self-forming polynucleotide nanoparticle is particularly useful in situations, e.g., where one allele is mutated but another is not. However, in other embodiments, this sequence would not necessarily comprise the mutation and may, therefore, comprise only wild-type sequence. Such a self-forming polynucleotide nanoparticle is particularly useful in situations, e.g., where all alleles are mutated. A variety of diseases and disorders are known in the art to be associated with or caused by gene mutation, and the invention encompasses the treatment of any such disease or disorder with a self-forming polynucleotide nanoparticle.

In certain embodiments, a gene of a pathogen is targeted for inhibition. For example, the gene could cause immunosuppression of the host directly or be essential for replication of the pathogen, transmission of the pathogen, or maintenance of the infection. In addition, the target gene may be a pathogen gene or host gene responsible for entry of a pathogen into its host, drug metabolism by the pathogen or host, replication or integration of the pathogen's genome, establishment or spread of an infection in the host, or assembly of the next generation of pathogen. Methods of prophylaxis (i.e., prevention or decreased risk of infection), as well as reduction in the frequency or severity of symptoms associated with infection are included in the present invention. For example, cells at risk for infection by a pathogen or already infected cells, particularly human immunodeficiency virus (HIV) infections, may be targeted for treatment by introduction of a self-forming polynucleotide nanoparticle according to the invention.

In other specific embodiments, the present invention is used for the treatment or development of treatments for cancers of any type. Examples of tumors that can be treated using the methods described herein include, but are not limited to, neuroblastomas, myelomas, prostate cancers, small cell lung cancer, colon cancer, ovarian cancer, non-small cell lung cancer, brain tumors, breast cancer, leukemias, lymphomas, and others.

The self-forming polynucleotide nanoparticles and expression vectors (including viral vectors and viruses) may be introduced into cells in vitro or ex vivo and then subsequently placed into an animal to affect therapy, or they may be directly introduced to a patient by in vivo administration. Thus, the invention provides methods of gene therapy, in certain embodiments. Compositions of the invention may be administered to a patient in any of a number of ways, including parenteral, intravenous, systemic, local, oral, intratumoral, intramuscular, subcutaneous, intraperitoneal, inhalation, or any such method of delivery. In one embodiment, the compositions are administered parenterally, i.e., intraarticularly, intravenously, intraperitoneally, subcutaneously, or intramuscularly. In a specific embodiment, the liposomal compositions are administered by intravenous infusion or intraperitoneally by a bolus injection.

Compositions of the invention may be formulated as pharmaceutical compositions suitable for delivery to a subject. The pharmaceutical compositions of the invention will often further comprise one or more buffers (e.g., neutral buffered saline or phosphate buffered saline), carbohydrates (e.g., glucose, mannose, sucrose, dextrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The amount of self-forming polynucleotide nanoparticles administered to a patient can be readily determined by a physician based upon a variety of factors, including, e.g., the disease and the level of self-forming polynucleotide nanoparticles expressed from the vector being used (in cases where a vector is administered). The amount administered per dose is typically selected to be above the minimal therapeutic dose but below a toxic dose. The choice of amount per dose will depend on a number of factors, such as the medical history of the patient, the use of other therapies, and the nature of the disease. In addition, the amount administered may be adjusted throughout treatment, depending on the patient's response to treatment and the presence or severity of any treatment-associated side effects.

The invention further includes a method of identifying gene function in an organism comprising the use of a self-forming polynucleotide nanoparticle to inhibit the activity of a target gene of previously unknown function. Instead of the time consuming and laborious isolation of mutants by traditional genetic screening, functional genomics envisions determining the function of uncharacterized genes by employing the invention to reduce the amount and/or alter the timing of target gene activity. The invention may be used in determining potential targets for pharmaceutics, understanding normal and pathological events associated with development, determining signaling pathways responsible for postnatal development/aging, and the like. The increasing speed of acquiring nucleotide sequence information from genomic and expressed gene sources, including total sequences for the yeast, *D. melanogaster*, and *C. elegans* genomes, can be coupled with the invention to determine gene function in an organism (e.g., nematode). The preference of different organisms to use particular codons, searching sequence databases for related gene products, correlating the linkage map of genetic traits with the physical map from which the nucleotide sequences are derived, and artificial intelligence methods may be used to define putative open reading frames from the nucleotide sequences acquired in such sequencing projects.

In one embodiment, a self-forming polynucleotide nanoparticle is used to inhibit gene expression based upon a partial sequence available from an expressed sequence tag (EST), e.g., in order to determine the gene's function or biological activity. Functional alterations in growth, development, metabolism, disease resistance, or other biological processes would be indicative of the normal role of the EST's gene product.

The ease with which a self-forming polynucleotide nanoparticle can be introduced into an intact cell/organism containing the target gene allows the present invention to be used in high throughput screening (HTS). For example, solutions containing self-forming polynucleotide nanoparticle that are capable of inhibiting different expressed genes can be placed into individual wells positioned on a microtiter plate as an ordered array, and intact cells/organisms in each well can be assayed for any changes or modifications in behavior or development due to inhibition of target gene activity. The function of the target gene can be assayed from the effects it has on the cell/organism when gene activity is inhibited. In one embodiment, self-forming polynucleotide nanoparticles of the invention are used for chemocogenomic screening, i.e., testing compounds for their ability to reverse a disease modeled by the reduction of gene expression using a self-forming polynucleotide nanoparticle of the invention.

If a characteristic of an organism is determined to be genetically linked to a polymorphism through RFLP or QTL analysis, the present invention can be used to gain insight regarding whether that genetic polymorphism may be directly responsible for the characteristic. For example, a fragment defining the genetic polymorphism or sequences in the vicinity of such a genetic polymorphism can be amplified to produce an RNA, a self-forming polynucleotide nanoparticle can be introduced to the organism, and whether an alteration in the characteristic is correlated with inhibition can be determined.

The present invention is also useful in allowing the inhibition of essential genes. Such genes may be required for cell or organism viability at only particular stages of development or cellular compartments. The functional equivalent of conditional mutations may be produced by inhibiting activity of the target gene when or where it is not required for viability. The invention allows addition of a self-forming polynucleotide nanoparticle at specific times of development and locations in the organism without introducing permanent mutations into the target genome. Similarly, the invention contemplates the use of inducible or conditional vectors that express a self-forming polynucleotide nanoparticle only when desired.

The present invention also relates to a method of validating whether a gene product is a target for drug discovery or development. A self-forming polynucleotide nanoparticle that targets the mRNA that corresponds to the gene for degradation is introduced into a cell or organism. The cell or organism is maintained under conditions in which degradation of the mRNA occurs, resulting in decreased expression of the gene. Whether decreased expression of the gene has an effect on the cell or organism is determined. If decreased expression of the gene has an effect, then the gene product is a target for drug discovery or development.

Methods of Designing and Producing the Self-Forming Polynucleotide Nanoparticle

The self-forming polynucleotide nanoparticles of the present invention comprise a novel and unique set of functional sequences as MV-RNA, arranged in a manner end-to-end so as to generally adopt a sphere-like secondary structure during transcription, which imparts the advantages of the polynucleotide nanoparticles. Accordingly, in certain embodiments, the present invention includes methods of designing the polynucleotide of the present invention. Such methods typically involve appropriate orientation of the various MV-RNA components contained within the polynucleotide nanoparticle.

In one illustrative example of producing an isolated polynucleotide nanoparticle of the invention, individual MV-RNA molecule sequences of the format shown in section "III" below are then adjoined into a chain of two or more MV-RNA molecules using a 5' to 3' pattern interleaving the 'Molecule' with the 'Linkage' (I) into a single isolated oligonucleotide sequence which is optionally closed in the manner described in section 'IV' below. Non-limiting examples of MV-RNA nanoparticles produced in this manner are shown in FIGS. 4 and 6A-D.

The resulting oligonucleotide is constructed using a linear or circular pattern of a given repetition (plurality) of MV-RNA. Optionally, a fully circularized (lacking a 5' phosphate) version can be created by inserting the isolated oligonucleotide sequence of (IV) in between the inverted ribozyme sequences (a) & (b) of (V).

Features of the nanoparticle assembly are:

I. Illustrative Linkage Features:

Linkage features for use in isolated polynucleotides of the invention, for expression in eukaryotic and prokaryotic organisms, are set forth illustratively below:
 a. mono-linkage: <mononucleotide>
 b. di-linkage: <dinucleotide>
 c. pH-linkage: <pH-linkage>

II. Illustrative mV-RNA Loop Features:

Loop features within an MV-RNA for use in isolated polynucleotides of the invention, for expression in eukaryotic and prokaryotic organisms, are set forth illustratively below:
 a. dicer1: <5-12 nt loop>
 b. rnt1: <13 nt stem, tetra-loop>
 c. aptamer: <aptamer>

III. Illustrative MV-RNA Molecule Features:

features for use in isolated polynucleotides of the invention are set forth illustratively below:
 a. targeting MV-RNA I: <Primary Guide><loop><Secondary Guide><aptamer><Key Guide>
 b. targeting MV-RNA II: <Primary Guide><aptamer><Secondary Guide><loop><Key Guide>
 c. targeting MV-RNA III: <Primary Guide><aptamer><Secondary Guide><aptamer><Key Guide>
 d. non-targeting MV-RNA II: <Primary Guide><loop><Secondary Guide><loop><Key Guide>

IV. Illustrative Nanoparticle Open/Close Features:

Features for use in closing 5' to 3' ends of isolated polynucleotides of the invention are set forth illustratively below by defining an 'opening sequence' and a 'closing sequence':
 a. Opening MV-RNA Fragment: <Primary Guide><loop><Secondary Guide>
 b. Closing MV-RNA Fragment: <Key Guide>
 c. Opening MV-RNA Fragment II: <Primary Guide>
 d. Closing MV-RNA Fragment II: <Secondary Guide><loop><Key Guide>
 e. Opening RNA Fragment: <ssRNA 1-400 nt>
 f. Closing RNA Fragment: <ssRNA 1-400 nt partially to fully complementary to 'c' above>

V. Illustrative Design of Connecting mV-RNA Molecule into Nanoparticle Format:
 a. 5' to 3' General Patterns: For Linear, <RNAi Molecule 1><Linkage><RNAi Molecule 2><Linkage>,,,...repeat. For Circular, <Opening Sequence><RNAi Molecule 1><Linkage><RNAi Molecule 2><Linkage>,,,...repeat, <Closing Sequence>
 b. STACKED MV-RNA NANOPARTICLE EXCEPTION (FIG. 3B): Stacking MV-RNA molecules have a unique pattern to ensure the integrity of the structured transcript and creates a higher surface-to-core stem ratio. In general, additional MV-RNA sequences are inserted into the loops of a preceding MV-RNA after the P strand overhang and before the S strand, and an additional MV-RNA inserted after the S strand overhang and before the K strand. <MV-RNA_1 Primary Strand><2 nt OH><MV-RNA_2><2 nt OH><MV-RNA_1 Secondary Strand><2 nt OH><MV-RNA_3><2 nt OH><MV-RNA_1 Key Strand><Linkage>,,,,,,,,repeating. When linking multiple versions of the same sequence, one can switch the sequence orientation of (P, S, K or S, K, P or K, P, S) while interleaving the RNAi Molecules. This will aide in nearest neighbor Watson-Crick interactions during transcription over intra-molecular bonds that may result in alternate structures.

V. Ribozyme Based Circularization of the Polynucleotide Nanoparticle:

One can circularize an RNA transcript in situ as part of the transcription reaction by using methods described in the art (Perriman 1998). For the removal of the 5' phosphate and complete circularization of the nanoparticle, insert the nanoparticle sequence designed using the motifs above in between the 'Cir_5' and 'Cir_3' sequences below to define the whole transcript:

a. Cir_5:
(SEQ ID NO: 1)
GAAAATTTCGTCTGGATTAGTTACTTATCGTGTAAAATCTGATA

AATGGAATTGGTTCTACATAAATGCCTAACGACTATCCCTTTGG

GGAGTAGGGTCAAGTGACTCGAAACGATAGACAACTTGCTTTA

ACAAGTTGGAGATATAGTCTGCTCTGCATGGTGACATGCAGCTG

GATATAATTCCGGGGTAAGATTAACGACCTTATCTGAACATAAT

G *CTA* b. Cir_3:
(SEQ ID NO: 2)
*CAGGT*CAATTGAGGCCTGAGTATAAGGTGACTTATACTTGTAAT

CTATCTAAACGGGGAACCTCTCTAGTAGACAATCCCGTGCTAAA

TTGTAGGACTGCCCTTTAATAAATACTTCTATATTTAAAGAGGT

ATTTATGAAAAGCGGAATTTATCAGATTAAAAATACTTTCT

IV. Verifying the Connecting RNAi Molecules:

Once the full sequence is designed using one of the patterns above, folding the RNA in a computer program like cofold, Vienna RNAfold, mFold, or specifically Multivalent RNAi Cloud computationally verifies the integrity of the secondary structure. The resulting fold notation or art will indicates free nucleotides as "." and bound nucleotides as "(" or ")". Relative Free-energy and melting temperature will also give indication as to the stability of the precise transcript. One can view the resulting art representing the precisely structured transcript.

Also provided herein are computer programs, as well as computer readable media and computers containing these programs, and the use thereof to select MV-RNA sequences of the nanoparticle, based upon the complementarity characteristics described herein. In certain embodiments, a user provides a computer with information regarding the sequences, locations or names of the target gene(s). The computer uses this input in a program of the present invention to identify one or more appropriate regions of the target gene to target in MV-RNA formats, and outputs or provides complementary sequences to use for the assembly of the a polynucleotide nanoparticle of the invention. Typically, the program will select a series of sequences that are not complementary to a genomic sequence, including the target gene, or the region of the polynucleotide nanoparticle that is complementary to the target gene. When desired, the program also provides sequences of gap regions, fold notations, and fold art. Upon selection of appropriate MV-RNA orientations, plurality, aptamers, loops, linkages, Opening/

Closing sequence, cloning sites, and necessary transcription elements, the computer program outputs or provides this information to the user.

The programs of the present invention may further use input regarding the genomic sequence of the organism containing the target gene, e.g., public or private databases, as well as additional programs that predict secondary structure and/or hybridization characteristics of particular sequences, in order to ensure that the polynucleotide nanoparticle adopts the correct secondary structure (i.e., mFold, RNAfold, cofold) and does not hybridize to non-target genes (BLASTn).

The practice of the present invention will employ a variety of conventional techniques of cell biology, molecular biology, microbiology, and recombinant DNA, which are within the skill of the art. Such techniques are fully described in the literature. See, for example, Molecular Cloning: A Laboratory Manual, 2nd Ed., ed. by Sambrook, Fritsch, and Maniatis (Cold Spring Harbor Laboratory Press, 1989); and DNA Cloning, Volumes I and II (D. M. Glover, IRL Press, 1985.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

Example 1: Self-Forming Single-Stranded Polynucleotide MV-RNA Nanoparticle for the Treatment of Human Prostate Cancer This example describes the assembly of a nanoparticle sequence according to the invention targeting multiple genes contributing to human castration-resistant prostate cancer. Each nanoparticle utilizes both a PSMA targeting aptamer sequence for cell-specific uptake and a clathrin-pit endocytosis aptamer sequence for endosomal movement. The entire nanoparticle delivers multiple active MV-RNA RNAi triggers per endocytosis event and is scalable by increasing plurality of MV-RNA within the nanoparticle polynucleotide. Two multi-gene pathways are targeted by this example: (1) human AKT (SEQ ID NO:89), human MAP3K (SEQ ID NO:90; NM_005921), and human PLK1 (SEQ ID NO:91; NM_005030); and (2) human Androgen Receptor (SEQ ID NO:92 and SEQ ID NO:93 (variant transcripts))/cMET (SEQ ID NO:94; X54559). Each target set can represent part or all of a nanoparticle of this invention in a wide spectrum of targeting MV-RNA, or repetitive plurality to increase molarity of highly efficacious MV-RNA triggers.

The selected MV-RNA contained various Dicer loops and targeting aptamer sequences that were assigned while picking target sites. Such loops are shown in BOLD on each MV-RNA sequence below. These loop sequences can be readily moved around while assembling the nanoparticle sequence to distribute the targeting aptamers in any preferred manner. Each MV-RNA also contained 3' "UU" overhangs which can be changed to "AG" in order to be less susceptible to ssRNA endonucleases, or changed to "AC," "GC," "AU," or "GU" in order to increase the probability of ssRNA endonuclease cleavage after the second nucleotide of the overhang.

Loops in the Selected MV-RNA:

```
Loop Dicer 1:
                                              (SEQ ID NO: 3)
UCAAGAAAC Loop Dicer 2:
                                              (SEQ ID NO: 4)
GGAUCUUAUU Loop Dicer 3:
                                              (SEQ ID NO: 5)
UUCAUAGAGA Loop PSMA:
                                              (SEQ ID NO: 6)
GGGAGGACGAUGCGGAUCAGCCAUGUUUACGUCACUCCUUGUCAAUCCU

CAUCGGCAGACGACUCGCCCGA

Loop clathrin-pit:
                                              (SEQ ID NO: 7)
UUCCUCUAUCCGUUCUAAACGCUUUAUGAU
```

The selected example MV-RNA of each of the two pathways are set forth below. "Project #" refers to the project number from the Multivalent RNAi Cloud software application. Each MV-RNA sequence is assigned a three number series indicating the binding site of each guide strand on the target strand.

AR (Primary Pathway of Interest):

```
Androgen receptor/cMET, Project #P00900:
MV-RNA 1269/2030/2896:
CGCCGGGAGGUGCUGCGCUUUGGGAUCUUAUUCAAGGUGCAGCUCUCAU

UUCCUUGGAUCUUAUUAAGGAAGUGAGAACUUCUCGGCG (SEQ ID

NO: 8, Loop Dicer 2 in bold)

MV-RNA 5124/3363/4456:
CACUGAGGUCAAUGUGGACGGAGGAUCUUAUUUCGUCCACAUCGAGCAC

UUUAUGGGAGGACGAUGCGGAUCAGCCAUGUUUACGUCACUCCUUGUCAA

UCCUCAUCGGCAGACGACUCGCCCGAAUAAGGUGCUUGUGGCUUCAGUG (SEQ ID NO: 9, Loop Dicer 2 in bold, Loop PSMA underlined)

MV-RNA 7276/4095/6235:
CCUUUCUCAGAGUAAGGGAGAAGGAUCUUAUUUCUCCCUUGCAACAAGU

AAGACGGAUCUUAUUGUCUUGUUUGUUCUGAGAGAGGUU (SEQ

ID NO: 10, Loop Dicer 2 in bold)

Androgen receptor V.1-2, Project #P00901:
MV-RNA 2854/1186/9722:
CAGCUUCCACAUGUGAGAGAGCUCAAGAAACGCUCUCUCGCAAUAGGCUG

CUUGUUCCUCUAUCCGUUCUAAACGCUUUAUGAUUAAGUAGCUUAUGUGG

GAGCUG (SEQ ID NO: 11, Loop Dicer 1 in bold, Loop clathrin-pit underlined)

MV-RNA 298/585/1473:
CAAAGGCAGCCGUCAGUCCAUCUCAAGAAACGAUGGGCUGACAUUCAUAG

CCGUUCAAGAAACGCGGCUGUGAAGGUUGCUUUUG (SEQ ID

NO: 12, Loop Dicer 1 in bold)
```

-continued

Hs androgen receptor, Project #P00963:
MV-RNA 6820/7230/9832:
GUGUGUUCUAGUCUUUGGUGGUUCUCAAGAAACGAACCACCAGAGAAAC

AGUGUAGUUGACUCAAGAAACGUCAAUUACAUUGGCUAGAACAUAC (SEQ ID NO: 13, Loop Dicer 1 in bold)

Open/Close MV-RNA
MV-RNA 3900/3304:
GGGAAAUAGGGUUUCCAAUGCUUUGCUCAAGAAACGCAAAGUAUUGGAG

CCACACCAACCAGUCAAGAAACCUGGUUGGUGUGGAACCCUAUUUCCC (SEQ ID NO: 14, Loop Dicer 1 in bold)

Androgen receptor/cMetII, Project #P00962
MV-RNA 392/2356/375:
GGCUGAGAGUAGCCGACUGAGUUUGCUCAAGAAACGCAAACUCAGUUGA

AAUGGUUGCGCUUCAAGAAACAGUGCAAUCAUUUCUGCUCUCGGCC (SEQ ID NO: 15, Loop Dicer 1 in bold)

MV-RNA 936/1727/7518:
AAAGUCUCGUGCAGAAGAAGAUCACGUUCAUAGAGACGUGAUCUUCUUC

CCAGUGAUACCUUUUCAAGAAACAAGGUGUCACUGGGUUGUACGGGACUUU (SEQ ID NO: 16, Loop Dicer 3 and Loop Dicer 1 in bold)

MV-RNA 1826/3186/4274:
CUUGGCGUUGUCAGAAAUGGUUUCAGUCAAGAAACUUGAAACCAUUUCU

GUAGUUGACAGAUCAAGAAACUCUGUCAAUUACAUUGGCGACGCCAAGUU (SEQ ID NO: 17, Loop Dicer 1 in bold)

PI3K/AKT/MTOR (secondary pathway of interest):
AKT1/MAP3K/PLK1, Project #P00840
Effective PLK1 site
MV-RNA 153/1425/1504:
CUGCUUCUUGAGGCCGUCGUGUUUUCAAGAAACAACACGGCGGUUUGUUUC

CGCAGGGGAGGACGAUGCGGAUCAGCCAUGUUUACGUCACUCCUUGUCAA

UCCUCAUCGGCAGACGACUCGCCCGAUUGCGGAAAUAUUUAAGGAGCGG
(SEQ ID NO: 18, Loop Dicer 1 in bold, Loop PSMA underlined)

MV-RNA 481/1478/1802:
AGAGGCGGUCGUGGGUCUGGCUCUCAAGAAACGAGUUAGGCCCUAUCUGC

UGCGCUUUCCUCUAUCCGUUCUAAACGCUUUAUGAUGGCGUAGCGGAGCC
GGCUGCCUCU (SEQ ID NO: 19, Loop Dicer 1 in bold, Loop clathrin-pit underlined)

The nanoparticle of this example can be produced by in vitro transcription using T7 polymerase from a DNA template digested for fall-off transcription.

Assembling a Dodecahedron Polynucleotide Nanoparticle with Targeting Aptamers

Using the 12 MV-RNA listed above (SEQ ID NOs:8-19), one can make the nanoparticles of this invention by defining an open/close MV-RNA, and a series of linked MV-RNA as a core. The plurality can range from two to upper limits of gene synthesis or the transcription environment. This example assembles a 12 unit (Dodecahedron) nanoparticle as a simplified model.

The "Linkage," "Open," "Close," and "Core" components of the nanoparticle are as follows:

Linkage Component: AC

Open component:
GGGAAAUAGGGUUUCCAAUGCUUUGCUCAAGAAACGCAAAGUAUUGGAGC

CACACCAACCAGAC (SEQ ID NO: 20, Loop Dicer 1 in bold, linkage component in italics)

Prostate cancer nanoparticle core component assembled from MV-RNA above with linkages (not included open/close MV-RNA sequence):

CAAAGGCAGCCGUCAGUCCAUCUCAAGAAACGAUGGGCUGAC

AUUCAUAGCCGUUUCCUCUAUCCGUUCUAAACGCUUUAUGAU

GCGGCUGUGAAGGUUGCUUUUGACCGCCGGGAGGUGCUGCGC

UUUGGGAUCUUAUUCAAGGUGCAGCUCUCAUUUCCUUGGAU

CUUAUUAAGGAAGUGAGAACUUCUCGGCGACCACUGAGGUCA

AUGUGGACGGAGGAUCUUAUUUUCGUCCACAUCGAGCACUU

UAUGGGAGGACGAUGCGGAUCAGCCAUGUUUACGUCACUCCU

UGUCAAUCCUCAUCGGCAGACGACUCGCCCGAAUAAGGUGCU

UGUGGCUUCAGUGACCCUUUCUCAGAGUAAGGGAGAAGGAUC

UUAUUUUCUCCCUUGCAACAAGUAAGACGGAUCUUAUUGUC

UUGUUUGUUCUGAGAGAGGACCAGCUUCCACAUGUGAGAGAG

CUCAAGAAACGCUCUCUCGCAAUAGGCUGCUUGUUCCUCUAU

CCGUUCUAAACGCUUUAUGAUUAAGUAGCUUAUGUGGGAGCU

GACGUGUGUUCUAGUCUUUGGUGGUUCUCAAGAAACGAACCA

CCAGAGAAACAGUGUAGUUGACUCAAGAAACGUCAAUUACA

UUGGCUAGAACAUACACCUGCUUCUUGAGGCCGUCGUGUUUC

AAGAAACAACACGGCGGUUUGUUUCCGCAGGGGAGGACGAU

GCGGAUCAGCCAUGUUUACGUCACUCCUUGUCAAUCCUCAUC

GGCAGACGACUCGCCCGAUUGCGGAAAUAUUUAAGGAGCGGA

CGGCUGAGAGUAGCCGACUGAGUUUGCUCAAGAAACGCAAAC

UCAGUUGAAAUGGUUGCGCUUCAAGAAACAGUGCAAUCAUU

UCUGCUCUCGGCCACAGAGGCGGUCGUGGGUCUGGCUCUCAA

GAAACGAGUUAGGCCCUAUCUGCUGCGCUUUCCUCUAUCCGU

UCUAAACGCUUUAUGAUGGCGUAGCGGAGCCGGCUGCCUCUA

CAAAGUCUCGUGCAGAAGAAGAUCACGUUCAUAGAGACGUG

AUCUUCUUCCCAGUGAUACCUUGGGAGGACGAUGCGGAUCAG

CCAUGUUUACGUCACUCCUUGUCAAUCCUCAUCGGCAGACGA

CUCGCCCGAAAGGUGUCACUGGGUUGUACGGGACUUUACCUU

GGCGUUGUCAGAAAUGGUUUCAGUCAAGAAACUUGAAACCA

UUUCUGUAGUUGACAGAUCAAGAAACUCUGUCAAUUACAUU

GGCGACGCCAAGUUAC (SEQ ID NO: 21; Loop Dicer 1,

Loop Dicer 2, and Loop Dicer 3 in bold, Loop PSMA and Loop clathrin pit underlined, linkage component in italics).

Close component:
CUGGUUGGUGUGGAACCCUAUUUCCC (SEQ ID NO: 22)

The final polynucleotide sequence can be converted into an in vitro transcription template by converting the sequence to DNA, adding a 5' T7 transcription start site (AAT-TAATACGACTCACTATAGGN; SEQ ID NO:23, "N" indicates start nucleotides of a T7 transcript, preferably "G"), then restriction enzyme sites for cloning. In this example, the pUC57 (Genscript, NJ) vector is used for gene synthesis and template amplification by cloning the fragment into EcoRI, XbaI sites.

Final nucleotide sequence of the DNA transcription template cloned into pUC57 for the transcription of the Dodecahedron nanoparticle designed above (Prostate Cancer Nanoparticle):

AAT<u>*TAATACGACTCACTATAGG*</u>GGAAATAGGGTTTCCAATGCTTTG
CTCAAGAAACGCAAAGTATTGGAGCCACACCAACCAGACCAAA
GGCAGCCGTCAGTCCATCTCAAGAAACGATGGGCTGACATTCAT
AGCCGT<u>TTCCTCTATCCGTTCTAAACGCTTT</u>ATGATGCGGCTGTG
AAGGTTGCTTTTGACCGCCGGGAGGTGCTGCGCTTTGGATCTT
ATTCAAGGTGCAGCTCTCATTTCCTTGGATCTTATTAAGGAAGT
GAGAACTTCTCGGCGACCACTGAGGTCAATGTGGACGGAGGAT
CTTATTTTCGTCCACATCGAGCACTTTATGGGAGGACGATGCGG
<u>ATCAGCCATGTTTACGTCACTCCTTGTCAATCCTCATCGGCAGAC</u>
<u>GACTCGCCCGAA</u>TAAGGTGCTTGTGGCTTCAGTGACCCTTTCTC
AGAGTAAGGGAGAAGGATCTTATTTTCTCCCTTGCAACAAGTA
AGACGGATCTTATTGTCTTGTTTGTTCTGAGAGAGGACCAGCTT
CCACATGTGAGAGAGCTCAAGAAACGCTCTCTCGCAATAGGCT
GCTTGT<u>TCCTCTATCCGTTCTAAACGCTTT</u>ATGATTAAGTAGCTTA
TGTGGGAGCTGACGTGTGTTCTAGTCTTTGGTGGTTCTCAAGAA
ACGAACCACCAGAGAAACAGTGTAGTTGACTCAAGAAACGTC
AATTACATTGGCTAGAACATACACCTGCTTCTTGAGGCCGTCGTG
TTTCAAGAAACAACACGGCGGTTTGTTTCCGCAG<u>GGGAGGACG</u>
<u>ATGCGGATCAGCCATGTTTACGTCACTCCTTGTCAATCCTCATCG</u>
<u>GCAGACGACTCGCCCGA</u>TTGCGGAAATATTTAAGGAGCGGACGG
CTGAGAGTAGCCGACTGAGTTTGCTCAAGAAACGCAAACTCAG
TTGAAATGGTTGCGCTTCAAGAAACAGTGCAATCATTTCTGCTC
TCGGCCACAGAGGCGGTCGTGGGTCTGGCTTCAAGAAACGAG
TTAGGCCCTATCTGCTGCGCT<u>TTCCTCTATCCGTTCTAAACGCTTT</u>
<u>ATGAT</u>GCGTAGCGGAGCCGGCTGCCTCTacAAAGTCTCGTGCAG
AAGAAGATCACGTTCATAGAGACGTGATCTTCTTCCCAGTGATA
CCTTGGGAGGACGATGCGGATCAGCCATGTTTACGTCACTCCTT
<u>GTCAATCCTCATCGGCAGACGACTCGCCCGA</u>AAGGTGTCACTGG
GTTGTACGGGACTTTACCTTGGCGTTGTCAGAAATGGTTTCAGT
CAAGAAACTTGAAACCATTTCTGTAGTTGACAGATCAAGAAAC
TCTGTCAATTACATTGGCGACGCCAAGTTACCTGGTTGGTGTGG
AACCCTATTTCCCT (SEQ ID NO: 24; Loop Dicer 1, Loop Dicer 2, and Loop Dicer 3 in bold, Loop PSMA and Loop clathrin pit underlined, EcoRI restriction site/T7 transcription start site in italics and underlined, and linkage component in italics)

One of ordinary skill in the art can will recognize that this can easily be utilized under different promoters, and as such this example is not meant to be limiting. For example, in vivo expression of these same examples by Mammalian H1 promoter could easily be accomplished by utilizing "GGG" as the transcription start site after the TATA box (pSUPER), and "TTTTT" as the stop signal.

Resulting RNA transcript of Prostate Cancer Dodecahedron polynucleotide nanoparticle with targeting aptamers:

GGGAAAUAGGGUUUCCAAUGCUUUGCUCAAGAAACGCAAAG
UAUUGGAGCCACACCAACCAGACCAAAGGCAGCCGUCAGUCC
AUCUCAAGAAACGAUGGGCUGACAUUCAUAGCCGU<u>UUCCUCU</u>
<u>AUCCGUUCUAAACGCUUUAUGAUGCGGCUGUGAAGGUUGCUU</u>
UUGACCGCCGGGAGGUGCUGCGCUUUGGGAUCUUAUUCAAG
GUGCAGCUCUCAUUUCCUUGGAUCUUAUUAAGGAAGUGAGA
ACUUCUCGGCGACCACUGAGGUCAAUGUGGACGGAGGAUCUU
AUUUUCGUCCACAUCGAGCACUUUAU<u>GGGAGGACGAUGCGGA</u>
<u>UCAGCCAUGUUUACGUCACUCCUUGUCAAUCCUCAUCGGCAG</u>
<u>ACGACUCGCCCGAA</u>UAAGGUGCUUGUGGCUUCAGUGACCCUU
UCUCAGAGUAAGGGAGAAGGAUCUUAUUUUCUCCCUUGCAA
CAAGUAAGACGGAUCuUAUUGUCUUGUUUGUUCUGAGAGAG
GACCAGCUUCCACAUGUGAGAGAGCUCAAGAAACGCUCUCUC
GCAAUAGGCUGCUUG<u>UUCCUCUAUCCGUUCUAAACGCUUUAU</u>
<u>GAU</u>UAAGUAGCUUAUGUGGGAGCUGACGUGUGUUCUAGUCU
UUGGUGGUUCUCAAGAAACGAACCACCAGAGAAACAGUGUA
GUUGACUCAAGAAACGUCAAUUACAUUGGCUAGAACAUACA
CCUGCUUCUUGAGGCCGUCGUGUUUCAAGAAACAACACGGCG
GUUUGUUUCCGCAG<u>GGGAGGACGAUGCGGAUCAGCCAUGUUU</u>
<u>ACGUCACUCCUUGUCAAUCCUCAUCGGCAGACGACUCGCCCG</u>
<u>A</u>UUGCGGAAAUAUUUAAGGAGCGGACGGCUGAGAGUAGCCGA
CUGAGUUUGCUCAAGAAACGCAAACUCAGUUGAAAUGGUUG
CGCUUCAAGAAACAGUGCAAUCAUUUCUGCUCUCGGCCACAG
AGGCGGUCGUGGGUCUGGCUCUCAAGAAACGAGUUAGGCCCU
AUCUGCUGCGCU<u>UUCCUCUAUCCGUUCUAAACGCUUUAUGAU</u>
GGCGUAGCGGAGCCGGCUGCCUCUACAAAGUCUCGUGCAGAA
GAAGAUCACGUUCAUAGAGACGUGAUCUUCUUCCCAGUGAU

```
ACCUUGGGAGGACGAUGCGGAUCAGCCAUGUUUACGUCACUC

CUUGUCAAUCCUCAUCGGCAGACGACUCGCCCGAAAGGUGUC

ACUGGGUUGUACGGGACUUUACCUUGGCGUUGUCAGAAAUGG

UUUCAGUCAAGAAACUUGAAACCAUUUCUGUAGUUGACAGA

UCAAGAAACUCUGUCAAUUACAUUGGCGACGCCAAGUUACCU

GGUUGGUGUGGAACCCUAUUUCCCU (SEQ ID NO: 25;

Loop Dicer 1, Loop Dicer 2, and Loop Dicer 3 in bold, Loop PSMA and Loop clathrin pit underlined, linkage component in italics)
```

Dodecahedron Polynucleotide Nanoparticle by Repetitive Plurality

Figure 19:
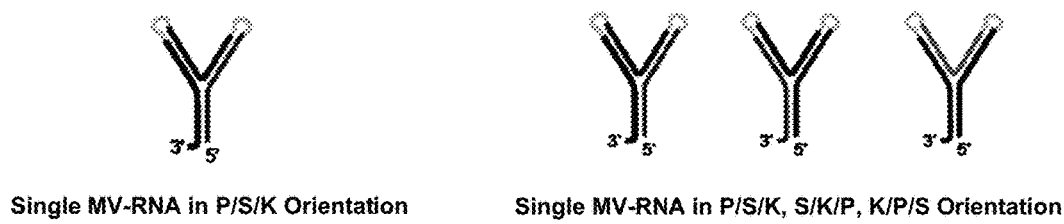
FIG. 19: Transcription orientations for repetitive plurality. Illustrates how a single MV-RNA sequence can be re-orientated for repetitive expression in a polynucleotide nanoparticle for effective transcription based RNA folding. (1) Individual MV-RNA guide strand orientations within the MV-RNA sequence. (2) Individual MV-RNA guide strand orientations in plurality within the transcript sequence.
Figure 19:
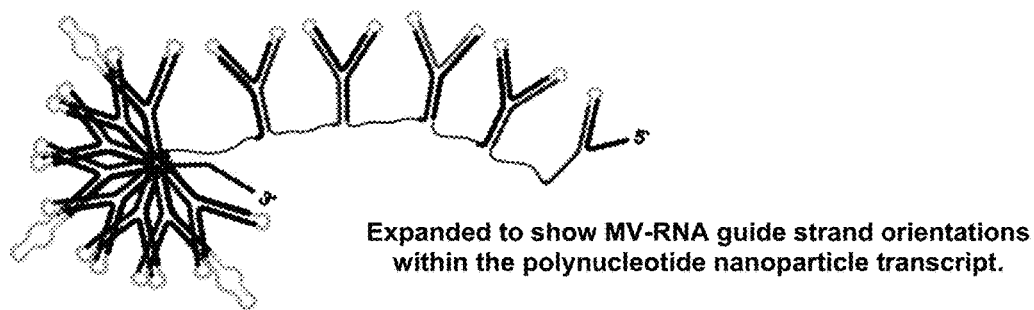

The ideal method to increase the molarity of a highly active MV-RNA is repetition within the polynucleotide nanoparticle sequence. To preserve the transcription based folding, interleaving a couple different MV-RNA or altering the orientation of a single MV-RNA when defining the nanoparticle sequence helps to preserve the secondary structure (see, e.g., FIG. 19). To confirm such transcription based structures, a computer program like 'cofold' (http://www.e-rna.org/cofold/) is suggested over the use of programs that rely on free energy to predict RNA secondary structure.

Interleaving a few MV-RNA in repetition is an effective manner to increase molarity.

```
MV-RNA 392/2356/375:
GGCUGAGAGUAGCCGACUGAGUUUGCUCAAGAAACGCAAACUCAGUUGAA

AUGGUUGCGCUUCAAGAAACAGUGCAAUCAUUUCUGCUCUCGGCC (SEQ ID NO: 15, Loop Dicer 1 in bold)

MV-RNA 936/1727/7518:
AAAGUCUCGUGCAGAAGAAGAUCACGUUCAUAGAGACGUGAUCUUCUUCC

CAGUGAUACCUUUCAAGAAACAAGGUGUCACUGGGUUGUACGGGACUUU (SEQ ID NO: 16, Loop Dicer 3 and Loop Dicer 1 in bold)

MV-RNA 1826/3186/4274:
CUUGGCGUUGUCAGAAAUGGUUUCAGUCAAGAAACUUGAAACCAUUUCUG

UAGUUGACAGAUCAAGAAACUCUGUCAAUUACAUUGGCGACGCCAAGUU (SEQ ID NO: 17, Loop Dicer 1 in bold)

Open component:
GGGAAAUAGGGUUUCCAAUGCUUUGCUCAAGAAACGCAAAGUAUUGGAGC

CACACCAACCAGAC (SEQ ID NO: 20, Loop Dicer 1 in bold, linkage component in italics)
```

Increased molarity nanoparticle generated by repeating the three MV-RNA of SEQ ID NOs:16, 17, and 20 while interleaving transcription order of each:

```
GGCUGAGAGUAGCCGACUGAGUUUGCUCAAGAAACGCAAAC

UCAGUUGAAAUGGUUGCGCUUCAAGAAACAGUGCAAUCAUU

UCUGCUCUCGGCCACAAAGUCUCGUGCAGAAGAAGAUCACGU

UCAUAGAGACGUGAUCUUCUUCCCAGUGAUACCUUUCAAGA

AACAAGGUGUCACUGGGUUGUACGGGACUUUACCUUGGCGUU

GUCAGAAAUGGUUUCAGUCAAGAAACUUGAAACCAUUUCUG

UAGUUGACAGAUCAAGAAACUCUGUCAAUUACAUUGGCGAC

GCCAAGUUACAAAGUCUCGUGCAGAAGAAGAUCACGUUCAUA

GAGACGUGAUCUUCUUCCCAGUGAUACCUUUCAAGAAACAA

GGUGUCACUGGGUUGUACGGGACUUUACCUUGGCGUUGUCAG

AAAUGGUUUCAGUCAAGAAACUUGAAACCAUUUCUGUAGUU

GACAGAUCAAGAAACUCUGUCAAUUACAUUGGCGACGCCAAG

UUACGGCUGAGAGUAGCCGACUGAGUUUGCUCAAGAAACGCA

AACUCAGUUGAAAUGGUUGCGCUUCAAGAAACAGUGCAAUC

AUUUCUGCUCUCGGCCACCUUGGCGUUGUCAGAAAUGGUUUC

AGUCAAGAAACUUGAAACCAUUUCUGUAGUUGACAGAUCAA

GAAACUCUGUCAAUUACAUUGGCGACGCCAAGUUACGGCUGA

GAGUAGCCGACUGAGUUUGCUCAAGAAACGCAAACUCAGUU

GAAAUGGUUGCGCUUCAAGAAACAGUGCAAUCAUUUCUGCU

CUCGGCCACAAAGUCUCGUGCAGAAGAAGAUCACGUUCAUAG

AGACGUGAUCUUCUUCCCAGUGAUACCUUUCAAGAAACAAG

GUGUCACUGGGUUGUACGGGACUUU (SEQ ID NO: 26;

Loop Dicer 1 and Loop Dicer 3 in bold, linkage component in italics)

Close component:
CUGGUUGGUGUGGAACCCUAUUUCCC (SEQ ID NO: 22)
```

Example of the nanoparticle sequence containing the "Open," "Close," and "Core" sequences made from repeating and interleaving the MV-RNA:

```
GGGAAAUAGGGUUUCCAAUGCUUUGCUCAAGAAACGCAAAG

UAUUGGAGCCACACCAACCAGACGGCUGAGAGUAGCCGACUG

AGUUUGCUCAAGAAACGCAAACUCAGUUGAAAUGGUUGCGC

UUCAAGAAACAGUGCAAUCAUUUCUGCUCUCGGCCACAAAGU

CUCGUGCAGAAGAAGAUCACGUUCAUAGAGACGUGAUCUUC

UUCCCAGUGAUACCUUUCAAGAAACAAGGUGUCACUGGGUU

GUACGGGACUUUACCUUGGCGUUGUCAGAAAUGGUUUCAGUC

AAGAAACUUGAAACCAUUUCUGUAGUUGACAGAUCAAGAAA

CUCUGUCAAUUACAUUGGCGACGCCAAGUUACAAAGUCUCGU

GCAGAAGAAGAUCACGUUCAUAGAGACGUGAUCUUCUUCCCA

GUGAUACCUUUCAAGAAACAAGGUGUCACUGGGUUGUACGG

GACUUUACCUUGGCGUUGUCAGAAAUGGUUUCAGUCAAGAAA

CUUGAAACCAUUUCUGUAGUUGACAGAUCAAGAAACUCUGU

CAAUUACAUUGGCGACGCCAAGUUACGGCUGAGAGUAGCCGA

CUGAGUUUGCUCAAGAAACGCAAACUCAGUUGAAAUGGUUG
```

-continued
CGCUUCAAGAAACAGUGCAAUCAUUUCUGCUCUCGGCCACCU

UGGCGUUGUCAGAAAUGGUUUCAGUCAAGAAACUUGAAACC

AUUUCUGUAGUUGACAGAUCAAGAAACUCUGUCAAUUACAU

UGGCGACGCCAAGUUACGGCUGAGAGUAGCCGACUGAGUUUG

CUCAAGAAACGCAAACUCAGUUGAAAUGGUUGCGCUUCAAG

AAACAGUGCAAUCAUUUCUGCUCUCGGCCACAAAGUCUCGUG

CAGAAGAAGAUCACGUUCAUAGAGACGUGAUCUUCUUCCCAG

UGAUACCUUUCAAGAAACAAGGUGUCACUGGGUUGUACGGG

ACUUUACCUGGUUGGUGUGGAACCCUAUUUCCC (SEQ ID

NO: 27; Loop Dicer 1 and Loop Dicer 3 in bold, linkage component in italics)

Cofold output (fold notations):
(((((((((((..(((((((((((.........)))))))))))).(((((((((((..
(((((((((((.(((((((((((.....          ....)))))))))))).
(((((((((((..........))))))))))))).))))))))))..(((((((((((.(((((((
(((((.......))))))))))))))(((((((((((..........))))))))))))).))))
)))))))..(((((((((((.(((((((         (((((.........)).)))))))
))).(((((((((((..........))))))))))))...)))))))))))....((((((((((
(((.(((((((((((......))))))))))))(((((((((((..........)))))))))))
))).)))))))))))..(((((((     (((.(((((((((((......)).)))))))
))).(((((((((((..........))))))))))))...)))))))))))....((((((((((.
(((((((((((..........))))))))))))).(((((((((..........))))))))))).))
)))))))))))..((      (((((((((((.(((((((((((......)).)))))))
))).(((((((((((..........))))))))))))...))))))))))  ....((((((((((.
(((((((((((..........))))))))))))).(((((((((..........))))))))))).))
))))))))     ))).((((((((((.(((((((((((......)))))))))))))
((((((((((((..........))))))))))))).)))       )))))))))..))))))))))
))))..)))))))))))

Circularization of a Polynucleotide Nanoparticle

Figure 12:
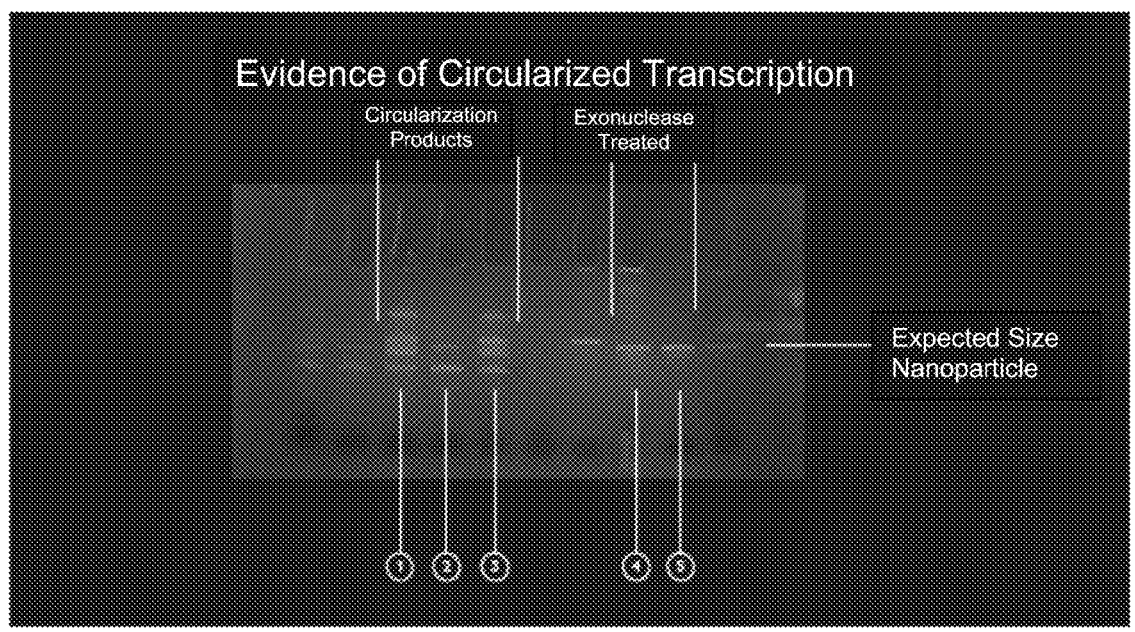
FIG. 12: Isolation of circularized self-forming MV-RNA nanoparticles. (1) All transcription by products of the circularization ribozyme during transcription, (2) a lower fractionation, (3) an upper fractionation, and (4-5) circularized RNA Nanoparticle confirmed by exo-nuclease digestion resistance.

An ideal polynucleotide nanoparticle for human use can be created using circularization ribozymes (Perriman 1998) to remove the immune stimulating 5' phosphate and reduce exonuclease degradation during in vivo use. Purification of the ribozyme products from the nanoparticle can be done by exonuclease digestion (FIG. 12), HPLC, Gel extraction, or in mg quantities using FPLC loaded with size exclusion columns (Kim 2007).

A sequence fragment was created using RNA cyclase ribozyme. Using a model of <5' cyclase ribozyme sequence><polynucleotide nanoparticle transcript><3' cyclase ribozyme sequence>, circularized nanoparticles can be made during transcription or thereafter utilizing a circularization reaction.

The cyclase ribozyme sequences are:

5' end w/ T7:
*AATTAATACGACTCACTATAGGG*GAAAATTTCGTCTGGATTAGTTACTT

ATCGTGTAAAATCTGATAAATGGAATTGGTTCTACATAAATGCCTAACG

ACTATCCCTTTGGGGAGTAGGGTCAAGTGACTCGAAACGATAGACAA

CTTGCTTTAACAAGTTGGAGATATAGTCTGCTCTGCATGGTGACATGC

AGCTGGATATAATTCCGGGGTAAGATTAACGACCTTATCTGAACATAA

TGCTA (SEQ ID NO: 28; EcoRI restriction site and

T7 transcription start cite in italics)

3' end:
CATGTCAATTGAGGCCTGAGTATAAGGTGACTTATACTTGTAATCTAT

CTAAACGGGGAACCTCTCTAGTAGACAATCCCGTGCTAAATTGTAGG

ACTGCCCTTTAATAAATACTTCTATATTTAAAGAGGTATTTATGAAAAG

CGGAATTTATCAGATTAAAAATACTTTCT (SEQ ID NO: 29)

The following sequence represents a prostate cancer-targeting circular dodecahedron nanoparticle generated by inserting a prostate cancer-targeting nanoparticle in between the above cyclase ribozyme sequences:

<u>AATTAATACGACTCACTATAGGG</u>GAAAATTTCGTCTGGATTAGTTAC

TTATCGTGTAAAATCTGATAAATGGAATTGGTTCTACATAAATGCC

TAACGACTATCCCTTTGGGGAGTAGGGTCAAGTGACTCGAAACG

ATAGACAACTTGCTTTAACAAGTTGGAGATATAGTCTGCTCTGCA

TGGTGACATGCAGCTGGATATAATTCCGGGGTAAGATTAACGACC

TTATCTGAACATAATGCTAGGGAAATAGGGTTTCCAATGCTTTGC

TCAAGAAACGCAAAGTATTGGAGCCACACCAACCAGACCAAAG

GCAGCCGTCAGTCCATCTCAAGAAACGATGGGCTGACATTCATA

GCCGTT<u>TTCCTCTATCCGTTCTAAACGCTTTATG</u>ATGCGGCTGTGA

AGGTTGCTTTTGACCGCCGGGAGGTGCTGCGCTTTGGATCTTA

TTCAAGGTGCAGCTCTCATTTCCTTGGATCTTATTAAGGAAGTG

AGAACTTCTCGGCGACCACTGAGGTCAATGTGGACGGAGGATC

TTATTTTCGTCCACATCGAGCACTTTAT<u>GGGAGGACGATGCGGAT</u>

<u>CAGCCATGTTTACGTCACTCCTTGTCAATCCTCATCGGCAGACGA</u>

<u>CTCGCCCGA</u>ATAAGGTGCTTGTGGCTTCAGTGACCCTTTCTCAG

AGTAAGGGAGAAGGATCTTATTTTCTCCCTTGCAACAAGTAAG

ACGGATCTTATTGTCTTGTTTGTTCTGAGAGAGGACCAGCTTCC

ACATGTGAGAGAGCTCAAGAAACGCTCTCTCGCAATAGGCTGC

TTG<u>TTCCTCTATCCGTTCTAAACGCTTTATGAT</u>TAAGTAGCTTATG

TGGGAGCTGACGTGTGTTCTAGTCTTTGGTGGTTCTCAAGAAAC

GAACCACCAGAGAAACAGTGTAGTTGACTCAAGAAACGTCAAT

TACATTGGCTAGAACATACACCTGCTTCTTGAGGCCGTCGTGTTT

CAAGAAACAACACGGCGGTTTGTTTCCGC<u>AGGGGAGGACGATG</u>

<u>CGGATCAGCCATGTTTACGTCACTCCTTGTCAATCCTCATCGGCA</u>

<u>GACGACTCGCCCGA</u>TTGCGGAAATATTTAAGGAGCGGACGGCTG

AGAGTAGCCGACTGAGTTTGCTCAAGAAACGCAAACTCAGTTG

AAATGGTTGCGCTTTCAAGAAACAGTGCAATCATTTCTGCTCTCG

GCCACAGAGGCGGTCGTGGGTCTGGCTCTCAAGAAACGAGTTA

GGCCCTATCTGCTGCGCT<u>TTCCTCTATCCGTTCTAAACGCTTTATG</u>

<u>AT</u>GGCGTAGCGGAGCCGGCTGCCTCTACAAAGTCTCGTGCAGAA

GAAGATCACGTTCATAGAGACGTGATCTTCTTCCCAGTGATACC

TTG<u>GGAGGACGATGCGGAT</u>CAGCCATGTTTACGTCACTCCTTGT

CAATCCTCATCGGCAGACGACTCGCCCGAAAGGTGTCACTGGGT

-continued

TGTACGGGACTTTACCTTGGCGTTGTCAGAAATGGTTTCAGTCA

AGAAACTTGAAACCATTTCTGTAGTTGACAGATCAAGAAACTC

TGTCAATTACATTGGCGACGCCAAGTTA*CC*TGGTTGGTGTGGAA

CCCTATTTCCCCATGTCAATTGAGGCCTGAGTATAAGGTGACTTA

TACTTGTAATCTATCTAAACGGGGAACCTCTCTAGTAGACAATCC

CGTGCTAAATTGTAGGACTGCCCTTTAATAAATACTTCTATATTTA

AAGAGGTATTTATGAAAAGCGGAATTTATCAGATTAAAAATACTT

TCT (SEQ ID NO: 30; Loop Dicer 1 in bold, Loop

PSMA and Loop clathrin pit underlined, linker component in italics, EcoRI restriction site/T7 transcription start site in italics and underlined)

Highly Structured Polynucleotide Nanoparticle for Increased Molarity

Repeating a core can be an effective manner in increasing molarity. The polynucleotide nanoparticle below forms a 40-60 nm diameter in a highly packed sphere. In this example, each nanoparticle delivers approximately 48 MV-RNA with each of the triggers in quadruplicate.

Open component:
GGGAAAUAGGGUUUCCAAUGCUUUGCUCAAGAAACGCAAAGUAUUGGAGC

CACACCAACCAGAC (SEQ ID NO: 20; Loop

Dicer 1 in bold)

Core component (collection of linked MV-RNA above):

Core 1:
CAAAGGCAGCCGUCAGUCCAUCUCAAGAAACGAUGGGCUGAC
AUUCAUAGCCGUUUCCUCUAUCCGUUCUAAACGCUUUAUGAU
GCGGCUGUGAAGGUUGCUUUUGacCGCCGGGAGGUGCUGCGCU
UUGGGAUCUUAUUCAAGGUGCAGCUCUCAUUUCCUUGGAUC
UUAUUAAGGAAGUGAGAACUUCUCGGCGACCACUGAGGUCAA
UGUGGACGGAGGAUCUUAUUUUCGUCCACAUCGAGCACUUU
AUGGGAGGACGAUGCGGAUCAGCCAUGUUUACGUCACUCCUU
GUCAAUCCUCAUCGGCAGACGACUCGCCCGAAUAAGGUGCUU
GUGGCUUCAGUGACCCUUUCUCAGAGUAAGGGAGAAGGAUCU
UAUUUUCUCCCUUGCAACAAGUAAGACGGAUCUUAUUGUCU
UGUUUGUUCUGAGAGAGGACCAGCUUCCACAUGUGAGAGAGC
UCAAGAAACGCUCUCUCGCAAUAGGCUGCUUGUUCCUCUAUC
CGUUCUAAACGCUUUAUGAUUAAGUAGCUUAUGUGGGAGCUG
ACGUGUGUUCUAGUCUUUGGUGGUUCUCAAGAAACGAACCAC
CAGAGAAACAGUGUAGUUGACUCAAGAAACGUCAAUUACAU
UGGCUAGAACAUACACCUGCUUCUUGAGGCCGUCGUGUUUCA
AGAAACAACACGGCGGUUUGUUUCCGCAGGGGAGGACGAUGC
GGAUCAGCCAUGUUUACGUCACUCCUUGUCAAUCCUCAUCGG
CAGACGACUCGCCCGAUUGCGGAAAUAUUUAAGGAGCGGACG
GCUGAGAGUAGCCGACUGAGUUUGCUCAAGAAACGCAAACUC
AGUUGAAAUGGUUGCGCUUCAAGAAACAGUGCAAUCAUUUC
UGCUCUCGGCCACAGAGGCGGUCGUGGGUCUGGCUCUCAAGA
AACGAGUUAGGCCCUAUCUGCUGCGCUUUCCUCUAUCCGUUC
UAAACGCUUUAUGAUGGCGUAGCGGAGCCGGCUGCCUCUACA
AAGUCUCGUGCAGAAGAAGAUCACGUUCAUAGAGACGUGAU
CUUCUUCCCAGUGAUACCUUGGGAGGACGAUGCGGAUCAGCC
AUGUUUACGUCACUCCUUGUCAAUCCUCAUCGGCAGACGACU
CGCCCGAAAGGUGUCACUGGGUUGUACGGGACUUUACCUUGG
CGUUGUCAGAAAUGGUUUCAGUCAAGAAACUUGAAACCAUU
UCUGUAGUUGACAGAUCAAGAAACUCUGUCAAUUACAUUGG
CGACGCCAAGUUAC (SEQ ID NO: 34; Loop Dicer 1, Loop Dicer 2, and Loop Dicer 3 in bold, Loop PSMA and Loop clathrin pit underlined, linker component in italics)

Core 2:
CAAAGGCAGCCGUCAGUCCAUCUCAAGAAACGAUGGGCUGAC
AUUCAUAGCCGUUUCCUCUAUCCGUUCUAAACGCUUUAUGAU
GCGGCUGUGAAGGUUGCUUUUGacCGCCGGGAGGUGCUGCGCU
UUGGGAUCUUAUUCAAGGUGCAGCUCUCAUUUCCUUGGAUC
UUAUUAAGGAAGUGAGAACUUCUCGGCGACCACUGAGGUCAA
UGUGGACGGAGGAUCUUAUUUUCGUCCACAUCGAGCACUUU
AUGGGAGGACGAUGCGGAUCAGCCAUGUUUACGUCACUCCUU
GUCAAUCCUCAUCGGCAGACGACUCGCCCGAAUAAGGUGCUU
GUGGCUUCAGUGACCCUUUCUCAGAGUAAGGGAGAAGGAUCU
UAUUUUCUCCCUUGCAACAAGUAUGACGGAUCUUAUUGUCU
UGUUUGUUCUGAGAGAGGACCAGCUUCCACAUGUGAGAGAGC
UCAAGAAACGCUCUCUCGCAAUAGGCUGCUUGUUCCUCUAUC
CGUUCUAAACGCUUUAUGAUUAAGUAGCUUAUGUGGGAGCUG
ACGUGUGUUCUAGUCUUUGGUGGUUCUCAAGAAACGAACCAC
CAGAGAAACAGUGUAGUUGACUCAAGAAACGUCAAUUACAU
UGGCUAGAACAUACACCUGCUUCUUGAGGCCGUCGUGUUUCA
AGAAACAACACGGCGGUUUGUUUCCGCAGGGGAGGACGAUGC
GGAUCAGCCAUGUUUACGUCACUCCUUGUCAAUCCUCAUCGG
CAGACGACUCGCCCGAUUGCGGAAAUAUUUAAGGAGCGGACG
GCUGAGAGUAGCCGACUGAGUUUGCUCAAGAAACGCAAACUC
AGUUGAAAUGGUUGCGCUUCAAGAAACAGUGCAAUCAUUUC
UGCUCUCGGCCACAGAGGCGGUCGUGGGUCUGGCUCUCAAGA
AACGAGUUAGGCCCUAUCUGCUGCGCUUUCCUCUAUCCGUUC -continued
UAAACGCUUUAUGAUGGCGUAGCGGAGCCGGCUGCCUCUACA

AAGUCUCGUGCAGAAGAAGAUCACGUUCAUAGAGACGUGAU

CUUCUUCCCAGUGAUACCUU<u>GGGAGGACGAUGCGGAUCAGCC</u>

<u>AUGUUUACGUCACUCCUUGUCAAUCCUCAUCGGCAGACGACU</u>

<u>CGCCCGA</u>AAGGUGUCACUGGGUUGUACGGGACUUUACCUUGG

CGUUGUCAGAAAUGGUUUCAGUCAAGAAACUUGAAACCAUU

UCUGUAGUUGACAGAUCAAGAAACUCUGUCAAUUACAUUGG

CGACGCCAAGUUA*C* (SEQ ID NO: 35; Loop Dicer 1 and Loop Dicer 3 in bold, Loop PSMA and Loop clathrin pit underlined, linker component in italics)

Core 3:
CAAAGGCAGCCGUCAGUCCAUCUCAAGAAACGAUGGGCUGAC

AUUCAUAGCCGUUUCCUCUA<u>UCCGUUCUAAACGCUUUAUGAU</u>

<u>GCGGCUGUGAAGGUUGCUUUUGACCGCCGGGAGGUGCUGCGC</u>

<u>UUU</u>GGGAUCUUAUUCAAGGUGCAGCUCUCAUUUCCUUGGAU

CUUAUUAAGGAAGUGAGAACUUCUCGGCGACCACUGAGGUCA

AUGUGGACGGAGGAUCUUAUUUUCGUCCACAUCGAGCACUU

UAU<u>GGGAGGACGAUGCGGAUCAGCCAUGUUUACGUCACUCCU</u>

<u>UGUCAAUCCUCAUCGGCAGACGACUCGCCCGA</u>UAAGGUGCU

UGUGGCUUCAGUGACCCUUUCUCAGAGUAAGGGAGAAGGAUC

UUAUUUUCUCCCUUGCAACAAGUAAGACGGAUCUUAUUGUC

UUGUUUGUUCUGAGAGAGGACCAGCUUCCACAUGUGAGAGAG

CUCAAGAAACGCUCUCUCGCAAUAGGCUGCUUG<u>UUCCUCUAU</u>

<u>CCGUUCUAAACGCUUUAUGAUUAAGUAGCUUAUGUGGGAGCU</u>

*GACGUGUGUUCUAGUCUUUGGUGGUUC*UCAAGAAAC*GAACCA*

*CCAGAGAAACAGUGUAGUUGAC*UCAAGAAAC*GUCAAUUACA*

*UUGGCUAGAACAUACACCUGCUUCUUGAGGCCGUCGUGUU*UC

AAGAAACAACACGGCGGUUUGUUUCCGCAG<u>GGGAGGACGAU</u>

<u>GCGGAUCAGCCAUGUUUACGUCACUCCUUGUCAAUCCUCAUC</u>

<u>GGCAGACGACUCGCCCGA</u>*UUGCGGAAAUAUUUAAGGAGCGGA*

*CGGCUGAGAGUAGCCGACUGAGUUUGC*UCAAGAAAC*GCAAAC*

*UCAGUUGAAAUGGUUGCGCU*UCAAGAAAC*AGUGCAAUCAUU*

*UCUGCUCUCGGCCACAGAGGCGGUCGUGGGUCUGGCUC*UCAA

GAAAC*GAGUUAGGCCCUAUCUGCUGCGCU*<u>UUCCUCUAUCCGU</u>

<u>UCUAAACGCUUUAUGAUGGCGUAGCGGAGCCGGCUGCCUCUA</u>

*CAAGUCUCGUGCAGAAGAAGAUCACG*UUCAUAGAGA*CGUG*

*AUCUUCUUCCCAGUGAUACCUU*<u>GGGAGGACGAUGCGGAUCAG</u>

<u>CCAUGUUUACGUCACUCCUUGUCAAUCCUCAUCGGCAGACGA</u>

<u>CUCGCCCGA</u>AAGGUGUCACUGGGUUGUACGGGACUUUACCUU

GGCGUUGUCAGAAAUGGUUUCAGUCAAGAAACUUGAAACCA

-continued
UUUCUGUAGUUGACAGAUCAAGAAACUCUGUCAAUUACAUU

GGCGACGCCAAGUUA*C* (SEQ ID NO: 36; Loop Dicer 1,

Loop Dicer 2, and Loop Dicer 3 in bold, Loop

PSMA and Loop clathrin pit underlined, linker component in italics)

Core 4:
CAAAGGCAGCCGUCAGUCCAUCUCAAGAAACGAUGGGCUGAC

AUUCAUAGCCGU<u>UUCCUCUAUCCGUUCUAAACGCUUUAUGAU</u>

<u>GCGGCUGUGAAGGUUGCUUUUGa</u>*cCGCCGGGAGGUGCUGCGCU*

*U*<u>UGGGAUCUUAUU</u>*CAAGGUGCAGCUCUCAUUUCCUU*GGAUC

UUAUUAAGGAAGUGAGAACUUCUCGGCGACCACUGAGGUCAA

UGUGGACGGAGGAUCUUAUUUUCGUCCACAUCGAGCACUUU

AU<u>GGGAGGACGAUGCGGAUCAGCCAUGUUUACGUCACUCCUU</u>

<u>GUCAAUCCUCAUCGGCAGACGACUCGCCCGA</u>AUAAGGUGCUU

GUGGCUUCAGUGACCCUUUCUCAGAGUAAGGGAGAAGGAUCU

UAUUUUCUCCCUUGCAACAAGUAAGACGGAUCUUAUUGUCU

UGUUUGUUCUGAGAGAGGACCAGCUUCCACAUGUGAGAGC

UCAAGAAACGCUCUCUCGCAAUAGGCUGCUUG<u>UUCCUCUAUC</u>

<u>CGUUCUAAACGCUUUAUGAUUAAGUAGCUUAUGUGGGAGCUG</u>

*ACGUGUGUUCUAGUCUUUGGUGGUUC*UCAAGAAAC*GAACCAC*

*CAGAGAAACAGUGUAGUUGAC*UCAAGAAAC*GUCAAUUACAU*

*UGGCUAGAACAUACACCUGCUUCUUGAGGCCGUCGUGUU*UCA

AGAAACAACACGGCGGUUUGUUUCCGCAG<u>GGGAGGACGAUGC</u>

<u>GGAUCAGCCAUGUUUACGUCACUCCUUGUCAAUCCUCAUCGG</u>

<u>CAGACGACUCGCCCGA</u>*UUGCGGAAAUAUUUAAGGAGCGGACG*

*GCUGAGAGUAGCCGACUGAGUUUGC*UCAAGAAAC*GCAAACUC*

*AGUUGAAAUGGUUGCGCU*UCAAGAAAC*AGUGCAAUCAUUUC*

*UGCUCUCGGCCACAGAGGCGGUCGUGGGUCUGGCUC*UCAAGA

AAC*GAGUUAGGCCCUAUCUGCUGCGCU*<u>UUCCUCUAUCCGUUC</u>

<u>UAAACGCUUUAUGAUGGCGUAGCGGAGCCGGCUGCCUCUACA</u>

*AAGUCUCGUGCAGAAGAAGAUCACG*UUCAUAGAGA*CGUGAU*

*CUUCUUCCCAGUGAUACCUU*<u>GGGAGGACGAUGCGGAUCAGCC</u>

<u>AUGUUUACGUCACUCCUUGUCAAUCCUCAUCGGCAGACGACU</u>

<u>CGCCCGA</u>AAGGUGUCACUGGGUUGUACGGGACUUUACCUUGG

CGUUGUCAGAAAUGGUUUCAGUCAAGAAACUUGAAACCAUU

UCUGUAGUUGACAGAUCAAGAAACUCUGUCAAUUACAUUGG

CGACGCCAAGUUA*C* (SEQ ID NO: 37; Loop Dicer 1,

Loop Dicer 2, and Loop Dicer 3 in bold, Loop

PSMA and Loop clathrin pit underlined, linker component in italics)

Close component:
CUGGUUGGUGUGGAACCCUAUUUCCC (SEQ ID NO: 22)

The final polynucleotide nanoparticle assembled from the repetitive regions and open/close components above:

GGGAAAUAGGGUUUCCAAUGCUUUGCUCAAGAAACGCAAAG
UAUUGGAGCCACACCAACCAGACCAAAGGCAGCCGUCAGUCC
AUCUCAAGAAACGAUGGGCUGACAUUCAUAGCCGUUUCCUCU
AUCCGUUCUAAACGCUUUAUGAUGCGGCUGUGAAGGUUGCUU
UUGACCGCCGGGAGGUGCUGCGCUUUGGGAUCUUAUUCAAGG
UGCAGCUCUCAUUUCCUUGGAUCUUAUUAAGGAAGUGAGAA
CUUCUCGGCGACCACUGAGGUCAAUGUGGACGGAGGAUCUUA
UUUUCGUCCACAUCGAGCACUUUAUGGGAGGACGAUGCGGAU
CAGCCAUGUUUACGUCACUCCUUGUCAAUCCUCAUCGGCAGA
CGACUCGCCCGAAUAAGGUGCUUGUGGCUUCAGUGACCCUUU
CUCAGAGUAAGGGAGAAGGAUCUUAUUUUCUCCCUUGCAAC
AAGUAAGACGGAUCUUAUUGUCUUGUUUGUUCUGAGAGAGG
ACCAGCUUCCACAUGUGAGAGAGCUCAAGAAACGCUCUCUCG
CAAUAGGCUGCUUGUUCCUCUAUCCGUUCUAAACGCUUUAUG
AUUAAGUAGCUUAUGUGGGAGCUGACGUGUGUUCUAGUCUUU
GGUGGUUCUCAAGAAACGAACCACCAGAGAAACAGUGUAGU
UGACUCAAGAAACGUCAAUUACAUUGGCUAGAACAUACACCU
GCUUCUUGAGGCCGUCGUGUUUCAAGAAACAACACGGCGGUU
UGUUUCCGCAGGGGAGGACGAUGCGGAUCAGCCAUGUUUACG
UCACUCCUUGUCAAUCCUCAUCGGCAGACGACUCGCCCGAUU
GCGGAAAUAUUUAAGGAGCGGACGGCUGAGAGUAGCCGACUG
AGUUUGCUCAAGAAACGCAAACUCAGUUGAAAUGGUUGCGC
UUCAAGAAACAGUGCAAUCAUUUCUGCUCUCGGCCACAGAGG
CGGUCGUGGGUCUGGCUCUCAAGAAACGAGUUAGGCCCUAUC
UGCUGCGCUUUCCUCUAUCCGUUCUAAACGCUUUAUGAUGGC
GUAGCGGAGCCGGCUGCCUCUACAAAGUCUCGUGCAGAAGAA
GAUCACGUUCAUAGAGACGUGAUCUUCUUCCCAGUGAUACCU
UGGGAGGACGAUGCGGAUCAGCCAUGUUUACGUCACUCCUUG
UCAAUCCUCAUCGGCAGACGACUCGCCCGAAAGGUGUCACUG
GGUUGUACGGGACUUUACCUUGGCGUUGUCAGAAAUGGUUUC
AGUCAAGAAACUUGAAACCAUUUCUGUAGUUGACAGAUCAA
GAAACUCUGUCAAUUACAUUGGCGACGCCAAGUUACCAAAGG
CAGCCGUCAGUCCAUCUCAAGAAACGAUGGGCUGACAUUCAU
AGCCGUUUCCUCUAUCCGUUCUAAACGCUUUAUGAUGCGGCU
GUGAAGGUUGCUUUUGACCGCCGGGAGGUGCUGCGCUUUGGG
AUCUUAUUCAAGGUGCAGCUCUCAUUUCCUUGGAUCUUAUU
AAGGAAGUGAGAACUUCUCGGCGACCACUGAGGUCAAUGUGG
ACGGAGGAUCUUAUUUUCGUCCACAUCGAGCACUUUAUGGG
AGGACGAUGCGGAUCAGCCAUGUUUACGUCACUCCUUGUCAA

-continued

UCCUCAUCGGCAGACGACUCGCCCGAAUAAGGUGCUUGUGGC
UUCAGUGACCCUUUCUCAGAGUAAGGGAGAAGGAUCUUAUUU
UCUCCCUUGCAACAAGUAAGACGGAUCuUAUUGUCUUGUUUG
UUCUGAGAGAGGACCAGCUUCCACAUGUGAGAGAGCUCAAGA
AACGCUCUCUCGCAAUAGGCUGCUUGUUCCUCUAUCCGUUCU
AAACGCUUUAUGAUUAAGUAGCUUAUGUGGGAGCUGACGUGU
GUUCUAGUCUUUGGUGGUUCUCAAGAAACGAACCACCAGAG
AAACAGUGUAGUUGACUCAAGAAACGUCAAUUACAUUGGCU
AGAACAUACACCUGCUUCUUGAGGCCGUCGUGUUUCAAGAAA
CAACACGGCGGUUUGUUUCCGCAGGGGAGGACGAUGCGGAUC
AGCCAUGUUUACGUCACUCCUUGUCAAUCCUCAUCGGCAGAC
GACUCGCCCGAUUGCGGAAAUAUUUAAGGAGCGGACGGCUGA
GAGUAGCCGACUGAGUUUGCUCAAGAAACGCAAACUCAGUU
GAAAUGGUUGCGCUUCAAGAAACAGUGCAAUCAUUUCUGCU
CUCGGCCACAGAGGCGGUCGUGGGUCUGGCUCUCAAGAAACG
AGUUAGGCCCUAUCUGCUGCGCUUUCCUCUAUCCGUUCUAAA
CGCUUUAUGAUGGCGUAGCGGAGCCGGCUGCCUCUACAAAGU
CUCGUGCAGAAGAAGAUCACGUUCAUAGAGACGUGAUCUUC
UUCCCAGUGAUACCUUGGGAGGACGAUGCGGAUCAGCCAUGU
UUACGUCACUCCUUGUCAAUCCUCAUCGGCAGACGACUCGCC
CGAAAGGUGUCACUGGGUUGUACGGGACUUUACCUUGGCGUU
GUCAGAAAUGGUUUCAGUCAAGAAACUUGAAACCAUUUCUG
UAGUUGACAGAUCAAGAAACUCUGUCAAUUACAUUGGCGAC
GCCAAGUUACCAAAGGCAGCCGUCAGUCCAUCUCAAGAAACG
AUGGGCUGACAUUCAUAGCCGUUUCCUCUAUCCGUUCUAAAC
GCUUUAUGAUGCGGCUGUGAAGGUUGCUUUUGACCGCCGGGA
GGUGCUGCGCUUUGGGAUCUUAUUCAAGGUGCAGCUCUCAU
UUCCUUGGAUCUUAUUAAGGAAGUGAGAACUUCUCGGCGACC
ACUGAGGUCAAUGUGGACGGAGGAUCUUAUUUUCGUCCACA
UCGAGCACUUUAUGGGAGGACGAUGCGGAUCAGCCAUGUUUA
CGUCACUCCUUGUCAAUCCUCAUCGGCAGACGACUCGCCCGA
AUAAGGUGCUUGUGGCUUCAGUGACCCUUUCUCAGAGUAAGG
GAGAAGGAUCUUAUUUUCUCCCUUGCAACAAGUAAGACGGA
UCUUAUUGUCUUGUUUGUUCUGAGAGAGGACCAGCUUCCACA
UGUGAGAGAGCUCAAGAAACGCUCUCUCGCAAUAGGCUGCUU
GUUCCUCUAUCCGUUCUAAACGCUUUAUGAUUAAGUAGCUUA
UGUGGGAGCUGACGUGUGUUCUAGUCUUUGGUGGUUCUCAAG
AAACGAACCACCAGAGAAACAGUGUAGUUGACUCAAGAAAC
GUCAAUUACAUUGGCUAGAACAUACACCUGCUUCUUGAGGCC
GUCGUGUUUCAAGAAACAACACGGCGGUUUGUUUCCGCAGG

-continued

GGAGGACGAUGCGGAUCAGCCAUGUUUACGUCACUCCUUGUC

AAUCCUCAUCGGCAGACGACUCGCCCGAUUGCGGAAAUAUUU

AAGGAGCGGACGGCUGAGAGUAGCCGACUGAGUUUGCUCAAG

AAACGCAAACUCAGUUGAAAUGGUUGCGCUUCAAGAAACAG

UGCAAUCAUUUCUGCUCUCGGCCACAGAGGCGGUCGUGGGUC

UGGCUCUCAAGAAACGAGUUAGGCCCUAUCUGCUGCGCUUUC

CUCUAUCCGUUCUAAACGCUUUAUGAUGGCGUAGCGGAGCCG

GCUGCCUCUACAAAGUCUCGUGCAGAAGAAGAUCACGUUCAU

AGAGACGUGAUCUUCUUCCCAGUGAUACCUUGGGAGGACGAU

GCGGAUCAGCCAUGUUUACGUCACUCCUUGUCAAUCCUCAUC

GGCAGACGACUCGCCCGAAAGGUGUCACUGGGUUGUACGGGA

CUUUACCUUGGCGUUGUCAGAAAUGGUUUCAGUCAAGAAACU

UGAAACCAUUUCUGUAGUUGACAGAUCAAGAAACUCUGUCA

AUUACAUUGGCGACGCCAAGUUACCAAAGGCAGCCGUCAGUC

CAUCUCAAGAAACGAUGGGCUGACAUUCAUAGCCGUUUCCUC

UAUCCGUUCUAAACGCUUUAUGAUGCGGCUGUGAAGGUUGCU

UUUGACCGCCGGGAGGUGCUGCGCUUUGGGAUCUUAUUCAAG

GUGCAGCUCUCAUUUCCUUGGAUCUUAUUAAGGAAGUGAGA

ACUUCUCGGCGACCACUGAGGUCAAUGUGGACGGAGGAUCUU

AUUUUCGUCCACAUCGAGCACUUUAUGGGAGGACGAUGCGGA

UCAGCCAUGUUUACGUCACUCCUUGUCAAUCCUCAUCGGCAG

ACGACUCGCCCGAAUAAGGUGCUUGUGGCUUCAGUGA CCCUU

UCUCAGAGUAAGGGAGAAGGAUCUUAUUUUCUCCCUUGCAA

CAAGUAAGACGGAUCUUAUUGUCUUGUUUGUUCUGAGAGAG

GA CCAGCUUCCACAUGUGAGAGAGCUCAAGAAACGCUCUCUC

GCAAUAGGCUGCUUGUUCCUCUAUCCGUUCUAAACGCUUUAU

GAUUAAGUAGCUUAUGUGGGAGCUGA CGUGUGUUCUAGUCUU

UGGUGGUUCUCAAGAAACGAACCACCAGAGAAACAGUGUAG

UUGACUCAAGAAACGUCAAUUACAUUGGCUAGAACAUACACC

UGCUUCUUGAGGCCGUCGUGUUUCAAGAAACAACACGGCGGU

UUGUUUCCGCAGGGGAGGACGAUGCGGAUCAGCCAUGUUUAC

GUCACUCCUUGUCAAUCCUCAUCGGCAGACGACUCGCCCGAU

UGCGGAAAUAUUUAAGGAGCGGACGGCUGAGAGUAGCCGACU

GAGUUUGCUCAAGAAACGCAAACUCAGUUGAAAUGGUUGCG

CUUCAAGAAACAGUGCAAUCAUUUCUGCUCUCGGCCACAGAG

GCGGUCGUGGGUCUGGCUCUCAAGAAACGAGUUAGGCCCUAU

CUGCUGCGCUUUCCUCUAUCCGUUCUAAACGCUUUAUGAUGG

CGUAGCGGAGCCGGCUGCCUCUACAAAGUCUCGUGCAGAAGA

AGAUCACGUUCAUAGAGACGUGAUCUUCUUCCCAGUGAUACC

UUGGGAGGACGAUGCGGAUCAGCCAUGUUUACGUCACUCCUU

GUCAAUCCUCAUCGGCAGACGACUCGCCCGAAAGGUGUCACU

GGGUUGUACGGGACUUUACCUUGGCGUUGUCAGAAAUGGUUU

CAGUCAAGAAACUUGAAACCAUUUCUGUAGUUGACAGAUCA

AGAAACUCUGUCAAUUACAUUGGCGACGCCAAGUUACCUGGU

UGGUGUGGAACCCUAUUUCCC (SEQ ID NO: 38;

Loop Dicer 1, Loop Dicer 2, and Loop Dicer 3 in bold, Loop PSMA and Loop clathrin pit underlined, linker component in italics)

Cofold output (fold notations) showing secondary structure:

```
((((((((((((..(((((((((((((.........))))))))))))).(((((((((((..(((((
((((((((((((((.........             ))))))))))..(((((((((.((.......
(((......)))........)).)))))))))).))))))))))..(((((((((((((((
(((((......))))))))))).(((((((((......))))))))))).)))))))))..
((((((((((.(((((((((    (......))))))))))((((((((((.((((
(((..((((......))..))...)))).))))................(((((....))..))) ...))))
)))))))).)))))))))..(((((((((((((((((((......))))))))))))).
((((((((((((......)))              )))))))))))))))..(((((((
(((.(((((((((...........))))))))).((((((((.((........(((.....)
))......))).)))))))))).))))))))..((((((((((((((((
((.........))))))))))).((((((((((.........)))))))))).)))))
)))))..(((((((((((.((((((((((.........)))))))))).(((((((.(((((
((((((..(((((.....))..))...)))).))))..........((((((..((......))..)))))).))
))))))).))))))))..(((((((((((((.((((((((((.........))))))))))).
((((((((((.........)))))))))).))))))))))..((((((((((.(((((((
(((.........))))))))))).(((((((((((.((........(((......))))......)).)))))
)))))..))) )))))...((((((((((((((.(((((((((((......)))))))))))))
(((((((((((((.((((((((..(((.....))    ..))...)))))..))))................
((((((....)).)))...))))))))))))....))))))))))..(((((((((.(((((
(((((((......)).))))))))).(((((((((.........))))))))))...))))))
)))))....((((((((((((   ((((((.........)))))))).((((((((.
((......((((.....)))......).)))))))))..))))))))..((((((((((((((
(((((......)))))))))))).(((((((((((......)))))))))))..))))))))
)))..(((((((   ((.(((((((((......))))))))))((((((((.
((((((((..(((.....))..))...)))).))))................(((((....))..)))...))))
))))))).))))))))..((((((((((((((((((((((((......))))))))))))))).
((((((((((......))))))))))))))))))..((((((((.((((((
(((((.........))))))))))).((((((((.(  (......((.....))).......)).))))))
))))).))))))))..((((((((((((((((((((.........))))))))))      )..
((((((((((((......)))))))))))).((((((((((.(((((.((..(((.....))..))...))
))).))))))))))..   (((((((((((..(((((((((..(((((.((..(((.....))..))...))
))).))))))..........((((.((..(((....))))..)))))))))).))))   )))))..
(((((((((((.(((((((((.......))))))))))..(((((((
((..........))))))))))).)))             ))))))..((((((((.(((((((((
((..........))))))))))).((((((((((.((........(((......))))......)).)
)))))))))..))))))))..((((((((((((((((((((((......)))))))))))))
)))))))))))))))))))))))))))..)))))))))..(((((((((.(((((((((
((((......))))))))))))).((((((((((..........))))))))))..)))))))))))..
(((((((((.(((((((((((.......       ...))))))))))))..))))))))))..
((((((((.(((((((((((((.........)))))))))))))..((((((((((.((((((((((
(((......)))))))))))).(((((((((((((...(((.....))...)).))
)).))))))..........(((((..((.....)).)))))..                ))))))))))))
```

```
)))..(((((((((((.(((((((((..........))))))))))))).(((((((((
(..........))         ))))))))).)))))))))..(((((((((.(((((((((((((
(..........)))))))))))))..(((((((((.((........(((.....)))........)).)))))
)))))..)))))))))))..(((((((((.(((((((((((......)))))))))))))))
((((((((((((.(((((((..(((......))..))...)))))..)))).................((
(((.....)).)))...)))))))))))...))))) )))))))..(((((((((((.((((((
(((((((......))).)))))))))).(((((((((..........))))))))))...)
))))))))))....(((((((((((((((((((..........))))))))))))..
((((((((((.((........(((.....)))........))        .)))))))))).)))))))))..
((((((((((((((((((((((.....)))))))))))).(((((((((((......))))))
))))))).)))))))))..(((((((((.(((((((((((......))))))))))))
((((((((((.((((((((.((((...              ..))..))...)))).))))..............
(((((.....)).)))...)))))))))))..))))))))..((((((((((((((
(((((......))))))))))).(((((((((((......)))))))))))).)))))))))..
((((((((((.(((((((((((    .....)))))))))))..(((((((((.((........
(((......)))........)).)))))))))..))))))))))..((((((((((
((((((((((..........)))))))))))..(((((((((..........)))))))))).)))))
))))))..(((((((((.((       (((((((((..........))))))))))).((((((((.
(((((((((((..(((((.....))..))...)))).))))))).........(((((..((.....))..)))
))..)))))))))..)))))))))..((((((((((.(((((((((     ((..........)))))
))))))..(((((((( ((((..........)))))))))))..)))))))))..((((((((((.((
((((((((..........)))))))))).((((((((((.((........(((.....)))........)).))
))))))))..)))))))))..((((((((((.(((((((((((((((......))))))
)))))))))(((((((((((((.(((((((((..(((((.....))..))...)))))).)
)))...............(((((.....)).)))...)))))))        )))))))...))))))))))..
((((((((((.((((((((((((((......))).))))))))))).((((((((((
(..........)) ))))))))))...)))))))))))....))))))))))))..)))))))))))
```

Example 2: Self-Forming Single-Stranded Polynucleotide MV-RNA Nanoparticle Targeting *Diabrotica virgifera* (Western Corn Rootworm)

Figure 20:
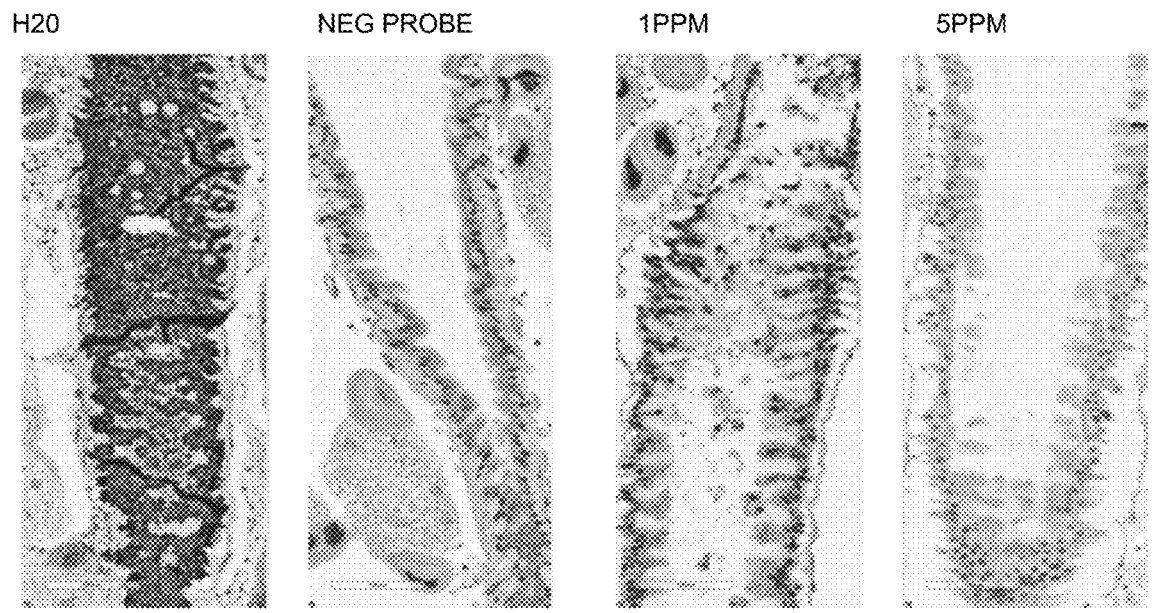
FIG. 20: In vivo activity in Western Corn Rootworm. ISH staining shows gene silencing effect of a target gene in Western Corn Rootworm after ingesting a polynucleotide nanoparticle provided herein at two different concentrations compared to a $H_2O$ control.
Figure 20:
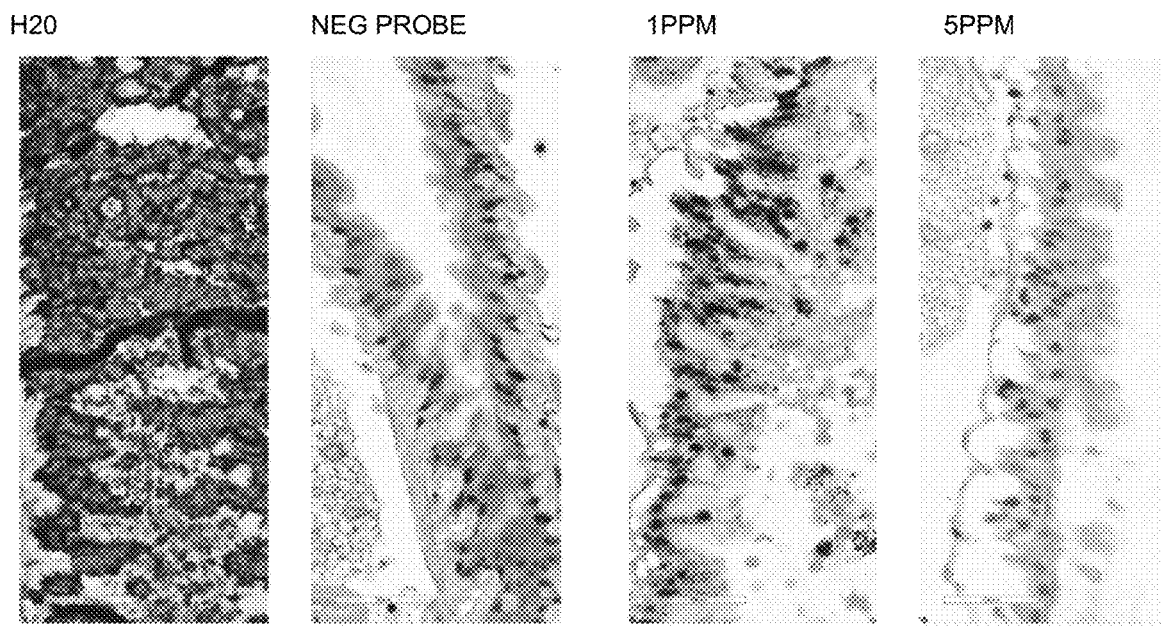

This example describes the assembly of a MV-RNA nanoparticle according to the invention as a stable and multivalent single-stranded RNA nanoparticle targeting multiple genes of Western Corn Rootworm. This example illustrates a novel size/activity relationships of ingested RNA that is contrary to the published requirement that only long dsRNA>60 bp can achieve activity in this insect (FIG. 20).

Additional benefits such as multivalency and transcript length can also be commercially realized. The invention triggers precise enzymatic biogenesis of long pre-cursor transcripts whose length can be optimized for promoter-driven production or size activity relationships of ingested RNA over canonical (post-biogenesis) forms (Turner 2006).

Collection of MV-RNA Utilized in the Polynucleotide Nanoparticle

"Project #" refers to the project number from the Multi-valent RNAi Cloud software application. MV-RNAs were generated targeting *Diabrotica virgifera* vATPase (CN498337.1, SEQ ID NO:96), cytochrome P450 (SEQ ID NO:97), COPI (SEQ ID NO:98), Ribo S4 (SEQ ID NO:99), Dvsnf7 (SEQ ID NO:100), ET3 (SEQ ID NO:101), part of ATPase D subunit 1 (SEQ ID NO:102), and ATPase E (SEQ ID NO:103).

MV-RNA WCR_SNF7_596 (Project #P00942):
ATTGGTTTAGTAGCAACTGCAAATTCAAAgAACATTTGTAGTTGGGTCTT

TTCCAATAGACTTAGGTGGATGTAGGATCCTTAGACTTAGGTGGATGTA

GGATCCAAATTGGAAAAGAACTAAACCAATtt (SEQ ID NO: 39)

MV-RNA WCR_RIBOS4_178 (Project #P00953):
ATCAATTGGTCATGTACTTCGTTTCAAAgAACAACGAAGTACATAACTA

GATTCGATTCCTCTATCCGTTCTAAACGCTTTATGATTCGAATCTAGTT

ATCAATTGGtt (SEQ ID NO: 40; Loop clathrin pit underlined)

MV-RNA WCR_COPI_242 (Project #P00950):
GGTTTCTGGTTTGACTTTCTAGTTCAAAgAACACTAGAAGGTCATGAG AAAGGCGTTCAAAgAACACGCCTTTCTCAACCAGAAACCtt (SEQ ID NO: 41)

MV-RNA WCR_RIBOS4_490 (Project #P00953):
TTTCATTCAAATTGTCTTTACTCAAAgAACGTGAAGACAGACAGTATTC

TTCTTCCTCTATCCGTTCTAAACGCTTTATGATGAAGAATACTGTTTGA

ATGAAAtt (SEQ ID NO: 42; Loop clathrin pit underlined)

MV-RNA WCR_SNF7_62 (Project #P00942):
TCCCCAGGACTAGGGGCTATTTATCAAAgAACTGAATAGCCTCCCCA

GGACTAGGGAGACTTAGGTGGATGTAGGATCCTTAGACTTAGGTGGA

TGTAGGATCCAACCCTAGTCCTGAGTCCTGGGGAtt (SEQ ID NO: 43)

MV-RNA WCR_SNF7_399 (Project #P00942):
GGCTATGTCATCCATGATATCGTTCAAAgAACATGATATCGTGAACAT CATCTACTTTCAAAgAACGTAGATGATGTATGACATAGCCtt (SEQ ID NO: 44)

MV-RNA WCR_RIBOS4_642 (Project #P00953):
ACATGATGGAATTGGAAATGGAATTCAAAgAACATTCGTTTTCATTCAA

ATTGTCTTTTCCTCTATCCGTTCTAAACGCTTTATGATAAGACAATTTG

AATTCCATCATGTtt (SEQ ID NO: 45; Loop clathrin pit underlined)

WCR_COPI_1249 (Project #P00950):
ACACAACCTTATATATTAACAGCTCAAAgAACGCTGTTAGTATGGATG

CCAGTGGAGACTTAGGTGGATGTAGGATCCTTAGACTTAGGTGGATG

TAGGATCCAACCACTGGCATCTAAGGTTGTGTtt (SEQ ID NO: 46)

MV-RNA WCR_RIBOS4_593 (Project #P00953):
GAAAGGGAGTAGGTGTATTTACATCAAAgAACTGTAGGTACAAGAT GCTAAGAGCTTCAAAgAACAGCTCTTAGCATCTACTCCCTTTCtt (SEQ ID NO: 47)

MV-RNA WCR_SNF7_472 (Project #P00942):
CATCCAGATCGTCGGTGAATTAGTCAAAgAACCTAATTCATCGTCAT

CCAGATCGTAGACTTAGGTGGATGTAGGATCCTTAGACTTAGGTGGA

TGTAGGATCCAAACGATCTGGATCGATCTGGATGtt (SEQ ID NO: 48)

-continued

MV-RNA WCR_COPI_780 (Project #P00950):
GAATTTCAAAGAGAAGAAGAATGGATCTTATTATTCTTCTTCTATAATT

TAAGCTTCCTCTATCCGTTCTAAACGCTTTATGATGCTTAAATTATGG

CTTTGAAATTCtt (SEQ ID NO: 49; Loop clathrin pit underlined)

MV-RNA WCR_RIBOS4_397 (Project #P00953):
GGTCGTGCATGTTAATTGGTAATCAAAgAACGTTATCAATTGGTCATG TACTTCGTCAAAgAACCGAAGTACATGCATGCACGACCtt (SEQ ID NO: 50)

MV-RNA WCR_COPI_125 (Project #P00950):

AGATAGCTACTTTATTCTTTCAAATCAAAgAACTTTGAAAGAGTATGG

ACTATTTTTCCTCTATCCGTTCTAAACGCTTTATGATAAATAGTCCAT

AGTAGCTATCTtt (SEQ ID NO: 51; Loop clathrin pit underlined)

MV-RNA WCR_SNF7_300 (Project #P00942):
AGTATTTGTGCTAGCTCCTAGTTCAAAgAACACTAGGGGCTATCTCT

TCCTTTTAGACTTAGGTGGATGTAGGATCCTTAGACTTAGGTGGATG

TAGGATCCAAAAAAGGAAGAGGCACAAATACTtt (SEQ ID NO: 52)

Assembling WCR Targeting Polynucleotide Nanoparticles with Clathrin-Pit & GalNac Uptake Aptamers The MV-RNA above were grouped into sets of three as TRI (FIGS. 1, 2) with one MV-RNA per nanoparticle targeting one of the target genes. The resulting 3 MV-RNA were linked into a single polynucleotide sequence according to the design instructions in this application. Two of the three MV-RNA contained aptamers (FIGS. 1, 2) on one loop as either 'Clathrin-Pit' or 'GalNac'.

GalNac:
(SEQ ID NO: 53)
AGACTTAGGTGGATGTAGGATCCTTAGACTTAGGTGGATGTAGGATCCAA

Clathrin-Pit:
(SEQ ID NO: 54)
TTCCTCTATCCGTTCTAAACGCTTTATGAT

Because in vitro T7 transcription was planned to produce these RNA nanoparticles, certain MV-RNA starting with nucleotides most suitable for T7 transcriptional yield ("Gnn," "GGn") were chosen to open/close the nanoparticle according to the instructions in this description of this invention.

Each nanoparticle below was prepared for in vitro transcription with the addition of the T7 transcription start site (BOLD) and a short random DNA fragment "AATT" to aide in transcription following template digestion. The DNA templates were cloned into pUC57 (Genscript, NJ) at the EcoRI/XbaI sites, amplified, then digested with the appropriate restriction enzymes before running an in vitro transcription reaction. One may alter the 3' restriction site to account for nucleotide additions due to a particular restriction enzyme. In this case, the final nucleotide of the nanoparticle was removed as a "T" will be added back to the template following XbaI digestion.

T7_initiation: TAATACGACTCACTATAGGN (SEQ ID NO:23)

The MV-RNA above were grouped into sets of three as TRI nanoparticles for feeding to WCR larva. For each TRI nanoparticle, the open/close MV-RNA were selected as described above based on T7 transcription.

TRI_c636c596r178:
*AATTAATACGACTCACTATAGG*TATGTTTGGCCACAGAAGATAGTCAAA

AAACCTATCTTCTGTCCAAATAATTTttATTGGTTTAGTAGCAACTGCA

AATTCAAAAAACATTTGTAGTTGGGTCTTTTCCAATAGACTTAGGTGGA

TGTAGGATCCTTAGACTTAGGTGGATGTAGGATCCAAATTGGAAAAG

AACTAAACCAATTTATCAATTGGTCATGTACTTCGTTTCAAAAAACAAC

GAAGTACATAACTAGATTCGATTCCTCTATCCGTTCTAAACGCTTTAT

GATTCGAATCTAGTTATCAATTGGTTTAAATTATTTGGGCCAGACAT

ACT (SEQ ID NO: 55; Loop clathrin pit underlined,

EcoRI restriction site/T7 transcription start site in italics)

TRI_c2422r490s62:
*AATTAATACGACTCACTATAGG*TTTCTGGTTTGACTTTCTAGTTCAAAAA

ACACTAGAAGGTCATGAGAAAGGCGTttTTTCATTCAAATTGTCTTTACT

CaaaaaaCGTGAAGACAGACAGTATTCTTCTTCCTCTATCCGTTCTAAAC

GCTTTATGATGAAGAATACTGTTTGAATGAAATTTCCCCAGGACTAGGG

GCTATTTATCAAAAAACTGAATAGCCTCCCCAGGACTAGGGAGACTTA

GGTGGATGTAGGATCCTTAGACTTAGGTGGATGTAGGATCCAACCCTA

GTCCTGAGTCCTGGGGATTACGCCTTTCTCAACCAGAAACCT (SEQ ID

NO: 56; Loopclathrin pit underlined, EcoRI restriction site/T7 transcription start site in italics)

TRI_s399r642c1249:
*AATTAATACGACTCACTATAGG*CTATGTCATCCATGATATCGTTCAAAA

AACATGATATCGTGAACATCATCTACTTACATGATGGAATTGGAAATGG

AATTCAAAAAACATTCGTTTTCATTCAAATTGTCTTTTCCTCTATCCGTT

CTAAACGCTTTATGATAAGACAATTTGAATTCCATCATGTTTACACAAC

CTTATATATTAACAGCTCAAAAAACGCTGTTAGTATGGATGCCAGTGG

AGACTTAGGTGGATGTAGGATCCTTAGACTTAGGTGGATGTAGGATCC

AACCACTGGCATCTAAGGTTGTGTTTGTAGATGATGTATGACATAGCCT (SEQ ID NO: 57, EcoRI restriction site/T7 transcription start site in italics)

TRI_r593s472c780:
*AATTAATACGACTCACTATAGG*AAAGGGAGTAGGTGTATTTACATCaaa aaaCTGTAGGTACAAGATGCTAAGAGCTttCATCCAGATCGTCGGTGAA

TTAGTCAAAAAACCTAATTCATCGTCATCCAGATCGTAGACTTAGGTG

GATGTAGGATCCTTAGACTTAGGTGGATGTAGGATCCAAACGATCTGG

ATCGATCTGGATGTTGAATTTCAAAGAGAAGAAGAATGGATCTTATTAT

-continued

TCTTCTTCTATAATTTAAGCTTCCTCTATCCGTTCTAAACGCTTTATGAT

GCTTAAATTATGGCTTTGAAATTCTTAGCTCTTAGCATCTACTCCCTTTC

T (SEQ ID NO: 58, EcoRI restriction site/T7
transcription start site in italics)

TRI_r397c125s300:
AATTAATACGACTCACTATAGGTCGTGCATGTTAATTGGTAATCAAAAA

ACGTTATCAATTGGTCATGTACTTCGTTAGATAGCTACTTTATTCTTTCA

AATCAAAAAACTTTGAAAGAGTATGGACTATTTTTCCTCTATCCGTTCT

AAACGCTTTATGATAAATAGTCCATAGTAGCTATCTTTAGTATTTGTGCT

AGCTCCTAGTTCAAAAAACACTAGGGGCTATCTCTTCCTTTTAGACTT

AGGTGGATGTAGGATCCTTAGACTTAGGTGGATGTAGGATCCAAAAA

AGGAAGAGGCACAAATACTTTCGAAGTACATGCATGCACGACCT (SEQ ID NO: 59, EcoRI restriction site/T7
transcription start site in italics)

Cofold output (fold notations) showing secondary structure:

((((((((((((.(((((((((((........))))))))))))..((((((((((..(((((((((((.((((
(((((((((..........)))))) ))))).(((((((((.((........(((.....))).......)).))))
)))))..)))))))))).((((((((((.(((((((((......     ...)))))))))..
((((((((((((..(((((((((.....))))....))))))))(((......))))..))))))))
)))))))))))) ))..)))))))))))))))))))..

Increasing MV-RNA Trigger Molarity in Polynucleotide Nanoparticles with Clathrin-Pit & GalNac Uptake Aptamers The individual MV-RNA above were then linked into a single polynucleotide sequence according to the design instructions in this application into nanoparticles of a higher number of MV-RNA. A single MV-RNA was chose as the open/closing fragment for the nanoparticle based on compatible nucleotide for T7 transcriptional yield.

The open/close sequences are:

Nanoparticle Open Sequence (5' of 'WCR_COPI_636'):
WCR_COPI_636:
                                             (SEQ ID NO: 60)
TAATACGACTCACTATAGGTATGTTTGGCCACAGAAGATAGTCAAAGAAC

CTATCTTCTGTCCAAATAATTTTT

Core Close (3' end of 'WCR_COPI_636'):
                                             (SEQ ID NO: 61)
AAATTATTTGGGCCAGACATACT The resulting nanoparticle template for in vitro transcription by T7 (transcript underlined):

WCR_PRESCREEN_apt:
   (SEQ ID NO: 62; Loop clathrin pit underlined)
AATTAATACGACTCACTATAGGTATGTTTGGCCACAGAAGATAGTC

AAAGAACCTATCTTCTGTCCAAATAATTTTTATTGGTTTAGTAGCA

ACTGCAAATTCAAAGAACATTTGTAGTTGGGTCTTTTCCAATAGA

CTTAGGTGGATGTAGGATCCTTAGACTTAGGTGGATGTAGGATCC

AAATTGGAAAAGAACTAAACCAATTTATCAATTGGTCATGTACTT

CGTTTCAAAGAACAACGAAGTACATAACTAGATTCGATTCCTCTA

TCCGTTCTAAACGCTTTATGATTCGAATCTAGTTATCAATTGGTTT

GGTTTCTGGTTTGACTTTCTAGTTCAAAGAACACTAGAAGGTCA

TGAGAAAGGCGTTCAAAGAACACGCCTTTCTCAACCAGAAACC

TTTTTCATTCAAATTGTCTTTACTCAAAGAACGTGAAGACAGAC

AGTATTCTTCTTCCTCTATCCGTTCTAAACGCTTTATGATGAAGAA

TACTGTTTGAATGAAATTTCCCCAGGACTAGGGGCTATTTATCAA

AGAACTGAATAGCCTCCCCAGGACTAGGGAGACTTAGGTGGATG

TAGGATCCTTAGACTTAGGTGGATGTAGGATCCAACCCTAGTCCT

GAGTCCTGGGGATTGGCTATGTCATCCATGATATCGTTCAAAGAA

CATGATATCGTGAACATCATCTACTTTCAAAGAACGTAGATGATG

TATGACATAGCCTTACATGATGGAATTGGAAATGGAATTCAAAGA

ACATTCGTTTTCATTCAAATTGTCTTTTCCTCTATCCGTTCTAAAC

GCTTTATGATAAGACAATTTGAATTCCATCATGTTTACACAACCTT

ATATATTAACAGCTCAAAGAACGCTGTTAGTATGGATGCCAGTGG

AGACTTAGGTGGATGTAGGATCCTTAGACTTAGGTGGATGTAGGA

TCCAACCACTGGCATCTAAGGTTGTGTTTGAAAGGGAGTAGGTG

TATTTACATCAAAGAACTGTAGGTACAAGATGCTAAGAGCTTCA

AAGAACAGCTCTTAGCATCTACTCCCTTTCTTCATCCAGATCGTC

GGTGAATTAGTCAAAGAACCTAATTCATCGTCATCCAGATCGTAG

ACTTAGGTGGATGTAGGATCCTTAGACTTAGGTGGATGTAGGATC

CAAACGATCTGGATCGATCTGGATGTTGAATTTCAAAGAGAAGA

AGAATGGATCTTATTATTCTTCTTCTATAATTTAAGCTTCCTCTATC

CGTTCTAAACGCTTTATGATGCTTAAATTATGGCTTTGAAATTCTT

GGTCGTGCATGTTAATTGGTAATCAAAGAACGTTATCAATTGGTC

ATGTACTTCGTCAAAGAACCGAAGTACATGCATGCACGACCTTA

GATAGCTACTTTATTCTTTCAAATCAAAGAACTTTGAAAGAGTAT

GGACTATTTTTCCTCTATCCGTTCTAAACGCTTTATGATAAATAGT

CCATAGTAGCTATCTTTAGTATTTGTGCTAGCTCCTAGTTCAAAGA

ACACTAGGGGCTATCTCTTCCTTTTAGACTTAGGTGGATGTAGGA

TCCTTAGACTTAGGTGGATGTAGGATCCAAAAAAGGAAGAGGCA

CAAATACTTTAAATTATTTGGGCCAGACATACT

Cofold output (fold notations) showing secondary structure:

..(((((((..(((((((((((..........))))))))))))))......((((((((((((..((((((((
((((..........))))))))))..((((((((((..((((((((((((.....))))....)))
)))))    ((((......))))..))))))))))))))))))..((((((((((.((((((((((((
((..........)))))))))))).((((((((((.((........(((......))))........)).))
)))))))))).))))))    ))))..((((((((((.((((((((((((..........)))))))))))).
((((((((((((..........)))))))))).)))))))))..((((((((((..((((((
((..........)))))))).((((((((((.((........(((......))))........)).))))    ))))))
)))))   )))))..((((((((((..((((((((((((..........)))))))))))).((((((((
((..((((((((((((.....))))....)))))))    ))(((((......)))..)))))))))
)).)))))))))..((((((((((..((((((((((((...)))))..)))))))))).((((((((
(((.(((...))).))))))))))..)))))))))..((((((((((..(((((((((((((.
(((...)))..)))))))))).((((((((((((    .((........(((......)))........
)).))))))))))..)))))))))..((((((((((..((((((((((((..........))))
)))))    )((((((((((..((((((((((((.....))))....)))))))))((((.....
))))..))))))))))..))))))))))..((((((((((.((((((((((..........))

```
))))))..(((((((((((.........)))))))))))))))))))))..((((((((((.(
(((((((((.........))))))))).((((((((((..((((((((((((.....))))....)
))))))((((.....))))..))))          ))))))))))))))))..((((((((((.
((((((((((((......)))))))))))).((((((((((.((.......(((.....))).)
)).    .....)).))))))))..))))))))))..((((((((((.(((((((((((.........)
))))))))..((((((((((........    .)))))))))))))))))))))..((((((((((.
((((((((((((.........))))))))))).(((((((((.((.......(((...    ..)))........
)).)))))))))..))))))))))..((((((((((.((((((((((.........))))))))))..
((((((((((..(((((((((((((.....))))....))))))))((((.....))))..)))))
))))))))))))))))).........................
```

One can also design the same nanoparticle with both 'GalNac' and 'Clathrin-pit' aptamers removed:

```
WCR_PRESCREEN_NONE:
                                   (SEQ ID NO: 63)
AATTAATACGACTCACTATAGGTATGTTTGGCCACAGAAGATAGTC
AAAGAACCTATCTTCTGTCCAAATAATTTTTATTGGTTTAGTAGCA
ACTGCAAATTCAAAGAACATTTGTAGTTGGGTCTTTTCCAATTCA
AAGAACATTGGAAAAGAACTAAACCAATTTATCAATTGGTCATG
TACTTCGTTTCAAAGAACAACGAAGTACATAACTAGATTCGATC
AAAGAACTCGAATCTAGTTATCAATTGGTTTGGTTTCTGGTTTGA
CTTTCTAGTTCAAAGAACACTAGAAGGTCATGAGAAAGGCGTTC
AAAGAACACGCCTTTCTCAACCAGAAACCTTTTTCATTCAAATT
GTCTTTACTCAAAGAACGTGAAGACAGACAGTATTCTTCTCAAA
GAACGAAGAATACTGTTTGAATGAAATTTCCCCAGGACTAGGGG
CTATTTATCAAAGAACTGAATAGCCTCCCCAGGACTAGGGTCAA
AGAACCCCTAGTCCTGAGTCCTGGGGATTGGCTATGTCATCCATG
ATATCGTTCAAAGAACATGATATCGTGAACATCATCTACTTTCAA
AGAACGTAGATGATGTATGACATAGCCTTACATGATGGAATTGGA
AATGGAATTCAAAGAACATTCGTTTTCATTCAAATTGTCTTTCAA
AGAACAAGACAATTTGAATTCCATCATGTTTACACAACCTTATAT
ATTAACAGCTCAAAGAACGCTGTTAGTATGGATGCCAGTGGTCA
AAGAACCCACTGGCATCTAAGGTTGTGTTTGAAAGGGAGTAGGT
GTATTTACATCAAAGAACTGTAGGTACAAGATGCTAAGAGCTTC
AAAGAACAGCTCTTAGCATCTACTCCCTTTCTTCATCCAGATCGT
CGGTGAATTAGTCAAAGAACCTAATTCATCGTCATCCAGATCGTT
CAAAGAACACGATCTGGATCGATCTGGATGTTGAATTTCAAAGA
GAAGAAGAATGGATCTTATTATTCTTCTTCTATAATTTAAGCTCAA
AGAACGCTTAAATTATGGCTTTGAAATTCTTGGTCGTGCATGTTA
ATTGGTAATCAAAGAACGTTATCAATTGGTCATGTACTTCGTCAA
AGAACCGAAGTACATGCATGCACGACCTTAGATAGCTACTTTATT
CTTTCAAATCAAAGAACTTTGAAAGAGTATGGACTATTTTCAAA
GAACAAATAGTCCATAGTAGCTATCTTTAGTATTTGTGCTAGCTCC
TAGTTCAAAGAACACTAGGGGCTATCTCTTCCTTTTTCAAAGAA
CAAAGGAAGAGGCACAAATACTTTAAATTATTTGGGCCAGACA
TACT
```

Cofold output (fold notations) showing secondary structure:

```
((((((((((((.((((((((((.........))))))))))...............((((((((((..
  ((((((((((((.........)))))))              ))..(((((((((((.........)))))
  )))))))))))))..((((((((((.((((((((((((.........))))))))))).
  (((((((((((.........)))))))))).))))))))))..((((((((((.((((((
  (((((.........)))))))))))).((((((((((  ((.........)))))))))).))))))))))..
  ((((((((((..((((((((((.........))))))).(((((((((((((.........))
  )))))))))))))))))..((((((((((..(((((((((((.........)))))))))))..
  ((((((((((((.........)))))))              )).))))))))))..((((((((((..
  ((((((((((((((...))))..))))))))).((((((((((((.(((...))).))))))))))).)
  ))))))))..((((((((((((.((((((((((.(((...)))..)))))))))))).
  ((((((((((((.........))))))))))).)))))              ))))))..((((((((((.
  ((((((((((((.........)))))))))))((((((((((((.........)))))))))).)))))
  )))))..((((((((((((.((((((((((.........))))))))..((((((((((
  (.........)))))))))))))))))))))))))..((((((((((.((((((((((((......))))
  )))))))..((((((((((((.........))))))))))))))))))))))))..((((((((((
  (.((((((((((((......))))))))))))).((((((((((((.........))))))))))..))
  )))))))))..((((((((((..((((((((((.........)))))))))))..
  (((((((((((.)))))))))))))))))))))))))))))))))))))))))..((((((((((.
  ((((((((((        (.........))))))))))))).((((((((((.........))))))))))..))
  )))))))..((((((((((((.((((((((((.........))              )))))))..
  ((((((((((((.........))))))))))))))))))))))))))).........)))))))))).
```

Polynucleotide Nanoparticles with dsRBD Uptake Signal

The open/close sequence of the nanoparticle can also be changed to result in a dsRNA fragment or "tail" leading off of the nanoparticle (e.g., FIG. 14, "A").

```
T7 + GFP Open Sequence (SEQ ID NO: 95):
                                   (SEQ ID NO: 64)
AATTAATACGACTCACTATAGGGAGGATGGTGACTGGTATGAGACTGGGC
TACATATATTCTTTGGGGCATATCCAAATGTCCAAAATCTATTTGGAGAA
CTTGGTATAAATGACCGACTGCAATG GFP Close Sequence DNA (anneals to "GFP
Open" above):
                                   (SEQ ID NO: 65)
CATTGCAGTCGGTCATTTATACCAAGTTCTCCAAATAGATTTTGGACATT
TGGATATGCCCCAAAGAATATATGTAGCCCAGTCTCATACCAGTCACCAT
CCTC
```

DNA template for the production of WCR nanoparticle with dsRBD uptake signal:

```
AATTAATACGACTCACTATAGGGAGGATGGTGACTGGTATGAGACT
GGGCTACATATATTCTTTGGGGCATATCCAAATGTCCAAAATCTAT
TTGGAGAACTTGGTATAAATGACCGACTGCAATGGTATGTTTGGC
CACAGAAGATAGTCAAAgAACCTATCTTCTGTCCAAATAATTTttA
TTGGTTTAGTAGCAACTGCAAATTCAAAgAACATTTGTAGTTGGG
TCTTTTCCAATAGACTTAGGTGGATGTAGGATCCTTAGACTTAGG
TGGATGTAGGATCCAAATTGGAAAAGAACTAAACCAATttATCAA
TTGGTCATGTACTTCGTTTCAAAgAACAACGAAGTACATAACTAG
ATTCGATTCCTCTATCCGTTCTAAACGCTTTATGATTCGAATCTAG
TTATCAATTGGtttGGTTTCTGGTTTGACTTTCTAGTTCAAAgAACA
CTAGAAGGTCATGAGAAAGGCGTTCAAAgAACACGCCTTTCTCA
```

-continued

ACCAGAAACCttTTTCATTCAAATTGTCTTTACTCAAAgAACGTGA
AGACAGACAGTATTCTTCTTCCTCTATCCGTTCTAAACGCTTTAT

GATGAAGAATACTGTTTGAATGAAAttTCCCCAGGACTAGGGGCT

ATTTATCAAAgAACTGAATAGCCTCCCCAGGACTAGGGAGACTTA

GGTGGATGTAGGATCCTTAGACTTAGGTGGATGTAGGATCCAAC

CCTAGTCCTGAGTCCTGGGGAttGGCTATGTCATCCATGATATCGT

TCAAAgAACATGATATCGTGAACATCATCTACTTTCAAAgAACGT

AGATGATGTATGACATAGCCttACATGATGGAATTGGAAATGGAAT

TCAAAgAACATTCGTTTTCATTCAAATTGTCTTTTCCTCTATCCGT

TCTAAACGCTTTATGATAAGACAATTTGAATTCCATCATGTttACA

CAACCTTATATATTAACAGCTCAAAgAACGCTGTTAGTATGGATG

CCAGTGGAGACTTAGGTGGATGTAGGATCCTTAGACTTAGGTGG

ATGTAGGATCCAACCACTGGCATCTAAGGTTGTGTttGAAAGGGA

GTAGGTGTATTTACATCAAAgAACTGTAGGTACAAGATGCTAAGA

GCTTCAAAgAACAGCTCTTAGCATCTACTCCCTTTCttCATCCAGA

TCGTCGGTGAATTAGTCAAAgAACCTAATTCATCGTCATCCAGAT

CGTAGACTTAGGTGGATGTAGGATCCTTAGACTTAGGTGGATGTA

GGATCCAAACGATCTGGATCGATCTGGATGttGAATTTCAAAGAG

AAGAAGAATGGATCTTATTATTCTTCTTCTATAATTTAAGCTTCCT

CTATCCGTTCTAAACGCTTTATGATGCTTAAATTATGGCTTTGAAA

TTCttGGTCGTGCATGTTAATTGGTAATCAAAgAACGTTATCAATTG

GTCATGTACTTCGTCAAAgAACCGAAGTACATGCATGCACGACCtt

AGATAGCTACTTTATTCTTTCAAATCAAAgAACTTTGAAAGAGTA

TGGACTATTTTTCCTCTATCCGTTCTAAACGCTTTATGATAAATAG

TCCATAGTAGCTATCTttAGTATTTGTGCTAGCTCCTAGTTCAAAgA

ACACTAGGGGCTATCTCTTCCTTTTAGACTTAGGTGGATGTAGGA

TCCTTAGACTTAGGTGGATGTAGGATCCAAAAAAGGAAGAGGCA

CAAATACTttAAATTATTTGGGCCAGACATACttCATTGCAGTCGGT

CATTTATACCAAGTTCTCCAAATAGATTTTGGACATTTGGATATGC

CCCAAAGAATATATGTAGCCCAGTCTCATACCAGTCACCATCCTCt (SEQ ID NO: 66; Loop clathrin pit underlined, EcoRI restriction site/T7 transcription start site in italics)

Cofold output (fold notation) showing secondary structure:

((((((((((((((((((((((((((((((((((((((((((((((((((((((((((((
((((((((((((((((((((((((((((((((((((((((((((.((((((
(((.........))))))))).............((((((((((..((((((((((   ..   ........)
))))))))))..((((((((((..(((((((((((......)))).....))))))))
((((.....)))).)))))))))))))))           ))))))..((((((((((.((((((((((
(.........))))))))))).((((((((((.((........(((.....)))......)).))))
))))))).)))))))))))..((((((((((.(((((((((((.........))))))))))).
((((((((((.((.........))))))                     )).))))))))))..(((((((((..
((((((((((.........))))))))).((((((((((((.((.........(((.....)))......)).)
))))))))))))))))))))..((((((((((..((((((((((((.........))))))))))..
((((((((((((..((((((((((((.                    ....))))....))))))))((((.....))
))..)))))))))))).))))))))))..((((((((((..((((((((((((...)))).))) )))
))).(((((((((((.(((...))).))))))))))).))))))))))..(((((((((((.((
(((((((((.(((...)))..)))))))            ))).(((((((((((.((.......(((.....
)))......)).))))))))))))).))))))))))..(((((((((((.((((((((((((
(.   .........))))))))))))((((((((((..((((((((((((.....))))....)))))))
((((.....))))..))))))))))).)))                 )))))..((((((((((((.
((((((((((((.........)))))))))..(((((((((((((.........))))))))))))))
)))))..((((((((((.((((((((((((.........))))))))))..((((((((((..(((
(((((((((.....))))....))))))))    ((((.....))))..)))))))))))))))))))))..
((((((((((((.(((((((((((((......)))))))))))).(((((((((((.((.......(((.....
)))......)).))))))))))))..)))))))))..(((((((((((.((((((((((((.........)
))))))))).     .((((((((((((.........)))))))))))))))))))))..((((((((((((.
((((((((((((((.........))))))))))))).(((((((((.((.......(((.....)))......
)).))))))))))..))))))))))..(((((((((((.((((((((((.........))))))) ))..
((((((((((((..((((((((((((((.....))))...))))))))((((.....))))..)))))
)))))))))))))))).............))))))))))))..))))))))))))))))))))))
))))))))))))))))))))))))))))))))))))))))))))))))))))))
))))))))))))))))))))))))))))))

Circularization of Polynucleotide Nanoparticles In Vitro or In Vivo

An ideal nanoparticle for human use can be created using circularization ribozymes (Manny Ares, 1998) to remove the immune stimulating 5' phosphate and reduce exonuclease degradation during in vivo use. Purification of the ribozyme products from the nanoparticle can be done by exonuclease digestion (FIG. 12), HPLC, Gel extraction, or in mg quantities using FPLC loaded with size exclusion columns (Kim 2007).

A sequence fragment was created using RNA cyclase ribozyme. Using a model of <5' cyclase ribozyme sequence><polynucleotide nanoparticle transcript><3' cyclase ribozyme sequence>, circularized nanoparticles can be made during transcription or thereafter utilizing a circularization reaction.

The cyclase ribozyme sequences are:

5' end w/ T7:
(SEQ ID NO: 31)

*AATTAATACGACTCACTATAGG*GAAAATTTCGTCTGGATTAGTTACTTAT
CGTGTAAAATCTGATAAATGGAATTGGTTCTACATAAATGCCTAACGACT

ATCCCTTTGGGGAGTAGGGTCAAGTGACTCGAAACGATAGACAACTTGCT

TTAACAAGTTGGAGATATAGTCTGCTCTGCATGGTGACATGCAGCTGGAT

ATAATTCCGGGGTAAGATTAACGACCTTATCTGAACATAATGCTA

3' end:
(SEQ ID NO: 32)
CATGTCAATTGAGGCCTGAGTATAAGGTGACTTATACTTGTAATCTATCT

AAACGGGGAACCTCTCTAGTAGACAATCCCGTGCTAAATTGTAGGACTGC

CCTTTAATAAATACTTCTATATTTAAAGAGGTATTTATGAAAAGCGGAAT

TTATCAGATTAAAAATACTTTCT

This sequence example shows a TRI nanoparticle targeting WCR EST3, vATPase A, & Snf7 inserted in between the above cyclase ribozyme sequences resulting in a circular TRI nanoparticle targeting WCR vATPase following in vitro T7 transcription:

TRI nanoparticle circularizing DNA template (WCR-trlm_III.C):

(SEQ ID NO: 67; nanoparticle insert underlined)

*AATTAATACGACTCACTATAGG*GGAAAATTTCGTCTGGATTAGTTAC
TTATCGTGTAAAATCTGATAAATGGAATTGGTTCTACATAAATGCC

TAACGACTATCCCTTTGGGGAGTAGGGTCAAGTGACTCGAAACG

ATAGACAACTTGCTTTAACAAGTTGGAGATATAGTCTGCTCTGCA

TGGTGACATGCAGCTGGATATAATTCCGGGGTAAGATTAACGACC

TTATCTGAACATAATGCTA<u>ACTGGATGATGTCGATAGGTTTTGTTC</u>

<u>TCAAGAAGGACAGAATCTGTCATAAGAAGGCTAACAGCAAACT</u>

<u>CAGTTGCTGGGGAAATATGCATATTTTCTCAGCAGTAACGACTGT</u>

<u>TGAAATTCCTCTATCCGTTCTAAACGCTTTATGATTTTCAATAGTT</u>

<u>GTAAGGGTTTGCTGAAGATCCCAACTTGATGTTGAATTTGTTCAA</u>

<u>GAGACAAATTTAATATTTAGCTGTCGGTTGTTCAAGAGACAGCC</u>

<u>GGC</u>AGTTGAGTTGGGATTAAAGCTTTCTTAAGGGCATCATCCAG

TCATGTCAATTGAGGCCTGAGTATAAGGTGACTTATACTTGTAAT

CTATCTAAACGGGGAACCTCTCTAGTAGACAATCCCGTGCTAAAT

TGTAGGACTGCCCTTTAATAAATACTTCTATATTTAAAGAGGTATT

TATGAAAAGCGGAATTTATCAGATTAAAAATACTTTCT

Figure 22:
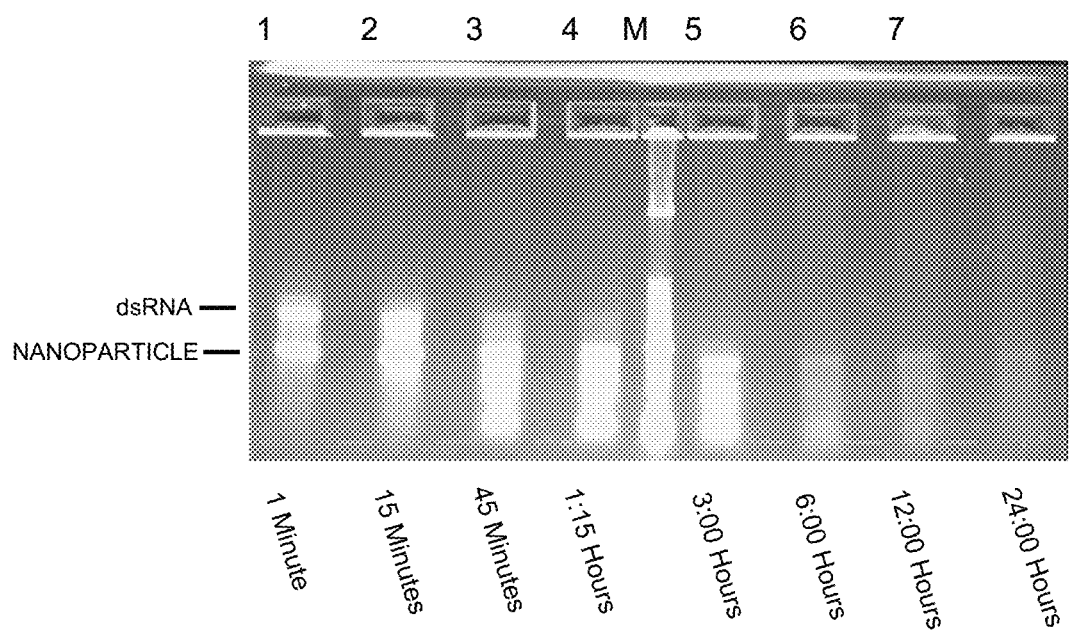
FIG. 22: Exo-nucleic stability of the polynucleotide nanoparticle in homogenized maize tissue compared to long dsRNA.

The same circularization can occur during in-planta (in vivo) expression. For example, on might chose to make the nanoparticles of this invention in Maize. Such nanoparticles expressed in corn have shown to be more stable within the tissue (FIG. 22)—leading to a higher concentration during pest ingestion. Promoters such as Ubiquitin or CMV can easily be used by inserting the 5' cyclase ribozyme, polynucleotide nanoparticle sequence, and 3' cyclase ribozyme above into the desired clone before transformation into the plant.

Example 3: Self-Forming Single-Stranded Polynucleotide MV-RNA Nanoparticle Targeting *Amaranthus palmeri* (Pigweed)

This example describes the assembly of a polynucleotide nanoparticle according to the invention as a stable and multivalent single-stranded RNA nanoparticle targeting one, two, or three plant genes simultaneously with increasing molarity and spectrum. This example illustrates in vitro production of the nanoparticles for exogenous (spray or drop) application on Palmer Amaranth.

Figure 21A:
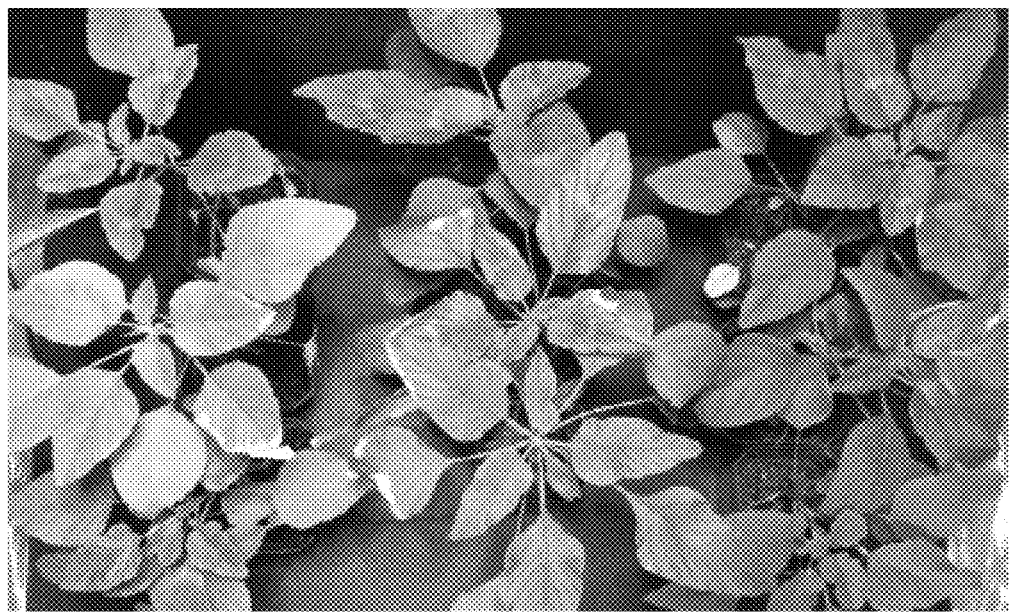
FIGS. 21A-C.
Figure 21B:
Figure 21C:
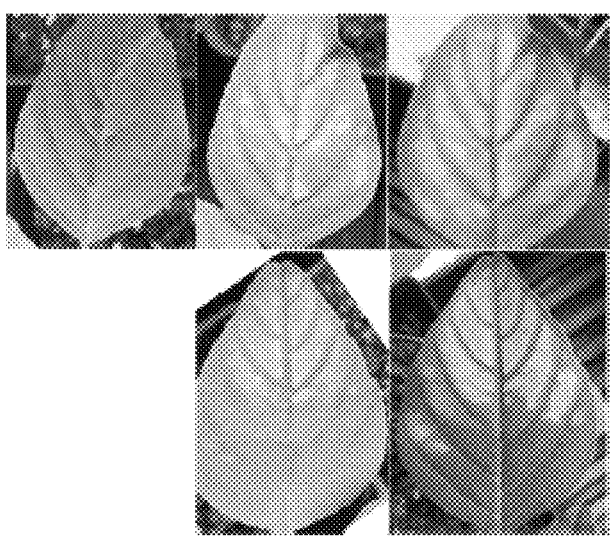

Benefits such as multivalency for spread spectrum bioherbicide, plant cell uptake, and formulation stability are realized by viewing the phenotype response (FIGS. 21A-C). In this case, photobleaching (de-greening) is observable on the treated plants 10 days after application due to reduced expression of pytoene desaturase (SEQ ID NO:104). Additional Palmer Amaranth targets in this example are EPSPS (SEQ ID NO:105) and HPPD (SEQ ID NO:106).

```
Clathrin-Pit:
                                    (SEQ ID NO: 54)
TTCCTCTATCCGTTCTAAACGCTTTATGAT T7_initiation:
                                    (SEQ ID NO: 23)
TAATACGACTCACTATAGGN
```

MV-RNA Examples Utilized in the Design of the Polynucleotide Nanoparticle

Individual Divalent MV-RNA composing the nanoparticle:

PDS divalents:
MV-RNA 655/1089:
GGUCAUAUGUAUUCUUUAAUUGGAUCUUAUUAAUUAAAGAAGCACAA GAUU < divide sequence here indicating the 5'

"Open" and 3' "Close" sequences for the nanoparticle> UCUUGUGCUUCAACAUAUGACUUU (SEQ ID NO:

68; Loop Dicer 2 in bold)

MV-RNA 430/1173:
AUAUAAGGAUGAACUUGGUAUCAAGAAACUACCAAGUUCUCCAAAUAGAU

UUUU<u>CCUCUAUCCGUUCUAAACGCUUUAUGAU</u>GGAUCUAUUUGGAUCCUU

AUAUUU (SEQ ID NO: 69; Loop Dicer 1 in bold, Loop clathrin pit underlined)

MV-RNA 1095/388:
UAGAUGGUCAUAUGUAUUCUUUUCAAGAAACAAAGAAUAUAUGUAGCCCA

GUCUCAUC<u>UUCCUCUAUCCGUUCUAAACGCUUUAUGAU</u>CUGAGACUGGGC

UAUGACCAUCUA (SEQ ID NO: 70; Loop Dicer 1 in bold,

Loop clathrin pit underlined)

MV-RNA 736/888:
GAUGUGUUUAACAAUAGGCAUUUCAAGAAACAUGCUUAUUGGCCAUGUCAA

AG<u>UUCCUCUAUCCGUUCUAAACGCUUUAUGAU</u>CUUUGACAUGGCAAUAAA

CACAUCUU (SEQ ID NO: 71; Loop Dicer 1 in bold,

Loop clathrin pit underlined)

EPSPS divalents:
MV-RNA 1430/989:
UGAUCGUCAUAAGUUUCAAGUGCUCAAGAAACGCACUUGAAGCAUCACCC

UCAACUCAAGAAACGUUGAGGGUGAUAUGACGAUCAUU (SEQ ID NO:

72; Loop Dicer 1 in bold)

MV-RNA 546/1437:
UGUCAAUGGGCGCAUCGCUGAAUGGGAUCUUAUUCAUUCGGUGAUCGUCA

UAAGU<u>UUCCUCUAUCCGUUCUAAACGCUUUAUGAU</u>AACUUAUGACGGCC

CAUUGACAUU (SEQ ID NO: 73; Loop Dicer 2 in bold,

Loop clathrin pit underlined)

MV-RNA 854/947:
UUGUAUUUCUGACCACCUCGAAUGGGAUCUUAUUCAUUCGAGGUGCCGUA

UGUUGAUCAAGAAACUCAACAUACGGUACAGAAAUACAAUU (SEQ ID

NO: 74; Loop Dicer 1 and Loop Dicer 2 in bold)

MV-RNA 1165/1317:
CAGAUGAAUCCCUGGGUGGUUGCCUCAAGAAACGGCAAUCAUCCGUUCGG

UUUC<u>CUUCCUCUAUCCGUUCUAAACGCUUUAUGAU</u>GGAAACCGAACGGAU

UCAUCUGUU (SEQ ID NO: 75; Loop Dicer 1 in bold,

Loop clathrin pit underlined)

HPPD_DIVALENT:
MV-RNA 492/984:
UAAUAUGAUGAAAGUAUGCCAUUAGAUCAAAAAACUCUAAUGGCAUAGGC

UGGUGUACA<u>UUCCUCUAUCCGUUCUAAACGCUUUAUGAU</u>UGUACACCAGC

CCCUUCAUUAUGUUAUU (SEQ ID NO: 76; Loop clathrin pit underlined)

* "655/1089" used as opening T7 transcript start and closing sequence for particle.

Individual Trivalent MV-RNA composing the nanoparticle:

```
MV-RNA 792/949/1156:
GGAGUAGCCAUGAGAAGUGCAGAUUCAAGAAACAUUUGUAUUUCUGACCA

CCUAGGGUU< divide sequence here indicating the

5' "Open" and 3' "Close" sequences for the nanoparticle >CCCUGGGUGGUCCAGUGGCUGUUCCUU (SEQ ID NO: 77; Loop Dicer 1 in bold)

MV-RNA 263/1112/1521:
GUCCGGGAAGGUUUUAAGGGGGUCUCUCAAGAAACGAGAUCUCUUUGAUG

GGUUGUAAGGUUUCCUCUAUCCGUUCUAAACGCUUUAUGAUACCUUGCAA

CCCAUCUUCUCGGGCUU (SEQ ID NO: 78; Loop Dicer 1 in bold, Loop clathrin pit underlined)

MV-RNA 1365/1146/1490:
AGAUCCUUCCUCAACUGUUGCUGGAUCAAGAAACUCCAGUAACAGUUACA

CUAUUCUUGGUUCCUCUAUCCGUUCUAAACGCUUUAUGAUUCAAGGAUAG

UGACGGGGAGGGAUCUUU (SEQ ID NO: 79; Loop Dicer 1 in bold, Loop clathrin pit underlined)

MV-RNA 370/586/958:
CAUCACUAUACAGCAAGUUGUGUGCUCAAGAAACGCACAUAACUUGAAUU

UCCUGGAGUUCAUAGAGAUUCCAGGAGAUUUGUAUGGUGAUGUU (SEQ ID NO: 80; Loop Dicer 1 and Loop Dicer 3 in bold)
```

* "792/949/1156" used as opening T7 transcript start and closing sequence for particle.

```
PDS TRIVALENT:
MV-RNA 544/1496/1340:
GAUAGCCUGUGCACAAAGCUUCAAGGUCAAGAAACCCUUGGAGUUUUGAC

GUUAAAUGGUAUCAAGAAACUGCCAUUUAAUGGUGCAGGCUGUCUU (SEQ ID NO: 81; Loop Dicer 1 in bold)

MV-RNA 84/294/538:
UCUUUGCUUUGCUCCAUAAACUUAUAUCAAGAAACUAUGGGUUUGUGACC

UGCAUCAUUAAUUCCUCUAUCCGUUCUAAACGCUUUAUGAUUUAAUGGUG

CAGGCAGGGUAAAGGUU (SEQ ID NO: 82; Loop Dicer 1 in bold, Loop clathrin pit underlined)

MV-RNA 93/512/503:
CGACUGAAUUCACCGGGAAUGGGCACUCAAGAAACGUGCCCAUUUCUUUG

CUUUGAUUUUCAAGAAACAAAUCAAAGCGACUGAAUUCAGUCGUU (SEQ ID NO: 83; Loop Dicer 1 in bold)

MV-RNA 1185/423/971:
CAGCUUCAAGAUGUCAUGCUGGGAUUCAAGAAACAUUCCAGCAUGGAUCU

AUUUGGAGAAUUCCUCUAUCCGUUCUAAACGCUUUAUGAUUUCUCCAAAU

AGAUUUGGAGCUGUU (SEQ ID NO: 84; Loop Dicer 1 in bold, Loop clathrin pit underlined)
```

TRI Polynucleotide Nanoparticle with Clathrin-Pit Endocytosis Signals for Topical Plant Application Targeting Palmer Amaranth Pytoene Desaturase

```
PA_pds_TRI DNA template:
AATTAATACGACTCACTATAGGGTCATATGTATTCTTTAATTGGATCT

TATTAATTAAAGAAGAAGCACAAGATcATATAAGGATGAACTTGG

TATCAAGAAACTACCAAGTTCTCCAAATAGATTTTTCCTCTATCC

GTTCTAAACGCTTTATGATGGATCTATTTGGATCCTTATATTcTAGA

TGGTCATATGTATTCTTTTCAAGAAACAAAGAATATATGTAGCCC

AGTCTCATCTTCCTCTATCCGTTCTAAACGCTTTATGATCTGAGAC

TGGGCTATGACCATCTATcTCTTGTGCTTCAACATATGACCT (SEQ ID NO: 85; Loop Dicer 1 and Loop Dicer 2 in bold, Loop clathrin pit underlined)
```

Cofold output (fold notation) showing secondary structure:

((((((((((..((((((((((.......)))))))))).((((((((((..(((((((.
((((((((((..........)))))))))).((((((((((..((........(((......)))........
))..))))))))))).))))))))..((((((((.((((((((((((..........))) ))))))))
(((((((((((((...((........(((......)))........))..))))))))))))).))))))
)))).. ))))))))))).)))) )))))..

TRI Polynucleotide Nanoparticle with Clathrin-Pit Endocytosis Signals for Topical Plant Application Targeting Palmer Amaranth PDS, EPSPS, and HPPD as a Bioherbicide

```
PA_pds,epsps,hppd_TRI DNA template:
AATTAATACGACTCACTATAGGGTCATATGTATTCTTTAATTGGATCT

TATTAATTAAAGAAGAAGCACAAGATTTGTCAATGGGCGCATCG

CTGAATGGGATCTTATTCATTCGGTGATCGTCATAAGTTTTCCTCT

ATCCGTTCTAAACGCTTTATGATAACTTATGACGGCCCATTGACA

TTTAATATGATGAAAGTATGCCATTAGATCAAAAAACTCTAATGG

CATAGGCTGGTGTACATTCCTCTATCCGTTCTAAACGCTTTATGAT

TGTACACCAGCCCCTTCATTATGTTATTTCTTGTGCTTCAACATAT

GACTT (SEQ ID NO: 86; Loop Dicer 2 in bold,

Loop clathrin pit underlined)
```

Cofold output (fold notations) showing secondary structure:

((((((((((..((((((((((......)))))))))).((((((((((..(((((((.
((((((((((..........)))))))))).((((((((((..((........(((......)))........
))..))))))))))).))))))))..((((((((.((((((((((((..........))) ))))))))
(((((((((((((...((........(((......)))........))..))))))))))))).))))))
))).. ))))))))))).)))) )))))..

Dodecahedron Polynucleotide Nanoparticles with Clathrin-Pit Endocytosis Signals for Topical Plant Application Targeting Palmer Amaranth PDS, EPSPS as a Bioherbicide

```
PA_pds_epsps_D8 DNA template:
AATTAATACGACTCACTATAGGGTCATATGTATTCTTTAATTGGATCT

TATTAATTAAAGAAGAAGCACAAGATTATATAAGGATGAACTTG

GTATCAAGAAACTACCAAGTTCTCCAAATAGATTTTTCCTCTATC

CGTTCTAAACGCTTTATGATGGATCTATTTGGATCCTTATATTTTCT
```

-continued

GGAGGGTTTCCGTCTAGGAAGTCAAGAAACCTTCCTAGACGGT

ATTTAGCTGGTTCAAGAAACACCAGCTAAATAGAAACCCTCTAG

ATTGATGTGTTTAACAATAGGCATTCAAGAAACATGCTTATTGGC

CATGTCAAAG<u>TTCCTCTATCCGTTCTAAACGCTTTATGATC</u>TTTGA

CATGGCAATAAACACATCTTTGATCGTCATAAGTTTCAAGTGCTC

AAGAAACGCACTTGAAGCATCACCCTCAACTCAAGAAACGTTG

AGGGTGATATGACGATCATTTGTCAATGGGCGCATCGCTGAATGG

GATCTTATTCATTCGGTGATCGTCATAAGT<u>TTTCCTCTATCCGTTC</u>

<u>TAAACGCTTTATGAT</u>AACTTATGACGGCCCATTGACATTTGTATT

TCTGACCACCTCGAATGGGATCTTATTCATTCGAGGTGCCGTAT

GTTGATCAAGAAACTCAACATACGGTACAGAAATACAATTCAGA

TGAATCCCTGGGTGGTTGCCTCAAGAAACGGCAATCATCCGTTC

GGTTTCC<u>TTCCTCTATCCGTTCTAAACGCTTTATGAT</u>GGAAACCG

AACGGATTCATCTGTTTCTTGTGCTTCAACATATGACTT (SEQ

ID NO: 87; Loop Dicer 1 and Loop Dicer 2 in bold,

Loop clathrin pit underlined)

Cofold output (fold notations) showing secondary structure:

(((((((((..(((((((((......))))))))))).(((((((((..(((((((.
((((((((((.........))))))))).(((((((((..((........(((......)))......
))..)))))))))))).)))))))..(((((((((((((((((((..........)
)))))))))).(((((((((..........))))))))))))))))))))..(((((((((.
((((((((((.........)))))))       ))))(((((((((.((........(((.....
)))......)..)))))))))))..)))))))))..(((((((((.(((((((((.       ........)
)))))))))).(((((((((..........)))))))))))))))))))))..(((((((((..
(((((((((((.....)       )))))))))).(((((((((.((........(((.....))).......
))..)))))))))))))))))..(((((((((..(((((((((......)
)))))))))))((((((((((..........)))))))))..)))))))))..(((((((((..
((((((((((.........)))))))))((((((((((.((........(((.....)))......
))..))))))))))))))))))..)))))))))). )))))))))..

PA_pds_epsps_T8 DNA template:
AATTAATACGACTCACTATAGGGAGTAGCCATGAGAAGTGCAGATT

CAAGAAACATTTGTATTTCTGACCACCTAGGGTTGTCCGGGAAG

GTTTTAAGGGGGTCTCTCAAGAAACGAGATCTCTTTGATGGGTT

GTAAGG<u>TTCCTCTATCCGTTCTAAACGCTTTATGATA</u>CCTTGCA

ACCCATCTTCTCGGGCTTCATCACTATACAGCAAGTTGTGTGCTC

AAGAAACGCACATAACTTGAATTTCCTGGAGTTCATAGAGATTC

CAGGAGATTTGTATGGTGATGTTAGATCCTTCCTCAACTGTTGCT

GGATCAAGAAACTCCAGTAACAGTTACACTATTCTTGG<u>TTCCTC</u>

<u>TATCCGTTCTAAACGCTTTATGATT</u>CAAGGATAGTGACGGGGAGG

GATCTTTGATAGCCTGTGCACAAAGCTTCAAGGTCAAGAAACCC

TTGGAGTTTTGACGTTAAATGGTATCAAGAAACTGCCATTTAAT

GGTGCAGGCTGTCTTTCTTTGCTTTGCTCCATAAACTTATATCAA

GAAACTATGGGTTTGTGACCTGCATCATTAA<u>TTCCTCTATCCGTT</u>

<u>CTAAACGCTTTATGATT</u>TAATGGTGCAGGCAGGGTAAAGGTTCG

ACTGAATTCACCGGGAATGGGCACTCAAGAAACGTGCCCATTT

CTTTGCTTTGATTTTCAAGAAACAAATCAAAGCGACTGAATTCA

GTCGTTCAGCTTCAAGATGTCATGCTGGGATTCAAGAAACATTC

CAGCATGGATCTATTTGGAGA<u>ATTCCTCTATCCGTTCTAAACGCT</u>

<u>TTATGATT</u>TCTCCAAATAGATTTTGGAGCTGTTCCCTGGGTGGTC

CAGTGGCTGTTCCT (SEQ ID NO: 88; Loop Dicer 1 and

Loop Dicer 3 in bold, Loop clathrin pit underlined)

Cofold output (fold notations) showing secondary structure:

((((((((..(((((((((......))))))))))).(((((((((..(((((((.
((((((((((.........))))))))).(((((((((..((........(((......)))......
))..)))))))))).)))))))..(((((((((((((((((((..........)
)))))))))).(((((((((..........)))))))))))))))))))..(((((((((.
((((((((((.........))))))       )))((((((((((.((........(((.....
)))......)..)))))))))))..))))))))..(((((((((.(((((((((.       ........)
)))))))))).(((((((((..........)))))))))))))))))))..(((((((((..
((((((((((.....)       )))))))))).(((((((((.((........(((.....))).......
))..)))))))))))))))))..(((((((((..(((((((((......)
)))))))))))((((((((((..........)))))))))..)))))))))..(((((((((..
((((((((( (..........))))))))))(((((((((.((........(((.....)))......
))..))))))))))))))))))..))))))))). )))))))))..

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Adolph & Butler. J Mol Biol 109:345-357 (1977)
2. Allison et al. J Virol 62:3581-3588 (1988)
3. Annamalai & Rao. Virology 332:650-658 (2005)
4. Annamalai & Rao Virology 80:10096-10108 (2006)
5. Annamalai et al. J Virol 82:1484-1490 (2008)
6. Bamunusinghe & Seo J Virol 85:2953-2963 (2011)
7. Bancroft Adv Virus Res 16:99-134 (1970)
8. Bancroft & Hiebert Virology 32:354-356 (1967)
9. Bancroft et al. Virology 39:924-930 (1969)
10. Basnak et al J Mol Biol 395:924-936 (2010)
11. Bernstein et al. Nature 409:363-6 (2001)
12. Briddon & Markham. Family Geminiviridae, pp. 158-165 in Murphy F A, et al., editors. (ed), Virus taxonomy: archives in virology. Springer-Verlag, New York, N.Y. (1995)
13. Brummelkamp et al. Science 296:550 (2002a)
14. Brummelkamp et al. Cancer Cell 2:243 (2002b)
15. Cadena-Nava et al. J Phys Chem 115:2386-2391 (2011)
16. Caspar & Klug Cold Spring Harbor Symp Quant Biol 27:1-24 (1962)
17. Choi & Rao Virology 275:207-217 (2000)
18. Choi & Rao Virology 275:249-257 (2000)
19. deHaseth et al. Biochemistry 16:4783-4790 (1977)

20. Denli et al. Nature 432:231-5 (2004)
21. Dreher et al. J Mol Biol 206:425-438 (1989)
22. Dzianott & Bujarski Virology 185:553-562 (1991)
23. Elrad & Hagan Phys Biol 7:045003 (2010)
24. Filippov et al. Gene 245:213-221 (2000)
25. Fire et al. Nature 391:806-11 (1998)
26. Fox et al. Virology 244:212-218 (1998)
27. Frischmuth et al. J Gen Virol 82:673-676 (2001)
28. Han et al. Cell 125:887-901 (2006)
29. Hiebert et al. Virology 34:492-508 (1968)
30. Hu et al. Biophys J 94:1428-1436 (2008)
31. Jaronczyk et al. Biochem J 387:561-71 (2005)
32. Johnson et al. J Mol Biol 335:455-464 (2004)
33. Johnson et al. J Gen Virol 19:263-273 (1973)
34. Jung et al. ACS Nano 5:1243-1252 (2011)
35. Kim RNA 13:289-294 (2007)
36. Kobayashi & Ehara Ann Phytopathol Soc Jpn 61:99-102 (1995)
37. Kroll et al. Proc Natl Acad Sci USA 96:13650-13655 (1999)
38. Lamontagne J Biol Chem 279:2231-2241 (2004)
39. Lavelle et al. J Phys Chem B 113:3813-3820 (2009)
40. Logan & Shenk Proc Natl Acad Sci USA 81:3655-3659 (1984)
41. Lustig et al. J Virol 62:2329-2336 (1988)
42. Macrae et al. Science 311:195-8 (2006)
43. Mascotti & Lohman Proc Natl Acad Sci USA 87:3142-3146 (1990)
44. Meister & Tuschl Nature 431:343-9 (2004)
45. Nugent et al. J Virol 73:427-435 (1997)
46. Obenauer-Kutner et al. Hum Gene Ther 13:1687-1696 (2002)
47. Perriman & Ares RNA 4:1047-1054 (1998)
48. Pfeifer et al. Philos Trans R Soc Lond B Biol Sci 276:99-107 (1976)
49. Porterfield et al. J Virol 84:7174-7184 (2010)
50. Prinsen et al. J Phys Chem B 114:5522-5533 (2010)
51. Qu & Morris J Virol 71:1428-1435 (1997)
52. Rao Annu Rev Phytopathol 44:61-87 (2006)
53. Sambrook et al. Molecular cloning: a laboratory manual. Cold Spring Harbor Laboratory Press, Cold Spring Harbor, N.Y. (1989)
54. Sidahmed & Bruce Methods Mol Biol 623:3-19 (2010)
55. Sikkema et al. Org Biomol Chem 5:54-57 (2007)
56. Song et al. Nat Struct Biol 10:1026-32 (2003)
57. Sorger et al. J Mol Biol 191:639-658 (1986)
58. Speir et al. Structure 3:63-78 (1995)
59. Sun et al. Proc Natl Acad Sci USA 104:1354-1359 (2007)
60. Tang et al. J Struct Biol 154:59-67 (2006)
61. Turner et al. Insect Mol Biol 15:383-391 (2006)
62. van der Graaf et al. Biochem 3:9177-9182 (1992)
63. Venter et al. J Virol 79:6239-6248 (2005)
64. Verduin & Bancroft Virology 37:501-506 (1969)
65. Yoffe et al. Proc Natl Acad Sci USA 105:16153-16158 (2008)
66. Zandi & van der Schoot Biophys J. 96:9-20 (2009)
67. Zhang et al. Virology 279:471-477 (2001)
68. Zlotnick et al. Virology 277:450-456 (2000)

SEQ ID NO: 89: AKT (X61037 H. sapiens mRNA for protein kinase B):
ATGAAGACGGAGCGGCCCCGGCCCAACACCTTCATCATCCGCT

GCCTGCAGTGGACCACTGTCATCGAACGCACCTTCCATGTGGA

GACTCCTGAGGAGCGGGAGGAGTGGACAACCGCCATCCAGACT

GTGGCCGACGGCCTCAAGAAGCAGGAGGAGGAGGAGATGGAC

TTCCGGTCGGGCTCACCCAGCGACAACTCAGGGGCCGAAGAGA

TGGAGGTGTCCCTGGCCAAGCCCAAGCACCGCGTGACCATGAA

CGAGTTTGAGTACCTGAAGCTGCTGGGCAAGGGCACTTTCGGC

AAGGTGATCCTGGTGAAGGAGAAGGCCACAGCGTACTACGCCA

TGAAGATCCTCAAGAAGGAAGTCATCGTGGCCAAGGACGAGGT

GGCCCACACACTCACCGAGAACCGCGTCCAGCAGAACTCCAGG

CACCCCTTCCTCACTCGCCTGAAGTACTCTTTCCAGACCCACGA

CCGCCTCTGCTTTGTCATGGAGTACGCCAACGGGGGCGAGCTGT

TCTTCCACCTGTCCCGGGAGCGTGTGTTCGCCGAGGACCGGGCC

CGCTTCTATGGCGCTGAGATTGTGTCAGCCCTGGACTACCTGCA

CTCGGAGAAGAACGTGGTGTACCGGGACCTCAAGCTGGAGAAC

CTCATGCTGGACAAGGACGGGCACATTAAGATCACAGACTTCG

GGCTGTGCAAGGAGGGGATCAAGGACGGTGCCACCATGAAGAC

CTTTTGCGGCACACCTGAGTACCTGGCCCCCGAGGTGCTGGAG

GACAATGACTACGGCCGTGCAGTGGACTGGTGGGGCTGGGCG

TGGTCATGTACGAGATGATGTGCGGTCGCCTGCCCTTCTACAAC

CAGGACCATGAGAAGCTTTTTGAGCTCATCCTCATGGAGGAGA

TCCGCTTCCCGCGCACGCTTGGTCCCGAGGCCAAGTCCTTGCTT

TCAGGGCTGCTCAAGAAGGACCCCAAGCAGAGGCTTGGCGGGG

GCTCCGAGGACGCCAAGGAGATCATGCAGCATCGCTTCTTTAC

CGGTATCGTGTGGCAGCACGTGTACGAGAAGAAGCTCAGCCCA

CCCTTCAAGCCCCAGGTCACGTCGGAGACTGACACCAGGTATTT

TGATGAGGAGTTCACGGCCCAGATGATCACCATCACACCACCT

GACCAAGATGACAGCATGGAGTGTGTGGACAGCGAGCGCAGGC

CCCACTTCCCCCAGTTCTCCTACTCGCCCAGCGCGACGGCCTGA

SEQ ID NO: 90: MAP3K (NM_005921 Homo sapiens mitogen-activated protein kinase 1, E3 ubiquitin protein ligase (MAP3K1), mRNA):
CACCAGAAACCCAAGTTGGAACTAATTCTTTCTTTCGGAAGGTG

CAACTCCCCTCCCGCGAGCTCCGCGGTGCCGGGCCGAGATTGC

CGAGAGGAAGCGGCGCAGCGCTGCCGCCAAGGCTCCTCCTGTC

GCCGGTGCGGCCGGGACTACCTGGCGGCGCGGCGCGTGCAGCG

CGCAGAGTCCCGGGAGCCCACGCCTCCGCCTCCGCCCCCGCCC

CCTCCGCCTCCCAGTCCACCTCGCCCGCCCGCCCTCTCGCCCGG

CGGAGAGCACAGCCCACTCCCTCCCACCTGCGGCCGCCGGGCC

GCCCTCCACCCACACCTCTGCCGCAGGCCGGACCCAGTGCGCC

CGCCCGTCGGTCAGTCCAGGCCAGGCGCCCGGCGGGCCGCT

CACGCAGTTGGCGCAGGAGGCCTTACGCTGGCGGCGCAGTGCC

CGCCCCCTGCGCTCTCCCCGCCCCCTCCCTCCCTCGCAGGGGCC

GAGCGAATGTAGCCCGCGAGAGAAAATGGCGGCGGCGGCGGG

-continued

```
GAATCGCGCCTCGTCGTCGGGATTCCCGGGCGCCAGGGCTACG
AGCCCTGAGGCAGGCGGCGGCGGAGGAGCCCTCAAGGCGAGC
AGCGCGCCCGCGGCTGCCGCGGGACTGCTGCGGGAGGCGGGCA
GCGGGGGCCGCGAGCGGGCGGACTGGCGGCGGCGGCAGCTGC
GCAAAGTGCGGAGTGTGGAGCTGGACCAGCTGCCTGAGCAGCC
GCTCTTCCTTGCCGCCTCACCGCCGGCCTCCTCGACTTCCCCGTC
GCCGGAGCCCGCGGACGCAGCGGGGAGTGGGACCGGCTTCCAG
CCTGTGGCGGTGCCGCCGCCCCACGGAGCCGCGAGCCGCGGCG
GCGCCCACCTTACCGAGTCGGTGGCGGCGCCGGACAGCGGCGC
CTCGAGTCCCGCAGCGGCCGAGCCCGGGGAGAAGCGGGCGCCC
GCCGCCGAGCCGTCTCCTGCAGCGGCCCCCGCCGGTCGTGAGA
TGGAGAATAAAGAAACTCTCAAAGGGTTGCACAAGATGGATGA
TCGTCCAGAGGAACGAATGATCAGGAGAAACTGAAGGCAACC
TGTATGCCAGCCTGGAAGCACGAATGGTTGGAAAGGAGAAATA
GGCGAGGGCCTGTGGTGGTAAAACCAATCCCAGTTAAAGGAGA
TGGATCTGAAATGAATCACTTAGCAGCTGAGTCTCCAGGAGAG
GTCCAGGCAAGTGCGGCTTCACCAGCTTCCAAAGGCCGACGCA
GTCCTTCTCCTGGCAACTCCCCATCAGGTCGCACAGTGAAATCA
GAATCTCCAGGAGTAAGGAGAAAAAGAGTTTCCCCAGTGCCTT
TTCAGAGTGGCAGAATCACACCACCCCGAAGAGCCCCTTCACC
AGATGGCTTCTCACCATATAGCCCTGAGGAAACAAACCGCCGT
GTTAACAAAGTGATGCGGGCCAGACTGTACTTACTGCAGCAGA
TAGGGCCTAACTCTTTCCTGATTGGAGGAGACAGCCCAGACAA
TAAATACCGGGTGTTTATTGGGCCTCAGAACTGCAGCTGTGCAC
GTGGAACATTCTGTATTCATCTGCTATTTGTGATGCTCCGGGTG
TTTCAACTAGAACCTTCAGACCCAATGTTATGGAGAAAAACTTT
AAAGAATTTTGAGGTTGAGAGTTTGTTCCAGAAATATCACAGTA
GGCGTAGCTCAAGGATCAAAGCTCCATCTCGTAACACCATCCA
GAAGTTTGTTTCACGCATGTCAAATTCTCATACATTGTCATCAT
CTAGTACTTCTACGTCTAGTTCAGAAAACAGCATAAAGGATGA
AGAGGAACAGATGTGTCCTATTTGCTTGTTGGGCATGCTTGATG
AAGAAAGTCTTACAGTGTGTGAAGACGGCTGCAGGAACAAGCT
GCACCACCACTGCATGTCAATTTGGGCAGAAGAGTGTAGAAGA
AATAGAGAACCTTTAATATGTCCCCTTTGTAGATCTAAGTGGAG
ATCTCATGATTTCTACAGCCACGAGTTGTCAAGTCCTGTGGATT
CCCCTTCTTCCCTCAGAGCTGCACAGCAGCAAACCGTACAGCA
GCAGCCTTTGGCTGGATCACGAAGGAATCAAGAGAGCAATTTT
AACCTTACTCATTATGGAACTCAGCAAATCCCTCCTGCTTACAA
AGATTTAGCTGAGCCATGGATTCAGGTGTTTGGAATGGAACTCG
TTGGCTGCTTATTTTCTAGAAACTGGAATGTGAGAGAGATGCC
CTCAGGCGTCTTTCCCATGATGTCAGTGGGGCCCTGCTGTTGGC
```

```
AAATGGGGAGAGCACTGGAAATTCTGGGGGCAGCAGTGGAAG
CAGCCCGAGTGGGGGAGCCACCAGTGGGTCTTCCCAGACCAGT
ATCTCAGGAGATGTGGTGGAGGCATGCTGCAGCGTTCTGTCAAT
GGTCTGTGCTGACCCTGTCTACAAAGTGTACGTTGCTGCTTTAA
AAACATTGAGAGCCATGCTGGTATATACTCCTTGCCACAGTTTA
GCGGAAAGAATCAAACTTCAGAGACTTCTCCAGCCAGTTGTAG
ACACCATCCTAGTCAAATGTGCAGATGCCAATAGCCGCACAAG
TCAGCTGTCCATATCAACACTGTTGGAACTGTGCAAAGGCCAA
GCAGGAGAGTTGGCAGTTGGCAGAGAAATACTAAAAGCTGGAT
CCATTGGTATTGGTGGTGTTGATTATGTCTTAAATTGTATTCTTG
GAAACCAAACTGAATCAAACAATTGGCAAGAACTTCTTGGCCG
CCTTTGTCTTATAGATAGACTGTTGTTGGAATTTCCTGCTGAATT
TTATCCTCATATTGTCAGTACTGATGTTTCACAAGCTGAGCCTG
TTGAAATCAGGTATAAGAAGCTGCTGTCCCTCTTAACCTTTGCT
TTGCAGTCCATTGATAATTCCCACTCAATGGTTGGCAAACTTTC
CAGAAGGATCTACTTGAGTTCTGCAAGAATGGTTACTACAGTAC
CCCATGTGTTTTCAAAACTGTTAGAAATGCTGAGTGTTTCCAGT
TCCACTCACTTCACCAGGATGCGTCGCCGTTTGATGGCTATTGC
AGATGAGGTGGAAATTGCCGAAGCCATCCAGTTGGGCGTAGAA
GACACTTTGGATGGTCAACAGGACAGCTTCTTGCAGGCATCTGT
TCCCAACAACTATCTGGAAACCACAGAGAACAGTTCCCCTGAG
TGCACAGTCCATTTAGAGAAAACTGGAAAAGGATTATGTGCTA
CAAAATTGAGTGCCAGTTCAGAGGACATTTCTGAGAGACTGGC
CAGCATTTCAGTAGGACCTTCTAGTTCAACAACAACAACAACA
ACAACAACAGAGCAACCAAAGCCAATGGTTCAAACAAAAGGC
AGACCCCACAGTCAGTGTTTGAACTCCTCTCCTTTATCTCATCAT
TCCCAATTAATGTTTCCAGCCTTGTCAACCCCTTCTTCTTCTACC
CCATCTGTACCAGCTGGCACTGCAACAGATGTCTCTAAGCATAG
ACTTCAGGGATTCATTCCCTGCAGAATACCTTCTGCATCTCCTC
AAACACAGCGCAAGTTTTCTCTACAATTCCACAGAAACTGTCCT
GAAAACAAAGACTCAGATAAACTTTCCCCAGTCTTTACTCAGTC
AAGACCCTTGCCCTCCAGTAACATACACAGGCCAAAGCCATCT
AGACCTACCCCAGGTAATACAAGTAAACAGGGAGATCCCTCAA
AAAATAGCATGACACTTGATCTGAACAGTAGTTCCAAATGTGA
TGACAGCTTTGGCTGTAGCAGCAATAGTAGTAATGCTGTTATAC
CCAGTGACGAGACAGTGTTCACCCCAGTAGAGGAGAAATGCAG
ATTAGATGTCAATACAGAGCTCAACTCCAGTATTGAGGACCTTC
TTGAAGCATCTATGCCTTCAAGTGATACAACAGTAACTTTTAAG
TCAGAAGTTGCTGTCCTGTCTCCTGAAAAGGCTGAAAATGATGA
TACCTACAAAGATGATGTGAATCATAATCAAAAGTGCAAAGAG
```

```
AAGATGGAAGCTGAAGAAGAAGAAGCTTTAGCAATTGCCATGG
CAATGTCAGCGTCTCAGGATGCCCTCCCCATAGTTCCTCAGCTG
CAGGTTGAAAATGGAGAAGATATCATCATTATTCAACAGGATA
CACCAGAGACTCTACCAGGACATACCAAAGCAAACAACCGTA
TAGAGAAGACACTGAATGGCTGAAAGGTCAACAGATAGGCCTT
GGAGCATTTTCTTCTTGTTATCAGGCTCAAGATGTGGGAACTGG
AACTTTAATGGCTGTTAAACAGGTGACTTATGTCAGAAACACAT
CTTCTGAGCAAGAAGAAGTAGTAGAAGCACTAAGAGAAGAGAT
AAGAATGATGAGCCATCTGAATCATCCAAACATCATTAGGATG
TTGGGAGCCACGTGTGAGAAGAGCAATTACAATCTCTTCATTGA
ATGGATGGCAGGGGATCGGTGGCTCATTTGCTGAGTAAATAT
GGAGCCTTCAAAGAATCAGTAGTTATTAACTACACTGAACAGTT
ACTCCGTGGCCTTTCGTATCTCCATGAAAACCAAATCATTCACA
GAGATGTCAAAGGTGCCAATTTGCTAATTGACAGCACTGGTCA
GAGACTAAGAATTGCAGATTTTGGAGCTGCAGCCAGGTTGGCA
TCAAAAGGAACTGGTGCAGGAGAGTTTCAGGGACAATTACTGG
GGACAATTGCATTTATGGCACCTGAGGTACTAAGAGGTCAACA
GTATGGAAGGAGCTGTGATGTATGGAGTGTTGGCTGTGCTATTA
TAGAAATGGCTTGTGCAAAACCACCATGGAATGCAGAAAAACA
CTCCAATCATCTTGCTTTGATATTTAAGATTGCTAGTGCAACTA
CTGCTCCATCGATCCCTTCACATTTGTCTCCTGGTTTACGAGATG
TGGCTCTTCGTTGTTTAGAACTTCAACCTCAGGACAGACCTCCA
TCAAGAGAGCTACTGAAGCATCCAGTCTTTCGTACTACATGGTA
GCCAATTATGCAGATCAACTACAGTAGAAACAGGATGCTCAAC
AAGAGAAAAAAACTTGTGGGGAACCACATTGATATTCTACTG
GCCATGATGCCACTGAACAGCTATGAACGAGGCCAGTGGGGAA
CCCTTACCTAAGTATGTGATTGACAAATCATGATCTGTACCTAA
GCTCAGTATGCAAAAGCCCAAACTAGTGCAGAAACTGTAAACT
GTGCCTTTCAAAGAACTGGCCCTAGGTGAACAGGAAAACAATG
AAGTTTGCATGACTAAATTGCAGAAGCATAATTTTATTTTTTG
GAGCACTTTTTCAGCAATATTAGCGGCTGAGGGGCTCAGGATCT
ATTTTAATATTTCAATTATTCTTCCATTTCATATAGTGATCACAA
GCAGGGGGTTCTGCAATTCCGTTCAAATTTTTGTCACTGGCTA
TAAAATCAGTATCTGCCTCTTTTAGGTCAGAGTATGCTATGAGT
AGCAATACATACATATATTTTAAAAGTTGATACTTCTTTATGA
CCCACAGTTGACCTTTATTTTCTTAAATACCAGGGCAGTTGTGG
CTCATTGTGCATTTACTGTTGGCCCATTCATTTCGTTTTTGGAA
ATTATGGTTTTGTATTTTCATGTTTATTTACATTCATTTTTGTTTA
TTCAGGGAAAGCTGATCTTTTTTTCAAACCAGAAAAAAAAAAT
GAACTAGATATGAAGTAGAGTTCATTAAATATCTTGCTATTGTC
AGAGTTTTTAAAATATAGACTTAATTTTGTTTTTTTAAATTGGAA
```
```
TACAATAAAGTACTACCTACATTTGAGTCAGTCACCACTCTTAT
TGTGCAGGTTAAGTACAAGTTAACTAAAAATAAACTGTCCTCTC
TGGTGCAACTCACAACCAAGATCAAGATTACCTTAAAATTTATT
TGAATTTTTAGATGTTTTGGTTGTCAAACTGTAGGAAACTTCA
CAACATTTAAGTCTTACTCTGTATGTAACAATCCATCATTCACC
TTCACTACTGGTAGTAACATAGAGCTGCCATTTTCCTTTTACCAT
GCATCATCTCTTTACAGTAGGCCTGGCAGATCATTTTTTAAAAA
GATTATTCAACTACCAATCAGTAATGTTTTTAAACAGTACATTT
GCTTTGAACTTGGAAAATGTGTTCAGAAAGAAAAATGGAATTG
AATTTCATTTATACACTAATTCCTTGGATTTTGCACAGTTACCTA
ACGGTTTTAGTCTGGAGTTAAATTCAGATGCATGGAATCCTGAA
GGAAAATGGTAGCTTTTTAATCTTTTTGTGTGTGTGAGTCTTT
TAAATCAAGTACTGATTAACTATTAAGTACAACTTTGAGATTTT
AGTTTTAACTCTTCAGAAGCCAGTGTGAAATAGAATTGGTTATT
CTCAAAGACTCAGGATAAACTAAATAAGCTATATATAGAGTAC
ATTTAAAATGTACAACACAAATTGGAAATAAAATAAGTTACAA
GATAAGTTTACAGGGATATATTGCTTACAATTTTTAAAAGGCAG
TTTGTTTTTTATGTGAATATGTTTCTTAGTGAAATTTTACATTCC
TTTGTTTTGGAAGATTGGCGATATTTGAAGAGTTAAAAATAGTA
CAGAAATGTGAAGTTTGGTATCTCTAAATGTGTTGTACTTGACT
TTCTTTTTTATTTTGTTTTTTTTTTTTTTGACTACTTAGAATTTTC
ACAATTCTAATAAGATTGTTTCCAAGTCTCTCATGTGCAAGCTT
TAAAGGATGCACTCTTGCCATTTTATGTACTGGAAGATCATTGG
TCAGATGAATACTGTGTCTGACAAAAATGTAAACTGTATAAACT
GAGGAACCTCAGCTAATCAGTATTACTTTGTAGATCACCATGCC
CACCACATTTCAAACTCAAACTATCTGTAGATTTCAAAATCCAT
TGTGTTTGAGTTTGTTTGCAGTTCCCTCAGCTTGCTGGTAATTGT
GGTGTTTTGTTTTTGTTTGTTTTCAATGCAAATGTGATGTAAT
ATTCTTATTTTCTTTGGATCAAAGCTGGACTGGAAATTGTATCG
TGTAATTATTTTTGTGTTCTTAATGTTATTTGGTACTCAAGTTGT
AAATAACGTCTACTACTGTTTATTCCAGTTTCTACTACCTCAGGT
GTCCTATAGATTTTTCTTCTACCAAAGTTCACTTTCACAATGAA
ATTATATTTGCTGTGTGACTATGATTCCTAAGATTTCCAGGGCTT
AAGGGCTAACTTCTATTAGCACCTTACTGTGTAAGCAAATGTTA
CAAAAAAAAAAAAAAAAATCTCTGGGTTAAGAAAATTTGGCT
TAAATGTATCCTTTGTTATTTTAAATATATTGAGATATTTTAATT
AAAATTTTTACCCCATTGAACCGATTTTATAGTATTTGTACCTAT
TTTGGTGTTTTTGTCTTTATAGTAAATAAAAGTTTTTGAACAAA
AAAAAAAAA
```

SEQ ID NO: 91: PLK1 (NM_005030 Homo sapiens
polo-like kinase 1):
GAGCGGTGCGGAGGCTCTGCTCGGATCGAGGTCTGCAGCGCAG

CTTCGGGAGCATGAGTGCTGCAGTGACTGCAGGGAAGCTGGCA

CGGGCACCGGCCGACCCTGGGAAAGCCGGGGTCCCCGGAGTTG

CAGCTCCCGGAGCTCCGGCGGCGGCTCCACCGGCGAAAGAGAT

CCCGGAGGTCCTAGTGGACCCACGCAGCCGGCGGCGCTATGTG

CGGGGCCGCTTTTTGGGCAAGGGCGGCTTTGCCAAGTGCTTCGA

GATCTCGGACGCGGACACCAAGGAGGTGTTCGCGGGCAAGATT

GTGCCTAAGTCTCTGCTGCTCAAGCCGCACCAGAGGGAGAAGA

TGTCCATGGAAATATCCATTCACCGCAGCCTCGCCCACCAGCAC

GTCGTAGGATTCCACGGCTTTTTCGAGGACAACGACTTCGTGTT

CGTGGTGTTGGAGCTCTGCCGCCGGAGGTCTCTCCTGGAGCTGC

ACAAGAGGAGGAAAGCCCTGACTGAGCCTGAGGCCCGATACTA

CCTACGGCAAATTGTGCTTGGCTGCCAGTACCTGCACCGAAACC

GAGTTATTCATCGAGACCTCAAGCTGGGCAACCTTTTCCTGAAT

GAAGATCTGGAGGTGAAAATAGGGGATTTTGGACTGGCAACCA

AAGTCGAATATGACGGGGAGAGGAAGAAGACCCTGTGTGGGA

CTCCTAATTACATAGCTCCCGAGGTGCTGAGCAAGAAAGGGCA

CAGTTTCGAGGTGGATGTGTGGTCCATTGGGTGTATCATGTATA

CCTTGTTAGTGGGCAAACCACCTTTTGAGACTTCTTGCCTAAAA

GAGACCTACCTCCGGATCAAGAAGAATGAATACAGTATTCCCA

AGCACATCAACCCCGTGGCCGCCTCCCTCATCCAGAAGATGCTT

CAGACAGATCCCACTGCCCGCCCAACCATTAACGAGCTGCTTA

ATGACGAGTTCTTTACTTCTGGCTATATCCCTGCCCGTCTCCCA

TCACCTGCCTGACCATTCCACCAAGGTTTTCGATTGCTCCCAGC

AGCCTGGACCCCAGCAACCGGAAGCCCCTCACAGTCCTCAATA

AAGGCTTGGAGAACCCCCTGCCTGAGCGTCCCCGGGAAAAGA

AGAACCAGTGGTTCGAGAGACAGGTGAGGTGGTCGACTGCCAC

CTCAGTGACATGCTGCAGCAGCTGCACAGTGTCAATGCCTCCA

AGCCCTCGGAGCGTGGGCTGGTCAGGCAAGAGGAGGCTGAGGA

TCCTGCCTGCATCCCCATCTTCTGGGTCAGCAAGTGGGTGGACT

ATTCGGACAAGTACGGCCTTGGGTATCAGCTCTGTGATAACAGC

GTGGGGGTGCTCTTCAATGACTCAACACGCCTCATCCTCTACAA

TGATGGTGACAGCCTGCAGTACATAGAGCGTGACGGCACTGAG

TCCTACCTCACCGTGAGTTCCCATCCCAACTCCTTGATGAAGAA

GATCACCCTCCTTAAATATTTCCGCAATTACATGAGCGAGCACT

TGCTGAAGGCAGGTGCCAACATCACGCCGCGCGAAGGTGATGA

GCTCGCCCGGCTGCCCTACCTACGGACCTGGTTCCGCACCCGCA

GCGCCATCATCCTGCACCTCAGCAACGGCAGCGTGCAGATCAA

CTTCTTCCAGGATCACACCAAGCTCATCTTGTGCCCACTGATGG

CAGCCGTGACCTACATCGACGAGAAGCGGGACTTCCGCACATA

CCGCCTGAGTCTCCTGGAGGAGTACGGCTGCTGCAAGGAGCTG

GCCAGCCGGCTCCGCTACGCCCGCACTATGGTGGACAAGCTGC

TGAGCTCACGCTCGGCCAGCAACCGTCTCAAGGCCTCCTAATA

GCTGCCCTCCCCTCCGGACTGGTGCCCTCCTCACTCCCACCTGC

ATCTGGGCCCATACTGGTTGGCTCCCGCGGTGCCATGTCTGCA

GTGTGCCCCCAGCCCCGGTGGCTGGGCAGAGCTGCATCATCCT

TGCAGGTGGGGGTTGCTGTGTAAGTTATTTTTGTACATGTTCGG

GTGTGGGTTCTACAGCCTTGTCCCCCTCCCCCTCAACCCCACCA

TATGAATTGTACAGAATATTTCTATTGAATTCGGAACTGTCCTT

TCCTTGGCTTTATGCACATTAAACAGATGTGAATATTCAAAAAA

AAAAAAAAAAAAAAAAAAAAAAAAAAAAA

SEQ ID NO: 92: androgen receptor variant 1
(NM_000044.3 Homo sapiens androgen
receptor (AR), transcript variant 1):
CGAGATCCCGGGGAGCCAGCTTGCTGGGAGAGCGGGACGGTCC

GGAGCAAGCCCAGAGGCAGAGGAGGCGACAGAGGGAAAAGG

GCCGAGCTAGCCGCTCCAGTGCTGTACAGGAGCCGAAGGGACG

CACCACGCCAGCCCCAGCCCGGCTCCAGCGACAGCCAACGCCT

CTTGCAGCGCGGCGGCTTCGAAGCCGCCGCCCGGAGCTGCCCT

TTCCTCTTCGGTGAAGTTTTTAAAAGCTGCTAAAGACTCGGAGG

AAGCAAGGAAAGTGCCTGGTAGGACTGACGGCTGCCTTTGTCC

TCCTCCTCTCCACCCCGCCTCCCCCCACCCTGCCTTCCCCCCCTC

CCCCGTCTTCTCTCCCGCAGCTGCCTCAGTCGGCTACTCTCAGC

CAACCCCCTCACCACCCTTCTCCCCACCCGCCCCCCCGCCCCC

GTCGGCCCAGCGCTGCCAGCCCGAGTTTGCAGAGAGGTAACTC

CCTTTGGCTGCGAGCGGGCGAGCTAGCTGCACATTGCAAAGAA

GGCTCTTAGGAGCCAGGCGACTGGGGAGCGGCTTCAGCACTGC

AGCCACGACCCGCCTGGTTAGGCTGCACGCGGAGAGAACCCTC

TGTTTTCCCCCACTCTCTCTCCACCTCCTCCTGCCTTCCCCACCC

CGAGTGCGGAGCCAGAGATCAAAAGATGAAAAGGCAGTCAGG

TCTTCAGTAGCCAAAAAACAAAACAAACAAAAACAAAAAAGC

CGAAATAAAAGAAAAGATAATAACTCAGTTCTTATTTGCACC

TACTTCAGTGGACACTGAATTTGGAAGGTGGAGGATTTTGTTTT

TTTCTTTTAAGATCTGGGCATCTTTTGAATCTACCCTTCAAGTAT

TAAGAGACAGACTGTGAGCCTAGCAGGGCAGATCTTGTCCACC

GTGTGTCTTCTTCTGCACGAGACTTTGAGGCTGTCAGAGCGCTT

TTTGCGTGGTTGCTCCCGCAAGTTTCCTTCTCTGGAGCTTCCCGC

AGGTGGGCAGCTAGCTGCAGCGACTACCGCATCATCACAGCCT

GTTGAACTCTTCTGAGCAAGAGAAGGGGAGGCGGGGTAAGGGA

AGTAGGTGGAAGATTCAGCCAAGCTCAAGGATGGAAGTGCAGT

TAGGGCTGGGAAGGGTCTACCCTCGGCCGCCGTCCAAGACCTA

-continued

```
CCGAGGAGCTTTCCAGAATCTGTTCCAGAGCGTGCGCGAAGTG
ATCCAGAACCCGGGCCCCAGGCACCCAGAGGCCGCGAGCGCAG
CACCTCCCGGCGCCAGTTTGCTGCTGCTGCAGCAGCAGCAGCA
GCAGCAGCAGCAGCAGCAGCAGCAGCAGCAGCAGCAGCAGCA
GCAGCAGCAGCAAGAGACTAGCCCCAGGCAGCAGCAGCAGCA
GCAGGGTGAGGATGGTTCTCCCCAAGCCCATCGTAGAGGCCCC
ACAGGCTACCTGGTCCTGGATGAGGAACAGCAACCTTCACAGC
CGCAGTCGGCCCTGGAGTGCCACCCCGAGAGAGGTTGCGTCCC
AGAGCCTGGAGCCGCCGTGGCCGCCAGCAAGGGGCTGCCGCAG
CAGCTGCCAGCACCTCCGGACGAGGATGACTCAGCTGCCCCAT
CCACGTTGTCCCTGCTGGGCCCCACTTTCCCCGGCTTAAGCAGC
TGCTCCGCTGACCTTAAAGACATCCTGAGCGAGGCCAGCACCA
TGCAACTCCTTCAGCAACAGCAGCAGGAAGCAGTATCCGAAGG
CAGCAGCAGCGGGAGAGCGAGGGAGGCCTCGGGGGCTCCCAC
TTCCTCCAAGGACAATTACTTAGGGGGCACTTCGACCATTTCTG
ACAACGCCAAGGAGTTGTGTAAGGCAGTGTCGGTGTCCATGGG
CCTGGGTGTGGAGGCGTTGGAGCATCTGAGTCCAGGGGAACAG
CTTCGGGGGATTGCATGTACGCCCCACTTTTGGGAGTTCCACC
CGCTGTGCGTCCCACTCCTTGTGCCCCATTGGCCGAATGCAAAG
GTTCTCTGCTAGACGACAGCGCAGGCAAGAGCACTGAAGATAC
TGCTGAGTATTCCCCTTTCAAGGGAGGTTACACCAAAGGGCTAG
AAGGCGAGAGCCTAGGCTGCTCTGGCAGCGCTGCAGCAGGGAG
CTCCGGGACACTTGAACTGCCGTCTACCCTGTCTCTCTACAAGT
CCGGAGCACTGGACGAGGCAGCTGCGTACCAGAGTCGCGACTA
CTACAACTTTCCACTGGCTCTGGCCGGACCGCCGCCCCCTCCGC
CGCCTCCCCATCCCCACGCTCGCATCAAGCTGGAGAACCCGCTG
GACTACGGCAGCGCCTGGGCGGCTGCGGCGGCGCAGTGCCGCT
ATGGGGACCTGGCGAGCCTGCATGGCGCGGGTGCAGCGGGACC
CGGTTCTGGGTCACCCTCAGCCGCCGCTTCCTCATCCTGGCACA
CTCTCTTCACAGCCGAAGAAGGCCAGTTGTATGGACCGTGTGGT
GGTGGTGGGGGTGGTGGCGGCGGCGGCGGCGGCGGCGGCGGC
GGCGGCGGCGGCGGCGGCGGCGGCGAGGCGGGAGCTGTAGCC
CCCTACGGCTACACTCGGCCCCCTCAGGGGCTGGCGGGCCAGG
AAAGCGACTTCACCGCACCTGATGTGTGGTACCCTGGCGGCAT
GGTGAGCAGAGTGCCCTATCCCAGTCCCACTTGTGTCAAAAGC
GAAATGGGCCCCTGGATGGATAGCTACTCCGGACCTTACGGGG
ACATGCGTTTGGAGACTGCCAGGGACCATGTTTTGCCCATTGAC
TATTACTTTCCACCCCAGAAGACCTGCCTGATCTGTGGAGATGA
AGCTTCTGGGTGTCACTATGGAGCTCTCACATGTGGAAGCTGCA
AGGTCTTCTTCAAAAGAGCCGCTGAAGGGAAACAGAAGTACCT
GTGCGCCAGCAGAAATGATTGCACTATTGATAAATTCCGAAGG
```

-continued

```
AAAAATTGTCCATCTTGTCGTCTTCGGAAATGTTATGAAGCAGG
GATGACTCTGGGAGCCCGGAAGCTGAAGAAACTTGGTAATCTG
AAACTACAGGAGGAAGGAGAGGCTTCCAGCACCACCAGCCCCA
CTGAGGAGACAACCCAGAAGCTGACAGTGTCACACATTGAAGG
CTATGAATGTCAGCCCATCTTTCTGAATGTCCTGGAAGCCATTG
AGCCAGGTGTAGTGTGTGCTGGACACGACAACAACCAGCCCGA
CTCCTTTGCAGCCTTGCTCTCTAGCCTCAATGAACTGGGAGAGA
GACAGCTTGTACACGTGGTCAAGTGGGCCAAGGCCTTGCCTGG
CTTCCGCAACTTACACGTGGACGACCAGATGGCTGTCATTCAGT
ACTCCTGGATGGGGCTCATGGTGTTTGCCATGGGCTGGCGATCC
TTCACCAATGTCAACTCCAGGATGCTCTACTTCGCCCCTGATCT
GGTTTTCAATGAGTACCGCATGCACAAGTCCCGGATGTACAGCC
AGTGTGTCCGAATGAGGCACCTCTCTCAAGAGTTTGGATGGCTC
CAAATCACCCCCCAGGAATTCCTGTGCATGAAAGCACTGCTACT
CTTCAGCATTATTCCAGTGGATGGGCTGAAAAATCAAAAATTCT
TTGATGAACTTCGAATGAACTACATCAAGGAACTCGATCGTATC
ATTGCATGCAAAAGAAAAAATCCCACATCCTGCTCAAGACGCT
TCTACCAGCTCACCAAGCTCCTGGACTCCGTGCAGCCTATTGCG
AGAGAGCTGCATCAGTTCACTTTTGACCTGCTAATCAAGTCACA
CATGGTGAGCGTGGACTTTCCGGAAATGATGGCAGAGATCATC
TCTGTGCAAGTGCCCAAGATCCTTTCTGGGAAAGTCAAGCCCAT
CTATTTCCACACCCAGTGAAGCATTGGAAACCCTATTTCCCCAC
CCCAGCTCATGCCCCCTTTCAGATGTCTTCTGCCTGTTATAACTC
TGCACTACTCCTCTGCAGTGCCTTGGGGAATTTCCTCTATTGAT
GTACAGTCTGTCATGAACATGTTCCTGAATTCTATTTGCTGGGC
TTTTTTTTTCTCTTTCTCTCCTTTCTTTTTCTTCTTCCCTCCCTATC
TAACCCTCCCATGGCACCTTCAGACTTTGCTTCCCATTGTGGCT
CCTATCTGTGTTTTGAATGGTGTTGTATGCCTTTAAATCTGTGAT
GATCCTCATATGCCCAGTGTCAAGTTGTGCTTGTTTACAGCAC
TACTCTGTGCCAGCCACACAAACGTTTACTTATCTTATGCCACG
GGAAGTTTAGAGAGCTAAGATTATCTGGGGAAATCAAAACAAA
AACAAGCAAACAAAAAAAAAAAGCAAAAACAAAACAAAAAAT
AAGCCAAAAAACCTTGCTAGTGTTTTTTCCTCAAAAATAAATAA
ATAAATAAATAAATACGTACATACATACACACATACATACAAA
CATATAGAAATCCCCAAAGAGGCCAATAGTGACGAGAAGGTGA
AAATTGCAGGCCCATGGGAGTTACTGATTTTTTCATCTCCTCC
CTCCACGGGAGACTTTATTTTCTGCCAATGGCTATTGCCATTAG
AGGGCAGAGTGACCCCAGAGCTGAGTTGGGCAGGGGGGTGGA
CAGAGAGGAGAGGACAAGGAGGGCAATGGAGCATCAGTACCT
GCCCACAGCCTTGGTCCCTGGGGGCTAGACTGCTCAACTGTGG
```

-continued

AGCAATTCATTATACTGAAAATGTGCTTGTTGTTGAAATTTGT
CTGCATGTTAATGCCTCACCCCCAAACCCTTTTCTCTCTCACTCT
CTGCCTCCAACTTCAGATTGACTTTCAATAGTTTTTCTAAGACCT
TTGAACTGAATGTTCTCTTCAGCCAAAACTTGGCGACTTCCACA
GAAAAGTCTGACCACTGAGAAGAAGGAGAGCAGAGATTTAACC
CTTTGTAAGGCCCCATTTGGATCCAGGTCTGCTTTCTCATGTGTG
AGTCAGGGAGGAGCTGGAGCCAGAGGAGAAGAAAATGATAGC
TTGGCTGTTCTCCTGCTTAGGACACTGACTGAATAGTTAAACTC
TCACTGCCACTACCTTTTCCCCACCTTTAAAAGACCTGAATGAA
GTTTTCTGCCAAACTCCGTGAAGCCACAAGCACCTTATGTCCTC
CCTTCAGTGTTTTGTGGGCCTGAATTTCATCACACTGCATTTCAG
CCATGGTCATCAAGCCTGTTTGCTTCTTTTGGGCATGTTCACAG
ATTCTCTGTTAAGAGCCCCCACCACCAAGAAGGTTAGCAGGCC
AACAGCTCTGACATCTATCTGTAGATGCCAGTAGTCACAAAGAT
TTCTTACCAACTCTCAGATCGCTGGAGCCCTTAGACAAACTGGA
AAGAAGGCATCAAAGGGATCAGGCAAGCTGGGCGTCTTGCCCT
TGTCCCCAGAGATGATACCCTCCCAGCAAGTGGAGAAGTTCT
CACTTCCTTCTTTAGAGCAGCTAAAGGGGCTACCCAGATCAGGG
TTGAAGAGAAAACTCAATTACCAGGGTGGGAAGAATGAAGGCA
CTAGAACCAGAAACCCTGCAAATGCTCTTCTTGTCACCCAGCAT
ATCCACCTGCAGAAGTCATGAGAAGAGAGAAGGAACAAAGAG
GAGACTCTGACTACTGAATTAAAATCTTCAGCGGCAAAGCCTA
AAGCCAGATGGACACCATCTGGTGAGTTTACTCATCATCCTCCT
CTGCTGCTGATTCTGGGCTCTGACATTGCCCATACTCACTCAGA
TTCCCCACCTTTGTTGCTGCCTCTTAGTCAGAGGGAGGCCAAAC
CATTGAGACTTTCTACAGAACCATGGCTTCTTTCGGAAAGGTCT
GGTTGGTGTGGCTCCAATACTTTGCCACCCATGAACTCAGGGTG
TGCCCTGGGACACTGGTTTTATATAGTCTTTTGGCACACCTGTG
TTCTGTTGACTTCGTTCTTCAAGCCCAAGTGCAAGGGAAAATGT
CCACCTACTTTCTCATCTTGGCCTCTGCCTCCTTACTTAGCTCTT
AATCTCATCTGTTGAACTCAAGAAATCAAGGGCCAGTCATCAA
GCTGCCCATTTTAATTGATTCACTCTGTTTGTTGAGAGGATAGTT
TCTGAGTGACATGATATGATCCACAAGGGTTTCCTTCCCTGATT
TCTGCATTGATATTAATAGCCAAACGAACTTCAAAACAGCTTTA
AATAACAAGGGAGAGGGAACCTAAGATGAGTAATATGCCAAT
CCAAGACTGCTGGAGAAAACTAAAGCTGACAGGTTCCCTTTTG
GGGTGGGATAGACATGTTCTGGTTTTCTTTATTATTACACAATC
TGGCTCATGTACAGGATCACTTTTAGCTGTTTTAAACAGAAAAA
AATATCCACCACTCTTTTCAGTTACACTAGGTTACATTTTAATA
GGTCCTTTACATCTGTTTTGGAATGATTTTCATCTTTTGTGATAC
ACAGATTGAATTATATCATTTTCATATCTCTCCTTGTAAATACTA

-continued

GAAGCTCTCCTTTACATTTCTCTATCAAATTTTTCATCTTTATGG
GTTTCCCAATTGTGACTCTTGTCTTCATGAATATATGTTTTTCAT
TTGCAAAAGCCAAAAATCAGTGAAACAGCAGTGTAATTAAAAG
CAACAACTGGATTACTCCAAATTTCCAAATGACAAAACTAGGG
AAAAATAGCCTACACAAGCCTTTAGGCCTACTCTTTCTGTGCTT
GGGTTTGAGTGAACAAAGGAGATTTTAGCTTGGCTCTGTTCTCC
CATGGATGAAAGGAGGAGGATTTTTTTTTTCTTTTGGCCATTGA
TGTTCTAGCCAATGTAATTGACAGAAGTCTCATTTTGCATGCGC
TCTGCTCTACAAACAGAGTTGGTATGGTTGGTATACTGTACTCA
CCTGTGAGGGACTGGCCACTCAGACCCACTTAGCTGGTGAGCT
AGAAGATGAGGATCACTCACTGGAAAAGTCACAAGGACCATCT
CCAAACAAGTTGGCAGTGCTCGATGTGGACGAAGAGTGAGGAA
GAGAAAAAGAAGGAGCACCAGGGAGAAGGCTCCGTCTGTGCT
GGGCAGCAGACAGCTGCCAGGATCACGAACTCTGTAGTCAAAG
AAAAGAGTCGTGTGGCAGTTTCAGCTCTCGTTCATTGGGCAGCT
CGCCTAGGCCCAGCCTCTGAGCTGACATGGGAGTTGTTGGATTC
TTTGTTTCATAGCTTTTTCTATGCCATAGGCAATATTGTTGTTCT
TGGAAAGTTTATTATTTTTTTAACTCCCTTACTCTGAGAAAGGG
ATATTTTGAAGGACTGTCATATATCTTTGAAAAAAGAAAATCTG
TAATACATATATTTTTATGTATGTTCACTGGCACTAAAAAATAT
AGAGAGCTTCATTCTGTCCTTTGGGTAGTTGCTGAGGTAATTGT
CCAGGTTGAAAAATAATGTGCTGATGCTAGAGTCCCTCTCTGTC
CATACTCTACTTCTAAATACATATAGGCATACATAGCAAGTTTT
ATTTGACTTGTACTTTAAGAGAAAATATGTCCACCATCCACATG
ATGCACAAATGAGCTAACATTGAGCTTCAAGTAGCTTCTAAGTG
TTTGTTTCATTAGGCACAGCACAGATGTGGCCTTTCCCCCCTTCT
CTCCCTTGATATCTGGCAGGGCATAAAGGCCCAGGCCACTTCCT
CTGCCCCTTCCCAGCCCTGCACCAAAGCTGCATTTCAGGAGACT
CTCTCCAGACAGCCCAGTAACTACCCGAGCATGGCCCCTGCAT
AGCCCTGGAAAAATAAGAGGCTGACTGTCTACGAATTATCTTGT
GCCAGTTGCCCAGGTGAGAGGGCACTGGGCCAAGGGAGTGGTT
TTCATGTTTGACCCACTACAAGGGGTCATGGGAATCAGGAATG
CCAAAGCACCAGATCAAATCCAAAACTTAAAGTCAAAATAAGC
CATTCAGCATGTTCAGTTTCTTGGAAAAGGAAGTTTCTACCCCT
GATGCCTTTGTAGGCAGATCTGTTCTCACCATTAATCTTTTGAA
AATCTTTTAAAGCAGTTTTTAAAAAGAGAGATGAAAGCATCAC
ATTATATAACCAAAGATTACATTGTACCTGCTAAGATACCAAAA
TTCATAAGGGCAGGGGGGAGCAAGCATTAGTGCCTCTTTGAT
AAGCTGTCAAAGACAGACTAAAGGACTCTGCTGGTGACTGAC
TTATAAGAGCTTTGTGGGTTTTTTTTTCCCTAATAATATACATGT

```
TTAGAAGAATTGAAAATAATTTCGGGAAAATGGGATTATGGGT
CCTTCACTAAGTGATTTTATAAGCAGAACTGGCTTTCCTTTTCTC
TAGTAGTTGCTGAGCAAATTGTTGAAGCTCCATCATTGCATGGT
TGGAAATGGAGCTGTTCTTAGCCACTGTGTTTGCTAGTGCCCAT
GTTAGCTTATCTGAAGATGTGAAACCCTTGCTGATAAGGGAGC
ATTTAAAGTACTAGATTTTGCACTAGAGGGACAGCAGGCAGAA
ATCCTTATTTCTGCCCACTTTGGATGGCACAAAAAGTTATCTGC
AGTTGAAGGCAGAAAGTTGAAATACATTGTAAATGAATATTTG
TATCCATGTTTCAAAATTGAAATATATATATATATATATATATA
TATATATATATATATAGTGTGTGTGTGTGTTCTGATAGCTTTA
ACTTTCTCTGCATCTTTATATTTGGTTCCAGATCACACCTGATGC
CATGTACTTGTGAGAGAGGATGCAGTTTTGTTTTGGAAGCTCTC
TCAGAACAAACAAGACACCTGGATTGATCAGTTAACTAAAAGT
TTTCTCCCCTATTGGGTTTGACCCACAGGTCCTGTGAAGGAGCA
GAGGGATAAAAAGAGTAGAGGACATGATACATTGTACTTTACT
AGTTCAAGACAGATGAATGTGGAAAGCATAAAAACTCAATGGA
ACTGACTGAGATTTACCACAGGGAAGGCCCAAACTTGGGGCCA
AAAGCCTACCCAAGTGATTGACCAGTGGCCCCCTAATGGGACC
TGAGCTGTTGGAAGAAGAGAACTGTTCCTTGGTCTTCACCATCC
TTGTGAGAGAAGGGCAGTTTCCTGCATTGGAACCTGGAGCAAG
CGCTCTATCTTTCACACAAATTCCCTCACCTGAGATTGAGGTGC
TCTTGTTACTGGGTGTCTGTGTGCTGTAATTCTGGTTTTGGATAT
GTTCTGTAAAGATTTTGACAAATGAAAATGTGTTTTTCTCTGTT
AAAACTTGTCAGAGTACTAGAAGTTGTATCTCTGTAGGTGCAGG
TCCATTTCTGCCCACAGGTAGGGTGTTTTCTTTGATTAAGAGA
TTGACACTTCTGTTGCCTAGGACCTCCCAACTCAACCATTTCTA
GGTGAAGGCAGAAAAATCCACATTAGTTACTCCTCTTCAGACAT
TTCAGCTGAGATAACAAATCTTTTGGAATTTTTTCACCCATAGA
AAGAGTGGTAGATATTTGAATTTAGCAGGTGGAGTTTCATAGTA
AAAACAGCTTTTGACTCAGCTTTGATTTATCCTCATTTGATTTGG
CCAGAAAGTAGGTAATATGCATTGATTGGCTTCTGATTCCAATT
CAGTATAGCAAGGTGCTAGGTTTTTTCCTTTCCCCACCTGTCTCT
TAGCCTGGGGAATTAAATGAGAAGCCTTAGAATGGGTGGCCCT
TGTGACCTGAAACACTTCCCACATAAGCTACTTAACAAGATTGT
CATGGAGCTGCAGATTCCATTGCCCACCAAAGACTAGAACACA
CACATATCCATACACCAAAGGAAAGACAATTCTGAAATGCTGT
TTCTCTGGTGGTTCCCTCTCTGGCTGCTGCCTCACAGTATGGGA
ACCTGTACTCTGCAGAGGTGACAGGCCAGATTTGCATTATCTCA
CAACCTTAGCCCTTGGTGCTAACTGTCCTACAGTGAAGTGCCTG
GGGGGTTGTCCTATCCCATAAGCCACTTGGATGCTGACAGCAGC
CACCATCAGAATGACCCACGCAAAAAAAGAAAAAAAAATT

AAAAAGTCCCCTCACAACCCAGTGACACCTTTCTGCTTTCCTCT
AGACTGGAACATTGATTAGGGAGTGCCTCAGACATGACATTCTT
GTGCTGTCCTTGGAATTAATCTGGCAGCAGGAGGGAGCAGACT
ATGTAAACAGAGATAAAAATTAATTTTCAATATTGAAGGAAAA
AAGAAATAAGAAGAGAGAGAGAAAGAAAGCATCACACAAAGA
TTTTCTTAAAAGAAACAATTTTGCTTGAAATCTCTTTAGATGGG
GCTCATTTCTCACGGTGGCACTTGGCCTCCACTGGGCAGCAGGA
CCAGCTCCAAGCGCTAGTGTTCTGTTCTCTTTTTGTAATCTTGGA
ATCTTTTGTTGCTCTAAATACAATTAAAAATGGCAGAAACTTGT
TTGTTGGACTACATGTGTGACTTTGGGTCTGTCTCTGCCTCTGCT
TTCAGAAATGTCATCCATTGTGTAAAATATTGGCTTACTGGTCT
GCCAGCTAAAACTTGGCCACATCCCCTGTTATGGCTGCAGGATC
GAGTTATTGTTAACAAAGAGACCCAAGAAAGCTGCTAATGTC
CTCTTATCATTGTTGTTAATTTGTTAAAACATAAAGAAATCTAA
AATTTCAAAAAA

SEQ ID NO: 93: androgen receptor variant 2
(NM_001011645.2 Homo sapiens androgen
receptor (AR), transcript variant):
GCTGCGAGCAGAGAGGGATTCCTCGGAGGTCATCTGTTCCATCT
TCTTGCCTATGCAAATGCCTGCCTGAAGCTGCTGGAGGCTGGCT
TTGTACCGGACTTTGTACAGGGAACCAGGGAAACGAATGCAGA
GTGCTCCTGACATTGCCTGTCACTTTTTCCCATGATACTCTGGCT
TCACAGTTTGGAGACTGCCAGGGACCATGTTTTGCCCATTGACT
ATTACTTTCCACCCCAGAAGACCTGCCTGATCTGTGGAGATGAA
GCTTCTGGGTGTCACTATGGAGCTCTCACATGTGGAAGCTGCAA
GGTCTTCTTCAAAAGAGCCGCTGAAGGGAAACAGAAGTACCTG
TGCGCCAGCAGAAATGATTGCACTATTGATAAATTCCGAAGGA
AAAATTGTCCATCTTGTCGTCTTCGGAAATGTTATGAAGCAGGG
ATGACTCTGGGAGCCCGGAAGCTGAAGAAACTTGGTAATCTGA
AACTACAGGAGGAAGGAGAGGCTTCCAGCACCACCAGCCCCAC
TGAGGAGACAACCCAGAAGCTGACAGTGTCACACATTGAAGGC
TATGAATGTCAGCCCATCTTTCTGAATGTCCTGGAAGCCATTGA
GCCAGGTGTAGTGTGTGCTGGACACGACAACAACCAGCCCGAC
TCCTTTGCAGCCTTGCTCTCTAGCCTCAATGAACTGGGAGAGAG
ACAGCTTGTACACGTGGTCAAGTGGGCCAAGGCCTTGCCTGGCT
TCCGCAACTTACACGTGGACGACCAGATGGCTGTCATTCAGTAC
TCCTGGATGGGGCTCATGGTGTTTGCCATGGGCTGGCGATCCTT
CACCAATGTCAACTCCAGGATGCTCTACTTCGCCCCTGATCTGG
TTTTCAATGAGTACCGCATGCACAAGTCCCGGATGTACAGCCAG
TGTGTCCGAATGAGGCACCTCTCTCAAGAGTTTGGATGGCTCCA
AATCACCCCCCAGGAATTCCTGTGCATGAAAGCACTGCTACTCT
TCAGCATTATTCCAGTGGATGGGCTGAAAAATCAAAAATTCTTT
```

-continued

```
GATGAACTTCGAATGAACTACATCAAGGAACTCGATCGTATCA
TTGCATGCAAAAGAAAAAATCCCACATCCTGCTCAAGACGCTT
CTACCAGCTCACCAAGCTCCTGGACTCCGTGCAGCCTATTGCGA
GAGAGCTGCATCAGTTCACTTTTGACCTGCTAATCAAGTCACAC
ATGGTGAGCGTGGACTTTCCGGAAATGATGGCAGAGATCATCT
CTGTGCAAGTGCCCAAGATCCTTTCTGGGAAAGTCAAGCCCATC
TATTTCCACACCCAGTGAAGCATTGGAAACCCTATTTCCCCACC
CCAGCTCATGCCCCCTTTCAGATGTCTTCTGCCTGTTATAACTCT
GCACTACTCCTCTGCAGTGCCTTGGGGAATTTCCTCTATTGATG
TACAGTCTGTCATGAACATGTTCCTGAATTCTATTTGCTGGCTT
TTTTTTTCTCTTTCTCTCCTTTCTTTTTCTTCTTCCCTCCCTATCTA
ACCCTCCCATGGCACCTTCAGACTTTGCTTCCCATTGTGGCTCCT
ATCTGTGTTTTGAATGGTGTTGTATGCCTTTAAATCTGTGATGAT
CCTCATATGGCCCAGTGTCAAGTTGTGCTTGTTTACAGCACTAC
TCTGTGCCAGCCACACAAACGTTTACTTATCTTATGCCACGGGA
AGTTTAGAGAGCTAAGATTATCTGGGGAAATCAAAACAAAAAC
AAGCAAACAAAAAAAAAAAGCAAAAACAAAACAAAAAATAAG
CCAAAAAACCTTGCTAGTGTTTTTTCCTCAAAAATAAATAAATA
AATAAATAAATACGTACATACATACACACATACATACAAACAT
ATAGAAATCCCCAAAGAGGCCAATAGTGACGAGAAGGTGAAA
ATTGCAGGCCCATGGGGAGTTACTGATTTTTTCATCTCCTCCCTC
CACGGGAGACTTTATTTTCTGCCAATGGCTATTGCCATTAGAGG
GCAGAGTGACCCCAGAGCTGAGTTGGGCAGGGGGTGGACAG
AGAGGAGAGGACAAGGAGGGCAATGGAGCATCAGTACCTGCC
CACAGCCTTGGTCCCTGGGGCTAGACTGCTCAACTGTGGAGC
AATTCATTATACTGAAAATGTGCTTGTTGTTGAAAATTTGTCTG
CATGTTAATGCCTCACCCCCAAACCCTTTTCTCTCTCACTCTCTG
CCTCCAACTTCAGATTGACTTTCAATAGTTTTTCTAAGACCTTTG
AACTGAATGTTCTCTTCAGCCAAAACTTGGCGACTTCCACAGAA
AAGTCTGACCACTGAGAAGAAGGAGAGCAGAGATTTAACCCTT
TGTAAGGCCCCATTTGGATCCAGGTCTGCTTTCTCATGTGTGAG
TCAGGGAGGAGCTGGAGCCAGAGGAGAAGAAAATGATAGCTT
GGCTGTTCTCCTGCTTAGGACACTGACTGAATAGTTAAACTCTC
ACTGCCACTACCTTTTCCCCACCTTTAAAAGACCTGAATGAAGT
TTTCTGCCAAACTCCGTGAAGCCACAAGCACCTTATGTCCTCCC
TTCAGTGTTTTGTGGGCCTGAATTTCATCACACTGCATTTCAGCC
ATGGTCATCAAGCCTGTTTGCTTCTTTTGGGCATGTTCACAGATT
CTCTGTTAAGAGCCCCCACCACCAAGAAGGTTAGCAGGCCAAC
AGCTCTGACATCTATCTGTAGATGCCAGTAGTCACAAAGATTTC
TTACCAACTCTCAGATCGCTGGAGCCCTTAGACAAACTGGAAA
GAAGGCATCAAAGGGATCAGGCAAGCTGGGCGTCTTGCCCTTG
TCCCCCAGAGATGATACCCTCCCAGCAAGTGGAGAAGTTCTCA
CTTCCTTCTTTAGAGCAGCTAAAGGGGCTACCCAGATCAGGGTT
GAAGAGAAAACTCAATTACCAGGGTGGGAAGAATGAAGGCAC
TAGAACCAGAAACCCTGCAAATGCTCTTCTTGTCACCCAGCATA
TCCACCTGCAGAAGTCATGAGAAGAGAGAAGGAACAAAGAGG
AGACTCTGACTACTGAATTAAAATCTTCAGCGGCAAAGCCTAA
AGCCAGATGGACACCATCTGGTGAGTTTACTCATCATCCTCCTC
TGCTGCTGATTCTGGGCTCTGACATTGCCCATACTCACTCAGAT
TCCCCACCTTTGTTGCTGCCTCTTAGTCAGAGGGAGGCCAAACC
ATTGAGACTTTCTACAGAACCATGGCTTCTTTCGGAAAGGTCTG
GTTGGTGTGGCTCCAATACTTTGCCACCCATGAACTCAGGGTGT
GCCCTGGGACACTGGTTTTATATAGTCTTTTGGCACACCTGTGT
TCTGTTGACTTCGTTCTTCAAGCCCAAGTGCAAGGGAAAATGTC
CACCTACTTTCTCATCTTGGCCTCTGCCTCCTTACTTAGCTCTTA
ATCTCATCTGTTGAACTCAAGAAATCAAGGGCCAGTCATCAAG
CTGCCCATTTTAATTGATTCACTCTGTTTGTTGAGAGGATAGTTT
CTGAGTGACATGATATGATCCACAAGGGTTTCCTTCCCTGATTT
CTGCATTGATATTAATAGCCAAACGAACTTCAAAACAGCTTTAA
ATAACAAGGGAGAGGGAACCTAAGATGAGTAATATGCCAATC
CAAGACTGCTGGAGAAAACTAAAGCTGACAGGTTCCCTTTTTG
GGGTGGGATAGACATGTTCTGGTTTTCTTTATTATTACACAATC
TGGCTCATGTACAGGATCACTTTTAGCTGTTTTAAACAGAAAAA
AATATCCACCACTCTTTTCAGTTACACTAGGTTACATTTTAATA
GGTCCTTTACATCTGTTTTGGAATGATTTTCATCTTTTGTGATAC
ACAGATTGAATTATATCATTTTCATATCTCTCCTTGTAAATACTA
GAAGCTCTCCTTTACATTTCTCTATCAAATTTTTCATCTTTATGG
GTTTCCCAATTGTGACTCTTGTCTTCATGAATATATGTTTTTCAT
TTGCAAAAGCCAAAAATCAGTGAAACAGCAGTGTAATTAAAAG
CAACAACTGGATTACTCCAAATTTCCAAATGACAAAACTAGGG
AAAAATAGCCTACACAAGCCTTTAGGCCTACTCTTTCTGTGCTT
GGGTTTGAGTGAACAAAGGAGATTTTAGCTTGGCTCTGTTCTCC
CATGGATGAAAGGAGGAGGATTTTTTTTTCTTTTGGCCATTGA
TGTTCTAGCCAATGTAATTGACAGAAGTCTCATTTTGCATGCGC
TCTGCTCTACAAACAGAGTTGGTATGGTTGGTATACTGTACTCA
CCTGTGAGGGACTGGCCACTCAGACCCACTTAGCTGGTGAGCT
AGAAGATGAGGATCACTCACTGGAAAAGTCACAAGGACCATCT
CCAAACAAGTTGGCAGTGCTCGATGTGGACGAAGAGTGAGGAA
GAGAAAAAGAAGGAGCACCAGGGAGAAGGCTCCGTCTGTGCT
GGGCAGCAGACAGCTGCCAGGATCACGAACTCTGTAGTCAAAG
AAAAGAGTCGTGTGGCAGTTTCAGCTCTCGTTCATTGGGCAGCT
```

```
CGCCTAGGCCCAGCCTCTGAGCTGACATGGGAGTTGTTGGATTC
TTTGTTTCATAGCTTTTTCTATGCCATAGGCAATATTGTTGTTCT
TGGAAAGTTTATTATTTTTTTAACTCCCTTACTCTGAGAAAGGG
ATATTTTGAAGGACTGTCATATATCTTTGAAAAAAGAAAATCTG
TAATACATATATTTTTATGTATGTTCACTGGCACTAAAAAATAT
AGAGAGCTTCATTCTGTCCTTTGGGTAGTTGCTGAGGTAATTGT
CCAGGTTGAAAAATAATGTGCTGATGCTAGAGTCCCTCTCTGTC
CATACTCTACTTCTAAATACATATAGGCATACATAGCAAGTTTT
ATTTGACTTGTACTTTAAGAGAAAATATGTCCACCATCCACATG
ATGCACAAATGAGCTAACATTGAGCTTCAAGTAGCTTCTAAGTG
TTTGTTTCATTAGGCACAGCACAGATGTGGCCTTTCCCCCCTTCT
CTCCCTTGATATCTGGCAGGGCATAAAGGCCCAGGCCACTTCCT
CTGCCCCTTCCCAGCCCTGCACCAAAGCTGCATTTCAGGAGACT
CTCTCCAGACAGCCCAGTAACTACCCGAGCATGGCCCCTGCAT
AGCCCTGGAAAAATAAGAGGCTGACTGTCTACGAATTATCTTGT
GCCAGTTGCCCAGGTGAGAGGGCACTGGGCCAAGGGAGTGGTT
TTCATGTTTGACCCACTACAAGGGGTCATGGGAATCAGGAATG
CCAAAGCACCAGATCAAATCCAAAACTTAAAGTCAAAATAAGC
CATTCAGCATGTTCAGTTTCTTGGAAAAGGAAGTTTCTACCCCT
GATGCCTTTGTAGGCAGATCTGTTCTCACCATTAATCTTTTTGAA
AATCTTTTAAAGCAGTTTTTAAAAAGAGAGATGAAAGCATCAC
ATTATATAACCAAAGATTACATTGTACCTGCTAAGATACCAAAA
TTCATAAGGGCAGGGGGGAGCAAGCATTAGTGCCTCTTTGAT
AAGCTGTCCAAAGACAGACTAAAGGACTCTGCTGGTGACTGAC
TTATAAGAGCTTTGTGGGTTTTTTTTCCCTAATAATATACATGT
TTAGAAGAATTGAAAATAATTTCGGGAAAATGGGATTATGGGT
CCTTCACTAAGTGATTTTATAAGCAGAACTGGCTTTCCTTTTCTC
TAGTAGTTGCTGAGCAAATTGTTGAAGCTCCATCATTGCATGGT
TGGAAATGGAGCTGTTCTTAGCCACTGTGTTTGCTAGTGCCCAT
GTTAGCTTATCTGAAGATGTGAAACCCTTGCTGATAAGGGAGC
ATTTAAAGTACTAGATTTTGCACTAGAGGGACAGCAGGCAGAA
ATCCTTATTTCTGCCCACTTTGGATGGCACAAAAAGTTATCTGC
AGTTGAAGGCAGAAAGTTGAAATACATTGTAAATGAATATTTG
TATCCATGTTTCAAAATTGAAATATATATATATATATATATATA
TATATATATATATATAGTGTGTGTGTGTTCTGATAGCTTTA
ACTTTCTCTGCATCTTTATATTTGGTTCCAGATCACACCTGATGC
CATGTACTTGTGAGAGAGGATGCAGTTTTGTTTGGAAGCTCTC
TCAGAACAAACAAGACACCTGGATTGATCAGTTAACTAAAAGT
TTTCTCCCCTATTGGGTTTGACCCACAGGTCCTGTGAAGGAGCA
GAGGGATAAAAAGAGTAGAGGACATGATACATTGTACTTTACT
AGTTCAAGACAGATGAATGTGGAAAGCATAAAAACTCAATGGA
ACTGACTGAGATTTACCACAGGGAAGGCCCAAACTTGGGGCCA
AAAGCCTACCCAAGTGATTGACCAGTGGCCCCCTAATGGGACC
TGAGCTGTTGGAAGAAGAACTGTTCCTTGGTCTTCACCATCC
TTGTGAGAGAAGGGCAGTTTCCTGCATTGGAACCTGGAGCAAG
CGCTCTATCTTTCACACAAATTCCCTCACCTGAGATTGAGGTGC
TCTTGTTACTGGGTGTCTGTGTGCTGTAATTCTGGTTTTGGATAT
GTTCTGTAAAGATTTTGACAAATGAAAATGTGTTTTTCTCTGTT
AAAACTTGTCAGAGTACTAGAAGTTGTATCTCTGTAGGTGCAGG
TCCATTTCTGCCCACAGGTAGGGTGTTTTTCTTTGATTAAGAGA
TTGACACTTCTGTTGCCTAGGACCTCCCAACTCAACCATTTCTA
GGTGAAGGCAGAAAAATCCACATTAGTTACTCCTCTTCAGACAT
TTCAGCTGAGATAACAAATCTTTTGGAATTTTTTCACCCATAGA
AAGAGTGGTAGATATTTGAATTTAGCAGGTGGAGTTTCATAGTA
AAAACAGCTTTTGACTCAGCTTTGATTTATCCTCATTTGATTTGG
CCAGAAAGTAGGTAATATGCATTGATTGGCTTCTGATTCCAATT
CAGTATAGCAAGGTGCTAGGTTTTTTCCTTTCCCCACCTGTCTCT
TAGCCTGGGGAATTAAATGAGAAGCCTTAGAATGGGTGGCCCT
TGTGACCTGAAACACTTCCCACATAAGCTACTTAACAAGATTGT
CATGGAGCTGCAGATTCCATTGCCCACCAAAGACTAGAACACA
CACATATCCATACACCAAAGGAAAGACAATTCTGAAATGCTGT
TTCTCTGGTGGTTCCCTCTCTGGCTGCTGCCTCACAGTATGGGA
ACCTGTACTCTGCAGAGGTGACAGGCCAGATTTGCATTATCTCA
CAACCTTAGCCCTTGGTGCTAACTGTCCTACAGTGAAGTGCCTG
GGGGGTTGTCCTATCCCATAAGCCACTTGGATGCTGACAGCAGC
CACCATCAGAATGACCCACGCAAAAAAAAGAAAAAAAAATT
AAAAAGTCCCCTCACAACCCAGTGACACCTTTCTGCTTTCCTCT
AGACTGGAACATTGATTAGGGAGTGCCTCAGACATGACATTCTT
GTGCTGTCCTTGGAATTAATCTGGCAGCAGGAGGGAGCAGACT
ATGTAAACAGAGATAAAAATTAATTTTCAATATTGAAGGAAAA
AAGAAATAAGAAGAGAGAGAGAAAGAAAGCATCACACAAAGA
TTTTCTTAAAAGAAACAATTTTGCTTGAAATCTCTTTAGATGGG
GCTCATTTCTCACGGTGGCACTTGGCCTCCACTGGGCAGCAGGA
CCAGCTCCAAGCGCTAGTGTTCTGTTCTCTTTTTGTAATCTTGGA
ATCTTTTGTTGCTCTAAATACAATTAAAAATGGCAGAAACTTGT
TTGTTGGACTACATGTGTGACTTTGGGTCTGTCTCTGCCTCTGCT
TTCAGAAATGTCATCCATTGTGTAAAATATTGGCTTACTGGTCT
GCCAGCTAAAACTTGGCCACATCCCCTGTTATGGCTGCAGGATC
GAGTTATTGTTAACAAAGAGACCCAAGAAAAGCTGCTAATGTC
CTCTTATCATTGTTGTTAATTTGTTAAAACATAAAGAAATCTAA
AATTTCAAAAAA
```

SEQ ID NO: 94: cMET (X54559 Homo sapiens mRNA for met proto-oncogene):
GAATTCCGCCCTCGCCGCCCGCGGCGCCCCGAGCGCTTTGTGAG
CAGATGCGGAGCCGAGTGGAGGGCGCGAGCCAGATGCGGGGC
GACAGCTGACTTGCTGAGAGGAGGCGGGGAGGCGCGGAGCGC
GCGTGTGGTCCTTGCGCCGCTGACTTCTCCACTGGTTCCTGGGC
ACCGAAAGATAAACCTCTCATAATGAAGGCCCCCGCTGTGCTT
GCACCTGGCATCCTCGTGCTCCTGTTTACCTTGGTGCAGAGGAG
CAATGGGGAGTGTAAAGAGGCACTAGCAAAGTCCGAGATGAAT
GTGAATATGAAGTATCAGCTTCCCAACTTCACCGCGGAAACAC
CCATCCAGAATGTCATTCTACATGAGCATCACATTTTCCTTGGT
GCCACTAACTACATTTATGTTTTAAATGAGGAAGACCTTCAGAA
GGTTGCTGAGTACAAGACTGGGCCTGTGCTGGAACACCCAGAT
TGTTTCCCATGTCAGGACTGCAGCAGCAAAGCCAATTTATCAGG
AGGTGTTTGGAAAGATAACATCAACATGGCTCTAGTTGTCGAC
ACCTACTATGATGATCAACTCATTAGCTGTGGCAGCGTCAACAG
AGGGACCTGCCAGCGACATGTCTTTCCCCACAATCATACTGCTG
ACATACAGTCGGAGGTTCACTGCATATTCTCCCCACAGATAGAA
GAGCCCAGCCAGTGTCCTGACTGTGTGGTGAGCGCCCTGGGAG
CCAAAGTCCTTTCATCTGTAAAGGACCGGTTCATCAACTTCTTT
GTAGGCAATACCATAAATTCTTCTTATTTCCCAGATCATCCATT
GCATTCGATATCAGTGAGAAGGCTAAAGGAAACGAAAGATGGT
TTTATGTTTTTGACGGACCAGTCCTACATTGATGTTTTACCTGAG
TTCAGAGATTCTTACCCCATTAAGTATGTCCATGCCTTTGAAAG
CAACAATTTTATTTACTTCTTGACGGTCCAAAGGGAAACTCTAG
ATGCTCAGACTTTTCACACAAGAATAATCAGGTTCTGTTCCATA
AACTCTGGATTGCATTCCTACATGGAAATGCCTCTGGAGTGTAT
TCTCACAGAAAAGAGAAAAAAGAGATCCACAAAGAAGGAAGT
GTTTAATATACTTCAGGCTGCGTATGTCAGCAAGCCTGGGGCCC
AGCTTGCTAGACAAATAGGAGCCAGCCTGAATGATGACATTCT
TTTCGGGGTGTTCGCACAAAGCAAGCCAGATTCTGCCGAACCA
ATGGATCGATCTGCCATGTGTGCATTCCCTATCAAATATGTCAA
CGACTTCTTCAACAAGATCGTCAACAAAAACAATGTGAGATGT
CTCCAGCATTTTTACGGACCCAATCATGAGCACTGCTTTAATAG
GACACTTCTGAGAAATTCATCAGGCTGTGAAGCGCGCCGTGAT
GAATATCGAACAGAGTTTACCACAGCTTTGCAGCGCGTTGACTT
ATTCATGGGTCAATTCAGCGAAGTCCTCTTAACATCTATATCCA
CCTTCATTAAAGGAGACCTCACCATAGCTAATCTTGGGACATCA
GAGGGTCGCTTCATGCAGGTTGTGGTTTCTCGATCAGGACCATC
AACCCCTCATGTGAATTTTCTCCTGGACTCCCATCCAGTGTCTC
CAGAAGTGATTGTGGAGCATACATTAAACCAAATGGCTACAC ACTGGTTATCACTGGGAAGAAGATCACGAAGATCCCATTGAAT
GGCTTGGGCTGCAGACATTTCCAGTCCTGCAGTCAATGCCTCTC
TGCCCCACCCTTTGTTCAGTGTGGCTGGTGCCACGACAAATGTG
TGCGATCGGAGGAATGCCTGAGCGGGACATGGACTCAACAGAT
CTGTCTGCCTGCAATCTACAAGGTTTTCCCAAATAGTGCACCCC
TTGAAGGAGGGACAAGGCTGACCATATGTGGCTGGGACTTTGG
ATTTCGGAGGAATAATAAATTTGATTTAAAGAAAACTAGAGTT
CTCCTTGGAAATGAGAGCTGCACCTTGACTTTAAGTGAGAGCAC
GATGAATACATTGAAATGCACAGTTGGTCCTGCCATGAATAAG
CATTTCAATATGTCCATAATTATTTCAAATGGCCACGGGACAAC
ACAATACAGTACATTCTCCTATGTGGATCCTGTAATAACAAGTA
TTTCGCCGAAATACGGTCCTATGGCTGGTGGCACTTTACTTACT
TTAACTGGAAATTACCTAAACAGTGGGAATTCTAGACACATTTC
AATTGGTGGAAAAACATGTACTTTAAAAAGTGTGTCAAACAGT
ATTCTTGAATGTTATACCCCAGCCCAAACCATTTCAACTGAGTT
TGCTGTTAAATTGAAAATTGACTTAGCCAACCGAGAGACAAGC
ATCTTCAGTTACCGTGAAGATCCCATTGTCTATGAAATTCATCC
AACCAAATCTTTTATTAGTGGTGGGAGCACAATAACAGGTGTTG
GGAAAAACCTGAATTCAGTTAGTGTCCCGAGAATGGTCATAAA
TGTGCATGAAGCAGGAAGGAACTTTACAGTGGCATGTCAACAT
CGCTCTAATTCAGAGATAATCTGTTGTACCACTCCTTCCCTGCA
ACAGCTGAATCTGCAACTCCCCCTGAAAACCAAAGCCTTTTTCA
TGTTAGATGGGATCCTTTCCAAATACTTTGATCTCATTTATGTAC
ATAATCCTGTGTTTAAGCCTTTTGAAAAGCCAGTGATGATCTCA
ATGGGCAATGAAAATGTACTGGAAATTAAGGGAAATGATATTG
ACCCTGAAGCAGTTAAAGGTGAAGTGTTAAAAGTTGGAAATAA
GAGCTGTGAGAATATACACTTACATTCTGAAGCCGTTTTATGCA
CGGTCCCCAATGACCTGCTGAAATTGAACAGCGAGCTAAATAT
AGAGTGGAAGCAAGCAATTTCTTCAACCGTCCTTGGAAAAGTA
ATAGTTCAACCAGATCAGAATTTCACAGGATTGATTGCTGGTGT
TGTCTCAATATCAACAGCACTGTTATTACTACTTGGGTTTTTCCT
GTGGCTGAAAAAGAGAAAGCAAATTAAAGATCTGGGCAGTGA
ATTAGTTCGCTACGATGCAAGAGTACACACTCCTCATTTGGATA
GGCTTGTAAGTGCCCGAAGTGTAAGCCCAACTACAGAAATGGT
TTCAAATGAATCTGTAGACTACCGAGCTACTTTTCCAGAAGATC
AGTTTCCTAATTCATCTCAGAACGGTTCATGCCGACAAGTGCAG
TATCCTCTGACAGACATGTCCCCCATCCTAACTAGTGGGACTC
TGATATATCCAGTCCATTACTGCAAAATACTGTCCACATTGACC
TCAGTGCTCTAAATCCAGAGCTGGTCCAGGCAGTGCAGCATGT
AGTGATTGGGCCCAGTAGCCTGATTGTGCATTTCAATGAAGTCA
TAGGAAGAGGGCATTTTGGTTGTGTATATCATGGGACTTTGTTG

GACAATGATGGCAAGAAAATTCACTGTGCTGTGAAATCCTTGA

ACAGAATCACTGACATAGGAGAAGTTTCCCAATTTCTGACCGA

GGGAATCATCATGAAAGATTTTAGTCATCCCAATGTCCTCTCGC

TCCTGGGAATCTGCCTGCGAAGTGAAGGGTCTCCGCTGGTGGTC

CTACCATACATGAAACATGGAGATCTTCGAAATTTCATTCGAAA

TGAGACTCATAATCCAACTGTAAAAGATCTTATTGGCTTTGGTC

TTCAAGTAGCCAAAGGCATGAAATATCTTGCAAGCAAAAAGTT

TGTCCACAGAGACTTGGCTGCAAGAAACTGTATGCTGGATGAA

AAATTCACAGTCAAGGTTGCTGATTTTGGTCTTGCCAGAGACAT

GTATGATAAAGAATACTATAGTGTACACAACAAAACAGGTGCA

AAGCTGCCAGTGAAGTGGATGGCTTTGGAAAGTCTGCAAACTC

AAAAGTTTACCACCAAGTCAGATGTGTGGTCCTTTGGCGTCGTC

CTCTGGGAGCTGATGACAAGAGGAGCCCCACCTTATCCTGACG

TAAACACCTTTGATATAACTGTTTACTTGTTGCAAGGGAGAAGA

CTCCTACAACCCGAATACTGCCCAGACCCCTTATATGAAGTAAT

GCTAAAATGCTGGCACCCTAAAGCCGAAATGCGCCCATCCTTTT

CTGAACTGGTGTCCCGGATATCAGCGATCTTCTCTACTTTCATT

GGGGAGCACTATGTCCATGTGAACGCTACTTATGTGAACGTAA

AATGTGTCGCTCCGTATCCTTCTCTGTTGTCATCAGAAGATAAC

GCTGATGATGAGGTGGACACACGACCAGCCTCCTTCTGGGAGA

CATCATAGTGCTAGTACTATGTCAAAGCAACAGTCCACACTTTG

TCCAATGGTTTTTTCACTGCCTGACCTTTAAAAGGCCATCGATA

TTCTTTGCTCCTTGCCAAATTGCACTATTAATAGGACTTGTATTG

TTATTTAAATTACTGGATTCTAAGGAATTTCTTATCTGACAGAG

CATCAGAACCAGAGGCTTGGTCCCACAGGCCAGGGACCAATGC

GCTGCAG

SEQ ID NO: 95: GFP:
ATGGGCAAGGGCGAGGAACTGTTCACTGGCGTGGTCCCAATCC

TGGTGGAACTGGATGGTGATGTGAACGGGCACAAGTTCTCCGT

CAGCGGAGAGGGTGAAGGTGATGCCACCTACGGAAAGCTCACC

CTGAAGTTCATCTGCACTACCGGAAAGCTCCCTGTTCCGTGGCC

AACCCTCGTCACCACTTTCACCTACGGTGTTCAGTGCTTCTCCC

GGTACCCAGATCACATGAAGCAGCATGACTTCTTCAAGAGCGC

CATGCCCGAAGGCTACGTGCAAGAAAGGACTATCTTCTTCAAG

GATGACGGGAACTACAAGACACGTGCCGAAGTCAAGTTCGAAG

GTGATACCCTGGTGAACCGCATCGAGCTGAAAGGTAAGTTTCT

GCTTCTACCTTTGATATATATATAATAATTATCATTAATTAGTAG

TAATATAATATTTCAAATATTTTTTCAAAATAAAGAATGTAG

TATATAGCAATTGCTTTTCTGTAGTTTATAAGTGTGTATATTTTA

ATTTATAACTTTTCTAATATATGACCAAAATTTGTTGATGTGCA

GGTATCGATTTCAAGGAAGATGGAAACATCCTCGGACACAAGC

TGGAGTACAACTACAACTCCCACAACGTATACATCATGGCCGA

CAAGCAGAAGAACGGCATCAAGGTGAACTTCAAGATCAGGCAC

AACATCGAAGATGGAAGCGTGCAACTGGCGGACCACTACCAGC

AGAACACGCCCATCGGCGATGGCCCTGTCCTGCTGCCGGACAA

CCATTACCTGTCCACGCAATCTGCCCTCTCCAAGGACCCCAACG

AGAAGAGGGACCACATGGTCCTGCTGGAGTTCGTGACGGCTGC

TGGGATCACGCATGGCATGGATGAACTCTACAAGTGA

SEQ ID NO: 96: Diabrotica virgifera v. vATPase,
CN498337.1:
CGGAATATTCCAACTCTGATGTCATTATCTACGTCGGTTGCGGA

GAAAGAGGTAACGAAATGTCTGAAGTATTGAGAGATTTCCCTG

AATTGACTGTTGAAATTGACGGGCACACTGAATCTATTATGAAA

CGTACCGCATTGGTCGCCAACACATCTAACATGCCTGTAGCTGC

TCGTGAAGCTTCTATCTATACTGGnATTACTCTTTCTGAATACTT

CCGTGATATGGGTTACAACGTATCTATGATGGCTGACTCGACAT

CACGTTGGGCCGAAGCTTTGAGAGAAATTTCAGGTCGTTTGGCT

GAAATGCCTGCCGATTCCGGTTATCCGGCTTACTTAGGTGCCCG

TTTGGCTTCCTTCTACGAACGTGCTGGTCGCGTTAAATGTTTAG

GTAATCCAGACAGAGAAGGATCCGTTTCAATTGTAGGAGCCGT

ATCACCTCCTGGTGGTGATTTCTCAGATCCTGTTACCACTGCTA

CTCTTGGTATTGTACAGGTGTTCTGGGGTTTGGACAAGAAACTT

GCCCAACGTAAGCACTTCCCTTCAGTAGACTGGCTTGGATCATA

TTCCAAATATTTAAGAGCATTGGACGACTTTTATGACAAAAACT

TCCAAGAGTTTATTCCTCTTAGAACCAAAGTTAAGGAAATTCTT

CAGGAAGAAGATGATCTAGCCGAAATTGTGCAnCTTGGTAGGT

AAAGCATCTCTGGCAGAAACGGACAAAATCACCCTTGGAAATT

GCCAGGCTTCTTnAAGAAnAATTTCTTGCAACAAAACTC

SEQ ID NO: 97: Diabrotica virgifera v.
Cytochrome P450:
ATGGATGTTTTAAAAACTTATCTGCCGTGTTAGCAGCAGTGTT

TGTTATTTATATTGTTTACAAATTTTTAAAAATACGTAGTGTTTT

AAGAAAAGTTTACAAGTTGCCAGGTCCTCCGAAACTTCCGATTT

TGGGGAACTTCAATGATTTATTCTACTCTGATTCAGTGCAACTA

TTTAAAAATTTTCGAGAATGGAGTCGAAAATATTCACCACTTTA

TTCAGTCGTTGTACTTGACATACCCGTAGTAGTTGTCACTGGAC

CTGATGAGTTTGAAAAAATCGCATCTGGATCAAAACATATTACC

AAAGGAATGATTTACGGTCTTGTAGAACCATGGCTTGGAAAAG

GTCTTCTGACAAATTCAGGTTCCCTGTGGCAACAAGAAGGAA

GATTTTGACACCTGCATTTCACTTCAGTATTCTACAGGAGTTCG

TTAAAGTGTTTAATAAAGAAACTGCTAGGTTGGTCGAGACCATC

AAACAAGAAAATAAGAAATCAGCAACAAATATAATTCCACTAA

TTTCTCAGACCGCTTTAAACACTATTGCAGAAACATCTTTCGGA

ACAACGCTCGATTTGACCAAAAAAGACGACAAAAATTATGTCT
CTGCAATTCATGAAATGGGAAAAATCTTGATATATAGAATGGT
AAGGCCTTGGTTCTATTCTTTATTTGTATTTTATATATTATCTTCT
GTTGGCGCTAAACTCAAACAAGTCTTATCAACGCTGCATAGCTT
TACAGAACGTATTATACCAGAACGATCAAAAGATTTTAAACCTT
TCGAAGTTAATACAGATGGCGAAACAAAGAGAAAGAAACTAG
CTTTTCTAGATTTATTGTTGAATGCAAAACTCTCCAAGGGCATC
ATCGATGACCAAGGTATTAAGGATGAAGTGAATACATTTATGTT
TGAAGGACACGATACAACTGCCACTGGAATATCATGGATTTTA
CGTCAATTGGCAACACATAGCGAATATCAGGATCAAATTTATG
AAGAAATCATAACTGTATTAGGAGATGCACAAAAACAGCCAGA
CCTGAACGACCTAAATGAACTAAAGGTAATGGAAAGATTTATC
AAAGAAACTTTACGTCTTTTCCCTCCTGTACCATATATAGCAAG

GACGTTGGACGAAGACATTGAGCTGAATGGATATTTGATTCCTA

AGGAGGCGTCTATTGATATCTGGATATATGACATTCACAGAAA

CCCGAAACATTGGCCAGAACCTGAGAAATTTGATCCGGATCGG

TTTTTACCTGAAAATTGTGTTAACAGACATCCATTTGCTTATGTA

CCCTTCAGTGCTGGACCCAGAAATTGCATTGGTCAGAGATTTGC

CATGTACGAGATGAAGGCCATTATTTGTGGAATTATGCAGAACT

TCTCAGTGAAACTCGCTGATAAAAATGAAAAAGTTGAAATAAT

GACTGATTTGGTGCTAAGAAGTGCACACGAAATTAATTTGAACT

TCATACCTCGTACTAACTAA

SEQ ID NO: 98: *Diabrotica virgifera* v. COPI:
GCACTGATTCGTTTATTTCACCTAGAAGATTGAAAGCCGATTCT

ACTCCATCATCCGCAACCTGATTGTTATCTCTGGCTTTTTGAACT

TCATCAGAATCATAAGAAAGAATAAAGTAGCTATCTTCTGTGG

CCAAACATACTAATTTACCACTATCTGACCAGTAAACTGCTTTT

GGTTGTATCTCGATTCTTCTGACTAAATCGAGAGTTTCCCAATC

ATAGAAAGTCAAACCAGAAACCGATTTGACTCCCAAAAGGTAT

CCACCGTATATACCTTCAGCTCCAAAATCGGACTTAAAATTCTT

CTTCTCTTTGAAATTCTTAAAAATTCTGATAGTAGATCCGGATT

CTCTGATGGCATATTCGCTGGAATCTTGAGCCCACACAAATTCT

TGTGCGCTACCAAACGCTTTGTTTCTTAAAGCCATTGCTGTGTA

GATTATGTATTCTCCATCCCCACAGACAACAACAAAACGGCCA

TTGGGATTGTGTTGAATTGTCTGAGGGTATATCTCGCAAGCACC

CATATCTTTTACAGAAACTGGAAGGCGTTCTCCATCTCTTATTTC

CGCACCTTCAGCTAACGCCTTGAGATTTGCCTGTTGAAGTTCAG

AGTGTCTGGCCCAAATAATTTTGCCTCCACTGGCATCCATACTA

ACAGCTGGTTCTTCTCTACCAACTTTAACCAAAATGCTACCTTC

ATCATAACCCAATGCCACGTTATTGGATCCCTTTAGGCAGAAAA

TAGTCCATACTCTTTCAAAGCCATAATTTAAGCTACTTTCTAAC

-continued

CTATGGGTGTTGGCATGCCACACTCTGACAGTACCATCTTCACT

TCCAGTAAGAGCTACAGGAAGTTCTGGATGGAAACATGCAGCG

GTTACATTTTGAGCATGTCCTTCCAAAGTTTGAACACAAGTTTT

GTTTTGATAATCCCAGATTTTTACTAATCTATCATCAGCGCCTG

AGATTAAATAAGGTTTATCTCCACCGTGATAATAGTCCACACAG

TTAACGCCTTTCTCATGACCTTCTAGTGTGAAATTCGCTGTGGA

CGCTCCCAATTGCCATACTTTCAATGTTCTATCTAGGGATGCAC

TGGCAAATGTGTTGTTGTCTTTTGGATTTATGGCGATTTGCATA

ATATAATGAGTGTGTCCTTCGAAAACTTGCTGACAAGCCCATGC

TTTTTCCCAATTCCAAAGCTTGATAAGCATATCATCACTACTTGT

TAATATATAAGGTTGTGTAGGGTGTACGACAATACATCTCACAT

AATCCGAATG

SEQ ID NO: 99: *Diabrotica virgifera* v. Ribo S4:
GTGTTTTGGCCTCTTGGGAGTAGTAGCAAAGACGTTCCCTATAA

GTTTCCGGATGGTGTCTCACCAAGAAATTTTGCTTCGACGGAAG

AATACTGTCTGTCTTCACTGTTATTCTCTCAACCAACATCCATGC

TAACCTCGGAAACGAAGTACATGACCAATTGATAACTAGATTC

GAACATTGACTTTGTGGAATTCCTTTCAGCGGTATTCACCAGTC

TCTGACTTTTCTTGTGAGGATGCTTGTCTCTCTGCCTTAGCTCTT

AGCATCTTGTACCTACACTTAATGTAGTATGTTTGGGTTTTGGTC

CAGATACGGTGAATTCTCAATAGCCATCGACTTTACTTTAGTCC

CGGTGGATGCTTCAGCAATCCTTACCAATTAACATGCACGACCC

AAATTCTAGAATTTTCAGGGTATCTTTTGGACTCTTGGCAAATC

TTAATAACATCTAATTAATCTTGTTTCTTAAAGACAATTTGAAT

GAAAACGAATATCAAAGTCTTCCTCCAAGATGTGGCATCGTACT

TTGACCTTTAACACATAAATCCTTTGCATAACAGAAAATTACTA

AATACACCTACTCCCTTTCTTATTTAACCGATCCAGGATGTGAT

CATACATTTCCAATTCCATCATGTGCAGAGTTTGTTCATAGATA

AGCAGGATAGTATTTTTGTGAAATGGTAAAGCCCAATTTGT

SEQ ID NO: 100: *Diabrotica virgifera* v. Dvsnf7:
ATGAGCTTTTTTGGAAAATTGTTCGGGGGGAAAAAGGAAGAGA

TAGCCCCTAGTCCTGGGGAGGCTATTCAAAAACTCAGAGAGAC

TGAAGAAATGTTAATAAAAAAACAGGATTTTTTAGAAAAGAAG

ATAGAAGAATTTACCATGGTAGCAAAGAAAAATGCGTCGAAAA

ATAAAAGAGTTGCACTCCAAGCCCTCAAAAAGAAGAAACGATT

GGAAAAGACCCAACTACAAATAGATGGAACCCTTACAACTATT

GAAATGCAGAGGGAAGCCCTCGAAGGAGCTAGCACAAATACTG

CTGTATTAGATTCTATGAAAAATGCTGCAGATGCCCTTAAGAAA

GCTCATAAGAATTTGAATGTAGATGATGTTCACGATATCATGGA

TGACATAGCCGAACAACACGACATAGCCAACGAAATCACAAAC

GCTATTAGCAATCCTGTCGGATTCACCGACGATCTGGATGACGA

TGAATTAGAAAAAGAATTAGAAGAGCTCGAACAAGAAGGATTG

GAAGAAGACCTGCTCCAAGTGCCAGGTCCAACTCAACTGCCGG
CTGTGCCTGCTGATGCAGTTGCTACTAAACCAATCAAACCAGCA
GCTAAAAAAGTTGAAGATGATGACGATATGAAAGAATTGGAAG
CCTGGGCCTCGTAA.

SEQ ID NO: 101: *Diabrotica virgifera* v. ET3:
ACACACGCTATAATTTGATCTTTGATCGGTCACAATGTTGTAGT
GTTTTTAGTTTATTGTGCCTCGAAGAGACAAAATCTAACCATGG
CTCATGTGGTGCAACTAGCGGAAGGAAAAATTTCTGGAGGCAC
TAGGACAGATCTCAATGGGGATAAGTTTCATTCGTTTTTATGTA
TCCCATACGGAAAAGCTCCAGTAGGCGACCTACGGTTTAAGGC
GCCATTACCTGTTGAACCATGGGAAGGGGTAAAACAAGTTATC
ACAGAAGACAAAACGCCATTCCAGAAGAACATTGTTCTGAAGG
AATATACTGGAGAAGAAGATTGCTTGTCTCTTCATGTATTTACA
AAGAAACTTCCCCATGAAGAATCCAAACTGAAACCTGTGATGG
TGTACATTCATGGAGGAGGTTTTATAATGGGATCTCACGAAACT
ACGATGTATGGTCCAGAATACCTTATGACTGAAGACATAGTTCT
CGTAAGCATCACTTACCGAGTTGGTCTACTGGGTTTTCTTAGTA
TAGAAGACGAATCACTGGACGTTCCTGGAAATGCAGGTCTAAA
AGATCAAGTACTGGCTTTAAAGTGGGTCCAGCGAAACATAAGA
AATTTCAATGGAGATCCCAATAACATTACCATATTTGGAGAAA
GTGCGGGAGGGCATCTGTTGAATTTTTGCTGTTATCTCCTTCA
GCCAAAGGTTTATTTCATAAAGCCATACTTCAGAGCGGGTCGAC
TTTAAATCCATGGACTCTTAAAAACTCCCCAGCAACTGAGTTTG
CTGAGTTTACCAAACTACATAACTTGCCTGATATTGACATTTTG
AAAAGCTTGAGGCGTATGACTGTTAGGGAGCTGTACGATCAAC
AAAATCAATATATTAAGTCTAAGAAGCTATTTGTAGATTTCGGT
CTAATAACCCCAGTGATAGAAAAACCCAACCCAACAGCATTTT
TGACAGAGAAACCTATCGACATCATCCAGTCAGGGAAATACAA
CAATGTGCCAGTGATAATGGGTTACACCGACAGTGAAGGTCTT
CTTCTAGACTTCTTGTCGGCACTTGGAATGAACGGGGCAAAAG
AGGGAGAAGATATACCTATTGAGCAGATACTACCATACGAGAC
AAATTTAACAGATGCACAACAAGTCAAACGATTAGTTGAAAAG
TTAAGAAATTTTTATCGTCCAGAAGCTGATCCGGTTGGACGAAT
TAATTTATCTACGGATGCCTTGTTTGCGGCTGGAATAATCACTT
CTGCAAAAAATCAAGCGAAAGTGTCAAAGAACCCTGTATATTT
TTATAGATTTTCATTGGACGCAGGCCTTAACATGCTGAAGAAAA
TGGTGAATGATACACGTCCAGGAGCTTGTCACGGGGATGAACT
GGGATACCTATTTAAAAACCTTTTGACAACAGACATTGGAGAT
GAAGATAAAACTTATATACATCGAATGGTAACACTATGGACAA
ACTTTGCCAAATATGGAAATCCAACACCACCAGGAAATAATCT
AAACATTGAATGGAAGCCGATACAGAATGGTCAGTTGAATTTC TTAGATATTGGAAAACAACTAAAGATGGATGTGAATCCAGACG
CTGACAGGATGAAAATTTGGAATGAGCTTTACCAGTGTAATCC
ACTGACAGCTAAATATTAAATTTGTTTGCAACAACTCTCAGAAA
TACATGTTATTATATTTTTATATTATAAAAAATATTTATATCATA
TTTTAAGACTATACGAATAAAACTGATTACTTTATTTTAAAATA
AAGTTACTACACAAAAA SEQ ID NO: 102: PIC16005, *Diabrotica virgifera*
v., Part of vATPase D subunit 1:
AACGGTTATTTGGAAGGCCTGTGTCGTGGCTTTAAATGTGGGAT
CCTGAAACAATCCGATTATTTGAATTTGGTCCAGTGTGAAACTC
TTGAAGATTTAAAACTGCACTTGCAAGGCACTGACTATGGAACT
TTTTTGGCCAATGAACCTTCACCTTTGTCAGTATCCGTCATCGAT
TCAAGACTTCGAGAAAAACTCGTGATTGAGTTCCAGCACATGC
GTAACCAAGCAGTAGAGCCTCTCTCGACATTTATGGACTTCATT
ACCTACAGTTACATGATCGACAA SEQ ID NO: 103: PIC17505, *Diabrotica virgifera*
v. vATPase E:
ACAATAAATTTTCATCGGCGAAGATTTTCTCCACAAGAAAAAA
ATAATCTTTTTCACATCACATCATCAAACATCAAATCACGAATA
TCATTCTTCGAGAAAAAAAATCAAGGTAGTATCAACTCGAAAC
CTCAATAATTCTTCTCAAGGATCTTTCAAAAAATATTCTCGCTTC
GACAAGGATCACAATTAGGGTAACAACAAACTCTAACTCGTTT
AAAATACTCTCAAAAAAAGGAATCGGTTTATTATCATCATCATT
CGTATCATACATCAGTAGTTTAAAAGGTTTTTCGAAGATCTCGT
CTAAGCAACCAACAATCGTTTTACAATACTATATAAAATACAG
GGAATACACAGTATCCAAAAAATACTTAATCAGTGAATTTTCTG
GTTGACGTTGCGTCCGAACAGAGCATTACGGATCTGGGGAATC
AATTGTTGTGAGATGAGCTCAAGACGGGCTTCCAGAGTATTGTT
GATTTTGATCTTGTTTCTCAAGGCCAACAGTTCGATTCCTCCGGT
GGTTTCTTGAGAAAGGTGGCTCTCGTCGTCGATTTTTAGATTTA
CGTCTTTACCGGTTATGTCCTTGTACTTTTGGGAGACGTTAGGC
ATGATAGATTTTACCAATTCTCTGTCCTGAGGGCGTACTCTAAT
GGTGATGTCCTTTTCGAAGAGCTGATAGAGCCCTTGGAGGATG
AGACTTTCCAGGATTTGTGTATATTTGCCTGAATCTCTGGTTACC
TCACCAAGACGTTTGCGAGCATCTTCCAAAACGGCACGTACAT
GGTCTTCCCTTACTTTNCATACCCTTCATCTTGCCTGGTTCAACA
TGTTTTGATGATTGGATTTTTTTTCTGGAGTTCTACTTGCTTCTCT
TTTTTCTCGTAGTACTCCAT SEQ ID NO: 104: *Amaranthus palmeri* PDS:
TCAATTTCATCTATTGGAAGTGATTTTTTGGGTCATTCTGTGAGA
AATTTCAGTGTTAGTAAAGTTTATGGAGCAAAGCAAAGAAATG
GGCACTGCCCTTTAAAGGTTGTTTGTATAGATTATCCTAGGCCA
GAGCTTGAAAGTACATCCAATTTCTTGGAAGCCGCCTACTTATC

```
TTCTACTTTTCGGAATTCGCCTCGTCCTCAGAAGCCATTAGAAG
TTGTAATTGCTGGAGCAGGTTTGGCTGGTCTATCCACGGCAAAG
TATTTAGCTGATGCAGGTCACAAACCCATATTGTTGGAAGCACG
AGATGTTTTAGGAGGAAAGGTTGCAGCGTGGAAGGATGAGGAT
GGTGACTGGTATGAGACTGGGCTACATATATTCTTTGGGGCATA
TCCAAATGTCCAAAATCTATTTGGAGAACTTGGTATAAATGACC
GACTGCAATGGAAGGAGCACTCTATGATTTTTGCAATGCCCAGC
AAGCCCGGTGAATTCAGTCGCTTTGATTTTCCCGAAATCCTGCC
TGCACCATTAAATGGCATATGGGCAATCCTAAGAAATAATGAA
ATGCTAACCTGGCCAGAAAAAATCAAGTTTGCCATTGGCTTGTT
GCCTGCTATGGCAGGCGGACAGTCATATGTTGAAGCACAAGAT
GGTTTGAGTGTCCAAGAGTGGATGAGAAAACAAGGAGTACCCG
ATCGTGTAACTGATGATGTGTTTATTGCCATGTCAAAGGCACTG
AACTTCATAAATCCCGATGAACTTTCAATGCAGTGCATCTTGAT
TGCTCTGAACCGATTCCTGCAGGAGAAACATGGTTCTAAGATG
GCCTTCCTAGACGGAAACCCTCCAGAGAGGCTGTGCATGCCTA
TTGTTAAACACATCGAGTCACTAGGTGGTGAAGTTAAACTTAAC
TCTCGTATACAGATGCCTATGTTTTTGCCACCCCAGTTGACATCT
TGAAGCTGTTACTACCTGATACTTGGAAGGAAATCTCATACTTC
aagaaaCTTGAGAAATTAGTGGGCGTTCCTGTGATTAATGTTCACA
TATGGTTTGACAGAAAATTAAAGAATACATATGACCATCTACTC
TTCAGCAGGAGTCCTCTTTTGAGTGTCTATGCTGATATGTCGGA
GACATGCAAGGAATATAAGGATCCAAATAGATCCATGCTGGAA
TTGGTTTTTGCACCCGCGGAGGAATGGATTTCACGAAGCGACAC
TGATATTATAGAGGCAACAATGAAAGAGCTTGCCAAGCTTTTCC
CGGATGAAATCGCTGCCGATGGAAGCAAGGCCAAGATCCTCAA
ATATCATGTCGTCAAAACTCCAAGGTCGGTTTATAAGACTGTAC
CGGATTGTGAACCTTGTCGGCCGCTGCAAAGATCACCAATAGA
GGGTTTCTATTTAGCTGGTGATTACACAAAACAAAAATATTTGG
CTTCTATGGAAGGTGCTGTCTTATCTGGGAAGCTTTGTGCACAG
GCTATCGTACAGGATTATGATCTGCTGAGTTCTCGAGCACAAAG
AGAATTGGCG SEQ ID NO: 105: Amaranthus palmeri EPSPS:
ATGGCTAAGCTACTACCATCAACAATGGTGTCCATACTGGTCA
ATTGCACCATACTTTACCCAAAACCCAGTTACCCAAATCTTCAA
AAACTCTTAATTTTGGATCAAACTTGAGAATTTCTCCAAAGTTC
ATGTCTTTAACCAATAAAAGAGTTGGTGGGCAATCATCAATTGT
TCCCAAGATTCAAGCTTCTGTTGCTGCTGCAGCTGAGAAACCTT
CATCTGTCCCAGAAATTGTGTTACAACCCATCAAAGAGATCTCT
GGTACTGTTCAATTGCCTGGGTCAAAGTCTTTATCCAATCGAAT
CCTTCTTTTAGCTGCTTTGTCTGAGGGCACAACAGTGGTCGACA
```

```
ACTTGCTGTATAGTGATGATATTCTTTATATGTTGGACGCTCTCA
GAACTCTTGGTTTAAAAGTGGAGGATGATAGTACAGCCAAAAG
GGCAGTCGTAGAGGGTTGTGGTGGTCTGTTTCCTGTTGGTAAAG
ATGGAAAGGAAGAGATTCAACTTTTCCTTGGTAATGCAGGAAC
AGCGATGCGCCCATTGACAGCTGCGGTTGCCGTTGCTGGAGGA
AATTCAAGTTATGTGCTTGATGGAGTACCAAGAATGAGGGAGC
GCCCCATTGGGGATCTGGTAGCAGGTCTAAAGCAACTTGGTTCA
GATGTAGATTGTTTTCTTGGCACAAATTGCCCTCCTGTTCGGGT
CAATGCTAAAGGAGGCCTTCCAGGGGGCAAGGTCAAGCTCTCT
GGATCGGTTAGTAGCCAATATTTAACTGCACTTCTCATGGCTAC
TCCTTTGGGTCTTGGAGACGTGGAGATTGAGATAGTTGATAAAT
TGATTTCTGTACCGTATGTTGAAATGACAATAAAGTTGATGGAA
CGCTTTGGAGTATCCGTAGAACATAGTGATAGTTGGGACAGGTT
CTACATTCGAGGTGGTCAGAAATACAAATCTCCTGGAAAGGCA
TATGTTGAGGGTGATGCTTCAAGTGCTAGCTACTTCCTAGCCGG
AGCCGCCGTCACTGGTGGGACTGTCACTGTCAAGGGTTGTGGA
ACAAGCAGTTTACAGGGTGATGTAAAATTTGCCGAAGTTCTTGA
GAAGATGGGTTGCAAGGTCACCTGGACAGAGAATAGTGTAACT
GTTACTGGACCACCCAGGGATTCATCTGGAAAGAAACATCTGC
GTGCTATCGACGTCAACATGAACAAAATGCCAGATGTTGCTAT
GACTCTTGCAGTTGTTGCCTTGTATGCAGATGGGCCCACCGCCA
TCAGAGATGTGGCTAGCTGGAGAGTGAAGGAAACCGAACGGAT
GATTGCCATTTGCACAGAACTGAGAAAGCTTGGGGCAACAGTT
GAGGAAGGATCTGATTACTGTGTGATCACTCCGCCTGAAAAGC
TAAACCCCACCGCCATTGAACTTATGACGATCACCGAATGGC
CATGGCATTCTCTCTTGCTGCCTGTGCAGATGTTCCCGTCACTAT
CCTTGATCCGGGATGCACCCGTAAAACCTTCCCGGACTACTTTG
ATGTTTTAGAAAAGTTCGCCAAGCATTGA

SEQ ID NO: 106: Amaranthus palmeri HPPD:
CGTCGAAGTAGAAGACGCGGAAGCTGCTTTTAACATCAGCGTT
TCGCATGGGGCTATTCCCTGTGTTTCTCCTATTCAATTGGAAAA
CGGTGTCGTTTTATCTGAGGTTCATTTATATGGGGATGTTGTGCT
TCGGTATGTAAGCTACGGAAATGAATGTGGGGATGTGTTTTTTC
TTCCTGGGTTTGAGGAAATGCCGGAGGAATCATCGTTTAGAGG
ACTTGATTTTGGCATTCGAAGGTTGGATCATGCTGTAGGGAATG
TCCCTGAGTTGGCTCCTGCAATTGCTTATTTGAAGAAGTTTACT
GGGTTTCATGAGTTTGCTGAGTTTACAGCTGAAGATGTTGGGAC
GAGTGAAAGTGGATTGAATTCAGCCGTATTGGCAAACAATGAT
GAAATGGTGTTGTTTCCGATGAATGAACCTGTGTATGGGACAA
AAAGGAAGAGCCAAATTCAAACTTATTTGGAGCATAATGAAGG
GGCTGGTGTACAGCATTTGGCTTTGATGAGTGAAGACATATTTT
```

-continued

```
GGACTTTAAGGGAGATGAGGAAGAGAAGTGTTCTTGGTGGGTT

TGAGTTTATGCCGTCGCCGCCTCCGACTTATTACCGGAATTTGA

GGAACAGAGCTGCTGATGTATTGAGTGAGGAGCAGATGAAGGA

GTGTGAAGAGTTGGGGATTTTGGTGGATAAAGATGATCAGGGC

ACTTTGCTTCAAATCTTCACCAAACCTATTGGAGACAGGTAAAT

TTTAATCTTGCTTTCAATTGCTTTTGCTTGATGGATTGACTAGCA
```

-continued
```
AATTTGATCGCATTTTGTTGCTTATATGACTTGATGATACTTCCT

CTGTTTCGAAATACTCGCTACATTCGCTACATTTTGTTTTGTGCA

CTATTCATCGTTCAAGCTTATTTTACATATTGCGACTAATGTGTA

ACTAAAAATATAGTCAAGTGGGATCTTGTTTGAATCGTCTAATG

GCATACTTTCATCATATTAAATTTTTATAATTTTTAGATTAGTGT

AGTTTAAGATATTAATGCTCAAAATTGTGCATTGGATTGCGTAA

AAAAGTGAAATGTAGCAAGTATTATGAAA
```

---

The invention claimed is:

1. An isolated polynucleotide nanoparticle comprising a contiguous polynucleotide comprising two or more MV-RNA sequences, each MV-RNA sequence joined by at least one linkage nucleotide,
    wherein the contiguous polynucleotide is self-forming into the nanoparticle having a diameter of approximately 40-100 nm with approximately twice the ratio of stems near the surface of the nanoparticle than at the core of the nanoparticle.

2. An isolated polynucleotide nanoparticle approximately 100 nm diameter with at least four times the ratio of stems on the outer surface than at the center, comprising stacked sets of three MV-RNA, wherein each stacked MV-RNA set is separated by a linking element.

3. The isolated polynucleotide nanoparticle of claim 1, wherein the polynucleotide nanoparticle comprises aptamer or cellular uptake sequences on one or more surface loops.

4. The isolated polynucleotide nanoparticle of claim 1, wherein the polynucleotide nanoparticle has a general structure set forth in any one of FIG. 1 (2nd to 5th graphics counting from left to right), FIG. 2 (2nd to 6th graphics counting from left to right), and FIG. 3.

5. The isolated polynucleotide nanoparticle of claim 1, wherein (i) the 5' end of the contiguous polynucleotide hybridizes to a reverse complement sequence of the 3' end of the contiguous polynucleotide to form a stem or (ii) the first MV-RNA in the nanoparticle comprises both the 5' end and the 3' end of the contiguous polynucleotide to close the nanoparticle.

6. The isolated polynucleotide nanoparticle of claim 1, wherein the at least one linkage nucleotide comprises: (i) a stem-loop structure or (ii) dinucleotide or (iii) mononucleotide.

7. The isolated polynucleotide nanoparticle of claim 1, wherein the polynucleotide nanoparticle comprises natural or synthetic RNA or DNA.

8. The isolated polynucleotide nanoparticle of claim 1, wherein the at least one linkage nucleotide is 1-12 nucleotides.

9. The isolated polynucleotide nanoparticle of claim 1, wherein the polynucleotide nanoparticle is without a 5' phosphate end or 3' hydroxyl terminus.

10. The isolated polynucleotide nanoparticle of claim 1, wherein the polynucleotide nanoparticle is expressed within a host cell selected from a plant cell or human cell or yeast cell or bacterial cell, or in vitro transcription.

11. The isolated polynucleotide nanoparticle of claim 1, wherein the polynucleotide nanoparticle is expressed within a host cell and targets genes other than the host.

12. A composition comprising the isolated polynucleotide nanoparticle of claim 1, in combination with a physiologically acceptable excipient.

13. The isolated polynucleotide nanoparticle of claim 2, wherein the polynucleotide nanoparticle contains aptamer or cellular uptake sequences on one or more surface loops.

14. The isolated polynucleotide nanoparticle of claim 2, wherein the linkage element comprises: (i) a stem-loop structure or (ii) dinucleotide or (iii) mononucleotide cleavable by an endonuclease.

15. The isolated polynucleotide nanoparticle of claim 2, wherein the polynucleotide nanoparticle comprises natural or synthetic RNA or DNA.

16. The isolated polynucleotide nanoparticle of claim 2, wherein the linkage element sequence is 3-12 nucleotides.

17. The isolated polynucleotide nanoparticle of claim 2, wherein the polynucleotide nanoparticle is a single polynucleotide nanoparticle circularized with ribozyme cleavage.

18. The isolated polynucleotide nanoparticle of claim 2, wherein the polynucleotide nanoparticle is expressed within a host cell selected from a plant cell or human cell or yeast cell or bacterial cell, or in vitro transcription.

19. The isolated polynucleotide nanoparticle of claim 2, wherein the polynucleotide nanoparticle is expressed within a host cell and targets genes other than the host.

20. A composition comprising the isolated polynucleotide nanoparticle of claim 2, in combination with a physiologically acceptable excipient.

21. The isolated polynucleotide nanoparticle of claim 2, wherein the polynucleotide is single-stranded and the nanoparticle is self-forming.

* * * * *

SEQUENCE LISTING

<160> NUMBER OF SEQ ID NOS: 106

<210> SEQ ID NO 1
<211> LENGTH: 223
<212> TYPE: DNA
<213> ORGANISM: Artificial Sequence
<220> FEATURE:
<223> OTHER INFORMATION: Region of cyclase ribozyme

<400> SEQUENCE: 1
gaaaatttcg tctggattag ttacttatcg tgtaaaatct gataaatgga attggttcta      60
cataaatgcc taacgactat ccctttgggg agtagggtca agtgactcga aacgatagac     120
aacttgcttt aacaagttgg agatatagtc tgctctgcat ggtgacatgc agctggatat     180
aattccgggg taagattaac gaccttatct gaacataatg cta                       223

<210> SEQ ID NO 2
<211> LENGTH: 173
<212> TYPE: DNA
<213> ORGANISM: Artificial Sequence
<220> FEATURE:
<223> OTHER INFORMATION: Region of cyclase ribozyme

<400> SEQUENCE: 2
caggtcaatt gaggcctgag tataaggtga cttatacttg taatctatct aaacggggaa      60
cctctctagt agacaatccc gtgctaaatt gtaggactgc cctttaataa atacttctat     120
atttaaagag gtatttatga aaagcggaat ttatcagatt aaaaatactt tct            173

<210> SEQ ID NO 3
<211> LENGTH: 9
<212> TYPE: RNA
<213> ORGANISM: Artificial Sequence
<220> FEATURE:
<223> OTHER INFORMATION: Dicer loop

<400> SEQUENCE: 3 ucaagaaac                                                               9

<210> SEQ ID NO 4
<211> LENGTH: 10
<212> TYPE: RNA
<213> ORGANISM: Artificial Sequence
<220> FEATURE:
<223> OTHER INFORMATION: Dicer loop

<400> SEQUENCE: 4
ggaucuuauu                                                             10

<210> SEQ ID NO 5

```
<211> LENGTH: 10
<212> TYPE: RNA
<213> ORGANISM: Artificial Sequence
<220> FEATURE:
<223> OTHER INFORMATION: Dicer loop

<400> SEQUENCE: 5
uucauagaga                                                               10

<210> SEQ ID NO 6
<211> LENGTH: 71
<212> TYPE: RNA
<213> ORGANISM: Artificial Sequence
<220> FEATURE:
<223> OTHER INFORMATION: Loop PSMA

<400> SEQUENCE: 6
gggaggacga ugcggaucag ccauguuuac gucacuccuu gucaauccuc aucggcagac         60
gacucgcccg a                                                             71

<210> SEQ ID NO 7
<211> LENGTH: 30
<212> TYPE: RNA
<213> ORGANISM: Artificial Sequence
<220> FEATURE:
<223> OTHER INFORMATION: Loop clathrin-pit

<400> SEQUENCE: 7
uuccucuauc cguucuaaac gcuuuaugau                                         30

<210> SEQ ID NO 8
<211> LENGTH: 88
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (23)..(32)
<223> OTHER INFORMATION: Loop Dicer 2
<220> FEATURE:
<221> NAME/KEY: misc_feature
<222> LOCATION: (56)..(65)
<223> OTHER INFORMATION: Loop Dicer 2

<400> SEQUENCE: 8
cgccgggagg ugcugcgcuu ugggaucuua uucaaggugc agcucucauu uccuuggauc         60
uuauuaagga agugagaacu ucucggcg                                           88

<210> SEQ ID NO 9
<211> LENGTH: 149
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (23)..(32)
<223> OTHER INFORMATION: Loop Dicer 2
<220> FEATURE:
<221> NAME/KEY: misc_feature
<222> LOCATION: (56)..(126)
<223> OTHER INFORMATION: Loop PSMA

<400> SEQUENCE: 9
cacugagguc aauguggacg gaggaucuua uuuucgucca caucgagcac uuuaugggag         60
gacgaugcgg aucagccaug uuuacgucac uccuugcaau uccucaucgg cagacgacuc        120
```

```
gcccgaauaa ggugcuugug gcuucagug                                        149

<210> SEQ ID NO 10
<211> LENGTH: 89
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (23)..(32)
<223> OTHER INFORMATION: Loop Dicer 2
<220> FEATURE:
<221> NAME/KEY: misc_feature
<222> LOCATION: (56)..(65)
<223> OTHER INFORMATION: Loop Dicer 2

<400> SEQUENCE: 10
ccuuucucag aguaagggag aaggaucuua uuuucuccccu ugcaacaagu aagacggauc     60
uuauugucuu guuuguucug agagagguu                                        89

<210> SEQ ID NO 11
<211> LENGTH: 106
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (23)..(31)
<223> OTHER INFORMATION: Loop Dicer 1
<220> FEATURE:
<221> NAME/KEY: misc_feature
<222> LOCATION: (55)..(84)
<223> OTHER INFORMATION: Loop clathrin-pit

<400> SEQUENCE: 11
cagcuuccac augugagaga gcucaagaaa cgcucucucg caauaggcug cuuguuccuc     60
uauccguucu aaacgcuuua ugauuaagua gcuuaugugg gagcug                   106

<210> SEQ ID NO 12
<211> LENGTH: 85
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (23)..(31)
<223> OTHER INFORMATION: Loop Dicer 1
<220> FEATURE:
<221> NAME/KEY: misc_feature
<222> LOCATION: (55)..(63)
<223> OTHER INFORMATION: Loop Dicer 1

<400> SEQUENCE: 12
caaaggcagc cgucagucca ucucaagaaa cgaugggcug acauucauag ccguucaaga     60
aacgcggcug ugaagguugc uuuug                                            85

<210> SEQ ID NO 13
<211> LENGTH: 95
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (25)..(33)
```

```
<223> OTHER INFORMATION: Loop Dicer 1
<220> FEATURE:
<221> NAME/KEY: misc_feature
<222> LOCATION: (62)..(70)
<223> OTHER INFORMATION: Loop Dicer 1

<400> SEQUENCE: 13
guguguucua gucuuuggug guucucaaga aacgaaccac cagagaaaca guguaguuga      60
cucaagaaac gucaauuaca uuggcuagaa cauac                                95

<210> SEQ ID NO 14
<211> LENGTH: 97
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (27)..(35)
<223> OTHER INFORMATION: Loop Dicer 1
<220> FEATURE:
<221> NAME/KEY: misc_feature
<222> LOCATION: (63)..(71)
<223> OTHER INFORMATION: Loop Dicer 1

<400> SEQUENCE: 14
gggaaauagg guuccaaug cuuugcucaa gaaacgcaaa guauuggagc cacaccaacc      60
agucaagaaa ccugguuggu guggaacccu auuccc                               97

<210> SEQ ID NO 15
<211> LENGTH: 95
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (27)..(35)
<223> OTHER INFORMATION: Loop Dicer 1
<220> FEATURE:
<221> NAME/KEY: misc_feature
<222> LOCATION: (62)..(70)
<223> OTHER INFORMATION: Loop Dicer 1

<400> SEQUENCE: 15
ggcugagagu agccgacuga guuugcucaa gaaacgcaaa cucaguugaa augguugcgc      60
uucaagaaac agugcaauca uuucugcucu cggcc                                95

<210> SEQ ID NO 16
<211> LENGTH: 99
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (27)..(36)
<223> OTHER INFORMATION: Loop Dicer 3
<220> FEATURE:
<221> NAME/KEY: misc_feature
<222> LOCATION: (63)..(71)
<223> OTHER INFORMATION: Loop Dicer 1

<400> SEQUENCE: 16
aaagucucgu gcagaagaag aucacguuca uagagacgug aucuucuucc cagugauacc     60
uuucaagaaa caagguguca cugguuguga cgggacuuu                           99
```

```
<210> SEQ ID NO 17
<211> LENGTH: 99
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (27)..(35)
<223> OTHER INFORMATION: Loop Dicer 1
<220> FEATURE:
<221> NAME/KEY: misc_feature
<222> LOCATION: (62)..(70)
<223> OTHER INFORMATION: Loop Dicer 1

<400> SEQUENCE: 17
cuuggcguug ucagaaaugg uuucagucaa gaaacuugaa accauuucug uaguugacag    60
aucaagaaac ucugucaauu acauuggcga cgccaaguu                          99

<210> SEQ ID NO 18
<211> LENGTH: 149
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (24)..(32)
<223> OTHER INFORMATION: Loop Dicer 1
<220> FEATURE:
<221> NAME/KEY: misc_feature
<222> LOCATION: (56)..(126)
<223> OTHER INFORMATION: Loop PSMA

<400> SEQUENCE: 18
cugcuucuug aggccgucgu guuucaagaa acaacacggc gguuuguuuc cgcaggggag    60
gacgaugcgg aucagccaug uuuacgucac uccuugucaa uccucaucgg cagacgacuc   120
gcccgauugc ggaaauauuu aaggagcgg                                    149

<210> SEQ ID NO 19
<211> LENGTH: 110
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (24)..(32)
<223> OTHER INFORMATION: Loop Dicer 1
<220> FEATURE:
<221> NAME/KEY: misc_feature
<222> LOCATION: (57)..(86)
<223> OTHER INFORMATION: Loop clathrin-pit

<400> SEQUENCE: 19
agaggcgguc gugggucugg cucucaagaa acgaguuagg cccuaucugc ugcgcuuucc    60
ucuauccguu cuaaacgcuu uaugauggcg uagcggagcc ggcugccucu              110

<210> SEQ ID NO 20
<211> LENGTH: 64
<212> TYPE: RNA
<213> ORGANISM: Artificial Sequence
<220> FEATURE:
<223> OTHER INFORMATION: Open component
<220> FEATURE:
<221> NAME/KEY: misc_feature
<222> LOCATION: (27)..(35)
<223> OTHER INFORMATION: Loop Dicer 1
<220> FEATURE:
```

```
<221> NAME/KEY: misc_feature
<222> LOCATION: (63)..(64)
<223> OTHER INFORMATION: Linkage component

<400> SEQUENCE: 20
gggaaauagg guuccaaug cuuugcucaa gaaacgcaaa guauuggagc cacaccaacc      60
agac                                                                  64

<210> SEQ ID NO 21
<211> LENGTH: 1267
<212> TYPE: RNA
<213> ORGANISM: Artificial Sequence
<220> FEATURE:
<223> OTHER INFORMATION: Prostate cancer nanoparticle core component
<220> FEATURE:
<221> NAME/KEY: misc_feature
<222> LOCATION: (23)..(31)
<223> OTHER INFORMATION: Loop Dicer 1
<220> FEATURE:
<221> NAME/KEY: misc_feature
<222> LOCATION: (55)..(84)
<223> OTHER INFORMATION: Loop clathrin-pit
<220> FEATURE:
<221> NAME/KEY: misc_feature
<222> LOCATION: (131)..(140)
<223> OTHER INFORMATION: Loop Dicer 2
<220> FEATURE:
<221> NAME/KEY: misc_feature
<222> LOCATION: (164)..(173)
<223> OTHER INFORMATION: Loop Dicer 2
<220> FEATURE:
<221> NAME/KEY: misc_feature
<222> LOCATION: (221)..(230)
<223> OTHER INFORMATION: Loop Dicer 2
<220> FEATURE:
<221> NAME/KEY: misc_feature
<222> LOCATION: (254)..(324)
<223> OTHER INFORMATION: Loop PSMA
<220> FEATURE:
<221> NAME/KEY: misc_feature
<222> LOCATION: (372)..(381)
<223> OTHER INFORMATION: Loop Dicer 2
<220> FEATURE:
<221> NAME/KEY: misc_feature
<222> LOCATION: (405)..(414)
<223> OTHER INFORMATION: Loop Dicer 2
<220> FEATURE:
<221> NAME/KEY: misc_feature
<222> LOCATION: (461)..(469)
<223> OTHER INFORMATION: Loop Dicer 1
<220> FEATURE:
<221> NAME/KEY: misc_feature
<222> LOCATION: (493)..(522)
<223> OTHER INFORMATION: Loop clathrin-pit
<220> FEATURE:
<221> NAME/KEY: misc_feature
<222> LOCATION: (571)..(579)
<223> OTHER INFORMATION: Loop Dicer 1
<220> FEATURE:
<221> NAME/KEY: misc_feature
<222> LOCATION: (608)..(616)
<223> OTHER INFORMATION: Loop Dicer 1
<220> FEATURE:
<221> NAME/KEY: misc_feature
<222> LOCATION: (667)..(675)
<223> OTHER INFORMATION: Loop Dicer 1
<220> FEATURE:
<221> NAME/KEY: misc_feature
<222> LOCATION: (699)..(769)
<223> OTHER INFORMATION: Loop PSMA
<220> FEATURE:
<221> NAME/KEY: misc_feature
<222> LOCATION: (821)..(829)
<223> OTHER INFORMATION: Loop Dicer 1
<220> FEATURE:
<221> NAME/KEY: misc_feature
```

```
<222> LOCATION: (856)..(864)
<223> OTHER INFORMATION: Loop Dicer 1
<220> FEATURE:
<221> NAME/KEY: misc_feature
<222> LOCATION: (915)..(923)
<223> OTHER INFORMATION: Loop Dicer 1
<220> FEATURE:
<221> NAME/KEY: misc_feature
<222> LOCATION: (948)..(977)
<223> OTHER INFORMATION: Loop clathrin-pit
<220> FEATURE:
<221> NAME/KEY: misc_feature
<222> LOCATION: (1002)..(1003)
<223> OTHER INFORMATION: Linkage component
<220> FEATURE:
<221> NAME/KEY: misc_feature
<222> LOCATION: (1030)..(1039)
<223> OTHER INFORMATION: Loop Dicer 3
<220> FEATURE:
<221> NAME/KEY: misc_feature
<222> LOCATION: (1066)..(1136)
<223> OTHER INFORMATION: Loop PSMA
<220> FEATURE:
<221> NAME/KEY: misc_feature
<222> LOCATION: (1165)..(1166)
<223> OTHER INFORMATION: Linkage component
<220> FEATURE:
<221> NAME/KEY: misc_feature
<222> LOCATION: (1193)..(1201)
<223> OTHER INFORMATION: Loop Dicer 1
<220> FEATURE:
<221> NAME/KEY: misc_feature
<222> LOCATION: (1228)..(1236)
<223> OTHER INFORMATION: Loop Dicer 1
<220> FEATURE:
<221> NAME/KEY: misc_feature
<222> LOCATION: (1266)..(1267)
<223> OTHER INFORMATION: Linkage component

<400> SEQUENCE: 21
caaaggcagc cgucagucca ucucaagaaa cgaugggcug acauucauag ccguuccuc      60 uauccguucu aaacgcuuua ugaugcggcu gugaagguug cuuuugaccg ccggaggug    120 cugcgcuuug ggaucuuauu caaggugcag cucucauuuc cuuggaucuu auuaaggaag   180
ugagaacuuc ucggcgacca cugaggucaa uguggacgga ggaucuuauu uucguccaca   240
ucgagcacuu uaugggagga cgaugcggau cagccauguu uacgcacucu cuugucaauc   300
cucaucggca gacgacucgc ccgaauaagg ugcuugugge uucagugacc cuuucucaga   360
guaagggaga aggaucuuau uuucuccccuu gcaacaagua agacggaucu auugucuug   420 uuuguucuga gagaggacca gcuuccacau gugagagagc ucaagaaacg cucucucgca   480
auaggcugcu uguccucua uccguucuaa acgcuuuaug auuaaguagc uuaugugga    540 gcugacgugu guucuagucu uugguggue ucaagaaacg aaccaccaga gaaacagugu    600
aguugacuca agaaacguca auuacauugg cuagaacaua caccugcuuc uugaggccgu   660
cguguuucaa gaaacaacac ggcgguuugu uccgcaggg gaggacgaug cggaucagcc    720
auguuuacgu cacuccuugu caauccucau cggcagacga cucgcccgau ugcgaaaaua   780
uuuaaggagc ggacggcuga gaguagccga cugaguuugc ucaagaaacg caaacucagu   840
ugaaaugguu gcgcuucaag aaacagugca aucauuucug cucucggcca cagaggcggu   900 cguggggucug gcucucaaga aacgaguuag gcccuaucgg cugcgcuuuc cucuauccgu   960
ucuaaacgcu uuaugauggc guagcggagc cggcugccuc uacaaagucu cgugcagaag   1020
aagaucacgu ucauagagac gugaucuucu ucccagugau accuugggag gacgaugcgg   1080
aucagccaug uuuacgucac uccuugucaa uccucaucgg cagacgacuc gcccgaaagg   1140
```
ugucacuggg uuguacggga cuuuaccuug gcguugucag aaauugguuuc agucaagaaa    1200 cuugaaacca uuucuguagu ugacagauca agaaacucug ucaauuacau uggcgacgcc    1260
aaguuac                                                              1267

<210> SEQ ID NO 22
<211> LENGTH: 26
<212> TYPE: RNA
<213> ORGANISM: Artificial Sequence
<220> FEATURE:
<223> OTHER INFORMATION: Close component

<400> SEQUENCE: 22
cugguuggug uggaacccua uuuccc                                         26

<210> SEQ ID NO 23
<211> LENGTH: 23
<212> TYPE: DNA
<213> ORGANISM: Artificial Sequence
<220> FEATURE:
<223> OTHER INFORMATION: T7 transcription start site
<220> FEATURE:
<221> NAME/KEY: misc_feature
<222> LOCATION: (23)..(23)
<223> OTHER INFORMATION: n is a, c, g, or t

<400> SEQUENCE: 23
aattaatacg actcactata ggn                                            23

<210> SEQ ID NO 24
<211> LENGTH: 1379
<212> TYPE: DNA
<213> ORGANISM: Artificial Sequence
<220> FEATURE:
<223> OTHER INFORMATION: Prostate cancer nanoparticle - DNA
      transcription template
<220> FEATURE:
<221> NAME/KEY: misc_feature
<222> LOCATION: (4)..(22)
<223> OTHER INFORMATION: EcoRI restriction site/T7 transcription start
      site
<220> FEATURE:
<221> NAME/KEY: misc_feature
<222> LOCATION: (48)..(56)
<223> OTHER INFORMATION: Loop Dicer 1
<220> FEATURE:
<221> NAME/KEY: misc_feature
<222> LOCATION: (84)..(85)
<223> OTHER INFORMATION: Linkage component
<220> FEATURE:
<221> NAME/KEY: misc_feature
<222> LOCATION: (108)..(116)
<223> OTHER INFORMATION: Loop Dicer 1
<220> FEATURE:
<221> NAME/KEY: misc_feature
<222> LOCATION: (140)..(169)
<223> OTHER INFORMATION: Loop clathrin-pit
<220> FEATURE:
<221> NAME/KEY: misc_feature
<222> LOCATION: (192)..(193)
<223> OTHER INFORMATION: Linkage component
<220> FEATURE:
<221> NAME/KEY: misc_feature
<222> LOCATION: (216)..(225)
<223> OTHER INFORMATION: Loop Dicer 2
<220> FEATURE:
<221> NAME/KEY: misc_feature
<222> LOCATION: (249)..(258)
<223> OTHER INFORMATION: Loop Dicer 2
<220> FEATURE:
<221> NAME/KEY: misc_feature
<222> LOCATION: (282)..(283)
<223> OTHER INFORMATION: Linkage component -continued

```
<220> FEATURE:
<221> NAME/KEY: misc_feature
<222> LOCATION: (306)..(315)
<223> OTHER INFORMATION: Loop Dicer 2
<220> FEATURE:
<221> NAME/KEY: misc_feature
<222> LOCATION: (339)..(409)
<223> OTHER INFORMATION: Loop PSMA
<220> FEATURE:
<221> NAME/KEY: misc_feature
<222> LOCATION: (433)..(434)
<223> OTHER INFORMATION: Linkage component
<220> FEATURE:
<221> NAME/KEY: misc_feature
<222> LOCATION: (457)..(466)
<223> OTHER INFORMATION: Loop Dicer 2
<220> FEATURE:
<221> NAME/KEY: misc_feature
<222> LOCATION: (490)..(499)
<223> OTHER INFORMATION: Loop Dicer 2
<220> FEATURE:
<221> NAME/KEY: misc_feature
<222> LOCATION: (522)..(523)
<223> OTHER INFORMATION: Linkage component
<220> FEATURE:
<221> NAME/KEY: misc_feature
<222> LOCATION: (546)..(554)
<223> OTHER INFORMATION: Loop Dicer 1
<220> FEATURE:
<221> NAME/KEY: misc_feature
<222> LOCATION: (578)..(607)
<223> OTHER INFORMATION: Loop clathrin-pit
<220> FEATURE:
<221> NAME/KEY: misc_feature
<222> LOCATION: (630)..(631)
<223> OTHER INFORMATION: Linkage component
<220> FEATURE:
<221> NAME/KEY: misc_feature
<222> LOCATION: (656)..(664)
<223> OTHER INFORMATION: Loop Dicer 1
<220> FEATURE:
<221> NAME/KEY: misc_feature
<222> LOCATION: (693)..(701)
<223> OTHER INFORMATION: Loop Dicer 1
<220> FEATURE:
<221> NAME/KEY: misc_feature
<222> LOCATION: (727)..(728)
<223> OTHER INFORMATION: Linkage component
<220> FEATURE:
<221> NAME/KEY: misc_feature
<222> LOCATION: (752)..(760)
<223> OTHER INFORMATION: Loop Dicer 1
<220> FEATURE:
<221> NAME/KEY: misc_feature
<222> LOCATION: (784)..(854)
<223> OTHER INFORMATION: Loop PSMA
<220> FEATURE:
<221> NAME/KEY: misc_feature
<222> LOCATION: (878)..(879)
<223> OTHER INFORMATION: Linkage component
<220> FEATURE:
<221> NAME/KEY: misc_feature
<222> LOCATION: (906)..(914)
<223> OTHER INFORMATION: Loop Dicer 1
<220> FEATURE:
<221> NAME/KEY: misc_feature
<222> LOCATION: (940)..(948)
<223> OTHER INFORMATION: Loop Dicer 1
<220> FEATURE:
<221> NAME/KEY: misc_feature
<222> LOCATION: (975)..(976)
<223> OTHER INFORMATION: Linkage component
<220> FEATURE:
<221> NAME/KEY: misc_feature
<222> LOCATION: (1000)..(1008)
<223> OTHER INFORMATION: Loop Dicer 1
<220> FEATURE:
<221> NAME/KEY: misc_feature
<222> LOCATION: (1033)..(1062)
```

```
<223> OTHER INFORMATION: Loop clathrin-pit
<220> FEATURE:
<221> NAME/KEY: misc_feature
<222> LOCATION: (1087)..(1088)
<223> OTHER INFORMATION: Linkage component
<220> FEATURE:
<221> NAME/KEY: misc_feature
<222> LOCATION: (1115)..(1124)
<223> OTHER INFORMATION: Loop Dicer 3
<220> FEATURE:
<221> NAME/KEY: misc_feature
<222> LOCATION: (1151)..(1221)
<223> OTHER INFORMATION: Loop PSMA
<220> FEATURE:
<221> NAME/KEY: misc_feature
<222> LOCATION: (1250)..(1251)
<223> OTHER INFORMATION: Linkage component
<220> FEATURE:
<221> NAME/KEY: misc_feature
<222> LOCATION: (1278)..(1286)
<223> OTHER INFORMATION: Loop Dicer 1
<220> FEATURE:
<221> NAME/KEY: misc_feature
<222> LOCATION: (1313)..(1321)
<223> OTHER INFORMATION: Loop Dicer 1
<220> FEATURE:
<221> NAME/KEY: misc_feature
<222> LOCATION: (1351)..(1352)
<223> OTHER INFORMATION: Linkage component

<400> SEQUENCE: 24
aattaatacg actcactata ggggaaatag ggtttccaat gctttgctca agaaacgcaa      60
agtattggag ccacaccaac cagaccaaag gcagccgtca gtccatctca agaaacgatg     120
ggctgacatt catagccgtt tcctctatcc gttctaaacg ctttatgatg cggctgtgaa     180
ggttgctttt gaccgccggg aggtgctgcg ctttgggatc ttattcaagg tgcagctctc     240
atttccttgg atcttattaa ggaagtgaga acttctcggc gaccactgag gtcaatgtgg     300
acggaggatc ttattttcgt ccacatcgag cactttatgg gaggacgatg cggatcagcc     360
atgtttacgt cactccttgt caatcctcat cggcagacga ctcgcccgaa taaggtgctt     420
gtggcttcag tgaccctttc tcagagtaag ggagaaggat cttatttcct cccttgcaac     480
aagtaagacg gatcttattg tcttgtttgt tctgagagag gaccagcttc cacatgtgag     540
agagctcaag aaacgctctc tcgcaatagg ctgcttgttc ctctatccgt tctaaacgct     600
ttatgattaa gtagcttatg tgggagctga cgtgtgttct agtctttggt ggttctcaag     660
aaacgaacca ccagagaaac agtgtagttg actcaagaaa cgtcaattac attggctaga     720
acatacacct gcttcttgag gccgtcgtgt ttcaagaaac aacacggcgg tttgtttccg     780
caggggagga cgatgcggat cagccatgtt tacgtcactc cttgtcaatc ctcatcggca     840
gacgactcgc ccgattgcgg aaatatttaa ggagcggacg gctgagagta gccgactgag     900
tttgctcaag aaacgcaaac tcagttgaaa tggttgcgct tcaagaaaca gtgcaatcat     960
ttctgctctc ggccacagag gcggtcgtgg gtctggctct caagaaacga gttaggccct    1020
atctgctgcg ctttcctcta tccgttctaa acgctttatg atggcgtagc ggagccggct    1080
gcctctacaa agtctcgtgc agaagaagat cacgttcata gagacgtgat cttcttccca    1140
gtgataccct gggaggacga tgcggatcag ccatgtttac gtcactcctt gtcaatcctc    1200
atcggcagac gactcgcccg aaaggtgtca ctgggttgta cgggactttta ccttggcgtt    1260 gtcagaaatg gtttcagtca agaaacttga accatttct gtagttgaca gatcaagaaa    1320
ctctgtcaat tacattggcg acgccaagtt acctggttgg tgtggaaccc tatttccct    1379
```

```
<210> SEQ ID NO 25
<211> LENGTH: 1358
<212> TYPE: RNA
<213> ORGANISM: Artificial Sequence
<220> FEATURE:
<223> OTHER INFORMATION: Prostate cancer dodecahedron polynucleotide
      nanoparticle - RNA transcript
<220> FEATURE:
<221> NAME/KEY: misc_feature
<222> LOCATION: (27)..(35)
<223> OTHER INFORMATION: loop dicer 1
<220> FEATURE:
<221> NAME/KEY: misc_feature
<222> LOCATION: (87)..(95)
<223> OTHER INFORMATION: loop dicer 1
<220> FEATURE:
<221> NAME/KEY: misc_feature
<222> LOCATION: (119)..(148)
<223> OTHER INFORMATION: loop clathrin-pit
<220> FEATURE:
<221> NAME/KEY: misc_feature
<222> LOCATION: (195)..(204)
<223> OTHER INFORMATION: loop dicer 2
<220> FEATURE:
<221> NAME/KEY: misc_feature
<222> LOCATION: (228)..(237)
<223> OTHER INFORMATION: loop dicer 2
<220> FEATURE:
<221> NAME/KEY: misc_feature
<222> LOCATION: (285)..(294)
<223> OTHER INFORMATION: loop dicer 2
<220> FEATURE:
<221> NAME/KEY: misc_feature
<222> LOCATION: (318)..(388)
<223> OTHER INFORMATION: loop PSMA
<220> FEATURE:
<221> NAME/KEY: misc_feature
<222> LOCATION: (436)..(445)
<223> OTHER INFORMATION: loop dicer 2
<220> FEATURE:
<221> NAME/KEY: misc_feature
<222> LOCATION: (469)..(478)
<223> OTHER INFORMATION: loop dicer 2
<220> FEATURE:
<221> NAME/KEY: misc_feature
<222> LOCATION: (525)..(533)
<223> OTHER INFORMATION: loop dicer 1
<220> FEATURE:
<221> NAME/KEY: misc_feature
<222> LOCATION: (557)..(586)
<223> OTHER INFORMATION: loop clathrin-pit
<220> FEATURE:
<221> NAME/KEY: misc_feature
<222> LOCATION: (635)..(643)
<223> OTHER INFORMATION: loop dicer 1
<220> FEATURE:
<221> NAME/KEY: misc_feature
<222> LOCATION: (672)..(680)
<223> OTHER INFORMATION: loop dicer 1
<220> FEATURE:
<221> NAME/KEY: misc_feature
<222> LOCATION: (731)..(739)
<223> OTHER INFORMATION: loop dicer 1
<220> FEATURE:
<221> NAME/KEY: misc_feature
<222> LOCATION: (763)..(833)
<223> OTHER INFORMATION: loop PSMA
<220> FEATURE:
<221> NAME/KEY: misc_feature
<222> LOCATION: (885)..(893)
<223> OTHER INFORMATION: loop dicer 1
<220> FEATURE:
<221> NAME/KEY: misc_feature
<222> LOCATION: (920)..(928)
<223> OTHER INFORMATION: loop dicer 1
<220> FEATURE:
<221> NAME/KEY: misc_feature
<222> LOCATION: (979)..(987)
<223> OTHER INFORMATION: loop dicer 1
```

```
<220> FEATURE:
<221> NAME/KEY: misc_feature
<222> LOCATION: (1012)..(1041)
<223> OTHER INFORMATION: loop clathrin-pit
<220> FEATURE:
<221> NAME/KEY: misc_feature
<222> LOCATION: (1094)..(1103)
<223> OTHER INFORMATION: loop dicer 1
<220> FEATURE:
<221> NAME/KEY: misc_feature
<222> LOCATION: (1130)..(1200)
<223> OTHER INFORMATION: loop PSMA
<220> FEATURE:
<221> NAME/KEY: misc_feature
<222> LOCATION: (1257)..(1265)
<223> OTHER INFORMATION: loop dicer 1
<220> FEATURE:
<221> NAME/KEY: misc_feature
<222> LOCATION: (1292)..(1300)
<223> OTHER INFORMATION: loop dicer 1

<400> SEQUENCE: 25
```

| | | | | | |
|---|---|---|---|---|---|
| gggaaauagg | guuuccaaug | cuuugcucaa | gaaacgcaaa | guauuggagc | cacaccaacc | 60 |
| agaccaaagg | cagccgucag | uccaucucaa | gaaacgaugg | gcugacauuc | auagccguuu | 120 |
| ccucuauccg | uucuaaacgc | uuuaugaugc | ggcugugaag | guugcuuuug | accgccggga | 180 |
| ggugcugcgc | uuugggaucu | uauucaaggu | gcagcucuca | uuccuugga | ucuuauuaag | 240 |
| gaagugagaa | cuucucggcg | accacugagg | ucaaugugga | cggaggaucu | uauuucguc | 300 |
| cacaucgagc | acuuuauggg | aggacgaugc | ggaucagcca | uguuuacguc | acuccuuguc | 360 |
| aauccucauc | ggcagacgac | ucgcccgaau | aaggugcuug | uggcuucagu | gacccuuucu | 420 |
| cagaguaagg | gagaaggauc | uuauuuucuc | ccuugcaaca | aguaagacgg | aucuuauugu | 480 |
| cuuguuuguu | cugagagagg | accagcuucc | acaugugaga | gagcucaaga | aacgcucucu | 540 |
| cgcaauaggc | ugcuuguucc | ucuauccguu | cuaaacgcuu | uaugauuaag | uagcuuaugu | 600 |
| gggagcugac | guguguucua | gucuuuggug | guucucaaga | aacgaaccac | cagagaaaca | 660 |
| guguaguuga | cucaagaaac | gucaauuaca | uuggcuagaa | cauacaccug | cuucuugagg | 720 |
| ccgucuguu | ucaagaaaca | acacggcggu | uuguuuccgc | aggggaggac | gaugcggauc | 780 |
| agccauguuu | acgucacucc | uugucaauuc | ucaucggcag | acgacucgcc | cgauugcgga | 840 |
| aauauuuaag | gagcggacgg | cugagaguag | ccgacugagu | uugcucaaga | aacgcaaacu | 900 |
| caguugaaau | gguugcgcuu | caagaaacag | ugcaaucauu | ucugcucucg | gccacagagg | 960 |
| cggucguggg | ucuggcucuc | aagaaacgag | uuaggcccua | ucugcugcgc | uuccucuau | 1020 |
| ccguucuaaa | cgcuuuauga | uggcguagcg | gagccggcug | ccucuacaaa | gucucgugca | 1080 |
| gaagaagauc | acguucauag | agacgugauc | uucuucccag | ugauaccuug | ggaggacgau | 1140 |
| gcggaucagc | cauguuuacg | ucacuccuug | ucaauccuca | ucggcagacg | acucgcccga | 1200 |
| aaggugucac | ugggugauac | gggacuuuac | cuuggcguug | ucagaaaugg | uuucagucaa | 1260 |
| gaaacuugaa | accauuucug | uaguugacag | aucaagaaac | ucugucaauu | acauuggcga | 1320 |
| cgccaaguua | ccugguuggu | guggaacccu | auuucccu | | | 1358 |

```
<210> SEQ ID NO 26
<211> LENGTH: 895
<212> TYPE: RNA
<213> ORGANISM: Artificial Sequence
<220> FEATURE:
<223> OTHER INFORMATION: Increased molarity nanoparticle
<220> FEATURE:
<221> NAME/KEY: misc_feature
<222> LOCATION: (27)..(35)
```

```
<223> OTHER INFORMATION: loop dicer 1
<220> FEATURE:
<221> NAME/KEY: misc_feature
<222> LOCATION: (62)..(70)
<223> OTHER INFORMATION: loop dicer 1
<220> FEATURE:
<221> NAME/KEY: misc_feature
<222> LOCATION: (96)..(97)
<223> OTHER INFORMATION: linkage component
<220> FEATURE:
<221> NAME/KEY: misc_feature
<222> LOCATION: (124)..(133)
<223> OTHER INFORMATION: loop dicer 3
<220> FEATURE:
<221> NAME/KEY: misc_feature
<222> LOCATION: (160)..(168)
<223> OTHER INFORMATION: loop dicer 1
<220> FEATURE:
<221> NAME/KEY: misc_feature
<222> LOCATION: (197)..(198)
<223> OTHER INFORMATION: linkage component
<220> FEATURE:
<221> NAME/KEY: misc_feature
<222> LOCATION: (225)..(233)
<223> OTHER INFORMATION: loop dicer 1
<220> FEATURE:
<221> NAME/KEY: misc_feature
<222> LOCATION: (260)..(268)
<223> OTHER INFORMATION: loop dicer 1
<220> FEATURE:
<221> NAME/KEY: misc_feature
<222> LOCATION: (298)..(299)
<223> OTHER INFORMATION: linkage component
<220> FEATURE:
<221> NAME/KEY: misc_feature
<222> LOCATION: (326)..(335)
<223> OTHER INFORMATION: loop dicer 3
<220> FEATURE:
<221> NAME/KEY: misc_feature
<222> LOCATION: (362)..(370)
<223> OTHER INFORMATION: loop dicer 1
<220> FEATURE:
<221> NAME/KEY: misc_feature
<222> LOCATION: (399)..(400)
<223> OTHER INFORMATION: linkage component
<220> FEATURE:
<221> NAME/KEY: misc_feature
<222> LOCATION: (427)..(435)
<223> OTHER INFORMATION: loop dicer 1
<220> FEATURE:
<221> NAME/KEY: misc_feature
<222> LOCATION: (462)..(470)
<223> OTHER INFORMATION: loop dicer 1
<220> FEATURE:
<221> NAME/KEY: misc_feature
<222> LOCATION: (500)..(501)
<223> OTHER INFORMATION: linkage component
<220> FEATURE:
<221> NAME/KEY: misc_feature
<222> LOCATION: (528)..(536)
<223> OTHER INFORMATION: loop dicer 1
<220> FEATURE:
<221> NAME/KEY: misc_feature
<222> LOCATION: (563)..(571)
<223> OTHER INFORMATION: loop dicer 1
<220> FEATURE:
<221> NAME/KEY: misc_feature
<222> LOCATION: (597)..(598)
<223> OTHER INFORMATION: linkage component
<220> FEATURE:
<221> NAME/KEY: misc_feature
<222> LOCATION: (625)..(633)
<223> OTHER INFORMATION: loop dicer 1
<220> FEATURE:
<221> NAME/KEY: misc_feature
<222> LOCATION: (660)..(668)
<223> OTHER INFORMATION: loop dicer 1
<220> FEATURE:
<221> NAME/KEY: misc_feature
```

-continued

```
<222> LOCATION: (698)..(699)
<223> OTHER INFORMATION: linkage component
<220> FEATURE:
<221> NAME/KEY: misc_feature
<222> LOCATION: (726)..(734)
<223> OTHER INFORMATION: loop dicer 1
<220> FEATURE:
<221> NAME/KEY: misc_feature
<222> LOCATION: (761)..(769)
<223> OTHER INFORMATION: loop dicer 1
<220> FEATURE:
<221> NAME/KEY: misc_feature
<222> LOCATION: (795)..(796)
<223> OTHER INFORMATION: linkage component
<220> FEATURE:
<221> NAME/KEY: misc_feature
<222> LOCATION: (823)..(832)
<223> OTHER INFORMATION: loop dicer 3
<220> FEATURE:
<221> NAME/KEY: misc_feature
<222> LOCATION: (859)..(867)
<223> OTHER INFORMATION: loop dicer 1

<400> SEQUENCE: 26
ggcugagagu agccgacuga guuugcucaa gaaacgcaaa cucaguugaa augguugcgc      60
uucaagaaac agugcaauca uuucugcucu cggccacaaa gucucgugca gaagaagauc     120
acguucauag agacgugauc uucucccag ugauaccuuu caagaaacaa ggugucacug      180
gguuguacgg gacuuuaccu uggcguuguc agaaaugguu ucagcaaga aacuugaaac     240 cauuucugua guugacagau caagaaacuc ugucaauuac auuggcgacg ccaaguuaca     300
aagucucgug cagaagaaga ucacguucau agagacguga ucuucuuccc agugauaccu     360
uucaagaaac aaggugucac ugggguuguac gggacuuuac cuuggcguug ucagaaaugg    420
uuucagucaa gaaacuugaa accauuucug uaguugacag aucaagaaac ucugucaauu    480
acauuggcga cgccaaguua cggcugagag uagccgacug aguuugcuca agaaacgcaa    540
acucaguuga aauugguugcg cuucaagaaa cagugcaauc auuucugcuc ucggccaccu   600
uggcguuguc agaaaugguu ucagucaaga aacuugaaac cauuucugua guugacagau    660
caagaaacuc ugucaauuac auuggcgacg ccaaguuacg gcugagagua gccgacugag    720
uuugcucaag aaacgcaaac ucaguugaaa ugguugcgcu ucaagaaaca gugcaaucau    780
uucugcucuc ggccacaaag ucucgugcag aagaagauca cguucauaga gacgugaucu    840
ucuucccagu gauaccuuuc aagaaacaag gugucacugg guuguacggg acuuu         895
```

```
<210> SEQ ID NO 27
<211> LENGTH: 987
<212> TYPE: RNA
<213> ORGANISM: Artificial Sequence
<220> FEATURE:
<223> OTHER INFORMATION: Nanoparticle sequence
<220> FEATURE:
<221> NAME/KEY: misc_feature
<222> LOCATION: (27)..(35)
<223> OTHER INFORMATION: loop dicer 1
<220> FEATURE:
<221> NAME/KEY: misc_feature
<222> LOCATION: (63)..(64)
<223> OTHER INFORMATION: linkage component
<220> FEATURE:
<221> NAME/KEY: misc_feature
<222> LOCATION: (91)..(99)
<223> OTHER INFORMATION: loop dicer 1
<220> FEATURE:
<221> NAME/KEY: misc_feature
<222> LOCATION: (126)..(134)
<223> OTHER INFORMATION: loop dicer 1
<220> FEATURE:
```

```
-continued

<221> NAME/KEY: misc_feature
<222> LOCATION: (160)..(161)
<223> OTHER INFORMATION: linkage component
<220> FEATURE:
<221> NAME/KEY: misc_feature
<222> LOCATION: (188)..(197)
<223> OTHER INFORMATION: loop dicer 3
<220> FEATURE:
<221> NAME/KEY: misc_feature
<222> LOCATION: (224)..(232)
<223> OTHER INFORMATION: loop dicer 1
<220> FEATURE:
<221> NAME/KEY: misc_feature
<222> LOCATION: (261)..(262)
<223> OTHER INFORMATION: linkage component
<220> FEATURE:
<221> NAME/KEY: misc_feature
<222> LOCATION: (289)..(297)
<223> OTHER INFORMATION: loop dicer 1
<220> FEATURE:
<221> NAME/KEY: misc_feature
<222> LOCATION: (324)..(332)
<223> OTHER INFORMATION: loop dicer 1
<220> FEATURE:
<221> NAME/KEY: misc_feature
<222> LOCATION: (362)..(363)
<223> OTHER INFORMATION: linkage component
<220> FEATURE:
<221> NAME/KEY: misc_feature
<222> LOCATION: (390)..(399)
<223> OTHER INFORMATION: loop dicer 3
<220> FEATURE:
<221> NAME/KEY: misc_feature
<222> LOCATION: (426)..(434)
<223> OTHER INFORMATION: loop dicer 1
<220> FEATURE:
<221> NAME/KEY: misc_feature
<222> LOCATION: (463)..(464)
<223> OTHER INFORMATION: linkage component
<220> FEATURE:
<221> NAME/KEY: misc_feature
<222> LOCATION: (491)..(499)
<223> OTHER INFORMATION: loop dicer 1
<220> FEATURE:
<221> NAME/KEY: misc_feature
<222> LOCATION: (526)..(534)
<223> OTHER INFORMATION: loop dicer 1
<220> FEATURE:
<221> NAME/KEY: misc_feature
<222> LOCATION: (564)..(565)
<223> OTHER INFORMATION: linkage component
<220> FEATURE:
<221> NAME/KEY: misc_feature
<222> LOCATION: (592)..(600)
<223> OTHER INFORMATION: loop dicer 1
<220> FEATURE:
<221> NAME/KEY: misc_feature
<222> LOCATION: (627)..(635)
<223> OTHER INFORMATION: loop dicer 1
<220> FEATURE:
<221> NAME/KEY: misc_feature
<222> LOCATION: (661)..(663)
<223> OTHER INFORMATION: linkage component
<220> FEATURE:
<221> NAME/KEY: misc_feature
<222> LOCATION: (689)..(697)
<223> OTHER INFORMATION: loop dicer 1
<220> FEATURE:
<221> NAME/KEY: misc_feature
<222> LOCATION: (724)..(732)
<223> OTHER INFORMATION: loop dicer 1
<220> FEATURE:
<221> NAME/KEY: misc_feature
<222> LOCATION: (762)..(763)
<223> OTHER INFORMATION: linkage component
<220> FEATURE:
<221> NAME/KEY: misc_feature
<222> LOCATION: (790)..(798)
<223> OTHER INFORMATION: loop dicer 1
```

<220> FEATURE:
<221> NAME/KEY: misc_feature
<222> LOCATION: (825)..(833)
<223> OTHER INFORMATION: loop dicer 1
<220> FEATURE:
<221> NAME/KEY: misc_feature
<222> LOCATION: (859)..(860)
<223> OTHER INFORMATION: linkage component
<220> FEATURE:
<221> NAME/KEY: misc_feature
<222> LOCATION: (887)..(896)
<223> OTHER INFORMATION: loop dicer 3
<220> FEATURE:
<221> NAME/KEY: misc_feature
<222> LOCATION: (923)..(931)
<223> OTHER INFORMATION: loop dicer 1
<220> FEATURE:
<221> NAME/KEY: misc_feature
<222> LOCATION: (960)..(961)
<223> OTHER INFORMATION: linkage component

<400> SEQUENCE: 27

```
gggaauuagg guuccaaug cuuugcucaa gaaacgcaaa guauuggagc cacaccaacc      60
agacggcuga gaguagccga cugaguuugc ucaagaaacg caaacucagu ugaaaugguu    120
gcgcuucaag aaacagugca aucauuucug cucucggcca caaagucucg ugcagaagaa    180
gaucacguuc auagagacgu gaucuucuuc ccagugauac cuuucaagaa acaaggguguc   240
acugguugu  acgggacuuu accuuggcgu ugucagaaau gguuucaguc aagaaacuug    300
aaaccauuuc uguaguugac agaucaagaa acucugucaa uuacauuggc gacgccaagu    360
uacaaagucu cgugcagaag aagaucacgu ucauagagac gugaucuucu ucccagugau    420
accuuucaag aaacaaggug ucacuggguu guacgggacu uuaccuuggc guugucagaa    480
augguuucag ucaagaaacu ugaaaccauu ucuguaguug acagaucaag aaacucuguc    540
aauuacauug gcgacgccaa guuacggcug agaguagccg acgaguuug cucaagaaac     600
gcaaacucag uugaaaugguu ugcgcuucaa gaaacagugc aaucauuucu gcucucggcc   660
accuuggcgu ugucagaaau gguuucaguc aagaaacuug aaaccauuuc uguaguugac    720
agaucaagaa acucugucaa uuacauuggc gacgccaagu uacggcugag aguagccgac    780
ugaguuugcu caagaaacgc aaacucaguu gaaaugguu cgcuucaaga acagugcaa     840
ucauuucugc ucucggccac aaagucucgu gcagaagaag aucacguuca uagagacgug    900
aucuucuucc cagugauacc uuucaagaaa caaggguuca cuggguugua cgggacuuua    960
ccugguuggu guggaacccu auuuccc                                       987
```

<210> SEQ ID NO 28
<211> LENGTH: 246
<212> TYPE: DNA
<213> ORGANISM: Artificial Sequence
<220> FEATURE:
<223> OTHER INFORMATION: 5' end of cyclase ribozyme sequence w/ T7
      transcription start site
<220> FEATURE:
<221> NAME/KEY: misc_feature
<222> LOCATION: (1)..(23)
<223> OTHER INFORMATION: EcoRI site/T7 transcription start site

<400> SEQUENCE: 28

```
aattaatacg actcactata ggggaaaatt tcgtctggat tagttactta tcgtgtaaaa    60
tctgataaat ggaattggtt ctacataaat gcctaacgac tatcccttttg gggagtaggg  120
tcaagtgact cgaaacgata gacaacttgc tttaacaagt tggagatata gtctgctctg   180
catggtgaca tgcagctgga tataattccg gggtaagatt aacgaccttta tctgaacata  240
``` atgcta 246

<210> SEQ ID NO 29
<211> LENGTH: 173
<212> TYPE: DNA
<213> ORGANISM: Artificial Sequence
<220> FEATURE:
<223> OTHER INFORMATION: 3' end of cyclase ribozyme sequence

<400> SEQUENCE: 29
catgtcaatt gaggcctgag tataaggtga cttatacttg taatctatct aaacggggaa    60
cctctctagt agacaatccc gtgctaaatt gtaggactgc cctttaataa atacttctat   120
atttaaagag gtatttatga aaagcggaat ttatcagatt aaaaatactt tct          173

<210> SEQ ID NO 30
<211> LENGTH: 1776
<212> TYPE: DNA
<213> ORGANISM: Artificial Sequence
<220> FEATURE:
<223> OTHER INFORMATION: prostate cancer-targeting circular dodecahedron
      nanoparticle
<220> FEATURE:
<221> NAME/KEY: misc_feature
<222> LOCATION: (1)..(22)
<223> OTHER INFORMATION: EcoRI restriction site/T7 transcription start
      site
<220> FEATURE:
<221> NAME/KEY: misc_feature
<222> LOCATION: (273)..(281)
<223> OTHER INFORMATION: loop dicer 1
<220> FEATURE:
<221> NAME/KEY: misc_feature
<222> LOCATION: (309)..(310)
<223> OTHER INFORMATION: linkage component
<220> FEATURE:
<221> NAME/KEY: misc_feature
<222> LOCATION: (333)..(341)
<223> OTHER INFORMATION: loop dicer 1
<220> FEATURE:
<221> NAME/KEY: misc_feature
<222> LOCATION: (365)..(394)
<223> OTHER INFORMATION: loop clathrin-pit
<220> FEATURE:
<221> NAME/KEY: misc_feature
<222> LOCATION: (417)..(418)
<223> OTHER INFORMATION: linkage component
<220> FEATURE:
<221> NAME/KEY: misc_feature
<222> LOCATION: (441)..(450)
<223> OTHER INFORMATION: loop dicer 2
<220> FEATURE:
<221> NAME/KEY: misc_feature
<222> LOCATION: (474)..(483)
<223> OTHER INFORMATION: loop dicer 2
<220> FEATURE:
<221> NAME/KEY: misc_feature
<222> LOCATION: (507)..(508)
<223> OTHER INFORMATION: linkage component
<220> FEATURE:
<221> NAME/KEY: misc_feature
<222> LOCATION: (531)..(540)
<223> OTHER INFORMATION: loop dicer 2
<220> FEATURE:
<221> NAME/KEY: misc_feature
<222> LOCATION: (564)..(634)
<223> OTHER INFORMATION: loop PSMA
<220> FEATURE:
<221> NAME/KEY: misc_feature
<222> LOCATION: (658)..(659)
<223> OTHER INFORMATION: linkage component
<220> FEATURE:
<221> NAME/KEY: misc_feature
<222> LOCATION: (682)..(691)

```
<223> OTHER INFORMATION: loop dicer 2
<220> FEATURE:
<221> NAME/KEY: misc_feature
<222> LOCATION: (715)..(724)
<223> OTHER INFORMATION: loop dicer 2
<220> FEATURE:
<221> NAME/KEY: misc_feature
<222> LOCATION: (747)..(748)
<223> OTHER INFORMATION: linkage component
<220> FEATURE:
<221> NAME/KEY: misc_feature
<222> LOCATION: (771)..(779)
<223> OTHER INFORMATION: loop dicer 1
<220> FEATURE:
<221> NAME/KEY: misc_feature
<222> LOCATION: (803)..(832)
<223> OTHER INFORMATION: loop clathrin-pit
<220> FEATURE:
<221> NAME/KEY: misc_feature
<222> LOCATION: (855)..(856)
<223> OTHER INFORMATION: linkage component
<220> FEATURE:
<221> NAME/KEY: misc_feature
<222> LOCATION: (881)..(889)
<223> OTHER INFORMATION: loop dicer 1
<220> FEATURE:
<221> NAME/KEY: misc_feature
<222> LOCATION: (918)..(926)
<223> OTHER INFORMATION: loop dicer 1
<220> FEATURE:
<221> NAME/KEY: misc_feature
<222> LOCATION: (952)..(953)
<223> OTHER INFORMATION: linkage component
<220> FEATURE:
<221> NAME/KEY: misc_feature
<222> LOCATION: (977)..(985)
<223> OTHER INFORMATION: loop dicer 1
<220> FEATURE:
<221> NAME/KEY: misc_feature
<222> LOCATION: (1009)..(1079)
<223> OTHER INFORMATION: loop PSMA
<220> FEATURE:
<221> NAME/KEY: misc_feature
<222> LOCATION: (1103)..(1104)
<223> OTHER INFORMATION: linkage component
<220> FEATURE:
<221> NAME/KEY: misc_feature
<222> LOCATION: (1131)..(1139)
<223> OTHER INFORMATION: loop dicer 1
<220> FEATURE:
<221> NAME/KEY: misc_feature
<222> LOCATION: (1166)..(1174)
<223> OTHER INFORMATION: loop dicer 1
<220> FEATURE:
<221> NAME/KEY: misc_feature
<222> LOCATION: (1200)..(1201)
<223> OTHER INFORMATION: linkage component
<220> FEATURE:
<221> NAME/KEY: misc_feature
<222> LOCATION: (1225)..(1233)
<223> OTHER INFORMATION: loop dicer 1
<220> FEATURE:
<221> NAME/KEY: misc_feature
<222> LOCATION: (1258)..(1287)
<223> OTHER INFORMATION: loop clathrin-pit
<220> FEATURE:
<221> NAME/KEY: misc_feature
<222> LOCATION: (1312)..(1313)
<223> OTHER INFORMATION: linkage component
<220> FEATURE:
<221> NAME/KEY: misc_feature
<222> LOCATION: (1340)..(1349)
<223> OTHER INFORMATION: loop dicer 3
<220> FEATURE:
<221> NAME/KEY: misc_feature
<222> LOCATION: (1376)..(1446)
<223> OTHER INFORMATION: loop PSMA
<220> FEATURE:
<221> NAME/KEY: misc_feature
```

```
<222> LOCATION: (1475)..(1476)
<223> OTHER INFORMATION: linkage component
<220> FEATURE:
<221> NAME/KEY: misc_feature
<222> LOCATION: (1503)..(1511)
<223> OTHER INFORMATION: loop dicer 1
<220> FEATURE:
<221> NAME/KEY: misc_feature
<222> LOCATION: (1538)..(1546)
<223> OTHER INFORMATION: loop dicer 1
<220> FEATURE:
<221> NAME/KEY: misc_feature
<222> LOCATION: (1576)..(1577)
<223> OTHER INFORMATION: linkage component
<220> FEATURE:
<221> NAME/KEY: misc_feature
<222> LOCATION: (1604)..(1608)
<223> OTHER INFORMATION: linkage component

<400> SEQUENCE: 30
aattaatacg actcactata ggggaaaatt tcgtctggat tagttactta tcgtgtaaaa      60
tctgataaat ggaattggtt ctacataaat gcctaacgac tatccctttg gggagtaggg     120
tcaagtgact cgaaacgata gacaacttgc tttaacaagt tggagatata gtctgctctg     180
catggtgaca tgcagctgga tataattccg gggtaagatt aacgacctta tctgaacata     240
atgctaggga atagggtttt ccaatgcttt gctcaagaaa cgcaaagtat tggagccaca     300
ccaaccagac caaaggcagc cgtcagtcca tctcaagaaa cgatgggctg acattcatag     360
ccgtttcctc tatccgttct aaacgcttta tgatgcggct gtgaaggttg cttttgaccg     420
ccgggaggtg ctgcgctttg ggatcttatt caaggtgcag ctctcatttc cttggatctt     480
attaaggaag tgagaacttc tcggcgacca ctgaggtcaa tgtggacgga ggatcttatt     540
ttcgtccaca tcgagcactt tatgggagga cgatgcggat cagccatgtt tacgtcactc     600
cttgtcaatc ctcatcggca gacgactcgc ccgaataagg tgcttgtggc ttcagtgacc     660
ctttctcaga gtaagggaga aggatcttat tttctcccctt gcaacaagta agacggatct     720
tattgtcttg tttgttctga gagaggacca gcttccacat gtgagagagc tcaagaaacg     780
ctctctcgca ataggctgct tgttcctcta tccgttctaa acgctttatg attaagtagc     840
ttatgtggga gctgacgtgt gttctagtct ttggtggttc tcaagaaacg aaccaccaga     900
gaaacagtgt agttgactca agaaacgtca attacattgg ctagaacata cacctgcttc     960
ttgaggccgt cgtgtttcaa gaaacaacac ggcggtttgt ttccgcaggg gaggacgatg    1020
cggatcagcc atgtttacgt cactccttgt caatcctcat cggcagacga ctcgcccgat    1080
tgcggaaata tttaaggagc ggacggctga gagtagccga ctgagtttgc tcaagaaacg    1140
caaactcagt tgaaatggtt gcgcttcaag aaacagtgca atcatttctg ctctcggcca    1200
cagaggcggt cgtgggtctg gctctcaaga acgagttag gccctatctg ctgcgctttc    1260
ctctatccgt tctaaacgct ttatgatggc gtagcggagc cggctgcctc tacaaagtct    1320
cgtgcagaag aagatcacgt tcatagagac gtgatcttct tcccagtgat accttgggag    1380
gacgatgcgg atcagccatg tttacgtcac tccttgtcaa tcctcatcgg cagacgactc    1440
gcccgaaagg tgtcactggg ttgtacggga ctttaccttg gcgttgtcag aaatggtttc    1500
agtcaagaaa cttgaaacca tttctgtagt tgacagatca agaaactctg tcaattacat    1560
tggcgacgcc aagttacctg gttggtgtgg aaccctattt ccccatgtca attgaggcct    1620
gagtataagg tgacttatac ttgtaatcta tctaaacggg gaacctctct agtagacaat    1680
cccgtgctaa attgtaggac tgcccttaa taaatacttc tatatttaaa gaggtattta    1740
```

```
tgaaaagcgg aatttatcag attaaaaata ctttct                              1776

<210> SEQ ID NO 31
<211> LENGTH: 245
<212> TYPE: DNA
<213> ORGANISM: Artificial Sequence
<220> FEATURE:
<223> OTHER INFORMATION: 5' end of cyclase ribozyme sequence w/ T7
      transcription start site

<400> SEQUENCE: 31
aattaatacg actcactata gggaaaattt cgtctggatt agttacttat cgtgtaaaat    60
ctgataaatg gaattggttc tacataaatg cctaacgact atcccttgg ggagtagggt    120 caagtgactc gaaacgatag acaacttgct ttaacaagtt ggagatatag tctgctctgc   180
atggtgacat gcagctggat ataattccgg ggtaagatta acgaccttat ctgaacataa   240
tgcta                                                                245

<210> SEQ ID NO 32
<211> LENGTH: 173
<212> TYPE: DNA
<213> ORGANISM: Artificial Sequence
<220> FEATURE:
<223> OTHER INFORMATION: 3' end of cyclase ribozyme sequence

<400> SEQUENCE: 32
catgtcaatt gaggcctgag tataaggtga cttatacttg taatctatct aaacggggaa    60
cctctctagt agacaatccc gtgctaaatt gtaggactgc cctttaataa atacttctat   120
atttaaagag gtatttatga aaagcggaat ttatcagatt aaaaatactt tct           173

<210> SEQ ID NO 33

<400> SEQUENCE: 33

000

<210> SEQ ID NO 34
<211> LENGTH: 1267
<212> TYPE: RNA
<213> ORGANISM: Artificial Sequence
<220> FEATURE:
<223> OTHER INFORMATION: Core component 1
<220> FEATURE:
<221> NAME/KEY: misc_feature
<222> LOCATION: (23)..(31)
<223> OTHER INFORMATION: loop dicer 1
<220> FEATURE:
<221> NAME/KEY: misc_feature
<222> LOCATION: (55)..(84)
<223> OTHER INFORMATION: loop clathrin-pit
<220> FEATURE:
<221> NAME/KEY: misc_feature
<222> LOCATION: (131)..(140)
<223> OTHER INFORMATION: loop dicer 2
<220> FEATURE:
<221> NAME/KEY: misc_feature
<222> LOCATION: (164)..(173)
<223> OTHER INFORMATION: loop dicer 2
<220> FEATURE:
<221> NAME/KEY: misc_feature
<222> LOCATION: (197)..(198)
<223> OTHER INFORMATION: linkage component
<220> FEATURE:
<221> NAME/KEY: misc_feature
<222> LOCATION: (221)..(230)
<223> OTHER INFORMATION: loop dicer 2
<220> FEATURE:
<221> NAME/KEY: misc_feature
```

-continued

```
<222> LOCATION: (254)..(324)
<223> OTHER INFORMATION: loop PSMA
<220> FEATURE:
<221> NAME/KEY: misc_feature
<222> LOCATION: (348)..(349)
<223> OTHER INFORMATION: linkage component
<220> FEATURE:
<221> NAME/KEY: misc_feature
<222> LOCATION: (372)..(381)
<223> OTHER INFORMATION: loop dicer 2
<220> FEATURE:
<221> NAME/KEY: misc_feature
<222> LOCATION: (405)..(414)
<223> OTHER INFORMATION: loop dicer 2
<220> FEATURE:
<221> NAME/KEY: misc_feature
<222> LOCATION: (437)..(438)
<223> OTHER INFORMATION: linkage component
<220> FEATURE:
<221> NAME/KEY: misc_feature
<222> LOCATION: (461)..(469)
<223> OTHER INFORMATION: loop dicer 1
<220> FEATURE:
<221> NAME/KEY: misc_feature
<222> LOCATION: (493)..(522)
<223> OTHER INFORMATION: loop clathrin-pit
<220> FEATURE:
<221> NAME/KEY: misc_feature
<222> LOCATION: (545)..(546)
<223> OTHER INFORMATION: linkage component
<220> FEATURE:
<221> NAME/KEY: misc_feature
<222> LOCATION: (571)..(579)
<223> OTHER INFORMATION: loop dicer 1
<220> FEATURE:
<221> NAME/KEY: misc_feature
<222> LOCATION: (608)..(616)
<223> OTHER INFORMATION: loop dicer 1
<220> FEATURE:
<221> NAME/KEY: misc_feature
<222> LOCATION: (642)..(643)
<223> OTHER INFORMATION: linkage component
<220> FEATURE:
<221> NAME/KEY: misc_feature
<222> LOCATION: (667)..(675)
<223> OTHER INFORMATION: loop dicer 1
<220> FEATURE:
<221> NAME/KEY: misc_feature
<222> LOCATION: (699)..(769)
<223> OTHER INFORMATION: loop PSMA
<220> FEATURE:
<221> NAME/KEY: misc_feature
<222> LOCATION: (793)..(794)
<223> OTHER INFORMATION: linkage component
<220> FEATURE:
<221> NAME/KEY: misc_feature
<222> LOCATION: (821)..(829)
<223> OTHER INFORMATION: loop dicer 1
<220> FEATURE:
<221> NAME/KEY: misc_feature
<222> LOCATION: (856)..(864)
<223> OTHER INFORMATION: loop dicer 1
<220> FEATURE:
<221> NAME/KEY: misc_feature
<222> LOCATION: (890)..(891)
<223> OTHER INFORMATION: linkage component
<220> FEATURE:
<221> NAME/KEY: misc_feature
<222> LOCATION: (915)..(923)
<223> OTHER INFORMATION: loop dicer 1
<220> FEATURE:
<221> NAME/KEY: misc_feature
<222> LOCATION: (948)..(977)
<223> OTHER INFORMATION: loop clathrin-pit
<220> FEATURE:
<221> NAME/KEY: misc_feature
<222> LOCATION: (1002)..(1003)
<223> OTHER INFORMATION: linkage component
<220> FEATURE:
```

```
<221> NAME/KEY: misc_feature
<222> LOCATION: (1030)..(1039)
<223> OTHER INFORMATION: loop dicer 3
<220> FEATURE:
<221> NAME/KEY: misc_feature
<222> LOCATION: (1066)..(1136)
<223> OTHER INFORMATION: loop PSMA
<220> FEATURE:
<221> NAME/KEY: misc_feature
<222> LOCATION: (1165)..(1166)
<223> OTHER INFORMATION: linkage component
<220> FEATURE:
<221> NAME/KEY: misc_feature
<222> LOCATION: (1193)..(1201)
<223> OTHER INFORMATION: loop dicer 1
<220> FEATURE:
<221> NAME/KEY: misc_feature
<222> LOCATION: (1228)..(1236)
<223> OTHER INFORMATION: loop dicer 1
<220> FEATURE:
<221> NAME/KEY: misc_feature
<222> LOCATION: (1266)..(1267)
<223> OTHER INFORMATION: linkage component

<400> SEQUENCE: 34
caaaggcagc cgucagucca ucucaagaaa cgaugggcug acauucauag ccguuccuc      60 uauccguucu aaacgcuuua ugaugcggcu gugaagguuc cuuuugaccg ccggaggug    120 cugcgcuuug ggaucuuauu caaggugcag cuccauuuc cuuggaucuu auuaaggaag   180
ugagaacuuc ucggcgacca cugaggucaa uguggacgga ggaucuuauu ucguccaca    240 ucgagcacuu uaugggagga cgaugcggau cagccauguu uacgcacuc cuugucaauc    300 cucaucggca gacgacucgc ccgaauaagg ugcuugugge uucagugacc cuuucucaga   360
guaagggaga aggaucuuau uuucucccuu gcaacaagua agacggaucu uauugucuug   420
uuuguucuga gagaggacca gcuuccacau gugagagagc ucaagaaacg cucucucgca   480
auaggcugcu uguuccucua uccguucuaa acgcuuuaug auuaaguagc uuauguggga   540 gcugacugu guucuagucu uggguugguuc ucaagaaacg aaccaccaga gaaacagugu   600
aguugacuca agaaacguca auuacauugg cuagaacaua caccugcuuc uugaggccgu   660
cguguuucaa gaaacaacac ggcgguuugu uccgcaggg gaggacgaug cggaucagcc    720
auguuuacgu cacuccuugu caauccucau cggcagacga cucgcccgau ugcggaaaua   780
uuuaaggagc ggacggcuga gaguagccga cugaguuugc ucaagaaacg caaacucagu    840
ugaaaugguu gcgcuucaag aaacagugca aucauuucug cucucggcca cagaggcggu    900
cgugggucug gcucucaaga aacgaguuag gcccuaucug cugcgcuuuc cucuauccgu    960
ucuaaacgcu uuaugauggc guagcggagc cggcugccuc uacaaagucu cgugcagaag   1020
aagaucacgu ucauagagac gugaucuucu ucccagugau accuugggag gacgaugcgg   1080
aucagccaug uuuacgucac uccuugucaa uccucaucgg cagacgacuc gcccgaaagg   1140
ugucacuggg uuguacggga cuuuaccuug gcguugucag aaaugguuc agucaagaaa    1200 cuugaaacca uuucuguagu ugacagauca agaaacucug ucaauuacau uggcgacgcc    1260
aaguuac                                                             1267

<210> SEQ ID NO 35
<211> LENGTH: 1267
<212> TYPE: RNA
<213> ORGANISM: Artificial Sequence
<220> FEATURE:
<223> OTHER INFORMATION: Core component 2
<220> FEATURE:
<221> NAME/KEY: misc_feature
```

```
<222> LOCATION: (23)..(31)
<223> OTHER INFORMATION: loop dicer 1
<220> FEATURE:
<221> NAME/KEY: misc_feature
<222> LOCATION: (55)..(84)
<223> OTHER INFORMATION: loop clathrin-pit
<220> FEATURE:
<221> NAME/KEY: misc_feature
<222> LOCATION: (131)..(140)
<223> OTHER INFORMATION: loop dicer 2
<220> FEATURE:
<221> NAME/KEY: misc_feature
<222> LOCATION: (164)..(173)
<223> OTHER INFORMATION: loop dicer 2
<220> FEATURE:
<221> NAME/KEY: misc_feature
<222> LOCATION: (197)..(198)
<223> OTHER INFORMATION: linkage component
<220> FEATURE:
<221> NAME/KEY: misc_feature
<222> LOCATION: (221)..(230)
<223> OTHER INFORMATION: loop dicer 2
<220> FEATURE:
<221> NAME/KEY: misc_feature
<222> LOCATION: (254)..(324)
<223> OTHER INFORMATION: loop PSMA
<220> FEATURE:
<221> NAME/KEY: misc_feature
<222> LOCATION: (348)..(349)
<223> OTHER INFORMATION: linkage component
<220> FEATURE:
<221> NAME/KEY: misc_feature
<222> LOCATION: (372)..(381)
<223> OTHER INFORMATION: loop dicer 2
<220> FEATURE:
<221> NAME/KEY: misc_feature
<222> LOCATION: (405)..(414)
<223> OTHER INFORMATION: loop dicer 2
<220> FEATURE:
<221> NAME/KEY: misc_feature
<222> LOCATION: (437)..(438)
<223> OTHER INFORMATION: linkage component
<220> FEATURE:
<221> NAME/KEY: misc_feature
<222> LOCATION: (461)..(469)
<223> OTHER INFORMATION: loop dicer 1
<220> FEATURE:
<221> NAME/KEY: misc_feature
<222> LOCATION: (493)..(522)
<223> OTHER INFORMATION: loop clathrin-pit
<220> FEATURE:
<221> NAME/KEY: misc_feature
<222> LOCATION: (545)..(546)
<223> OTHER INFORMATION: linkage component
<220> FEATURE:
<221> NAME/KEY: misc_feature
<222> LOCATION: (571)..(579)
<223> OTHER INFORMATION: loop dicer 1
<220> FEATURE:
<221> NAME/KEY: misc_feature
<222> LOCATION: (608)..(616)
<223> OTHER INFORMATION: loop dicer 1
<220> FEATURE:
<221> NAME/KEY: misc_feature
<222> LOCATION: (642)..(643)
<223> OTHER INFORMATION: linkage component
<220> FEATURE:
<221> NAME/KEY: misc_feature
<222> LOCATION: (667)..(675)
<223> OTHER INFORMATION: loop dicer 1
<220> FEATURE:
<221> NAME/KEY: misc_feature
<222> LOCATION: (699)..(769)
<223> OTHER INFORMATION: loop PSMA
<220> FEATURE:
<221> NAME/KEY: misc_feature
<222> LOCATION: (793)..(794)
<223> OTHER INFORMATION: linkage component
<220> FEATURE:
```

```
<221> NAME/KEY: misc_feature
<222> LOCATION: (821)..(829)
<223> OTHER INFORMATION: loop dicer 1
<220> FEATURE:
<221> NAME/KEY: misc_feature
<222> LOCATION: (856)..(864)
<223> OTHER INFORMATION: loop dicer 1
<220> FEATURE:
<221> NAME/KEY: misc_feature
<222> LOCATION: (915)..(923)
<223> OTHER INFORMATION: loop dicer 1
<220> FEATURE:
<221> NAME/KEY: misc_feature
<222> LOCATION: (948)..(977)
<223> OTHER INFORMATION: loop clathrin-pit
<220> FEATURE:
<221> NAME/KEY: misc_feature
<222> LOCATION: (1002)..(1003)
<223> OTHER INFORMATION: linkage component
<220> FEATURE:
<221> NAME/KEY: misc_feature
<222> LOCATION: (1030)..(1039)
<223> OTHER INFORMATION: loop dicer 3
<220> FEATURE:
<221> NAME/KEY: misc_feature
<222> LOCATION: (1066)..(1136)
<223> OTHER INFORMATION: loop PSMA
<220> FEATURE:
<221> NAME/KEY: misc_feature
<222> LOCATION: (1165)..(1166)
<223> OTHER INFORMATION: linkage component
<220> FEATURE:
<221> NAME/KEY: misc_feature
<222> LOCATION: (1193)..(1201)
<223> OTHER INFORMATION: loop dicer 1
<220> FEATURE:
<221> NAME/KEY: misc_feature
<222> LOCATION: (1228)..(1236)
<223> OTHER INFORMATION: loop dicer 1
<220> FEATURE:
<221> NAME/KEY: misc_feature
<222> LOCATION: (1266)..(1267)
<223> OTHER INFORMATION: linkage component

<400> SEQUENCE: 35
caaaggcagc cgucagucca ucucaagaaa cgaugggcug acauucauag ccguuccuc      60 uauccguucu aaacgcuuua ugaugcggcu gugaagguug cuuuugaccg ccggagggug    120
cugcgcuuug ggaucuuauu caaggugcag cucucauuuc cuuggaucuu auuaaggaag    180
ugagaacuuc ucggcgacca cugaggucaa uguggacgga ggaucuuauu ucguccaca     240 ucgagcacuu uaugggagga cgaugcggau cagccauguu uacgucacuc cuugucaauc    300
cucaucggca gacgacucgc ccgaauaagg ugcuugguggc uucagugacc cuuucagga    360 guaagggaga aggaucuuau uuucuccccuu gcaacaagua ugacggaucu auugucuug    420 uuuguucuga gagaggacca gcuuccacau gugagagagc ucaagaaacg cucucucgca    480
auaggcugcu uguuccucua uccguucuaa acgcuuuaug auuaaguagc uuaugugga    540 gcugacugugu uucuagucu uugguggguuuc ucaagaaacg aaccaccaga gaaacagugu   600
aguugacuca agaaacguca auuacauugg cuagaacaua caccugcuuc uugaggccgu    660
cguguuucaa gaaacaacac ggcgguuugu uccgcaggg gaggacgaug cggaucagcc     720
auguuuacgu cacuccuugu caauccucau cggcagacga cucgcccgau ugcggaaaua    780
uuuaaggagc ggacggcuga gaguagccga cugaguuugc ucaagaaacg caaacucagu    840
ugaaaugguu gcgcuucaag aaacagugca aucauuucug cucucggcca cagaggcggu    900
cgugggucug gcucucaaga aacgaguuag gcccuaucug cugcgcuuuc ucuauccgu     960 ucuaaacgcu uuaugauggc guagcggagc cggcugccuc uacaaagucu cgucagaag    1020
```

-continued

```
aagaucacgu ucauagagac gugaucuucu ucccagugau accuugggag gacgaugcgg    1080
aucagccaug uuuacgucac uccuugucaa uccucaucgg cagacgacuc gcccgaaagg    1140
ugucacuggg uuguacggga cuuuaccuug gcguugucag aaaugguuuc agucaagaaa    1200
cuugaaacca uuucuguagu ugacagauca agaaacucug ucaauuacau uggcgacgcc    1260
aaguuac                                                              1267
```

```
<210> SEQ ID NO 36
<211> LENGTH: 1267
<212> TYPE: RNA
<213> ORGANISM: Artificial Sequence
<220> FEATURE:
<223> OTHER INFORMATION: Core component 3
<220> FEATURE:
<221> NAME/KEY: misc_feature
<222> LOCATION: (23)..(31)
<223> OTHER INFORMATION: loop dicer 1
<220> FEATURE:
<221> NAME/KEY: misc_feature
<222> LOCATION: (55)..(84)
<223> OTHER INFORMATION: loop clathrin-pit
<220> FEATURE:
<221> NAME/KEY: misc_feature
<222> LOCATION: (107)..(108)
<223> OTHER INFORMATION: linkage component
<220> FEATURE:
<221> NAME/KEY: misc_feature
<222> LOCATION: (131)..(140)
<223> OTHER INFORMATION: loop dicer 2
<220> FEATURE:
<221> NAME/KEY: misc_feature
<222> LOCATION: (164)..(173)
<223> OTHER INFORMATION: loop dicer 2
<220> FEATURE:
<221> NAME/KEY: misc_feature
<222> LOCATION: (197)..(198)
<223> OTHER INFORMATION: linkage component
<220> FEATURE:
<221> NAME/KEY: misc_feature
<222> LOCATION: (221)..(230)
<223> OTHER INFORMATION: loop dicer 2
<220> FEATURE:
<221> NAME/KEY: misc_feature
<222> LOCATION: (254)..(324)
<223> OTHER INFORMATION: loop PSMA
<220> FEATURE:
<221> NAME/KEY: misc_feature
<222> LOCATION: (348)..(349)
<223> OTHER INFORMATION: linkage component
<220> FEATURE:
<221> NAME/KEY: misc_feature
<222> LOCATION: (372)..(381)
<223> OTHER INFORMATION: loop dicer 2
<220> FEATURE:
<221> NAME/KEY: misc_feature
<222> LOCATION: (405)..(414)
<223> OTHER INFORMATION: loop dicer 2
<220> FEATURE:
<221> NAME/KEY: misc_feature
<222> LOCATION: (437)..(438)
<223> OTHER INFORMATION: linkage component
<220> FEATURE:
<221> NAME/KEY: misc_feature
<222> LOCATION: (461)..(469)
<223> OTHER INFORMATION: loop dicer 1
<220> FEATURE:
<221> NAME/KEY: misc_feature
<222> LOCATION: (493)..(522)
<223> OTHER INFORMATION: loop clathrin-pit
<220> FEATURE:
<221> NAME/KEY: misc_feature
<222> LOCATION: (545)..(546)
<223> OTHER INFORMATION: linkage component
<220> FEATURE:
```

```
<221> NAME/KEY: misc_feature
<222> LOCATION: (571)..(579)
<223> OTHER INFORMATION: loop dicer 1
<220> FEATURE:
<221> NAME/KEY: misc_feature
<222> LOCATION: (608)..(616)
<223> OTHER INFORMATION: loop dicer 1
<220> FEATURE:
<221> NAME/KEY: misc_feature
<222> LOCATION: (642)..(643)
<223> OTHER INFORMATION: linkage component
<220> FEATURE:
<221> NAME/KEY: misc_feature
<222> LOCATION: (667)..(675)
<223> OTHER INFORMATION: loop dicer 1
<220> FEATURE:
<221> NAME/KEY: misc_feature
<222> LOCATION: (699)..(769)
<223> OTHER INFORMATION: loop PSMA
<220> FEATURE:
<221> NAME/KEY: misc_feature
<222> LOCATION: (793)..(794)
<223> OTHER INFORMATION: linkage component
<220> FEATURE:
<221> NAME/KEY: misc_feature
<222> LOCATION: (821)..(829)
<223> OTHER INFORMATION: loop dicer 1
<220> FEATURE:
<221> NAME/KEY: misc_feature
<222> LOCATION: (856)..(864)
<223> OTHER INFORMATION: loop dicer 1
<220> FEATURE:
<221> NAME/KEY: misc_feature
<222> LOCATION: (890)..(891)
<223> OTHER INFORMATION: linkage component
<220> FEATURE:
<221> NAME/KEY: misc_feature
<222> LOCATION: (915)..(923)
<223> OTHER INFORMATION: loop dicer 1
<220> FEATURE:
<221> NAME/KEY: misc_feature
<222> LOCATION: (948)..(977)
<223> OTHER INFORMATION: loop clathrin-pit
<220> FEATURE:
<221> NAME/KEY: misc_feature
<222> LOCATION: (1002)..(1003)
<223> OTHER INFORMATION: linkage component
<220> FEATURE:
<221> NAME/KEY: misc_feature
<222> LOCATION: (1030)..(1039)
<223> OTHER INFORMATION: loop dicer 3
<220> FEATURE:
<221> NAME/KEY: misc_feature
<222> LOCATION: (1066)..(1136)
<223> OTHER INFORMATION: loop PSMA
<220> FEATURE:
<221> NAME/KEY: misc_feature
<222> LOCATION: (1165)..(1166)
<223> OTHER INFORMATION: linkage component
<220> FEATURE:
<221> NAME/KEY: misc_feature
<222> LOCATION: (1193)..(1201)
<223> OTHER INFORMATION: loop dicer 1
<220> FEATURE:
<221> NAME/KEY: misc_feature
<222> LOCATION: (1228)..(1236)
<223> OTHER INFORMATION: loop dicer 1
<220> FEATURE:
<221> NAME/KEY: misc_feature
<222> LOCATION: (1266)..(1267)
<223> OTHER INFORMATION: linkage component

<400> SEQUENCE: 36
caaaggcagc cgucagucca ucucaagaaa cgaugggcug acauucauag ccguuccuc      60 uauccguucu aaacgcuuua ugaugcggcu gugaagguug cuuuugaccg ccgggaggug    120
cugcgcuuug ggaucuuauu caaggugcag cucucauuuc cuuggaucuu auuaaggaag    180
```

```
ugagaacuuc ucggcgacca cugaggucaa uguggacgga ggaucuuauu uucguccaca    240
ucgagcacuu uaugggagga cgaugcggau cagccauguu uacgucacuc cuugucaauc    300
cucaucggca gacgacucgc ccgaauaagg ugcuugugge uucagugacc cuuucucaga    360
guaagggaga aggaucuuau uuucuccuu gcaacaagua agacggaucu uauugucuug     420
uuuguucuga gagaggacca gcuuccacau gugagagagc ucaagaaacg cucucucgca    480
auaggcugcu uguccucua uccguucuaa acgcuuuaug auuaaguagc uuaugugga      540 gcugacugu guucuagucu uuggugguuc ucaagaaacg aaccaccaga gaaacagugu     600
aguugacuca agaaacguca auuacauugg cuagaacaua caccugcuuc uugaggccgu    660
cguguuucaa gaaacaacac ggcgguuugu uccgcaggg gaggacgaug cggaucagcc     720
auguuuacgu cacuccuugu caauccucau cggcagacga cucgcccgau ugcggaaaua    780
uuuaaggagc ggacggcuga gaguagccga cugaguuugc ucaagaaacg caaacucagu    840
ugaaaugguu gcgcuucaag aaacagugca aucauuucug cucucggcca cagaggcggu    900 cguggggucug gcucucaaga aacgaguuag gcccuaucug cugcgcuuuc cucuauccgu   960
ucuaaacgcu uuaugaugge guagcggagc cggcugccuc acaaagucu cgucagaag      1020 aagaucacgu ucauagagac gugaucuucu ucccagugau accuugggag gacgaugcgg   1080
aucagccaug uuuacgucac uccuugucaa uccucaucgg cagacgacuc gcccgaaagg    1140
ugucacuggg uuguacggga cuuuaccuug gcguugucag aaauggguuc agucaagaaa    1200
cuugaaacca uuucuguagu ugacagauca agaaacucug ucaauuacau uggcgacgcc    1260
aaguuac                                                              1267
```

```
<210> SEQ ID NO 37
<211> LENGTH: 1267
<212> TYPE: RNA
<213> ORGANISM: Artificial Sequence
<220> FEATURE:
<223> OTHER INFORMATION: Core component 4
<220> FEATURE:
<221> NAME/KEY: misc_feature
<222> LOCATION: (23)..(31)
<223> OTHER INFORMATION: loop dicer 1
<220> FEATURE:
<221> NAME/KEY: misc_feature
<222> LOCATION: (55)..(84)
<223> OTHER INFORMATION: loop clathrin-pit
<220> FEATURE:
<221> NAME/KEY: misc_feature
<222> LOCATION: (131)..(140)
<223> OTHER INFORMATION: loop dicer 2
<220> FEATURE:
<221> NAME/KEY: misc_feature
<222> LOCATION: (164)..(173)
<223> OTHER INFORMATION: loop dicer 2
<220> FEATURE:
<221> NAME/KEY: misc_feature
<222> LOCATION: (197)..(198)
<223> OTHER INFORMATION: linkage component
<220> FEATURE:
<221> NAME/KEY: misc_feature
<222> LOCATION: (221)..(230)
<223> OTHER INFORMATION: loop dicer 2
<220> FEATURE:
<221> NAME/KEY: misc_feature
<222> LOCATION: (254)..(324)
<223> OTHER INFORMATION: loop PSMA
<220> FEATURE:
<221> NAME/KEY: misc_feature
<222> LOCATION: (348)..(349)
<223> OTHER INFORMATION: linkage component
<220> FEATURE:
```

-continued

```
<221> NAME/KEY: misc_feature
<222> LOCATION: (372)..(381)
<223> OTHER INFORMATION: loop dicer 2
<220> FEATURE:
<221> NAME/KEY: misc_feature
<222> LOCATION: (405)..(414)
<223> OTHER INFORMATION: loop dicer 2
<220> FEATURE:
<221> NAME/KEY: misc_feature
<222> LOCATION: (437)..(438)
<223> OTHER INFORMATION: linkage component
<220> FEATURE:
<221> NAME/KEY: misc_feature
<222> LOCATION: (461)..(469)
<223> OTHER INFORMATION: loop dicer 1
<220> FEATURE:
<221> NAME/KEY: misc_feature
<222> LOCATION: (493)..(522)
<223> OTHER INFORMATION: loop clathrin-pit
<220> FEATURE:
<221> NAME/KEY: misc_feature
<222> LOCATION: (545)..(546)
<223> OTHER INFORMATION: linkage component
<220> FEATURE:
<221> NAME/KEY: misc_feature
<222> LOCATION: (571)..(579)
<223> OTHER INFORMATION: loop dicer 1
<220> FEATURE:
<221> NAME/KEY: misc_feature
<222> LOCATION: (608)..(616)
<223> OTHER INFORMATION: loop dicer 1
<220> FEATURE:
<221> NAME/KEY: misc_feature
<222> LOCATION: (642)..(643)
<223> OTHER INFORMATION: linkage component
<220> FEATURE:
<221> NAME/KEY: misc_feature
<222> LOCATION: (667)..(675)
<223> OTHER INFORMATION: loop dicer 1
<220> FEATURE:
<221> NAME/KEY: misc_feature
<222> LOCATION: (699)..(769)
<223> OTHER INFORMATION: loop PSMA
<220> FEATURE:
<221> NAME/KEY: misc_feature
<222> LOCATION: (793)..(794)
<223> OTHER INFORMATION: linkage component
<220> FEATURE:
<221> NAME/KEY: misc_feature
<222> LOCATION: (821)..(829)
<223> OTHER INFORMATION: loop dicer 1
<220> FEATURE:
<221> NAME/KEY: misc_feature
<222> LOCATION: (856)..(864)
<223> OTHER INFORMATION: loop dicer 1
<220> FEATURE:
<221> NAME/KEY: misc_feature
<222> LOCATION: (890)..(891)
<223> OTHER INFORMATION: linkage component
<220> FEATURE:
<221> NAME/KEY: misc_feature
<222> LOCATION: (915)..(923)
<223> OTHER INFORMATION: loop dicer 1
<220> FEATURE:
<221> NAME/KEY: misc_feature
<222> LOCATION: (948)..(977)
<223> OTHER INFORMATION: loop clathrin-pit
<220> FEATURE:
<221> NAME/KEY: misc_feature
<222> LOCATION: (1002)..(1003)
<223> OTHER INFORMATION: linkage component
<220> FEATURE:
<221> NAME/KEY: misc_feature
<222> LOCATION: (1030)..(1039)
<223> OTHER INFORMATION: loop dicer 3
<220> FEATURE:
<221> NAME/KEY: misc_feature
<222> LOCATION: (1066)..(1136)
<223> OTHER INFORMATION: loop PSMA
```

```
<220> FEATURE:
<221> NAME/KEY: misc_feature
<222> LOCATION: (1165)..(1166)
<223> OTHER INFORMATION: linkage component
<220> FEATURE:
<221> NAME/KEY: misc_feature
<222> LOCATION: (1193)..(1201)
<223> OTHER INFORMATION: loop dicer 1
<220> FEATURE:
<221> NAME/KEY: misc_feature
<222> LOCATION: (1228)..(1236)
<223> OTHER INFORMATION: loop dicer 1
<220> FEATURE:
<221> NAME/KEY: misc_feature
<222> LOCATION: (1266)..(1267)
<223> OTHER INFORMATION: linkage component

<400> SEQUENCE: 37
caaaggcagc cgucagucca ucucaagaaa cgaugggcug acauucauag ccguuccuc      60
uauccguucu aaacgcuuua ugaugcggcu gugaagguug cuuuugaccg ccgggaggug    120
cugcgcuuug ggaucuuauu caaggugcag cucucauuuc cuggaucuu auuaaggaag     180
ugagaacuuc ucggcgacca cugaggucaa uguggacgga ggaucuuauu uucguccaca    240
ucgagcacuu uaugggagga cgaugcggau cagccauguu uacgucacuc cuugucaauc    300
cucaucggca gacgacucgc ccgaauaagg ugcuugugcc uucagugacc cuuucucaga    360
guaagggaga aggaucuuau uuucuccccuu gcaacaagua agacggaucu uauugucuug    420
uuuguucuga gagaggacca gcuuccacau gugagagagc ucaagaaacg cucucucgca    480
auaggcugcu uguuccucua uccguucaa acgcuuuaug auuaaguagc uuaugggga       540
gcugacugu guucuagucu uugguggugguuc ucaagaaacg aaccaccaga gaaacagugu   600
aguugacuca agaaacguca auuacauugg cuagaacaua caccugcuuc uugaggccgu   660
cguguuucaa gaaacaacac ggcgguuugu uccgcaggg gaggacgaug cggaucagcc    720
auguuuacgu cacuccuugu caauccucau cggcagacga cucgcccgau ugcgaaaua    780
uuuaaggagc ggacggcuga gaguagccga cugaguuugc ucaagaaacg caaacucagu    840
ugaaaugguu gcgcuucaag aaacagugca aucauuucug cucucggcca cagaggcguu    900
cgugggucug gcucucaaga aacgaguuag gcccuaucug cugcgcuuuc ucuauccgu    960
ucuaaacgcu uuaugauggc guagcggagc cggcugccuc uacaaagucu cgugcagaag   1020
aagaucacgu ucauagagac gugaucuucu ucccaguugau accuugggag gacgaugcgg   1080
aucagccaug uuuacgucac uccuugucaa uccucaucgg cagacgacuc gcccgaaagg    1140
ugucacuggg uuguacggga cuuuaccuug gcguugcag aaauggguuc agucaagaaa    1200
cuugaaacca uuucuguagu ugacagauca agaaacucug ucaauuacau uggcgacgcc    1260
aaguuac                                                             1267

<210> SEQ ID NO 38
<211> LENGTH: 5158
<212> TYPE: RNA
<213> ORGANISM: Artificial Sequence
<220> FEATURE:
<223> OTHER INFORMATION: Final polynucleotide nanoparticle
<220> FEATURE:
<221> NAME/KEY: misc_feature
<222> LOCATION: (27)..(35)
<223> OTHER INFORMATION: loop dicer 1
<220> FEATURE:
<221> NAME/KEY: misc_feature
<222> LOCATION: (63)..(64)
<223> OTHER INFORMATION: linkage component
<220> FEATURE:
```

```
<221> NAME/KEY: misc_feature
<222> LOCATION: (87)..(95)
<223> OTHER INFORMATION: loop dicer 1
<220> FEATURE:
<221> NAME/KEY: misc_feature
<222> LOCATION: (119)..(148)
<223> OTHER INFORMATION: loop clathrin-pit
<220> FEATURE:
<221> NAME/KEY: misc_feature
<222> LOCATION: (171)..(172)
<223> OTHER INFORMATION: linkage component
<220> FEATURE:
<221> NAME/KEY: misc_feature
<222> LOCATION: (195)..(204)
<223> OTHER INFORMATION: loop dicer 2
<220> FEATURE:
<221> NAME/KEY: misc_feature
<222> LOCATION: (228)..(237)
<223> OTHER INFORMATION: loop dicer 2
<220> FEATURE:
<221> NAME/KEY: misc_feature
<222> LOCATION: (261)..(262)
<223> OTHER INFORMATION: linkage component
<220> FEATURE:
<221> NAME/KEY: misc_feature
<222> LOCATION: (285)..(294)
<223> OTHER INFORMATION: loop dicer 2
<220> FEATURE:
<221> NAME/KEY: misc_feature
<222> LOCATION: (318)..(388)
<223> OTHER INFORMATION: loop PSMA
<220> FEATURE:
<221> NAME/KEY: misc_feature
<222> LOCATION: (412)..(413)
<223> OTHER INFORMATION: linkage component
<220> FEATURE:
<221> NAME/KEY: misc_feature
<222> LOCATION: (436)..(445)
<223> OTHER INFORMATION: loop dicer 2
<220> FEATURE:
<221> NAME/KEY: misc_feature
<222> LOCATION: (469)..(478)
<223> OTHER INFORMATION: loop dicer 2
<220> FEATURE:
<221> NAME/KEY: misc_feature
<222> LOCATION: (501)..(502)
<223> OTHER INFORMATION: linkage component
<220> FEATURE:
<221> NAME/KEY: misc_feature
<222> LOCATION: (525)..(533)
<223> OTHER INFORMATION: loop dicer 1
<220> FEATURE:
<221> NAME/KEY: misc_feature
<222> LOCATION: (557)..(586)
<223> OTHER INFORMATION: loop clathrin-pit
<220> FEATURE:
<221> NAME/KEY: misc_feature
<222> LOCATION: (609)..(610)
<223> OTHER INFORMATION: linkage component
<220> FEATURE:
<221> NAME/KEY: misc_feature
<222> LOCATION: (635)..(643)
<223> OTHER INFORMATION: loop dicer 1
<220> FEATURE:
<221> NAME/KEY: misc_feature
<222> LOCATION: (672)..(680)
<223> OTHER INFORMATION: loop dicer 1
<220> FEATURE:
<221> NAME/KEY: misc_feature
<222> LOCATION: (706)..(707)
<223> OTHER INFORMATION: linkage component
<220> FEATURE:
<221> NAME/KEY: misc_feature
<222> LOCATION: (731)..(739)
<223> OTHER INFORMATION: loop dicer 1
<220> FEATURE:
<221> NAME/KEY: misc_feature
<222> LOCATION: (763)..(833)
<223> OTHER INFORMATION: loop PSMA
```

-continued

```
<220> FEATURE:
<221> NAME/KEY: misc_feature
<222> LOCATION: (857)..(858)
<223> OTHER INFORMATION: linkage component
<220> FEATURE:
<221> NAME/KEY: misc_feature
<222> LOCATION: (885)..(893)
<223> OTHER INFORMATION: loop dicer 1
<220> FEATURE:
<221> NAME/KEY: misc_feature
<222> LOCATION: (920)..(928)
<223> OTHER INFORMATION: loop dicer 1
<220> FEATURE:
<221> NAME/KEY: misc_feature
<222> LOCATION: (954)..(955)
<223> OTHER INFORMATION: linkage component
<220> FEATURE:
<221> NAME/KEY: misc_feature
<222> LOCATION: (979)..(987)
<223> OTHER INFORMATION: loop dicer 1
<220> FEATURE:
<221> NAME/KEY: misc_feature
<222> LOCATION: (1012)..(1041)
<223> OTHER INFORMATION: loop clathrin-pit
<220> FEATURE:
<221> NAME/KEY: misc_feature
<222> LOCATION: (1066)..(1067)
<223> OTHER INFORMATION: linkage component
<220> FEATURE:
<221> NAME/KEY: misc_feature
<222> LOCATION: (1094)..(1103)
<223> OTHER INFORMATION: loop dicer 3
<220> FEATURE:
<221> NAME/KEY: misc_feature
<222> LOCATION: (1130)..(1200)
<223> OTHER INFORMATION: loop PSMA
<220> FEATURE:
<221> NAME/KEY: misc_feature
<222> LOCATION: (1229)..(1230)
<223> OTHER INFORMATION: linkage component
<220> FEATURE:
<221> NAME/KEY: misc_feature
<222> LOCATION: (1257)..(1265)
<223> OTHER INFORMATION: loop dicer 1
<220> FEATURE:
<221> NAME/KEY: misc_feature
<222> LOCATION: (1292)..(1300)
<223> OTHER INFORMATION: loop dicer 1
<220> FEATURE:
<221> NAME/KEY: misc_feature
<222> LOCATION: (1330)..(1331)
<223> OTHER INFORMATION: linkage component
<220> FEATURE:
<221> NAME/KEY: misc_feature
<222> LOCATION: (1354)..(1362)
<223> OTHER INFORMATION: loop dicer 1
<220> FEATURE:
<221> NAME/KEY: misc_feature
<222> LOCATION: (1386)..(1415)
<223> OTHER INFORMATION: loop clathrin-pit
<220> FEATURE:
<221> NAME/KEY: misc_feature
<222> LOCATION: (1438)..(1439)
<223> OTHER INFORMATION: linkage component
<220> FEATURE:
<221> NAME/KEY: misc_feature
<222> LOCATION: (1462)..(1471)
<223> OTHER INFORMATION: loop dicer 2
<220> FEATURE:
<221> NAME/KEY: misc_feature
<222> LOCATION: (1495)..(1504)
<223> OTHER INFORMATION: loop dicer 2
<220> FEATURE:
<221> NAME/KEY: misc_feature
<222> LOCATION: (1528)..(1529)
<223> OTHER INFORMATION: linkage component
<220> FEATURE:
<221> NAME/KEY: misc_feature
<222> LOCATION: (1552)..(1561)
```

```
<223> OTHER INFORMATION: loop dicer 2
<220> FEATURE:
<221> NAME/KEY: misc_feature
<222> LOCATION: (1585)..(1655)
<223> OTHER INFORMATION: loop PSMA
<220> FEATURE:
<221> NAME/KEY: misc_feature
<222> LOCATION: (1679)..(1680)
<223> OTHER INFORMATION: linkage component
<220> FEATURE:
<221> NAME/KEY: misc_feature
<222> LOCATION: (1703)..(1712)
<223> OTHER INFORMATION: loop dicer 2
<220> FEATURE:
<221> NAME/KEY: misc_feature
<222> LOCATION: (1736)..(1745)
<223> OTHER INFORMATION: loop dicer 2
<220> FEATURE:
<221> NAME/KEY: misc_feature
<222> LOCATION: (1768)..(1769)
<223> OTHER INFORMATION: linkage component
<220> FEATURE:
<221> NAME/KEY: misc_feature
<222> LOCATION: (1792)..(1800)
<223> OTHER INFORMATION: loop dicer 1
<220> FEATURE:
<221> NAME/KEY: misc_feature
<222> LOCATION: (1824)..(1853)
<223> OTHER INFORMATION: loop clathrin-pit
<220> FEATURE:
<221> NAME/KEY: misc_feature
<222> LOCATION: (1876)..(1877)
<223> OTHER INFORMATION: linkage component
<220> FEATURE:
<221> NAME/KEY: misc_feature
<222> LOCATION: (1902)..(1910)
<223> OTHER INFORMATION: loop dicer 1
<220> FEATURE:
<221> NAME/KEY: misc_feature
<222> LOCATION: (1939)..(1947)
<223> OTHER INFORMATION: loop dicer 1
<220> FEATURE:
<221> NAME/KEY: misc_feature
<222> LOCATION: (1973)..(1974)
<223> OTHER INFORMATION: linkage component
<220> FEATURE:
<221> NAME/KEY: misc_feature
<222> LOCATION: (1998)..(2006)
<223> OTHER INFORMATION: loop dicer 1
<220> FEATURE:
<221> NAME/KEY: misc_feature
<222> LOCATION: (2030)..(2100)
<223> OTHER INFORMATION: loop PSMA
<220> FEATURE:
<221> NAME/KEY: misc_feature
<222> LOCATION: (2124)..(2125)
<223> OTHER INFORMATION: linkage component
<220> FEATURE:
<221> NAME/KEY: misc_feature
<222> LOCATION: (2152)..(2160)
<223> OTHER INFORMATION: loop dicer 1
<220> FEATURE:
<221> NAME/KEY: misc_feature
<222> LOCATION: (2187)..(2195)
<223> OTHER INFORMATION: loop dicer 1
<220> FEATURE:
<221> NAME/KEY: misc_feature
<222> LOCATION: (2221)..(2222)
<223> OTHER INFORMATION: linkage component
<220> FEATURE:
<221> NAME/KEY: misc_feature
<222> LOCATION: (2246)..(2254)
<223> OTHER INFORMATION: loop dicer 1
<220> FEATURE:
<221> NAME/KEY: misc_feature
<222> LOCATION: (2279)..(2308)
<223> OTHER INFORMATION: loop clathrin-pit
<220> FEATURE:
<221> NAME/KEY: misc_feature
```

-continued

```
<222> LOCATION: (2333)..(2334)
<223> OTHER INFORMATION: linkage component
<220> FEATURE:
<221> NAME/KEY: misc_feature
<222> LOCATION: (2361)..(2370)
<223> OTHER INFORMATION: loop dicer 3
<220> FEATURE:
<221> NAME/KEY: misc_feature
<222> LOCATION: (2397)..(2467)
<223> OTHER INFORMATION: loop PSMA
<220> FEATURE:
<221> NAME/KEY: misc_feature
<222> LOCATION: (2496)..(2497)
<223> OTHER INFORMATION: linkage component
<220> FEATURE:
<221> NAME/KEY: misc_feature
<222> LOCATION: (2524)..(2532)
<223> OTHER INFORMATION: loop dicer 1
<220> FEATURE:
<221> NAME/KEY: misc_feature
<222> LOCATION: (2559)..(2567)
<223> OTHER INFORMATION: loop dicer 1
<220> FEATURE:
<221> NAME/KEY: misc_feature
<222> LOCATION: (2597)..(2598)
<223> OTHER INFORMATION: linkage component
<220> FEATURE:
<221> NAME/KEY: misc_feature
<222> LOCATION: (2621)..(2629)
<223> OTHER INFORMATION: loop dicer 1
<220> FEATURE:
<221> NAME/KEY: misc_feature
<222> LOCATION: (2653)..(2682)
<223> OTHER INFORMATION: loop clathrin-pit
<220> FEATURE:
<221> NAME/KEY: misc_feature
<222> LOCATION: (2705)..(2706)
<223> OTHER INFORMATION: linkage component
<220> FEATURE:
<221> NAME/KEY: misc_feature
<222> LOCATION: (2729)..(2738)
<223> OTHER INFORMATION: loop dicer 2
<220> FEATURE:
<221> NAME/KEY: misc_feature
<222> LOCATION: (2762)..(2771)
<223> OTHER INFORMATION: loop dicer 2
<220> FEATURE:
<221> NAME/KEY: misc_feature
<222> LOCATION: (2795)..(2796)
<223> OTHER INFORMATION: linkage component
<220> FEATURE:
<221> NAME/KEY: misc_feature
<222> LOCATION: (2819)..(2828)
<223> OTHER INFORMATION: loop dicer 2
<220> FEATURE:
<221> NAME/KEY: misc_feature
<222> LOCATION: (2852)..(2922)
<223> OTHER INFORMATION: loop PSMA
<220> FEATURE:
<221> NAME/KEY: misc_feature
<222> LOCATION: (2946)..(2947)
<223> OTHER INFORMATION: linkage component
<220> FEATURE:
<221> NAME/KEY: misc_feature
<222> LOCATION: (2970)..(2979)
<223> OTHER INFORMATION: loop dicer 2
<220> FEATURE:
<221> NAME/KEY: misc_feature
<222> LOCATION: (3003)..(3012)
<223> OTHER INFORMATION: loop dicer 2
<220> FEATURE:
<221> NAME/KEY: misc_feature
<222> LOCATION: (3035)..(3036)
<223> OTHER INFORMATION: linkage component
<220> FEATURE:
<221> NAME/KEY: misc_feature
<222> LOCATION: (3059)..(3067)
<223> OTHER INFORMATION: loop dicer 1
<220> FEATURE:
```

-continued

```
<221> NAME/KEY: misc_feature
<222> LOCATION: (3091)..(3120)
<223> OTHER INFORMATION: loop clathrin-pit
<220> FEATURE:
<221> NAME/KEY: misc_feature
<222> LOCATION: (3143)..(3144)
<223> OTHER INFORMATION: linkage component
<220> FEATURE:
<221> NAME/KEY: misc_feature
<222> LOCATION: (3169)..(3177)
<223> OTHER INFORMATION: loop dicer 1
<220> FEATURE:
<221> NAME/KEY: misc_feature
<222> LOCATION: (3206)..(3214)
<223> OTHER INFORMATION: loop dicer 1
<220> FEATURE:
<221> NAME/KEY: misc_feature
<222> LOCATION: (3240)..(3241)
<223> OTHER INFORMATION: linkage component
<220> FEATURE:
<221> NAME/KEY: misc_feature
<222> LOCATION: (3265)..(3273)
<223> OTHER INFORMATION: loop dicer 1
<220> FEATURE:
<221> NAME/KEY: misc_feature
<222> LOCATION: (3297)..(3367)
<223> OTHER INFORMATION: loop PSMA
<220> FEATURE:
<221> NAME/KEY: misc_feature
<222> LOCATION: (3391)..(3392)
<223> OTHER INFORMATION: linkage component
<220> FEATURE:
<221> NAME/KEY: misc_feature
<222> LOCATION: (3419)..(3427)
<223> OTHER INFORMATION: loop dicer 1
<220> FEATURE:
<221> NAME/KEY: misc_feature
<222> LOCATION: (3454)..(3462)
<223> OTHER INFORMATION: loop dicer 1
<220> FEATURE:
<221> NAME/KEY: misc_feature
<222> LOCATION: (3488)..(3489)
<223> OTHER INFORMATION: linkage component
<220> FEATURE:
<221> NAME/KEY: misc_feature
<222> LOCATION: (3513)..(3521)
<223> OTHER INFORMATION: loop dicer 1
<220> FEATURE:
<221> NAME/KEY: misc_feature
<222> LOCATION: (3546)..(3575)
<223> OTHER INFORMATION: loop clathrin-pit
<220> FEATURE:
<221> NAME/KEY: misc_feature
<222> LOCATION: (3600)..(3601)
<223> OTHER INFORMATION: linkage component
<220> FEATURE:
<221> NAME/KEY: misc_feature
<222> LOCATION: (3628)..(3637)
<223> OTHER INFORMATION: loop dicer 3
<220> FEATURE:
<221> NAME/KEY: misc_feature
<222> LOCATION: (3664)..(3734)
<223> OTHER INFORMATION: loop PSMA
<220> FEATURE:
<221> NAME/KEY: misc_feature
<222> LOCATION: (3763)..(3764)
<223> OTHER INFORMATION: linkage component
<220> FEATURE:
<221> NAME/KEY: misc_feature
<222> LOCATION: (3791)..(3799)
<223> OTHER INFORMATION: loop dicer 1
<220> FEATURE:
<221> NAME/KEY: misc_feature
<222> LOCATION: (3826)..(3834)
<223> OTHER INFORMATION: loop dicer 1
<220> FEATURE:
<221> NAME/KEY: misc_feature
<222> LOCATION: (3864)..(3865)
<223> OTHER INFORMATION: linkage component
```

```
<220> FEATURE:
<221> NAME/KEY: misc_feature
<222> LOCATION: (3888)..(3896)
<223> OTHER INFORMATION: loop dicer 1
<220> FEATURE:
<221> NAME/KEY: misc_feature
<222> LOCATION: (3920)..(3949)
<223> OTHER INFORMATION: loop clathrin-pit
<220> FEATURE:
<221> NAME/KEY: misc_feature
<222> LOCATION: (3972)..(3973)
<223> OTHER INFORMATION: linkage component
<220> FEATURE:
<221> NAME/KEY: misc_feature
<222> LOCATION: (3996)..(4005)
<223> OTHER INFORMATION: loop dicer 2
<220> FEATURE:
<221> NAME/KEY: misc_feature
<222> LOCATION: (4029)..(4038)
<223> OTHER INFORMATION: loop dicer 2
<220> FEATURE:
<221> NAME/KEY: misc_feature
<222> LOCATION: (4062)..(4063)
<223> OTHER INFORMATION: linkage component
<220> FEATURE:
<221> NAME/KEY: misc_feature
<222> LOCATION: (4086)..(4095)
<223> OTHER INFORMATION: loop dicer 2
<220> FEATURE:
<221> NAME/KEY: misc_feature
<222> LOCATION: (4119)..(4189)
<223> OTHER INFORMATION: loop PSMA
<220> FEATURE:
<221> NAME/KEY: misc_feature
<222> LOCATION: (4213)..(4214)
<223> OTHER INFORMATION: linkage component
<220> FEATURE:
<221> NAME/KEY: misc_feature
<222> LOCATION: (4237)..(4246)
<223> OTHER INFORMATION: loop dicer 2
<220> FEATURE:
<221> NAME/KEY: misc_feature
<222> LOCATION: (4270)..(4279)
<223> OTHER INFORMATION: loop dicer 2
<220> FEATURE:
<221> NAME/KEY: misc_feature
<222> LOCATION: (4302)..(4303)
<223> OTHER INFORMATION: linkage component
<220> FEATURE:
<221> NAME/KEY: misc_feature
<222> LOCATION: (4326)..(4334)
<223> OTHER INFORMATION: loop dicer 1
<220> FEATURE:
<221> NAME/KEY: misc_feature
<222> LOCATION: (4358)..(4387)
<223> OTHER INFORMATION: loop clathrin-pit
<220> FEATURE:
<221> NAME/KEY: misc_feature
<222> LOCATION: (4410)..(4411)
<223> OTHER INFORMATION: linkage component
<220> FEATURE:
<221> NAME/KEY: misc_feature
<222> LOCATION: (4436)..(4444)
<223> OTHER INFORMATION: loop dicer 1
<220> FEATURE:
<221> NAME/KEY: misc_feature
<222> LOCATION: (4473)..(4481)
<223> OTHER INFORMATION: loop dicer 1
<220> FEATURE:
<221> NAME/KEY: misc_feature
<222> LOCATION: (4507)..(4508)
<223> OTHER INFORMATION: linkage component
<220> FEATURE:
<221> NAME/KEY: misc_feature
<222> LOCATION: (4532)..(4540)
<223> OTHER INFORMATION: loop dicer 1
<220> FEATURE:
<221> NAME/KEY: misc_feature
<222> LOCATION: (4564)..(4634)
```

```
<223> OTHER INFORMATION: loop PSMA
<220> FEATURE:
<221> NAME/KEY: misc_feature
<222> LOCATION: (4658)..(4659)
<223> OTHER INFORMATION: linkage component
<220> FEATURE:
<221> NAME/KEY: misc_feature
<222> LOCATION: (4686)..(4694)
<223> OTHER INFORMATION: loop dicer 1
<220> FEATURE:
<221> NAME/KEY: misc_feature
<222> LOCATION: (4721)..(4729)
<223> OTHER INFORMATION: loop dicer 1
<220> FEATURE:
<221> NAME/KEY: misc_feature
<222> LOCATION: (4755)..(4756)
<223> OTHER INFORMATION: linkage component
<220> FEATURE:
<221> NAME/KEY: misc_feature
<222> LOCATION: (4780)..(4788)
<223> OTHER INFORMATION: loop dicer 1
<220> FEATURE:
<221> NAME/KEY: misc_feature
<222> LOCATION: (4813)..(4842)
<223> OTHER INFORMATION: loop clathrin-pit
<220> FEATURE:
<221> NAME/KEY: misc_feature
<222> LOCATION: (4867)..(4868)
<223> OTHER INFORMATION: linkage component
<220> FEATURE:
<221> NAME/KEY: misc_feature
<222> LOCATION: (4895)..(4904)
<223> OTHER INFORMATION: loop dicer 3
<220> FEATURE:
<221> NAME/KEY: misc_feature
<222> LOCATION: (4931)..(5001)
<223> OTHER INFORMATION: loop PSMA
<220> FEATURE:
<221> NAME/KEY: misc_feature
<222> LOCATION: (5030)..(5031)
<223> OTHER INFORMATION: linkage component
<220> FEATURE:
<221> NAME/KEY: misc_feature
<222> LOCATION: (5058)..(5066)
<223> OTHER INFORMATION: loop dicer 1
<220> FEATURE:
<221> NAME/KEY: misc_feature
<222> LOCATION: (5093)..(5101)
<223> OTHER INFORMATION: loop dicer 1
<220> FEATURE:
<221> NAME/KEY: misc_feature
<222> LOCATION: (5131)..(5132)
<223> OTHER INFORMATION: linkage component

<400> SEQUENCE: 38
gggaauuagg guuccaaug cuuugcucaa gaaacgcaaa guauuggagc cacaccaacc      60
agaccaaagg cagccgucag uccaucucaa gaaacgaugg gcugacauuc auagccguuu    120
ccucuauccg uucuaaacgc uuuaugaugc ggcugugaag guugcuuuug accgccggga    180
ggugcugcgc uuugggaucu uauucaaggu gcagcucuca uuccuugga ucuuauuaag     240 gaagugagaa cuucucggcg accacugagg ucaaugugga cggaggaucu uauuucguc     300 cacaucgagc acuuuauggg aggacagugc ggaucagcca uguuuacguc acuccuuguc    360
aauccucauc ggcagacgac ucgcccgaau aaggugcuug uggcuucagu gacccuuucu    420
cagaguaagg gagaaggauc uuauuuucuc ccuugcaaca aguaagacgg aucuauugu     480 cuuguuuguu cugagagagg accagcuucc acaugugaga gagcucaaga aacgcucucu    540
cgcaauaggc ugcuuguucc ucuauccguu cuaaacgcuu uaugauuaag uagcuuaugu    600
gggagcugac guguguucua gucuuuggug guucucaaga aacgaaccac cagagaaaca    660
guguaguuga cucaagaaac gucaauuaca uuggcuagaa cauacaccug cuucuugagg    720
```

-continued

```
ccgucguguu ucaagaaaca acacggcggu uuguuccgc aggggaggac gaugcggauc    780
agccauguuu acgucacucc uugucaaucc ucaucggcag acgacucgcc cgauugcgga    840
aauauuuaag gagcggacgg cugagaguag ccgacugagu uugcucaaga acgcaaacu    900 caguugaaau gguugcgcuu caagaaacag ugcaaucauu ucugcucucg gccacagagg    960
cggucguggg ucuggcucuc aagaaacgag uuaggcccua ucugcugcgc uuccucuau   1020 ccguucuaaa cgcuuuauga uggcguagcg gagccggcug ccucuacaaa gucucgugca   1080
gaagaagauc acguucauag agacgugauc uucuucccag ugauaccuug ggaggacgau   1140
gcggaucagc cauguuuacg ucacuccuug ucaauccuca ucggcagacg acucgcccga   1200
aaggugucac ugggguuguac gggacuuuac cuugcguug ucagaaaugg uuucagucaa   1260
gaaacuugaa accauuucug uaguugacag aucaagaaac ucugucaauu acauggcga   1320 cgccaaguua ccaaaggcag ccgucagucc aucucaagaa acgaugggcu gacauucaua   1380 gccguuccu cuauccguuc uaaacgcuuu augaugcggc ugugaagguu gcuuuugacc   1440
gccgggaggu gcugcgcuuu gggaucuuau ucaaggugca gcucucauuu ccuuggaucu   1500
uauuaaggaa gugagaacuu cucggcgacc acugaggaca auggacgg aggaucuuau   1560 uuucguccac aucgagcacu uuaugggagg acgaugcgga ucagccaugu uuacgucacu   1620
ccuugucaau cccuaucggc agacgacucg cccgaauaag gugcuugugg cuucagugac   1680
ccuuucucag aguaagggag aaggaucuua uuuucucccu ugcaacaagu aagacggauc   1740
uuauugucuu guuguucug agagaggacc agcuuccaca ugugagagag cucaagaaac   1800
gcucucucgc aauaggcugc uuguuccucu auccguucua aacgcuuuau gauuaaguag   1860 cuuaugggg agcugacgug uguucuaguc uuugggguu ucaagaaaac gaaccaccag   1920
agaaacagug uaguugacuc aagaaacguc aauuacauug gcagaacau acaccugcuu   1980 cuugaggccg ucguguuuca agaaacaaca cggcgguuug uuccgcagg ggaggacgau   2040 gcggaucagc cauguuuacg ucacuccuug ucaauccuca ucggcagacg acucgcccga   2100
uugcggaaau auuuaaggag cggacggcug agauagccg acugaguuug ucaagaaac   2160 gcaaacucag uugaaauggu ucgcuucaa gaaacagugc aaucauucu gcucucggcc   2220 acagaggcgg ucgugggucu ggcucucaag aaacgaguua ggcccuaucu gcugcguuu   2280 ccucuauccg uucuaaacgc uuuaugaugg cguagcggag ccggcugccu cuacaaaguc   2340
ucgugcagaa gaagaucacg uucauagaga cgugaucuuc uucccaguga uaccuuggga   2400
ggacgaugcg gaucagccau guuuacguca cuccuuguca auccucaucg gcagacgacu   2460
cgcccgaaag gugucacugg guuuacggg acuuaccuu ggcguuguca gaaaugguuu   2520
cagucaagaa acuugaaacc auuucuguag uugacagauc aagaaacucu gucaauuaca   2580
uuggcgacgc caaguuacca aaggcagccg ucagccauc ucaagaaacg augggcugac   2640
auucauagcc guuccucua uccguucuaa acgcuuuaug augcggcugu gaagguugcu   2700
uuugaccgcc gggaggugcu gcgcuuuggg aucuuauuca aggugcagcu cucauuuccu   2760
uggaucuuau uaaggaagug agaacucu ggcgaccacu gaggucaaug uggacgagg   2820 aucuuauuuu cguccacauc gagcacuuua ugggaggacg augcggauca gccauguuua   2880 cgcacuccu ugucaauccu caucggcaga cgacucgccc gaauaaggug cuugugcuu   2940 cagugacccu uucucagagu aagggagaag gaucuuauuu ucuccuugc aacaaguaag   3000 acggaucuua uugucuuguu uguucugaga gaggaccagc uuccacaugu gagagagcuc   3060
```

| | |
|---|---|
| aagaaacgcu cucucgcaau aggcugcuug uuccucuauc cguucuaaac gcuuuaugau | 3120 |
| uaaguagcuu augugggagc ugacgugugu ucuagucuuu ggugguucuc aagaaacgaa | 3180 |
| ccaccagaga aacaguguag uugacucaag aaacgucaau uacauuggcu agaacauaca | 3240 |
| ccugcuucuu gaggccgucg uguuucaaga acaacacgg cgguuuguuu ccgcagggga | 3300 |
| ggacgaugcg gaucagccau guuuacguca cuccuuguca auccucaucg gcagacgacu | 3360 |
| cgcccgauug cggaaauauu uaaggagcgg acggcugaga guagccgacu gaguuugcuc | 3420 |
| aagaaacgca aacucaguug aaauugguugc gcuucaagaa acagugcaau cauuucugcu | 3480 |
| cucggccaca gaggcggucg ugggucuggc ucucaagaaa cgaguuaggc ccuaucugcu | 3540 |
| gcgcuuuccu cuauccguuc uaaacgcuuu augauggcgu agcggagccg gcugccucua | 3600 |
| caaagucucg ugcagaagaa gaucacguuc auagagacgu gaucuucuuc ccagugauac | 3660 |
| cuugggagga cgaugcggau cagccauguu uacgucacuc cuugucaauc cucaucggca | 3720 |
| gacgacucgc ccgaaaggug ucacggguu guacgggacu uuaccuuggc guugucagaa | 3780 |
| augguuucag ucaagaaacu ugaaaccauu ucuguaguug acagaucaag aaacucuguc | 3840 |
| aauuacauug gcgacgccaa guuaccaaag gcagccguca guccaucuca agaaacgaug | 3900 |
| ggcugacauu cauagccguu uccucuaucc guucuaaacg cuuuaugaug cggcugugaa | 3960 |
| gguugcuuuu gaccgccggg aggugcugcg cuugggauc uuauucaagg ugcagcucuc | 4020 |
| auuccuugg aucuuauuaa ggaagugaga acuucgcggc gaccacgag gucaaugugg | 4080 |
| acggaggauc uuauuuucgu ccacaucgag cacuuuaugg gaggacgaug cggaucagcc | 4140 |
| auguuuacgu cacuccuugu caauccucau cggcagacga cucgcccgaa uaaggugcuu | 4200 |
| guggcuucag ugacccuuuc ucagaguaag ggagaaggau cuuauuuucu cccuugcaac | 4260 |
| aaguaagacg gaucuuauug ucuuguugu ucugagagag gaccagcuuc cacaugugag | 4320 |
| agagcucaag aaacgcucuc ucgcaauagg cugcuuguuc cucuauccgu ucuaaacgcu | 4380 |
| uuaugauuaa guagcuuaug ugggagcuga cguguguucu agucuuuggu gguucucaag | 4440 |
| aaacgaacca ccagagaaac aguguaguug acucaagaaa cgucaauuac auuggcuaga | 4500 |
| acauacaccu gcuucuugag gccgucgugu ucaagaaac aacacggcgg uuuguuccg | 4560 |
| caggggagga cgaugcggau cagccauguu uacgcacuc cuugucaauc cucaucggca | 4620 |
| gacgacucgc ccgauugcgg aaauauuuaa ggagcggacg gcugagagua gccgacugag | 4680 |
| uuugcucaag aaacgcaaac ucaguugaaa ugguugcgcu ucaagaaaca gugcaaucau | 4740 |
| uucugcucuc ggccacagag gcggucgugg ucuggcucu caagaaacga guuaggcccu | 4800 |
| aucugcugcg cuuccucua uccguucuaa acgcuuuaug auggcguagc ggagccggcu | 4860 |
| gccucuacaa agucucgugc agaagaagau cacguucaua gagacgugau cuucuuccca | 4920 |
| gugauaccuu gggaggacga ugcggaucag ccauguuuac gucacuccuu gucaauccuc | 4980 |
| aucggcagac gacucgcccg aaaggugca cugggugua cgggacuuua ccuuggcguu | 5040 |
| gucagaaaug guuucaguca agaaacuuga accauuucu guaguugaca gaucaagaaa | 5100 |
| cucugucaau uacauuggcg acgccaaguu accgguugg uguggaaccc uauuuccc | 5158 |

<210> SEQ ID NO 39
<211> LENGTH: 131
<212> TYPE: DNA
<213> ORGANISM: Artificial Sequence
<220> FEATURE:
<223> OTHER INFORMATION: MV-RNA

<400> SEQUENCE: 39

```
attggtttag tagcaactgc aaattcaaag aacatttgta gttgggtctt ttccaataga      60
cttaggtgga tgtaggatcc ttagacttag gtggatgtag gatccaaatt ggaaaagaac     120
taaaccaatt t                                                          131
```

<210> SEQ ID NO 40
<211> LENGTH: 109
<212> TYPE: DNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (57)..(86)
<223> OTHER INFORMATION: Loop clathrin-pit

<400> SEQUENCE: 40

```
atcaattggt catgtacttc gtttcaaaga acaacgaagt acataactag attcgattcc      60
tctatccgtt ctaaacgctt tatgattcga atctagttat caattggtt               109
```

<210> SEQ ID NO 41
<211> LENGTH: 89
<212> TYPE: DNA
<213> ORGANISM: Artificial Sequence
<220> FEATURE:
<223> OTHER INFORMATION: MV-RNA

<400> SEQUENCE: 41

```
ggtttctggt ttgactttct agttcaaaga acactagaag gtcatgagaa aggcgttcaa      60
agaacacgcc tttctcaacc agaaaccctt                                       89
```

<210> SEQ ID NO 42
<211> LENGTH: 106
<212> TYPE: DNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (53)..(82)
<223> OTHER INFORMATION: Loop clathrin-pit

<400> SEQUENCE: 42

```
tttcattcaa attgtcttta ctcaaagaac gtgaagacag acagtattct tcttcctcta      60
tccgttctaa acgctttatg atgaagaata ctgtttgaat gaaatt                    106
```

<210> SEQ ID NO 43
<211> LENGTH: 130
<212> TYPE: DNA
<213> ORGANISM: Artificial Sequence
<220> FEATURE:
<223> OTHER INFORMATION: MV-RNA

<400> SEQUENCE: 43

```
tccccaggac tagggctat ttatcaaaga actgaatagc ctccccagga ctagggagac       60
ttaggtggat gtaggatcct tagacttagg tggatgtagg atccaaccct agtcctgagt     120
cctggggatt                                                            130
```

<210> SEQ ID NO 44
<211> LENGTH: 90
<212> TYPE: DNA
<213> ORGANISM: Artificial Sequence
<220> FEATURE:

```
<223> OTHER INFORMATION: MV-RNA

<400> SEQUENCE: 44
ggctatgtca tccatgatat cgttcaaaga acatgatatc gtgaacatca tctactttca    60
aagaacgtag atgatgtatg acatagcctt                                      90

<210> SEQ ID NO 45
<211> LENGTH: 113
<212> TYPE: DNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (58)..(87)
<223> OTHER INFORMATION: Loop clathrin-pit

<400> SEQUENCE: 45
acatgatgga attggaaatg gaattcaaag aacattcgtt ttcattcaaa ttgtcttttc    60
ctctatccgt tctaaacgct ttatgataag acaatttgaa ttccatcatg ttt          113

<210> SEQ ID NO 46
<211> LENGTH: 129
<212> TYPE: DNA
<213> ORGANISM: Artificial Sequence
<220> FEATURE:
<223> OTHER INFORMATION: MV-RNA

<400> SEQUENCE: 46
acacaacctt atatattaac agctcaaaga acgctgttag tatggatgcc agtggagact    60
taggtggatg taggatcctt agacttaggt ggatgtagga tccaaccact ggcatctaag   120
gttgtgttt                                                            129

<210> SEQ ID NO 47
<211> LENGTH: 91
<212> TYPE: DNA
<213> ORGANISM: Artificial Sequence
<220> FEATURE:
<223> OTHER INFORMATION: MV-RNA

<400> SEQUENCE: 47
gaaagggagt aggtgtattt acatcaaaga actgtaggta caagatgcta agagcttcaa    60
agaacagctc ttagcatcta ctcccttct t                                   91

<210> SEQ ID NO 48
<211> LENGTH: 130
<212> TYPE: DNA
<213> ORGANISM: Artificial Sequence
<220> FEATURE:
<223> OTHER INFORMATION: MV-RNA

<400> SEQUENCE: 48
catccagatc gtcggtgaat tagtcaaaga acctaattca tcgtcatcca gatcgtagac    60
ttaggtggat gtaggatcct tagacttagg tggatgtagg atccaaacga tctggatcga   120
tctggatgtt                                                          130

<210> SEQ ID NO 49
<211> LENGTH: 110
<212> TYPE: DNA
<213> ORGANISM: Artificial Sequence
<220> FEATURE:
<223> OTHER INFORMATION: MV-RNA
```

```
<220> FEATURE:
<221> NAME/KEY: misc_feature
<222> LOCATION: (55)..(84)
<223> OTHER INFORMATION: Loop clathrin-pit

<400> SEQUENCE: 49
gaatttcaaa gagaagaaga atggatctta ttattcttct tctataattt aagcttcctc    60
tatccgttct aaacgcttta tgatgcttaa attatggctt tgaaattctt              110

<210> SEQ ID NO 50
<211> LENGTH: 88
<212> TYPE: DNA
<213> ORGANISM: Artificial Sequence
<220> FEATURE:
<223> OTHER INFORMATION: MV-RNA

<400> SEQUENCE: 50
ggtcgtgcat gttaattggt aatcaaagaa cgttatcaat tggtcatgta cttcgtcaaa    60
gaaccgaagt acatgcatgc acgacctt                                       88

<210> SEQ ID NO 51
<211> LENGTH: 109
<212> TYPE: DNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (56)..(85)
<223> OTHER INFORMATION: Loop clathrin-pit

<400> SEQUENCE: 51
agatagctac tttattcttt caaatcaaag aactttgaaa gagtatggac tattttcct     60 ctatccgttc taaacgcttt atgataaata gtccatagta gctatcttt               109

<210> SEQ ID NO 52
<211> LENGTH: 128
<212> TYPE: DNA
<213> ORGANISM: Artificial Sequence
<220> FEATURE:
<223> OTHER INFORMATION: MV-RNA

<400> SEQUENCE: 52
agtatttgtg ctagctccta gttcaaagaa cactagggc tatctcttcc ttttagactt     60
aggtggatgt aggatcctta gactaggtg gatgtaggat ccaaaaaagg aagaggcaca   120
aatacttt                                                           128

<210> SEQ ID NO 53
<211> LENGTH: 50
<212> TYPE: DNA
<213> ORGANISM: Artificial Sequence
<220> FEATURE:
<223> OTHER INFORMATION: GalNac

<400> SEQUENCE: 53
agacttaggt ggatgtagga tccttagact taggtggatg taggatccaa               50

<210> SEQ ID NO 54
<211> LENGTH: 30
<212> TYPE: DNA
<213> ORGANISM: Artificial Sequence
<220> FEATURE:
<223> OTHER INFORMATION: Clathrin-pit
```

<400> SEQUENCE: 54
ttcctctatc cgttctaaac gctttatgat                                           30

<210> SEQ ID NO 55
<211> LENGTH: 341
<212> TYPE: DNA
<213> ORGANISM: Artificial Sequence
<220> FEATURE:
<223> OTHER INFORMATION: TRI nanoparticle
<220> FEATURE:
<221> NAME/KEY: misc_feature
<222> LOCATION: (1)..(22)
<223> OTHER INFORMATION: EcoRI restriction site/T7 transcription start
      site
<220> FEATURE:
<221> NAME/KEY: misc_feature
<222> LOCATION: (265)..(294)
<223> OTHER INFORMATION: Loop clathrin-pit

<400> SEQUENCE: 55
aattaatacg actcactata ggtatgtttg gccacagaag atagtcaaaa aacctatctt         60
ctgtccaaat aatttttatt ggtttagtag caactgcaaa ttcaaaaaac atttgtagtt        120
gggtcttttc caatagactt aggtggatgt aggatcctta gacttaggtg gatgtaggat        180
ccaaattgga aaagaactaa accaatttat caattggtca tgtacttcgt ttcaaaaaac        240
aacgaagtac ataactagat tcgattcctc tatccgttct aaacgcttta tgattcgaat        300
ctagttatca attggtttaa attatttggg ccagacatac t                            341

<210> SEQ ID NO 56
<211> LENGTH: 337
<212> TYPE: DNA
<213> ORGANISM: Artificial Sequence
<220> FEATURE:
<223> OTHER INFORMATION: TRI nanoparticle
<220> FEATURE:
<221> NAME/KEY: misc_feature
<222> LOCATION: (1)..(22)
<223> OTHER INFORMATION: EcoRI restriction site/T7 transcription start
      site
<220> FEATURE:
<221> NAME/KEY: misc_feature
<222> LOCATION: (131)..(160)
<223> OTHER INFORMATION: Loop clathrin-pit

<400> SEQUENCE: 56
aattaatacg actcactata ggtttctggt ttgactttct agttcaaaaa acactagaag         60
gtcatgagaa aggcgttttt tcattcaaat tgtctttact caaaaaacgt gaagacagac        120
agtattcttc ttcctctatc cgttctaaac gctttatgat gaagaatact gtttgaatga        180
aatttcccca ggactagggg ctatttatca aaaaactgaa tagcctcccc aggactaggg        240
agacttaggt ggatgtagga tccttagact taggtggatg taggatccaa ccctagtcct        300
gagtcctggg gattacgcct ttctcaacca gaaacct                                 337

<210> SEQ ID NO 57
<211> LENGTH: 342
<212> TYPE: DNA
<213> ORGANISM: Artificial Sequence
<220> FEATURE:
<223> OTHER INFORMATION: TRI nanoparticle
<220> FEATURE:
<221> NAME/KEY: misc_feature
<222> LOCATION: (1)..(22)
<223> OTHER INFORMATION: EcoRI restriction site/T7 transcription start
      site
<220> FEATURE:

```
<221> NAME/KEY: misc_feature
<222> LOCATION: (135)..(164)
<223> OTHER INFORMATION: Loop clathrin-pit

<400> SEQUENCE: 57
aattaatacg actcactata ggctatgtca tccatgatat cgttcaaaaa acatgatatc    60
gtgaacatca tctacttaca tgatggaatt ggaaatggaa ttcaaaaaac attcgttttc   120
attcaaattg tcttttcctc tatccgttct aaacgcttta tgataagaca atttgaattc   180
catcatgttt acacaacctt atatattaac agctcaaaaa acgctgttag tatggatgcc   240
agtggagact taggtggatg taggatcctt agacttaggt ggatgtagga tccaaccact   300
ggcatctaag gttgtgtttg tagatgatgt atgacatagc ct                      342

<210> SEQ ID NO 58
<211> LENGTH: 344
<212> TYPE: DNA
<213> ORGANISM: Artificial Sequence
<220> FEATURE:
<223> OTHER INFORMATION: TRI nanoparticle
<220> FEATURE:
<221> NAME/KEY: misc_feature
<222> LOCATION: (1)..(22)
<223> OTHER INFORMATION: EcoRI restriction site/T7 transcription start
      site
<220> FEATURE:
<221> NAME/KEY: misc_feature
<222> LOCATION: (264)..(293)
<223> OTHER INFORMATION: Loop clathrin-pit

<400> SEQUENCE: 58
aattaatacg actcactata ggaaagggag taggtgtatt tacatcaaaa aactgtaggt    60
acaagatgct aagagctttc atccagatcg tcggtgaatt agtcaaaaaa cctaattcat   120
cgtcatccag atcgtagact taggtggatg taggatcctt agacttaggt ggatgtagga   180
tccaaacgat ctggatcgat ctggatgttg aatttcaaag agaagaagaa tggatcttat   240
tattcttctt ctataattta agcttcctct atccgttcta aacgctttat gatgcttaaa   300
ttatggcttt gaaattctta gctcttagca tctactccct ttct                    344

<210> SEQ ID NO 59
<211> LENGTH: 337
<212> TYPE: DNA
<213> ORGANISM: Artificial Sequence
<220> FEATURE:
<223> OTHER INFORMATION: TRI nanoparticle
<220> FEATURE:
<221> NAME/KEY: misc_feature
<222> LOCATION: (1)..(22)
<223> OTHER INFORMATION: EcoRI restriction site/T7 transcription start
      site
<220> FEATURE:
<221> NAME/KEY: misc_feature
<222> LOCATION: (133)..(162)
<223> OTHER INFORMATION: Loop clathrin-pit

<400> SEQUENCE: 59
aattaatacg actcactata ggtcgtgcat gttaattggt aatcaaaaaa cgttatcaat    60
tggtcatgta cttcgttaga tagctacttt attctttcaa atcaaaaaac tttgaaagag   120
tatggactat ttttcctcta tccgttctaa acgctttatg ataaatagtc catagtagct   180
atctttagta tttgtgctag ctcctagttc aaaaaacact agggctatc tcttcctttt    240 agacttaggt ggatgtagga tccttagact taggtggatg taggatccaa aaaaggaaga   300
ggcacaaata ctttcgaagt acatgcatgc acgacct                            337
```

<210> SEQ ID NO 60
<211> LENGTH: 74
<212> TYPE: DNA
<213> ORGANISM: Artificial Sequence
<220> FEATURE:
<223> OTHER INFORMATION: Nanoparticle open sequence

<400> SEQUENCE: 60

```
taatacgact cactataggt atgtttggcc acagaagata gtcaaagaac ctatcttctg    60
tccaaataat tttt                                                      74
```

<210> SEQ ID NO 61
<211> LENGTH: 23
<212> TYPE: DNA
<213> ORGANISM: Artificial Sequence
<220> FEATURE:
<223> OTHER INFORMATION: Core close

<400> SEQUENCE: 61

```
aaattatttg ggccagacat act                                            23
```

<210> SEQ ID NO 62
<211> LENGTH: 1654
<212> TYPE: DNA
<213> ORGANISM: Artificial Sequence
<220> FEATURE:
<223> OTHER INFORMATION: WCR prescreen apt
<220> FEATURE:
<221> NAME/KEY: misc_feature
<222> LOCATION: (265)..(294)
<223> OTHER INFORMATION: loop clathrin-pit
<220> FEATURE:
<221> NAME/KEY: misc_feature
<222> LOCATION: (460)..(489)
<223> OTHER INFORMATION: loop clathrin-pit
<220> FEATURE:
<221> NAME/KEY: misc_feature
<222> LOCATION: (791)..(820)
<223> OTHER INFORMATION: loop clathrin-pit
<220> FEATURE:
<221> NAME/KEY: misc_feature
<222> LOCATION: (1251)..(1280)
<223> OTHER INFORMATION: loop clathrin-pit
<220> FEATURE:
<221> NAME/KEY: misc_feature
<222> LOCATION: (1450)..(1479)
<223> OTHER INFORMATION: loop clathrin-pit

<400> SEQUENCE: 62

```
aattaatacg actcactata ggtatgtttg ccacagaag atagtcaaag aacctatctt     60
ctgtccaaat aattttatt ggtttagtag caactgcaaa ttcaaagaac atttgtagtt    120
gggtcttttc caatagactt aggtggatgt aggatcctta gacttaggtg gatgtaggat    180
ccaaattgga aaagaactaa accaatttat caattggtca tgtacttcgt ttcaaagaac    240
aacgaagtac ataactagat tcgattcctc tatccgttct aaacgcttta tgattcgaat    300
ctagttatca attggtttgg tttctggttt gactttctag ttcaaagaac actagaaggt    360
catgagaaag gcgttcaaag aacacgcctt tctcaaccag aaaccttttt cattcaaatt    420
gtctttactc aaagaacgtg aagacagaca gtattcttct tcctctatcc gttctaaacg    480
ctttatgatg aagaatactg tttgaatgaa atttccccag gactaggggc tatttatcaa    540
agaactgaat agcctcccca ggactaggga gacttaggtg gatgtaggat ccttagactt    600
aggtggatgt aggatccaac cctagtcctg agtcctgggg attggctatg tcatccatga    660
```

```
tatcgttcaa agaacatgat atcgtgaaca tcatctactt tcaaagaacg tagatgatgt      720
atgacatagc cttacatgat ggaattggaa atggaattca agaacattc gttttcattc       780 aaattgtctt ttcctctatc cgttctaaac gctttatgat aagacaattt gaattccatc     840
atgtttacac aaccttatat attaacagct caaagaacgc tgttagtatg gatgccagtg     900
gagacttagg tggatgtagg atccttagac ttaggtggat gtaggatcca accactggca     960
tctaaggttg tgtttgaaag ggagtaggtg tatttacatc aaagaactgt aggtacaaga    1020
tgctaagagc ttcaaagaac agctcttagc atctactccc tttcttcatc cagatcgtcg    1080
gtgaattagt caaagaacct aattcatcgt catccagatc gtagacttag gtggatgtag    1140
gatccttaga cttaggtgga tgtaggatcc aaacgatctg gatcgatctg gatgttgaat   1200
ttcaaagaga agaagaatgg atcttattat tcttcttcta taatttaagc ttcctctatc   1260
cgttctaaac gctttatgat gcttaaatta tggctttgaa attcttggtc gtgcatgtta   1320
attggtaatc aaagaacgtt atcaattggt catgtacttc gtcaaagaac cgaagtacat   1380
gcatgcacga cctagatag ctactttatt cttcaaatc aaagaacttt gaaagagtat     1440
ggactatttt tcctctatcc gttctaaacg ctttatgata aatagtccat agtagctatc   1500
tttagtattt gtgctagctc ctagttcaaa gaacactagg ggctatctct tcctttaga    1560 cttaggtgga tgtaggatcc ttagacttag gtggatgtag gatccaaaaa aggaagaggc   1620
acaaatactt taaattattt gggccagaca tact                                1654

<210> SEQ ID NO 63
<211> LENGTH: 1344
<212> TYPE: DNA
<213> ORGANISM: Artificial Sequence
<220> FEATURE:
<223> OTHER INFORMATION: WCR prescreen none

<400> SEQUENCE: 63
aattaatacg actcactata ggtatgtttg gccacagaag atagtcaaag aacctatctt      60
ctgtccaaat aattttttatt ggtttagtag caactgcaaa ttcaaagaac atttgtagtt    120
gggtcttttc caattcaaag aacattggaa aagaactaaa ccaatttatc aattggtcat    180
gtacttcgtt tcaaagaaca acgaagtaca taactagatt cgatcaaaga actcgaatct    240
agttatcaat tggtttggtt tctggtttga ctttctagtt caaagaacac tagaaggtca    300
tgagaaaggc gttcaaagaa cacgcctttc tcaaccagaa acctttttca ttcaaattgt    360
ctttactcaa agaacgtgaa gacagacagt attcttctca aagaacgaag aatactgttt    420
gaatgaaatt tccccaggac tagggctat ttatcaaaga actgaatagc ctccccagga    480
ctagggtcaa agaaccccta gtcctgagtc ctggggattg ctatgtcat ccatgatatc    540 gttcaaagaa catgatatcg tgaacatcat ctactttcaa agaacgtaga tgatgtatga   600
catagcctta catgatggaa ttggaaatgg aattcaaaga acattcgttt tcattcaaat    660
tgtctttcaa agaacaagac aatttgaatt ccatcatgtt tacacaacct tatatattaa    720
cagctcaaag aacgctgtta gtatggatgc cagtggtcaa agaacccact ggcatctaag    780
gttgtgtttg aaagggagta ggtgtattta catcaaagaa ctgtaggtac aagatgctaa    840
gagcttcaaa gaacagctct tagcatctac tccctttctt catccagatc gtcggtgaat   900
tagtcaaaga acctaattca tcgtcatcca gatcgttcaa agaacacgat ctggatcgat   960
ctggatgttg aatttcaaag agaagaagaa tggatcttat tattcttctt ctataattta   1020
agctcaaaga acgcttaaat tatggctttg aaattcttgg tcgtgcatgt taattggtaa   1080
```
tcaaagaacg ttatcaattg gtcatgtact tcgtcaaaga accgaagtac atgcatgcac 1140
gaccttagat agctacttta ttctttcaaa tcaaagaact ttgaaagagt atggactatt 1200
ttcaaagaac aaatagtcca tagtagctat ctttagtatt tgtgctagct cctagttcaa 1260
agaacactag gggctatctc ttcctttttc aaagaacaaa aggaagaggc acaaatactt 1320
taaattattt gggccagaca tact 1344

<210> SEQ ID NO 64
<211> LENGTH: 126
<212> TYPE: DNA
<213> ORGANISM: Artificial Sequence
<220> FEATURE:
<223> OTHER INFORMATION: T7 + GFP open sequence

<400> SEQUENCE: 64
aattaatacg actcactata gggaggatgg tgactggtat gagactgggc tacatatatt 60
ctttggggca tatccaaatg tccaaaatct atttggagaa cttggtataa atgaccgact 120
gcaatg 126

<210> SEQ ID NO 65
<211> LENGTH: 104
<212> TYPE: DNA
<213> ORGANISM: Artificial Sequence
<220> FEATURE:
<223> OTHER INFORMATION: GFP close sequence DNA

<400> SEQUENCE: 65
cattgcagtc ggtcatttat accaagttct ccaaatagat tttggacatt tggatatgcc 60
ccaaagaata tatgtagccc agtctcatac cagtcaccat cctc 104

<210> SEQ ID NO 66
<211> LENGTH: 1865
<212> TYPE: DNA
<213> ORGANISM: Artificial Sequence
<220> FEATURE:
<223> OTHER INFORMATION: WCR nanoparticle with dsRBD uptake signal
<220> FEATURE:
<221> NAME/KEY: misc_feature
<222> LOCATION: (1)..(22)
<223> OTHER INFORMATION: EcoRI restriction site/T7 transcription start site
<220> FEATURE:
<221> NAME/KEY: misc_feature
<222> LOCATION: (370)..(399)
<223> OTHER INFORMATION: loop clathrin-pit
<220> FEATURE:
<221> NAME/KEY: misc_feature
<222> LOCATION: (565)..(594)
<223> OTHER INFORMATION: loop clathrin-pit
<220> FEATURE:
<221> NAME/KEY: misc_feature
<222> LOCATION: (896)..(925)
<223> OTHER INFORMATION: loop clathrin-pit
<220> FEATURE:
<221> NAME/KEY: misc_feature
<222> LOCATION: (1356)..(1385)
<223> OTHER INFORMATION: loop clathrin-pit
<220> FEATURE:
<221> NAME/KEY: misc_feature
<222> LOCATION: (1555)..(1584)
<223> OTHER INFORMATION: loop clathrin-pit

<400> SEQUENCE: 66
aattaatacg actcactata gggaggatgg tgactggtat gagactgggc tacatatatt 60
ctttggggca tatccaaatg tccaaaatct atttggagaa cttggtataa atgaccgact 120

-continued

```
gcaatggtat gtttggccac agaagatagt caaagaacct atcttctgtc caaataattt      180
ttattggttt agtagcaact gcaaattcaa agaacatttg tagttgggtc ttttccaata      240
gacttaggtg gatgtaggat ccttagactt aggtggatgt aggatccaaa ttggaaaaga      300
actaaaccaa tttatcaatt ggtcatgtac ttcgtttcaa agaacaacga agtacataac      360
tagattcgat tcctctatcc gttctaaacg ctttatgatt cgatctagt tatcaattgg       420 tttggtttct ggtttgactt tctagttcaa agaacactag aaggtcatga gaaaggcgtt      480
caaagaacac gcctttctca accagaaacc ttttcattc aaattgtctt tactcaaaga       540
acgtgaagac agacagtatt cttcttcctc tatccgttct aaacgcttta tgatgaagaa      600
tactgtttga atgaaatttc cccaggacta ggggctattt atcaaagaac tgaatagcct      660
ccccaggact agggagactt aggtggatgt aggatcctta gacttaggtg gatgtaggat      720
ccaaccctag tcctgagtcc tggggattgg ctatgtcatc catgatatcg ttcaaagaac      780
atgatatcgt gaacatcatc tactttcaaa gaacgtagat gatgtatgac atagccttac      840
atgatggaat tggaaatgga attcaaagaa cattcgtttt cattcaaatt gtcttttcct      900
ctatccgttc taaacgcttt atgataagac aatttgaatt ccatcatgtt tacacaacct      960
tatatattaa cagctcaaag aacgctgtta gtatggatgc cagtggagac ttaggtggat     1020
gtaggatcct tagacttagg tggatgtagg atccaaccac tggcatctaa ggttgtgttt     1080
gaaagggagt aggtgtattt acatcaaaga actgtaggta caagatgcta agagcttcaa     1140
agaacagctc ttagcatcta ctcccttcct tcatccagat cgtcggtgaa ttagtcaaag     1200
aacctaattc atcgtcatcc agatcgtaga cttaggtgga tgtaggatcc ttagacttag     1260
gtggatgtag gatccaaacg atctggatcg atctggatgt tgaatttcaa agagaagaag     1320
aatggatctt attattcttc ttctataatt taagcttcct ctatccgttc taaacgcttt     1380
atgatgctta aattatggct ttgaaattct tggtcgtgca tgttaattgg taatcaaaga     1440
acgttatcaa ttggtcatgt acttcgtcaa agaaccgaag tacatgcatg cacgaccta      1500 gatagctact ttattctttc aaatcaaaga actttgaaag agtatggact attttttcctc    1560 tatccgttct aaacgcttta tgataaatag tccatagtag ctatctttag tatttgtgct     1620
agctcctagt tcaaagaaca ctaggggcta tctcttcctt ttagacttag gtggatgtag     1680
gatccttaga cttaggtgga tgtaggatcc aaaaaaggaa gaggcacaaa tactttaaat     1740
tatttgggcc agacatactt cattgcagtc ggtcatttat accaagttct ccaaatagat     1800
tttggacatt tggatatgcc ccaaagaata tatgtagccc agtctcatac cagtcaccat     1860
cctct                                                                  1865
```

<210> SEQ ID NO 67
<211> LENGTH: 714
<212> TYPE: DNA
<213> ORGANISM: Artificial Sequence
<220> FEATURE:
<223> OTHER INFORMATION: TRI nanoparticle
<220> FEATURE:
<221> NAME/KEY: misc_feature
<222> LOCATION: (247)..(501)
<223> OTHER INFORMATION: Nanoparticle insert

<400> SEQUENCE: 67

```
aattaatacg actcactata ggggaaaatt tcgtctggat tagttactta tcgtgtaaaa       60
tctgataaat ggaattggtt ctacataaat gcctaacgac tatcccttttg gggagtaggg     120
```

-continued

```
tcaagtgact cgaaacgata gacaacttgc tttaacaagt tggagatata gtctgctctg    180
catggtgaca tgcagctgga tataattccg gggtaagatt aacgacccta tctgaacata    240
atgctaactg gatgatgtcg ataggttttg ttctcaagaa ggacagaatc tgtcataaga    300
aggctaacag caaactcagt tgctggggaa atatgcatat ttctcagca gtaacgactg    360 ttgaaattcc tctatccgtt ctaaacgctt tatgattttc aatagttgta agggtttgct    420
gaagatccca acttgatgtt gaatttgttc aagagacaaa tttaatattt agctgtcggt    480
tgttcaagag acagccggca gttgagttgg gattaaagct ttcttaaggg catcatccag    540
tcatgtcaat tgaggcctga gtataaggtg acttatactt gtaatctatc taaacgggga    600
acctctctag tagacaatcc cgtgctaaat tgtaggactg ccctttaata aatacttcta    660
tatttaaaga ggtatttatg aaaagcggaa tttatcagat taaaaatact ttct           714
```

<210> SEQ ID NO 68
<211> LENGTH: 78
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (22)..(31)
<223> OTHER INFORMATION: Loop Dicer 2

<400> SEQUENCE: 68

```
ggucauaugu auucuuuaau uggaucuuau uaauuaaaga agaagcacaa gauuucuugu    60
gcuucaacau augacuuu                                                   78
```

<210> SEQ ID NO 69
<211> LENGTH: 106
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (21)..(29)
<223> OTHER INFORMATION: Loop Dicer 1
<220> FEATURE:
<221> NAME/KEY: misc_feature
<222> LOCATION: (53)..(82)
<223> OTHER INFORMATION: Loop clathrin-pit

<400> SEQUENCE: 69

```
auauaaggau gaacuuggua ucaagaaacu accaaguucu ccaaauagau uuuccucua     60 uccguucuaa acgcuuuaug auggaucuau uuggauccuu auauuu                   106
```

<210> SEQ ID NO 70
<211> LENGTH: 112
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (23)..(31)
<223> OTHER INFORMATION: Loop Dicer 1
<220> FEATURE:
<221> NAME/KEY: misc_feature
<222> LOCATION: (59)..(88)
<223> OTHER INFORMATION: Loop clathrin-pit

<400> SEQUENCE: 70

```
uagaugguca uauguauucu uuucaagaaa caaagaauau auguagccca gucucaucuu    60
```

```
ccucuauccg uucuaaacgc uuuaugaucu gagacugggc uaugaccauc ua          112
```

<210> SEQ ID NO 71
<211> LENGTH: 108
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (22)..(30)
<223> OTHER INFORMATION: Loop Dicer 1
<220> FEATURE:
<221> NAME/KEY: misc_feature
<222> LOCATION: (53)..(82)
<223> OTHER INFORMATION: Loop clathrin-pit

<400> SEQUENCE: 71

```
gauguguuua acaauaggca uucaagaaac augcuuauug gccaugucaa aguuccucua   60
uccguucuaa acgcuuuaug aucuuugaca uggcaauaaa cacaucuu              108
```

<210> SEQ ID NO 72
<211> LENGTH: 88
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (24)..(32)
<223> OTHER INFORMATION: Loop Dicer 1

<400> SEQUENCE: 72

```
ugaucgucau aaguuucaag ugcucaagaa acgcacuuga agcaucaccc ucaacucaag   60
aaacguugag ggugauauga cgaucauu                                    88
```

<210> SEQ ID NO 73
<211> LENGTH: 110
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (25)..(34)
<223> OTHER INFORMATION: Loop Dicer 2
<220> FEATURE:
<221> NAME/KEY: misc_feature
<222> LOCATION: (57)..(86)
<223> OTHER INFORMATION: Loop clathrin-pit

<400> SEQUENCE: 73

```
ugucaauggg cgcaucgcug aaugggaucu uauucauucg gugaucguca uaaguuuucc   60
ucuauccguu cuaaacgcuu uaugauaacu uaugacggcc cauugacauu            110
```

<210> SEQ ID NO 74
<211> LENGTH: 91
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (25)..(34)
<223> OTHER INFORMATION: Loop Dicer 2
<220> FEATURE:
<221> NAME/KEY: misc_feature
<222> LOCATION: (57)..(65)

<223> OTHER INFORMATION: Loop Dicer 1

<400> SEQUENCE: 74
uuguauuucu gaccaccucg aaugggaucu uauucauucg aggugccgua uguugaucaa    60
gaaacucaac auacgguaca gaaauacaau u    91

<210> SEQ ID NO 75
<211> LENGTH: 109
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (25)..(33)
<223> OTHER INFORMATION: Loop Dicer 1
<220> FEATURE:
<221> NAME/KEY: misc_feature
<222> LOCATION: (56)..(85)
<223> OTHER INFORMATION: Loop clathrin-pit

<400> SEQUENCE: 75
cagaugaauc ccuggguggu ugccucaaga acggcaauc auccguucgg uuccuuccu    60 cuauccguuc uaaacgcuuu augauggaaa ccgaacggau ucaucuguu    109

<210> SEQ ID NO 76
<211> LENGTH: 117
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (60)..(89)
<223> OTHER INFORMATION: Loop clathrin-pit

<400> SEQUENCE: 76
uaauaugaug aaaguaugcc auuagaucaa aaaacucuaa uggcauaggc ugguguacau    60
uccucuaucc guucuaaacg cuuuaugauu guacaccagc cccuucauua guuauu    117

<210> SEQ ID NO 77
<211> LENGTH: 86
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (1)..(59)
<223> OTHER INFORMATION: 5' Open sequence
<220> FEATURE:
<221> NAME/KEY: misc_feature
<222> LOCATION: (25)..(33)
<223> OTHER INFORMATION: Loop Dicer 1
<220> FEATURE:
<221> NAME/KEY: misc_feature
<222> LOCATION: (60)..(86)
<223> OTHER INFORMATION: 3' Close sequence

<400> SEQUENCE: 77
ggaguagcca ugagaagugc agauucaaga aacauuugua uuucugacca ccuaggguuc    60
ccuggguggu ccaguggcug uuccuu    86

<210> SEQ ID NO 78
<211> LENGTH: 117
<212> TYPE: RNA
<213> ORGANISM: Artificial Sequence

```
<220> FEATURE:
<223> OTHER INFORMATION: MV-RNA
<220> FEATURE:
<221> NAME/KEY: misc_feature
<222> LOCATION: (27)..(35)
<223> OTHER INFORMATION: Loop Dicer 1
<220> FEATURE:
<221> NAME/KEY: misc_feature
<222> LOCATION: (62)..(91)
<223> OTHER INFORMATION: Loop clathrin-pit

<400> SEQUENCE: 78
guccgggaag guuuaaggg ggucucucaa gaaacgagau cucuuugaug gguuguaagg      60
uuuccucuau ccguucuaaa cgcuuuauga uaccuugcaa cccaucuucu cgggcuu      117

<210> SEQ ID NO 79
<211> LENGTH: 118
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (26)..(34)
<223> OTHER INFORMATION: Loop Dicer 1
<220> FEATURE:
<221> NAME/KEY: misc_feature
<222> LOCATION: (61)..(90)
<223> OTHER INFORMATION: Loop clathrin-pit

<400> SEQUENCE: 79
agauccuucc ucaacuguug cuggaucaag aaacuccagu aacaguuaca cuauucuugg      60
uuccucuauc cguucuaaac gcuuuaugau ucaaggauag ugacggggag ggaucuuu     118

<210> SEQ ID NO 80
<211> LENGTH: 94
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (26)..(34)
<223> OTHER INFORMATION: Loop Dicer 1
<220> FEATURE:
<221> NAME/KEY: misc_feature
<222> LOCATION: (59)..(68)
<223> OTHER INFORMATION: Loop Dicer 3

<400> SEQUENCE: 80
caucacuaua cagcaaguug ugugcucaag aaacgcacau aacuugaauu uccuggaguu      60
cauagagauu ccaggagauu uguaugguga uguu      94

<210> SEQ ID NO 81
<211> LENGTH: 96
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (27)..(35)
<223> OTHER INFORMATION: Loop Dicer 1
<220> FEATURE:
<221> NAME/KEY: misc_feature
<222> LOCATION: (62)..(70)
<223> OTHER INFORMATION: Loop Dicer 1

<400> SEQUENCE: 81
```
gauagccugu gcacaaagcu ucaaggucaa gaaacccuug gaguuuugac guuaaauggu    60
aucaagaaac ugccauuuaa uggugcaggc ugucuu                              96

<210> SEQ ID NO 82
<211> LENGTH: 117
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (27)..(35)
<223> OTHER INFORMATION: Loop Dicer 1
<220> FEATURE:
<221> NAME/KEY: misc_feature
<222> LOCATION: (62)..(91)
<223> OTHER INFORMATION: Loop clathrin-pit

<400> SEQUENCE: 82
ucuuugcuuu gcuccauaaa cuuauaucaa gaaacuaugg guuugugacc ugcaucauua    60
auuccucuau ccguucuaaa cgcuuuauga uuuaauggug caggcagggu aaagguu      117

<210> SEQ ID NO 83
<211> LENGTH: 95
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (27)..(35)
<223> OTHER INFORMATION: Loop Dicer 1
<220> FEATURE:
<221> NAME/KEY: misc_feature
<222> LOCATION: (60)..(68)
<223> OTHER INFORMATION: Loop Dicer 1

<400> SEQUENCE: 83
cgacugaauu caccgggaau gggcacucaa gaaacgugcc cauuucuuug cuuugauuuu    60
caagaaacaa aucaaagcga cugaauucag ucguu                               95

<210> SEQ ID NO 84
<211> LENGTH: 116
<212> TYPE: RNA
<213> ORGANISM: Artificial Sequence
<220> FEATURE:
<223> OTHER INFORMATION: MV-RNA
<220> FEATURE:
<221> NAME/KEY: misc_feature
<222> LOCATION: (26)..(34)
<223> OTHER INFORMATION: Loop Dicer 1
<220> FEATURE:
<221> NAME/KEY: misc_feature
<222> LOCATION: (61)..(90)
<223> OTHER INFORMATION: Loop clathrin-pit

<400> SEQUENCE: 84
cagcuucaag augucaugcu gggauucaag aaacauucca gcauggaucu auuuggagaa    60
uuccucuauc cguucuaaac gcuuuaugau uucuccaaau agauuuugga gcuguu       116

<210> SEQ ID NO 85
<211> LENGTH: 318
<212> TYPE: DNA
<213> ORGANISM: Artificial Sequence
<220> FEATURE:
<223> OTHER INFORMATION: PA pds TRI DNA
<220> FEATURE:
<221> NAME/KEY: misc_feature

```
<222> LOCATION: (43)..(52)
<223> OTHER INFORMATION: Loop Dicer 2
<220> FEATURE:
<221> NAME/KEY: misc_feature
<222> LOCATION: (96)..(104)
<223> OTHER INFORMATION: Loop Dicer 1
<220> FEATURE:
<221> NAME/KEY: misc_feature
<222> LOCATION: (128)..(157)
<223> OTHER INFORMATION: Loop clathrin-pit
<220> FEATURE:
<221> NAME/KEY: misc_feature
<222> LOCATION: (204)..(212)
<223> OTHER INFORMATION: Loop Dicer 1
<220> FEATURE:
<221> NAME/KEY: misc_feature
<222> LOCATION: (240)..(269)
<223> OTHER INFORMATION: Loop clathrin-pit

<400> SEQUENCE: 85
aattaatacg actcactata gggtcatatg tattctttaa ttggatctta ttaattaaag    60
aagaagcaca agatcatata aggatgaact tggtatcaag aaactaccaa gttctccaaa   120
tagatttttc ctctatccgt tctaaacgct ttatgatgga tctatttgga tccttatatt   180
ctagatggtc atatgtattc ttttcaagaa acaaagaata tatgtagccc agtctcatct   240
tcctctatcc gttctaaacg ctttatgatc tgagactggg ctatgaccat ctatctcttg   300
tgcttcaaca tatgacct                                                 318

<210> SEQ ID NO 86
<211> LENGTH: 325
<212> TYPE: DNA
<213> ORGANISM: Artificial Sequence
<220> FEATURE:
<223> OTHER INFORMATION: PA pds, epsps, hppd TRI DNA
<220> FEATURE:
<221> NAME/KEY: misc_feature
<222> LOCATION: (43)..(52)
<223> OTHER INFORMATION: Loop Dicer 2
<220> FEATURE:
<221> NAME/KEY: misc_feature
<222> LOCATION: (132)..(161)
<223> OTHER INFORMATION: Loop clathrin-pit
<220> FEATURE:
<221> NAME/KEY: misc_feature
<222> LOCATION: (245)..(274)
<223> OTHER INFORMATION: Loop clathrin-pit

<400> SEQUENCE: 86
aattaatacg actcactata gggtcatatg tattctttaa ttggatctta ttaattaaag    60
aagaagcaca agatttgtca atgggcgcat cgctgaatgg gatcttattc attcggtgat   120
cgtcataagt tttcctctat ccgttctaaa cgctttatga taacttatga cggcccattg   180
acatttaata tgatgaaagt atgccattag atcaaaaaac tctaatggca taggctggtg   240
tacattcctc tatccgttct aaacgcttta tgattgtaca ccagcccctt cattatgtta   300
tttcttgtgc ttcaacatat gactt                                         325

<210> SEQ ID NO 87
<211> LENGTH: 803
<212> TYPE: DNA
<213> ORGANISM: Artificial Sequence
<220> FEATURE:
<223> OTHER INFORMATION: PA pds epsps D8 DNA
<220> FEATURE:
<221> NAME/KEY: misc_feature
<222> LOCATION: (43)..(52)
<223> OTHER INFORMATION: Loop Dicer 2
<220> FEATURE:
```

<221> NAME/KEY: misc_feature
<222> LOCATION: (96)..(104)
<223> OTHER INFORMATION: Loop Dicer 1
<220> FEATURE:
<221> NAME/KEY: misc_feature
<222> LOCATION: (128)..(157)
<223> OTHER INFORMATION: Loop clathrin-pit
<220> FEATURE:
<221> NAME/KEY: misc_feature
<222> LOCATION: (206)..(214)
<223> OTHER INFORMATION: Loop Dicer 1
<220> FEATURE:
<221> NAME/KEY: misc_feature
<222> LOCATION: (239)..(247)
<223> OTHER INFORMATION: Loop Dicer 1
<220> FEATURE:
<221> NAME/KEY: misc_feature
<222> LOCATION: (296)..(304)
<223> OTHER INFORMATION: Loop Dicer 1
<220> FEATURE:
<221> NAME/KEY: misc_feature
<222> LOCATION: (327)..(356)
<223> OTHER INFORMATION: Loop clathrin-pit
<220> FEATURE:
<221> NAME/KEY: misc_feature
<222> LOCATION: (406)..(414)
<223> OTHER INFORMATION: Loop Dicer 1
<220> FEATURE:
<221> NAME/KEY: misc_feature
<222> LOCATION: (438)..(446)
<223> OTHER INFORMATION: Loop Dicer 1
<220> FEATURE:
<221> NAME/KEY: misc_feature
<222> LOCATION: (495)..(504)
<223> OTHER INFORMATION: Loop Dicer 2
<220> FEATURE:
<221> NAME/KEY: misc_feature
<222> LOCATION: (527)..(556)
<223> OTHER INFORMATION: Loop clathrin-pit
<220> FEATURE:
<221> NAME/KEY: misc_feature
<222> LOCATION: (605)..(614)
<223> OTHER INFORMATION: Loop Dicer 2
<220> FEATURE:
<221> NAME/KEY: misc_feature
<222> LOCATION: (637)..(645)
<223> OTHER INFORMATION: Loop Dicer 1
<220> FEATURE:
<221> NAME/KEY: misc_feature
<222> LOCATION: (696)..(704)
<223> OTHER INFORMATION: Loop Dicer 1
<220> FEATURE:
<221> NAME/KEY: misc_feature
<222> LOCATION: (727)..(756)
<223> OTHER INFORMATION: Loop clathrin-pit

<400> SEQUENCE: 87

```
aattaatacg actcactata gggtcatatg tattctttaa ttggatctta ttaattaaag      60
aagaagcaca agattatata aggatgaact tggtatcaag aaactaccaa gttctccaaa     120 tagattttc  ctctatccgt tctaaacgct ttatgatgga tctatttgga tccttatatt     180
ttctggaggg tttccgtcta ggaagtcaag aaaccttcct agacggtatt tagctggttc     240
aagaaacacc agctaaatag aaaccctcta gattgatgtg tttaacaata ggcattcaag     300
aaacatgctt attggccatg tcaaagttcc tctatccgtt ctaaacgctt tatgatcttt     360
gacatggcaa taaacacatc tttgatcgtc ataagtttca agtgctcaag aaacgcactt     420
gaagcatcac cctcaactca agaaacgttg agggtgatat gacgatcatt tgtcaatggg     480
cgcatcgctg aatgggatct tattcattcg gtgatcgtca taagttttcc tctatccgtt     540
ctaaacgctt tatgataact tatgacggcc cattgacatt tgtatttct gaccacctcg      600 aatgggatct tattcattcg aggtgccgta tgttgatcaa gaaactcaac atacggtaca     660
```
gaaatacaat tcagatgaat ccctgggtgg ttgcctcaag aaacggcaat catccgttcg    720
gtttccttcc tctatccgtt ctaaacgctt tatgatggaa accgaacgga ttcatctgtt    780
tcttgtgctt caacatatga ctt    803

<210> SEQ ID NO 88
<211> LENGTH: 859
<212> TYPE: DNA
<213> ORGANISM: Artificial Sequence
<220> FEATURE:
<223> OTHER INFORMATION: PA pds epsps T8 DNA
<220> FEATURE:
<221> NAME/KEY: misc_feature
<222> LOCATION: (1)..(22)
<223> OTHER INFORMATION: EcoRI restriction site/T7 transcription start
      site
<220> FEATURE:
<221> NAME/KEY: misc_feature
<222> LOCATION: (46)..(54)
<223> OTHER INFORMATION: loop dicer 1
<220> FEATURE:
<221> NAME/KEY: misc_feature
<222> LOCATION: (107)..(115)
<223> OTHER INFORMATION: loop dicer 1
<220> FEATURE:
<221> NAME/KEY: misc_feature
<222> LOCATION: (142)..(171)
<223> OTHER INFORMATION: loop clathrin-pit
<220> FEATURE:
<221> NAME/KEY: misc_feature
<222> LOCATION: (223)..(231)
<223> OTHER INFORMATION: loop dicer 1
<220> FEATURE:
<221> NAME/KEY: misc_feature
<222> LOCATION: (256)..(265)
<223> OTHER INFORMATION: loop dicer 3
<220> FEATURE:
<221> NAME/KEY: misc_feature
<222> LOCATION: (317)..(325)
<223> OTHER INFORMATION: loop dicer 1
<220> FEATURE:
<221> NAME/KEY: misc_feature
<222> LOCATION: (352)..(381)
<223> OTHER INFORMATION: loop clathrin-pit
<220> FEATURE:
<221> NAME/KEY: misc_feature
<222> LOCATION: (436)..(444)
<223> OTHER INFORMATION: loop dicer 1
<220> FEATURE:
<221> NAME/KEY: misc_feature
<222> LOCATION: (471)..(479)
<223> OTHER INFORMATION: loop dicer 1
<220> FEATURE:
<221> NAME/KEY: misc_feature
<222> LOCATION: (532)..(540)
<223> OTHER INFORMATION: loop dicer 1
<220> FEATURE:
<221> NAME/KEY: misc_feature
<222> LOCATION: (567)..(596)
<223> OTHER INFORMATION: loop clathrin-pit
<220> FEATURE:
<221> NAME/KEY: misc_feature
<222> LOCATION: (649)..(657)
<223> OTHER INFORMATION: loop dicer 1
<220> FEATURE:
<221> NAME/KEY: misc_feature
<222> LOCATION: (682)..(690)
<223> OTHER INFORMATION: loop dicer 1
<220> FEATURE:
<221> NAME/KEY: misc_feature
<222> LOCATION: (743)..(751)
<223> OTHER INFORMATION: loop dicer 1
<220> FEATURE:
<221> NAME/KEY: misc_feature
<222> LOCATION: (778)..(807)
<223> OTHER INFORMATION: loop clathrin-pit

<400> SEQUENCE: 88

```
aattaatacg actcactata gggagtagcc atgagaagtg cagattcaag aaacatttgt    60
atttctgacc acctagggtt gtccgggaag gttttaaggg ggtctctcaa gaaacgagat   120
ctctttgatg ggttgtaagg tttcctctat ccgttctaaa cgctttatga taccttgcaa   180
cccatcttct cgggcttcat cactatacag caagttgtgt gctcaagaaa cgcacataac   240
ttgaatttcc tggagttcat agagattcca ggagatttgt atggtgatgt tagatccttc   300
ctcaactgtt gctggatcaa gaaactccag taacagttac actattcttg gttcctctat   360
ccgttctaaa cgctttatga ttcaaggata gtgacgggga gggatctttg atagcctgtg   420
cacaaagctt caaggtcaag aaaccccttgg agttttgacg ttaaatggta tcaagaaact   480
gccatttaat ggtgcaggct gtctttcttt gctttgctcc ataaactyat atcaagaaac   540
tatgggtttg tgacctgcat cattaattcc tctatccgtt ctaaacgctt tatgatttaa   600
tggtgcaggc agggtaaagg ttcgactgaa ttcaccggga atgggcactc aagaaacgtg   660
cccatttctt tgctttgatt ttcaagaaac aaatcaaagc gactgaattc agtcgttcag   720
cttcaagatg tcatgctggg attcaagaaa cattccagca tggatctatt tggagaattc   780
ctctatccgt tctaaacgct ttatgatttc tccaaataga ttttggagct gttccctggg   840
tggtccagtg gctgttcct                                                859
```

<210> SEQ ID NO 89
<211> LENGTH: 1254
<212> TYPE: DNA
<213> ORGANISM: Homo sapiens

<400> SEQUENCE: 89

```
atgaagacgg agcggccccg gcccaacacc ttcatcatcc gctgcctgca gtggaccact    60
gtcatcgaac gcaccttcca tgtggagact cctgaggagc gggaggagtg gacaaccgcc   120
atccagactg tggccgacgg cctcaagaag caggaggagg aggagatgga cttccggtcg   180
ggctcaccca cgacaactc aggggccgaa gagatggagg tgtccctggc caagcccaag   240
caccgcgtga ccatgaacga gtttgagtac ctgaagctgc tgggcaaggg cacttttcggc   300
aaggtgatcc tggtgaagga aggccacaca gcgtactacg ccatgaagat cctcaagaag   360
gaagtcatcg tggccaagga cgaggtggcc cacacactca ccgagaaccg cgtccagcag   420
aactccaggc accccttcct cactcgcctg aagtactctt tccagaccca cgaccgcctc   480
tgctttgtca tggagtacgc caacgggggc gagctgttct tccacctgtc ccgggagcgt   540
gtgttcgccg aggaccgggc ccgcttctat ggcgctgaga ttgtgtcagc cctggactac   600
ctgcactcgg agaagaacgt ggtgtaccgg gacctcaagc tggagaacct catgctggac   660
aaggacgggc acattaagat cacagacttc gggctgtgca aggagggat caaggacggt   720
gccaccatga gacctttttg cggcacacct gagtacctgg cccccgaggt gctggaggac   780
aatgactacg gccgtgcagt ggactggtgg gggctgggcg tggtcatgta cgagatgatg   840
tgcggtcgcc tgcccttcta caaccaggac catgagaagc tttttgagct catcctcatg   900
gaggagatcc gcttcccgcg cacgcttggt cccgaggcca gtccttgct tcagggctg    960
ctcaagaagg accccaagca gaggcttggc ggggctccg aggacgccaa ggagatcatg  1020
cagcatcgct tctttaccgg tatcgtgtgg cagcacgtgt acgagaagaa gctcagccca  1080
cccttcaagc cccaggtcac gtcggagact gacaccaggt attttgatga ggagttcacg  1140
```

| | |
|---|---|
| gcccagatga tcaccatcac accacctgac caagatgaca gcatggagtg tgtggacagc | 1200 |
| gagcgcaggc cccacttccc ccagttctcc tactcgccca gcgcgacggc ctga | 1254 |

<210> SEQ ID NO 90
<211> LENGTH: 7522
<212> TYPE: DNA
<213> ORGANISM: Homo sapiens

<400> SEQUENCE: 90

| | |
|---|---|
| caccagaaac ccaagttgga actaattctt tctttcggaa ggtgcaactc ccctcccgcg | 60 |
| agctccgcgg tgccgggccg agattgccga gaggaagcgg cgcagcgctg ccgccaaggc | 120 |
| tcctcctgtc gccggtgcgg ccgggactac ctggcggcgc ggcgcgtgca gcgcgcagag | 180 |
| tcccgggagc ccacgcctcc gcctccgccc ccgcccctc cgcctcccag tccacctcgc | 240 |
| ccgcccgccc tctcgcccgg cggagagcac agcccactcc ctcccacctg cggccgccgg | 300 |
| gccgccctcc acccacacct ctgccgcagg ccggacccag tgcgcccgcc cgtcggtcag | 360 |
| tccaggccag gcgcccggcg gccgcgctc acgcagttgg cgcaggaggc cttacgctgg | 420 |
| cggcgcagtg cccgcccct gcgctctccc cgcccctcc ctcctcgca ggggccgagc | 480 |
| gaatgtagcc cgcgagagaa aatggcggcg gcggcgggga atcgcgcctc gtcgtcggga | 540 |
| ttcccgggcg ccagggctac gagccctgag gcaggcggcg gcggaggagc cctcaaggcg | 600 |
| agcagcgcgc ccgcggctgc cgcgggactg ctgcgggagg cgggcagcgg gggccgcgag | 660 |
| cgggcggact ggcggcggcg gcagctgcgc aaagtgcgga gtgtggagct ggaccagctg | 720 |
| cctgagcagc cgctcttcct tgccgcctca ccgccggcct cctcgacttc cccgtcgccg | 780 |
| gagcccgcgg acgcagcggg gagtgggacc ggcttccagc ctgtggcggt gccgccgccc | 840 |
| cacggagccg cgagccgcgg cggcgcccac cttaccgagt cggtggcggc gccggacagc | 900 |
| ggcgcctcga gtcccgcagc ggccgagccc ggggagaagc gggcgcccgc cgccgagccg | 960 |
| tctcctgcag cggcccccgc cggtcgtgag atggagaata agaaaactct caaagggttg | 1020 |
| cacaagatgg atgatcgtcc agaggaacga atgatcaggg agaaactgaa ggcaacctgt | 1080 |
| atgccagcct ggaagcacga atggttggaa aggagaaata ggcgagggcc tgtggtggta | 1140 |
| aaaccaatcc cagttaaagg agatggatct gaaatgaatc acttagcagc tgagtctcca | 1200 |
| ggagaggtcc aggcaagtgc ggcttcacca gcttccaaag gccgacgcag tccttctcct | 1260 |
| ggcaactccc catcaggtcg cacagtgaaa tcagaatctc caggagtaag gagaaaaaga | 1320 |
| gtttccccag tgccttttca gagtggcaga atcacaccac cccgaagagc cccttcacca | 1380 |
| gatggcttct caccatatag ccctgaggaa acaaaccgcc gtgttaacaa agtgatgcgg | 1440 |
| gccagactgt acttactgca gcagataggg cctaactctt tcctgattgg aggagacagc | 1500 |
| ccagacaata ataccgggt gtttattggg cctcagaact gcagctgtgc acgtggaaca | 1560 |
| ttctgtattc atctgctatt tgtgatgctc cgggtgtttc aactagaacc ttcagaccca | 1620 |
| atgttatgga gaaaaacttt aaagaatttt gaggttgaga gtttgttcca gaaatatcac | 1680 |
| agtaggcgta gctcaaggat caaagctcca tctcgtaaca ccatccagaa gtttgtttca | 1740 |
| cgcatgtcaa attctcatac attgtcatca tctagtactt ctacgtctag ttcagaaaac | 1800 |
| agcataaagg atgaagagga acagatgtgt cctatttgct tgttgggcat gcttgatgaa | 1860 |
| gaaagtctta cagtgtgtga agacggctgc aggaacaagc tgcaccacca ctgcatgtca | 1920 |
| atttgggcag aagagtgtag aagaaataga gaacctttaa tatgtccctt ttgtagatct | 1980 |
| aagtggagat ctcatgattt ctacagccac gagttgtcaa gtcctgtgga ttccccttct | 2040 |

```
tccctcagag ctgcacagca gcaaaccgta cagcagcagc ctttggctgg atcacgaagg    2100
aatcaagaga gcaattttaa ccttactcat tatggaactc agcaaatccc tcctgcttac    2160
aaagatttag ctgagccatg gattcaggtg tttggaatgg aactcgttgg ctgcttattt    2220
tctagaaact ggaatgtgag agagatggcc ctcaggcgtc tttcccatga tgtcagtggg    2280
gccctgctgt tggcaaatgg ggagagcact ggaaattctg ggggcagcag tggaagcagc    2340
ccgagtgggg gagccaccag tgggtcttcc cagaccagta tctcaggaga gtggtggag     2400 gcatgctgca gcgttctgtc aatggtctgt gctgaccctg tctacaaagt gtacgttgct    2460
gctttaaaaa cattgagagc catgctggta tatactcctt gccacagttt agcggaaaga    2520
atcaaacttc agagacttct ccagccagtt gtagacacca tcctagtcaa atgtgcagat    2580
gccaatagcc gcacaagtca gctgtccata tcaacactgt tggaactgtg caaaggccaa    2640
gcaggagagt tggcagttgg cagagaaata ctaaaagctg gatccattgg tattggtggt    2700
gttgattatg tcttaaattg tattcttgga aaccaaactg aatcaaacaa ttggcaagaa    2760
cttcttggcc gcctttgtct tatagataga ctgttgttgg aatttcctgc tgaattttat    2820
cctcatattg tcagtactga tgtttcacaa gctgagcctg ttgaaatcag gtataagaag    2880
ctgctgtccc tcttaacctt tgcttttgcag tccattgata attcccactc aatggttggc    2940
aaactttcca gaaggatcta cttgagttct gcaagaatgg ttactacagt accccatgtg    3000
ttttcaaaac tgttagaaat gctgagtgtt tccagttcca ctcacttcac caggatgcgt    3060
cgccgtttga tggctattgc agatgaggtg gaaattgccg aagccatcca gttgggcgta    3120
gaagacactt tggatggtca acaggacagc ttcttgcagg catctgttcc caacaactat    3180
ctggaaacca cagagaacag ttcccctgag tgcacagtcc atttagagaa aactggaaaa    3240
ggattatgtg ctacaaaatt gagtgccagt tcagaggaca tttctgagag actggccagc    3300
atttcagtag gaccttctag ttcaacaaca acaacaacaa caacaacaga gcaaccaaag    3360
ccaatggttc aaacaaaagg cagaccccac agtcagtgtt tgaactcctc tcctttatct    3420
catcattccc aattaatgtt tccagccttg tcaaccccctt cttcttctac cccatctgta    3480
ccagctggca ctgcaacaga tgtctctaag catagacttc agggattcat tccctgcaga    3540
ataccttctg catctcctca aacacagcgc aagttttctc tacaattcca cagaaactgt    3600
cctgaaaaca aagactcaga taaactttcc ccagtcttta ctcagtcaag acccttgccc    3660
tccagtaaca tacacaggcc aaagccatct agacctaccc caggtaatac aagtaaacag    3720
ggagatccct caaaaaatag catgacactt gatctgaaca gtagttccaa atgtgatgac    3780
agctttggct gtagcagcaa tagtagtaat gctgttatac ccagtgacga gacagtgttc    3840
accccagtag aggagaaatg cagattagat gtcaatacag agctcaactc cagtattgag    3900
gaccttcttg aagcatctat gccttcaagt gatacaacag taactttttaa gtcagaagtt    3960 gctgtcctgt ctcctgaaaa ggctgaaaat gatgatacct acaaagatga tgtgaatcat    4020
aatcaaaagt gcaaagagaa gatggaagct gaagaagaag aagctttagc aattgccatg    4080
gcaatgtcag cgtctcagga tgccctcccc atagttcctc agctgcaggt tgaaaatgga    4140
gaagatatca tcattattca acaggataca ccagagactc taccaggaca taccaaagca    4200
aaacaaccgt atagagaaga cactgaatgg ctgaaggtc aacagatagg ccttggagca    4260
ttttcttctt gttatcaggc tcaagatgtg ggaactggaa cttttaatggc tgttaaacag    4320 gtgacttatg tcagaaacac atcttctgag caagaagaag tagtagaagc actaagagaa    4380
```

```
gagataagaa tgatgagcca tctgaatcat ccaaacatca ttaggatgtt gggagccacg   4440
tgtgagaaga gcaattacaa tctcttcatt gaatggatgg caggggatc ggtggctcat    4500 ttgctgagta aatatggagc cttcaaagaa tcagtagtta ttaactacac tgaacagtta   4560
ctccgtggcc tttcgtatct ccatgaaaac caaatcattc acagagatgt caaaggtgcc   4620
aatttgctaa ttgacagcac tggtcagaga ctaagaattg cagattttgg agctgcagcc   4680
aggttggcat caaaaggaac tggtgcagga gagtttcagg acaaattact ggggacaatt   4740
gcatttatgg cacctgaggt actaagaggt caacagtatg aaggagctg tgatgtatgg    4800 agtgttggct gtgctattat agaaatggct tgtgcaaaac caccatggaa tgcagaaaaa   4860
cactccaatc atcttgcttt gatatttaag attgctagtg caactactgc tccatcgatc   4920
ccttcacatt tgtctcctgg tttacgagat gtggctcttc gttgtttaga acttcaacct   4980
caggacagac ctccatcaag agagctactg aagcatccag tctttcgtac tacatggtag   5040
ccaattatgc agatcaacta cagtagaaac aggatgctca acaagagaaa aaaaacttgt   5100
ggggaaccac attgatattc tactggccat gatgccactg aacagctatg aacgaggcca   5160
gtggggaacc cttacctaag tatgtgattg acaaatcatg atctgtacct aagctcagta   5220
tgcaaaagcc caaactagtg cagaaactgt aaactgtgcc tttcaaagaa ctggccctag   5280
gtgaacagga aaacaatgaa gtttgcatga ctaaattgca gaagcataat tttatttttt   5340
tggagcactt tttcagcaat attagcggct gaggggctca ggatctattt taatatttca   5400
attattcttc catttcatat agtgatcaca agcaggggt tctgcaattc cgttcaaatt     5460
ttttgtcact ggctataaaa tcagtatctg cctcttttag gtcagagtat gctatgagta   5520
gcaatacata catatatttt taaaagttga tacttcttta tgacccacag ttgacctta    5580 ttttcttaaa taccagggca gttgtggctc attgtgcatt ttactgttgg cccattcatt   5640
tcgtttttgg aaattatggt tttgtatttt catgtttatt tacattcatt tttgtttatt   5700
cagggaaagc tgatcttttt ttcaaaccag aaaaaaaaaa tgaactagat atgaagtaga   5760
gttcattaaa tatcttgcta ttgtcagagt ttttaaaata tagacttaat tttgtttttt   5820
taaattggaa tacaataaag tactacctac atttgagtca gtcaccactc ttattgtgca   5880
ggttaagtac aagttaacta aaaataaact gtcctctctg gtgcaactca caaccaagat   5940
caagattacc ttaaaattta tttgaatttt ttagatgttt tggttgtcaa actgtaggaa   6000
acttcacaac atttaagtct tactctgtat gtaacaatcc atcattcacc ttcactactg   6060
gtagtaacat agagctgcca ttttcctttt accatgcatc atctctttac agtaggcctg   6120
gcagatcatt ttttaaaaag attattcaac taccaatcag taatgttttt aaacagtaca   6180
tttgctttga acttggaaaa tgtgttcaga agaaaaatg gaattgaatt tcatttatac    6240
actaattcct tggattttgc acagttacct aacggtttta gtctggagtt aaattcagat   6300
gcatggaatc ctgaaggaaa atggtagctt tttaatcttt ttgtgtgtgt gtgagtcttt   6360
taaatcaagt actgattaac tattaagtac aactttgaga ttttagtttt aactcttcag   6420
aagccagtgt gaaatagaat tggttattct caaagactca ggataaacta ataagctat    6480 atatagagta catttaaaat gtacaacaca aattggaaat aaaataagtt acaagataag   6540
tttacaggga tatattgctt acaattttta aaggcagtt tgtttttat gtgaatatgt      6600 ttcttagtga aattttacat tcctttgttt tggaagattg gcgatatttg aagagttaaa   6660
aatagtacag aaatgtgaag tttggtatct ctaaatgtgt tgtacttgac tttctttttt   6720
attttgtttt ttttttttt tgactactta gaattttcac aattctaata agattgtttc   6780
```

```
caagtctctc atgtgcaagc tttaaaggat gcactcttgc catttatgt actggaagat    6840
cattggtcag atgaatactg tgtctgacaa aaatgtaaac tgtataaact gaggaacctc    6900
agctaatcag tattactttg tagatcacca tgcccaccac atttcaaact caaactatct    6960
gtagatttca aaatccattg tgtttgagtt tgtttgcagt tccctcagct tgctggtaat    7020
tgtggtgttt tgttttttgt tttgttttca atgcaaatgt gatgtaatat tcttattttc    7080
tttggatcaa agctggactg gaaattgtat cgtgtaatta tttttgtgtt cttaatgtta    7140
tttggtactc aagttgtaaa taacgtctac tactgtttat tccagtttct actacctcag    7200
gtgtcctata gattttctct ctaccaaagt tcactttcac aatgaaatta tatttgctgt    7260
gtgactatga ttcctaagat ttccagggct taagggctaa cttctattag caccttactg    7320
tgtaagcaaa tgttacaaaa aaaaaaaaaa aaaatctctg ggttaagaaa atttggctta    7380
aatgtatcct ttgttatttt aaatatattg agatatttta attaaaattt ttaccccatt    7440
gaaccgattt tatagtattt gtacctattt tggtgttttt gtctttatag taaataaaag    7500
tttttgaaca aaaaaaaaaa aa                                             7522

<210> SEQ ID NO 91
<211> LENGTH: 2204
<212> TYPE: DNA
<213> ORGANISM: Homo sapiens

<400> SEQUENCE: 91
gagcggtgcg gaggctctgc tcggatcgag gtctgcagcg cagcttcggg agcatgagtg      60
ctgcagtgac tgcagggaag ctggcacggg caccggccga ccctgggaaa gccggggtcc     120
ccggagttgc agctcccgga gctccggcgg cggctccacc ggcgaaagag atcccggagg     180
tcctagtgga cccacgcagc cggcggcgct atgtgcgggg ccgcttttg ggcaagggcg      240
gctttgccaa gtgcttcgag atctcggacg cggacaccaa ggaggtgttc gcgggcaaga     300
ttgtgcctaa gtctctgctg ctcaagccgc accagaggga gaagatgtcc atggaaatat     360
ccattcaccg cagcctcgcc caccagcacg tcgtaggatt ccacggcttt tcgaggaca     420
acgacttcgt gttcgtggtg ttggagctct gccgccggag gtctctcctg gagctgcaca     480
agaggaggaa agccctgact gagcctgagg cccgatacta cctacggcaa attgtgcttg     540
gctgccagta cctgcaccga aaccgagtta ttcatcgaga cctcaagctg ggcaaccttt     600
tcctgaatga agatctggag gtgaaaatag gggattttgg actggcaacc aaagtcgaat     660
atgacgggga gaggaagaag accctgtgtg ggactcctaa ttacatagct cccgaggtgc     720
tgagcaagaa agggcacagt ttcgaggtgg atgtgtggtc cattgggtgt atcatgtata     780
ccttgttagt gggcaaacca ccttttgaga cttcttgcct aaaagagacc tacctccgga     840
tcaagaagaa tgaatacagt attcccaagc acatcaaccc cgtggccgcc tccctcatcc     900
agaagatgct tcagacagat cccactgccc gcccaaccat taacgagctg cttaatgacg     960
agttctttac ttctggctat atccctgccc gtctccccat cacctgcctg accattccac    1020
caaggttttc gattgctccc agcagcctgg accccagcaa ccggaagccc tcacagtcc     1080
tcaataaagg cttggagaac cccctgcctg agcgtccccg ggaaaagaa gaaccagtgg     1140
ttcgagagac aggtgaggtg gtcgactgcc acctcagtga catgctgcag cagctgcaca    1200
gtgtcaatgc ctccaagccc tcggagcgtg ggctggtcag gcaagaggag gctgaggatc    1260
ctgcctgcat ccccatcttc tgggtcagca agtgggtgga ctattcggac aagtacggcc    1320
```

```
ttgggtatca gctctgtgat aacagcgtgg gggtgctctt caatgactca acacgcctca    1380
tcctctacaa tgatggtgac agcctgcagt acatagagcg tgacggcact gagtcctacc    1440
tcaccgtgag ttcccatccc aactccttga tgaagaagat caccctcctt aaatatttcc    1500
gcaattacat gagcgagcac ttgctgaagg caggtgccaa catcacgccg cgcgaaggtg    1560
atgagctcgc ccggctgccc tacctacgga cctggttccg caccgcagc gccatcatcc    1620
tgcacctcag caacggcagc gtgcagatca acttcttcca ggatcacacc aagctcatct    1680
tgtgcccact gatggcagcc gtgacctaca tcgacgagaa gcgggacttc cgcacatacc    1740
gcctgagtct cctggaggag tacgctgct gcaaggagc ggccagccgg ctccgctacg    1800
cccgcactat ggtggacaag ctgctgagct cacgctcggc cagcaaccgt ctcaaggcct    1860
cctaatagct gccctcccct ccggactggt gccctcctca ctcccacctg catctggggc    1920
ccatactggt tggctcccgc ggtgccatgt ctgcagtgtg cccccagcc ccggtggctg    1980
ggcagagctg catcatcctt gcaggtgggg gttgctgtgt aagttatttt tgtacatgtt    2040
cgggtgtggg ttctacagcc ttgtcccct cccctcaac cccaccatat gaattgtaca    2100
gaatatttct attgaattcg gaactgtcct ttccttggct ttatgcacat taaacagatg    2160
tgaatattca aaaaaaaaaa aaaaaaaaaa aaaaaaaaaa aaaa                     2204
```

<210> SEQ ID NO 92
<211> LENGTH: 10661
<212> TYPE: DNA
<213> ORGANISM: Homo sapiens

<400> SEQUENCE: 92

```
cgagatcccg gggagccagc ttgctgggag agcgggacgg tccggagcaa gcccagaggc      60
agaggaggcg acagagggaa aaagggccga gctagccgct ccagtgctgt acaggagccg     120
aagggacgca ccacgccagc cccagcccgg ctccagcgac agccaacgcc tcttgcagcg     180
cggcggcttc gaagccgccg cccggagctg ccctttcctc ttcggtgaag ttttttaaaag    240
ctgctaaaga ctcggaggaa gcaaggaaag tgcctggtag gactgacggc tgcctttgtc     300
ctcctcctct ccaccccgcc tcccccacc ctgccttccc ccctccccc gtcttctctc      360
ccgcagctgc ctcagtcggc tactctcagc caaccccct caccacccttc tccccaccc     420
gcccccccgc cccgtcggc ccagcgctgc cagcccgagt ttgcagagag gtaactccct     480
ttggctgcga gcgggcgagc tagctgcaca ttgcaaagaa ggctcttagg agccaggcga    540
ctggggagcg gcttcagcac tgcagccacg accgcctgg ttaggctgca cgcggagaga    600
accctctgtt ttcccccact ctctctccac ctcctcctgc cttccccacc ccgagtgcgg    660
agccagagat caaagatga aaaggcagtc aggtcttcag tagccaaaaa acaaaacaaa    720
caaaaacaaa aagccgaaa taaagaaaa agataataac tcagttctta tttgcaccta     780
cttcagtgga cactgaattt ggaaggtgga ggattttgtt ttttctttt aagatctggg    840
catctttga atctacccctt caagtattaa gagacagact gtgagcctag cagggcagat     900
cttgtccacc gtgtgtcttc ttctgcacga gactttgagg ctgtcagagc gcttttttgcg    960
tggttgctcc cgcaagtttc cttctctgga gcttccgca ggtgggcagc tagctgcagc    1020
gactaccgca tcatcacagc ctgttgaact cttctgagca agagaaggg aggcggggta    1080
agggaagtag gtggaagatt cagccaagct caaggatgga agtgcagtta gggctgggaa    1140
gggtctaccc tcgccgccg tccaagacct accgaggagc tttccagaat ctgttccaga    1200
gcgtgcgcga agtgatccag aacccggggcc ccaggcaccc agaggccgcg agcgcagcac    1260
```

```
ctcccggcgc cagtttgctg ctgctgcagc agcagcagca gcagcagcag cagcagcagc   1320
agcagcagca gcagcagcag cagcagcagc agcaagagac tagccccagg cagcagcagc   1380
agcagcaggg tgaggatggt tctccccaag cccatcgtag aggccccaca ggctacctgg   1440
tcctggatga ggaacagcaa ccttcacagc cgcagtcggc cctggagtgc cacccccgaga  1500
gaggttgcgt cccagagcct ggagccgccg tggccgccag caaggggctg ccgcagcagc   1560
tgccagcacc tccggacgag gatgactcag ctgccccatc cacgttgtcc ctgctgggcc   1620
ccactttccc cggcttaagc agctgctccg ctgaccttaa agacatcctg agcgaggcca   1680
gcaccatgca actccttcag caacagcagc aggaagcagt atccgaaggc agcagcagcg   1740
ggagagcgag ggaggcctcg ggggctccca cttcctccaa ggacaattac ttaggggca    1800
cttcgaccat ttctgacaac gccaaggagt tgtgtaaggc agtgtcggtg tccatgggcc   1860
tgggtgtgga ggcgttggag catctgagtc caggggaaca gcttcggggg gattgcatgt   1920
acgccccact tttgggagtt ccacccgctg tgcgtcccac tccttgtgcc ccattggccg   1980
aatgcaaagg ttctctgcta gacgacagcg caggcaagag cactgaagat actgctgagt   2040
attcccctt caagggaggt tacaccaaag ggctagaagg cgagagccta ggctgctctg    2100
gcagcgctgc agcagggagc tccgggacac ttgaactgcc gtctaccctg tctctctaca   2160
agtccggagc actggacgag gcagctgcgt accagagtcg cgactactac aactttccac   2220
tggctctggc cggaccgccg cccctccgc cgcctcccca tccccacgct cgcatcaagc    2280
tggagaaccc gctggactac ggcagcgcct gggcggctgc ggcggcgcag tgccgctatg   2340
gggacctggc gagcctgcat ggcgcgggtg cagcgggacc cggttctggg tcaccctcag   2400
ccgccgcttc ctcatcctgg cacactctct tcacagccga agaaggccag ttgtatggac   2460
cgtgtggtgg tggtggggt ggtggcggcg gcggcggcgg cggcggcggc ggcggcggcg    2520
gcggcggcgg cggcgaggcg ggagctgtag cccctacgg ctacactcgg ccccctcagg    2580
ggctggcggg ccaggaaagc gacttcaccg cacctgatgt gtggtaccct ggcggcatgg   2640
tgagcagagt gccctatccc agtcccactt gtgtcaaaag cgaaatgggc ccctggatgg   2700
atagctactc cggaccttac gggacatgc gtttggagac tgccagggac catgttttgc    2760
ccattgacta ttactttcca ccccagaaga cctgctgat ctgtggagat gaagcttctg    2820
ggtgtcacta tggagctctc acatgtggaa gctgcaaggt cttcttcaaa agagccgctg   2880
aagggaaaca gaagtacctg tgcgccagca gaaatgattg cactattgat aaattccgaa   2940
ggaaaaattg tccatcttgt cgtcttcgga atgttatga agcagggatg actctggggag   3000
cccggaagct gaagaaactt ggtaatctga actacagga ggaaggagag gcttccagca    3060
ccaccagccc cactgaggag acaacccaga agctgacagt gtcacacatt gaaggctatg   3120
aatgtcagcc catctttctg aatgtcctgg aagccattga ccaggtgta gtgtgtgctg    3180
gacacgacaa caaccagccc gactcctttg cagccttgct ctctagcctc aatgaactgg   3240
gagagagaca gcttgtacac gtggtcaagt gggccaaggc cttgcctggc ttccgcaact   3300
tacacgtgga cgaccagatg gctgtcattc agtactcctg gatgggctc atggtgtttg    3360
ccatgggctg gcgatccttc accaatgtca actccaggat gctctacttc gcccctgatc   3420
tggttttcaa tgagtaccgc atgcacaagt cccggatgta cagccagtgt gtccgaatga   3480
ggcacctctc tcaagagttt ggatggctcc aaatcacccc caggaattc ctgtgcatga    3540
aagcactgct actcttcagc attattccag tggatgggct gaaaaatcaa aaattctttg   3600
```

```
atgaacttcg aatgaactac atcaaggaac tcgatcgtat cattgcatgc aaaagaaaaa    3660
atcccacatc ctgctcaaga cgcttctacc agctcaccaa gctcctggac tccgtgcagc    3720
ctattgcgag agagctgcat cagttcactt ttgacctgct aatcaagtca cacatggtga    3780
gcgtggactt tccggaaatg atggcagaga tcatctctgt gcaagtgccc aagatccttt    3840
ctgggaaagt caagcccatc tatttccaca cccagtgaag cattggaaac cctatttccc    3900
caccccagct catgccccct ttcagatgtc ttctgcctgt tataactctg cactactcct    3960
ctgcagtgcc ttggggaatt tcctctattg atgtacagtc tgtcatgaac atgttcctga    4020
attctatttg ctgggctttt tttttctctt tctctccttt cttttcttc ttccctccct     4080
atctaaccct cccatggcac cttcagactt tgcttcccat tgtggctcct atctgtgttt    4140
tgaatggtgt tgtatgcctt taaatctgtg atgatcctca tatggcccag tgtcaagttg    4200
tgcttgttta cagcactact ctgtgccagc cacacaaacg tttacttatc ttatgccacg    4260
ggaagtttag agagctaaga ttatctgggg aaatcaaaac aaaacaagc aaacaaaaaa     4320
aaaaagcaaa aacaaaacaa aaaataagcc aaaaaaccct tgctagtgttt tttcctcaaa   4380
aataaataaa taaataaata aatacgtaca tacatacaca catacataca aacatataga    4440
aatccccaaa gaggccaata gtgacgagaa ggtgaaaatt gcaggcccat ggggagttac    4500
tgatttttc atctcctccc tccacgggag actttatttt ctgccaatgg ctattgccat     4560
tagagggcag agtgaccccca gagctgagtt gggcaggggg gtggacagag aggagaggac   4620
aaggagggca atggagcatc agtacctgcc cacagccttg gtccctgggg gctagactgc    4680
tcaactgtgg agcaattcat tatactgaaa atgtgcttgt tgttgaaaat ttgtctgcat    4740
gttaatgcct cacccccaaa ccctttttctc tctcactctc tgcctccaac ttcagattga   4800
cttctcaatag ttttttctaag accttgtgaac tgaatgttct cttcagccaa aacttggcga  4860
cttccacaga aaagtctgac cactgagaag aaggagagca gagatttaac cctttgtaag    4920
gccccatttg gatccaggtc tgcttttctca tgtgtgagtc agggaggagc tggagccaga   4980
ggagaagaaa atgatagctt ggctgttctc ctgcttagga cactgactga atagttaaac    5040
tctcactgcc actacctttt ccccacccttt aaaagacctg aatgaagttt ctgccaaac    5100
tccgtgaagc cacaagcacc ttatgtcctc ccttcagtgt tttgtgggcc tgaatttcat    5160
cacactgcat ttcagccatg gtcatcaagc ctgtttgctt cttttgggca tgttcacaga    5220
ttctctgtta agagccccca ccaccaagaa ggttagcagg ccaacagctc tgacatctat    5280
ctgtagatgc cagtagtcac aaagatttct taccaactct cagatcgctg gagcccttag    5340
acaaactgga agaaggcat caaagggatc aggcaagctg ggcgtcttgc ccttgtcccc     5400
cagagatgat accctcccag caagtggaga agttctcact tccttcttta gagcagctaa    5460
aggggctacc cagatcaggg ttgaagagaa aactcaatta ccagggtggg aagaatgaag    5520
gcactagaac cagaaaccct gcaaatgctc ttcttgtcac ccagcatatc cacctgcaga    5580
agtcatgaga agagagaagg aacaaagagg agactctgac tactgaatta aaatcttcag    5640
cggcaaagcc taaagccaga tggacaccat ctggtgagtt tactcatcat cctcctctgc    5700
tgctgattct gggctctgac attgccata ctcactcaga ttccccacct tgttgctgc      5760
ctcttagtca gagggaggcc aaaccattga gactttctac agaaccatgg cttctttcgg    5820
aaaggtctgg ttggtgtggc tccaatactt tgccacccat gaactcaggg tgtgccctgg    5880
gacactggtt ttatatagtc ttttggcaca cctgtgttct gttgacttcg ttcttcaagc    5940
ccaagtgcaa gggaaaatgt ccacctactt tctcatcttg gcctctgcct ccttacttag    6000
```

| | |
|---|---|
| ctcttaatct catctgttga actcaagaaa tcaagggcca gtcatcaagc tgcccatttt | 6060 |
| aattgattca ctctgtttgt tgagaggata gtttctgagt gacatgatat gatccacaag | 6120 |
| ggtttccttc cctgatttct gcattgatat taatagccaa acgaacttca aaacagcttt | 6180 |
| aaataacaag ggagagggga acctaagatg agtaatatgc caatccaaga ctgctggaga | 6240 |
| aaactaaagc tgacaggttc ccttttgggg gtgggataga catgttctgg ttttctttat | 6300 |
| tattacacaa tctggctcat gtacaggatc acttttagct gttttaaaca gaaaaaaata | 6360 |
| tccaccactc ttttcagtta cactaggtta cattttaata ggtcctttac atctgttttg | 6420 |
| gaatgatttt catcttttgt gatacacaga ttgaattata tcattttcat atctctcctt | 6480 |
| gtaaatacta gaagctctcc tttacatttc tctatcaaat ttttcatctt tatgggtttc | 6540 |
| ccaattgtga ctcttgtctt catgaatata tgttttcat ttgcaaagc caaaatcag | 6600 |
| tgaaacagca gtgtaattaa agcaacaac tggattactc caaatttcca aatgacaaaa | 6660 |
| ctagggaaaa atagcctaca caagccttta ggcctactct ttctgtgctt gggtttgagt | 6720 |
| gaacaaagga gattttagct tggctctgtt ctcccatgga tgaaaggagg aggatttttt | 6780 |
| ttttcttttg gccattgatg ttctagccaa tgtaattgac agaagtctca ttttgcatgc | 6840 |
| gctctgctct acaaacagag ttggtatggt tggtatactg tactcacctg tgagggactg | 6900 |
| gccactcaga cccacttagc tggtgagcta gaagatgagg atcactcact ggaaaagtca | 6960 |
| caaggaccat ctccaaacaa gttggcagtg ctcgatgtgg acgaagagtg aggaagagaa | 7020 |
| aaagaaggag caccagggag aaggctccgt ctgtgctggg cagcagacag ctgccaggat | 7080 |
| cacgaactct gtagtcaaag aaaagagtcg tgtggcagtt tcagctctcg ttcattgggc | 7140 |
| agctcgccta ggcccagcct ctgagctgac atgggagttg ttggattctt tgtttcatag | 7200 |
| cttttttctat gccataggca atattgttgt tcttggaaag tttattattt ttttaactcc | 7260 |
| cttactctga gaaagggata ttttgaagga ctgtcatata tctttgaaaa agaaaatct | 7320 |
| gtaatacata tattttatg tatgttcact ggcactaaaa aatatagaga gcttcattct | 7380 |
| gtcctttggg tagttgctga ggtaattgtc caggttgaaa aataatgtgc tgatgctaga | 7440 |
| gtccctctct gtccatactc tacttctaaa tacatatagg catacatagc aagttttatt | 7500 |
| tgacttgtac tttaagagaa aatatgtcca ccatccacat gatgcacaaa tgagctaaca | 7560 |
| ttgagcttca agtagcttct aagtgtttgt ttcattaggc acagcacaga tgtggccttt | 7620 |
| ccccccttct ctcccttgat atctggcagg gcataaaggc ccaggccact tcctctgccc | 7680 |
| cttcccagcc ctgcaccaaa gctgcatttc aggagactct ctccagacag cccagtaact | 7740 |
| acccgagcat ggcccctgca tagccctgga aaaataagag gctgactgtc tacgaattat | 7800 |
| cttgtgccag ttgcccaggt gagagggcac tgggccaagg gagtggtttt catgtttgac | 7860 |
| ccactacaag gggtcatggg aatcaggaat gccaaagcac cagatcaaat ccaaaactta | 7920 |
| aagtcaaaat aagccattca gcatgttcag tttcttggaa aaggaagttt ctaccccctga | 7980 |
| tgcctttgta ggcagatctg ttctcaccat taatcttttt gaaaatcttt taaagcagtt | 8040 |
| tttaaaaaga gagatgaaag catcacatta tataaccaaa gattacattg tacctgctaa | 8100 |
| gataccaaaa ttcataaggg caggggggga gcaagcatta gtgcctcttt gataagctgt | 8160 |
| ccaaagacag actaaaggac tctgctggtg actgacttat aagagctttg tgggtttttt | 8220 |
| tttccctaat aatatacatg tttagaagaa ttgaaaataa tttcgggaaa atgggattat | 8280 |
| gggtccttca ctaagtgatt ttataagcag aactggcttt ccttttctct agtagttgct | 8340 |

```
gagcaaattg ttgaagctcc atcattgcat ggttggaaat ggagctgttc ttagccactg   8400
tgtttgctag tgcccatgtt agcttatctg aagatgtgaa acccttgctg ataagggagc   8460
atttaaagta ctagattttg cactagaggg acagcaggca gaaatcctta tttctgccca   8520
ctttggatgg cacaaaaagt tatctgcagt tgaaggcaga aagttgaaat acattgtaaa   8580
tgaatatttg tatccatgtt tcaaaattga aatatatata tatatatata tatatatata   8640
tatatatata tagtgtgtgt gtgtgttctg atagctttaa ctttctctgc atctttatat   8700
ttggttccag atcacacctg atgccatgta cttgtgagag aggatgcagt tttgttttgg   8760
aagctctctc agaacaaaca agacacctgg attgatcagt taactaaaag tttttctcccc   8820
tattgggttt gacccacagg tcctgtgaag gagcagaggg ataaaaagag tagaggacat   8880
gatacattgt actttactag ttcaagacag atgaatgtgg aaagcataaa aactcaatgg   8940
aactgactga gatttaccac agggaaggcc caaacttggg gccaaaagcc tacccaagtg   9000
attgaccagt ggcccctaa tgggacctga gctgttggaa gaagagaact gttccttggt    9060
cttcaccatc cttgtgagag aagggcagtt tcctgcattg gaacctggag caagcgctct   9120
atctttcaca caaattccct cacctgagat tgaggtgctc ttgttactgg gtgtctgtgt   9180
gctgtaattc tggttttgga tatgttctgt aaagattttg acaaatgaaa atgtgttttt   9240
ctctgttaaa acttgtcaga gtactagaag ttgtatctct gtaggtgcag gtccatttct   9300
gcccacaggt agggtgtttt tctttgatta agagattgac acttctgttg cctaggacct   9360
cccaactcaa ccatttctag gtgaaggcag aaaaatccac attagttact cctcttcaga   9420
catttcagct gagataacaa atcttttgga atttttcac ccatagaaag agtggtagat    9480
atttgaattt agcaggtgga gtttcatagt aaaaacagct tttgactcag ctttgattta   9540
tcctcatttg atttggccag aaagtaggta atatgcattg attggcttct gattccaatt   9600
cagtatagca aggtgctagg tttttcctt tccccacctg tctcttagcc tggggaatta    9660
aatgagaagc cttagaatgg gtggccctg tgacctgaaa cacttcccac ataagctact    9720
taacaagatt gtcatggagc tgcagattcc attgcccacc aaagactaga acacacacat   9780
atccatacac caaaggaaag acaattctga atgctgtttt ctctggtggt tccctctctg   9840
gctgctgcct cacagtatgg gaacctgtac tctgcagagg tgacaggcca gatttgcatt   9900
atctcacaac cttagccctt ggtgctaact gtcctacagt gaagtgcctg gggggttgtc   9960
ctatcccata agccacttgg atgctgacag cagccaccat cagaatgacc cacgcaaaaa  10020
aaagaaaaaa aaaattaaaa agtcccctca caacccagtg acacctttct gctttcctct  10080
agactggaac attgattagg gagtgcctca gacatgacat tcttgtgctg tccttggaat  10140
taatctggca gcaggaggga gcagactatg taaacagaga taaaaattaa ttttcaatat  10200
tgaaggaaaa aagaaataag aagagagaga gaaagaaagc atcacacaaa gatttcttaa  10260
aaagaaacaa ttttgcttga aatctcttta gatgggggctc atttctcacg gtggcacttg  10320
gcctccactg ggcagcagga ccagctccaa gcgctagtgt tctgttctct ttttgtaatc  10380
ttggaatctt tgttgctct aaatacaatt aaaaatggca gaaacttgtt tgttggacta   10440
catgtgtgac tttgggtctg tctctgcctc tgctttcaga aatgtcatcc attgtgtaaa  10500
atattggctt actggtctgc cagctaaaac ttggccacat cccctgttat ggctgcagga  10560
tcgagttatt gttaacaaag agacccaaga aaagctgcta atgtcctctt atcattgttg  10620
ttaatttgtt aaaacataaa gaaatctaaa atttcaaaaa a                      10661
```

<210> SEQ ID NO 93
<211> LENGTH: 8112
<212> TYPE: DNA
<213> ORGANISM: Homo sapiens

<400> SEQUENCE: 93

| | | | | | |
|---|---|---|---|---|---|
| gctgcgagca | gagagggatt | cctcggaggt | catctgttcc | atcttcttgc | ctatgcaaat | 60 |
| gcctgcctga | agctgctgga | ggctggcttt | gtaccggact | tgtacaggg | aaccagggaa | 120 |
| acgaatgcag | agtgctcctg | acattgcctg | tcacttttc | ccatgatact | ctggcttcac | 180 |
| agtttggaga | ctgccaggga | ccatgttttg | cccattgact | attactttcc | accccagaag | 240 |
| acctgcctga | tctgtggaga | tgaagcttct | gggtgtcact | atggagctct | cacatgtgga | 300 |
| agctgcaagg | tcttcttcaa | aagagccgct | gaagggaaac | agaagtacct | gtgcgccagc | 360 |
| agaaatgatt | gcactattga | taaattccga | aggaaaaatt | gtccatcttg | tcgtcttcgg | 420 |
| aaatgttatg | aagcagggat | gactctggga | gcccggaagc | tgaagaaact | tggtaatctg | 480 |
| aaactacagg | aggaaggaga | ggcttccagc | accaccagcc | ccactgagga | gacaacccag | 540 |
| aagctgacag | tgtcacacat | tgaaggctat | gaatgtcagc | ccatctttct | gaatgtcctg | 600 |
| gaagccattg | agccaggtgt | agtgtgtgct | ggacacgaca | acaaccagcc | cgactccttt | 660 |
| gcagccttgc | tctctagcct | caatgaactg | ggagagagac | agcttgtaca | cgtggtcaag | 720 |
| tgggccaagg | ccttgcctgg | cttccgcaac | ttacacgtgg | acgaccagat | ggctgtcatt | 780 |
| cagtactcct | ggatggggct | catggtgttt | gccatgggct | ggcgatcctt | caccaatgtc | 840 |
| aactccagga | tgctctactt | cgcccctgat | ctggttttca | atgagtaccg | catgcacaag | 900 |
| tcccggatgt | acagccagtg | tgtccgaatg | aggcacctct | ctcaagagtt | tggatggctc | 960 |
| caaatcaccc | cccaggaatt | cctgtgcatg | aaagcactgc | tactcttcag | cattattcca | 1020 |
| gtggatgggc | tgaaaaatca | aaaattcttt | gatgaacttc | gaatgaacta | catcaaggaa | 1080 |
| ctcgatcgta | tcattgcatg | caaaagaaaa | aatcccacat | cctgctcaag | acgcttctac | 1140 |
| cagctcacca | agctcctgga | ctccgtgcag | cctattgcga | gagagctgca | tcagttcact | 1200 |
| tttgacctgc | taatcaagtc | acacatggtg | agcgttggact | ttccggaaat | gatggcagag | 1260 |
| atcatctctg | tgcaagtgcc | caagatcctt | tctgggaaag | tcaagcccat | ctatttccac | 1320 |
| acccagtgaa | gcattggaaa | ccctatttcc | ccaccccagc | tcatgccccc | tttcagatgt | 1380 |
| cttctgcctg | ttataactct | gcactactcc | tctgcagtgc | cttggggaat | tcctctatt | 1440 |
| gatgtacagt | ctgtcatgaa | catgttcctg | aattctattt | gctgggcttt | ttttttctct | 1500 |
| ttctctcctt | tctttttctt | cttccctccc | tatctaaccc | tcccatggca | ccttcagact | 1560 |
| ttgcttccca | ttgtggctcc | tatctgtgtt | ttgaatggtg | ttgtatgcct | ttaaatctgt | 1620 |
| gatgatcctc | atatggccca | gtgtcaagtt | gtgcttgttt | acagcactac | tctgtgccag | 1680 |
| ccacacaaac | gtttacttat | cttatgccac | gggaagttta | gagagctaag | attatctggg | 1740 |
| gaaatcaaaa | caaaacaag | caaacaaaaa | aaaaagcaa | aacaaaaca | aaaataagc | 1800 |
| caaaaaacct | tgctagtgtt | ttttcctcaa | aaataaataa | ataaataaat | aaatacgtac | 1860 |
| atacatacac | acatacatac | aaacatatag | aaatccccaa | agaggccaat | agtgacgaga | 1920 |
| aggtgaaaat | tgcaggccca | tggggagtta | ctgattttt | catctcctcc | ctccacggga | 1980 |
| gactttattt | tctgccaatg | gctattgcca | ttagagggca | gagtgacccc | agagctgagt | 2040 |
| tgggcagggg | ggtggacaga | gaggagagga | caaggagggc | aatggagcat | cagtacctgc | 2100 |
| ccacagcctt | ggtccctggg | ggctagactg | ctcaactgtg | gagcaattca | ttatactgaa | 2160 |

```
aatgtgcttg ttgttgaaaa tttgtctgca tgttaatgcc tcaccccaa accctttct     2220 ctctcactct ctgcctccaa cttcagattg actttcaata gtttttctaa gaccttgaa     2280 ctgaatgttc tcttcagcca aaacttggcg acttccacag aaaagtctga ccactgagaa    2340
gaaggagagc agagatttaa ccctttgtaa ggccccattt ggatccaggt ctgctttctc    2400
atgtgtgagt cagggaggag ctggagccag aggagaagaa aatgatagct tggctgttct    2460
cctgcttagg acactgactg aatagttaaa ctctcactgc cactaccttt tccccacctt    2520
taaaagacct gaatgaagtt ttctgccaaa ctccgtgaag ccacaagcac cttatgtcct    2580
cccttcagtg ttttgtgggc ctgaatttca tcacactgca tttcagccat ggtcatcaag    2640
cctgtttgct tcttttgggc atgttcacag attctctgtt aagagccccc accaccaaga    2700
aggttagcag ccaacagct ctgacatcta tctgtagatg ccagtagtca caaagatttc     2760
ttaccaactc tcagatcgct ggagccctta gacaaactgg aaagaaggca tcaaagggat    2820
caggcaagct gggcgtcttg cccttgtccc cagagatga  taccctccca gcaagtggag    2880
aagttctcac ttccttcttt agagcagcta aaggggctac ccagatcagg gttgaagaga    2940
aaactcaatt accagggtgg gaagaatgaa ggcactagaa ccagaaaccc tgcaaatgct    3000
cttcttgtca cccagcatat ccacctgcag aagtcatgag aagagagaag gaacaaagag    3060
gagactctga ctactgaatt aaaatcttca gcggcaaagc ctaaagccag atggacacca    3120
tctggtgagt ttactcatca tcctcctctg ctgctgattc tgggctctga cattgcccat    3180
actcactcag attccccacc tttgttgctg cctcttagtc agagggaggc caaaccattg    3240
agactttcta cagaaccatg gcttctttcg gaaaggtctg gttggtgtgg ctccaatact    3300
ttgccaccca tgaactcagg gtgtgccctg ggacactggt tttatatagt cttttggcac    3360
acctgtgttc tgttgacttc gttcttcaag cccaagtgca agggaaaatg tccacctact    3420
ttctcatctt ggcctctgcc tccttactta gctcttaatc tcatctgttg aactcaagaa    3480
atcaagggcc agtcatcaag ctgcccattt taattgattc actctgttg ttgagaggat     3540 agtttctgag tgacatgata tgatccacaa gggtttcctt ccctgatttc tgcattgata    3600
ttaatagcca aacgaacttc aaaacagctt taaataacaa gggagagggg aacctaagat    3660
gagtaatatg ccaatccaag actgctggag aaaactaaag ctgacaggtt ccctttttgg    3720
ggtgggatag acatgttctg gttttcttta ttattacaca atctggctca tgtacaggat    3780
cacttttagc tgtttaaac agaaaaaaat atccaccact cttttcagtt acactaggtt     3840
acattttaat aggtcctta catctgtttt ggaatgattt tcatcttttg tgatacacag     3900
attgaattat atcattttca tatctctcct tgtaaatact agaagctctc ctttacattt    3960
ctctatcaaa tttttcatct ttatgggttt cccaattgtg actcttgtct tcatgaatat    4020
atgtttttca tttgcaaaag ccaaaaatca gtgaaacagc agtgtaatta aaagcaacaa    4080
ctggattact ccaaatttcc aaatgacaaa actaggaaaa aatagcctac aaagccttt     4140 aggcctactc tttctgtgct tgggtttgag tgaacaaagg agattttagc ttggctctgt    4200
tctcccatgg atgaaaggag gaggattttt ttttttcttt ggccattgat gttctagcca    4260
atgtaattga cagaagtctc attttgcatg cgctctgctc tacaaacaga gttggtatgg    4320
ttggtatact gtactcacct gtgagggact ggccactcag acccacttag ctggtgagct    4380
agaagatgag gatcactcac tggaaaagtc acaaggacca tctccaaaca agttggcagt    4440
gctcgatgtg gacgaagagt gaggaagaga aaagaaggga gcaccaggga gaaggctccg    4500
tctgtgctgg gcagcagaca gctgccagga tcacgaactc tgtagtcaaa gaaaagagtc    4560
```

```
gtgtggcagt tcagctctc gttcattggg cagctcgcct aggcccagcc tctgagctga   4620
catgggagtt gttggattct tgttcata gcttttcta tgccataggc aatattgttg     4680
ttcttggaaa gtttattatt ttttaactc ccttactctg agaaagggat atttgaagg    4740 actgtcatat atctttgaaa aagaaaatc tgtaatacat atatttttat gtatgttcac   4800
tggcactaaa aaatatagag agcttcattc tgtcctttgg gtagttgctg aggtaattgt   4860
ccaggttgaa aaataatgtg ctgatgctag agtccctctc tgtccatact ctacttctaa   4920
atacatatag gcatacatag caagttttat ttgacttgta ctttaagaga aaatatgtcc   4980
accatccaca tgatgcacaa atgagctaac attgagcttc aagtagcttc taagtgtttg   5040
tttcattagg cacagcacag atgtggcctt tccccccttc tctcccttga tatctggcag   5100
ggcataaagg cccaggccac ttcctctgcc ccttcccagc cctgcaccaa agctgcattt   5160
caggagactc tctccagaca gcccagtaac tacccgagca tggcccctgc atagccctgg   5220
aaaaataaga ggctgactgt ctacgaatta tcttgtgcca gttgcccagg tgagagggca   5280
ctgggccaag ggagtggttt tcatgtttga cccactacaa ggggtcatgg gaatcaggaa   5340
tgccaaagca ccagatcaaa tccaaaactt aaagtcaaaa taagccattc agcatgttca   5400
gtttcttgga aaaggaagtt tctacccctg atgcctttgt aggcagatct gttctcacca   5460
ttaatctttt tgaaaatctt ttaaagcagt ttttaaaaag agatgaaa gcatcacatt    5520 ataaccaa agattacatt gtacctgcta agataccaaa attcataagg gcaggggggg    5580
agcaagcatt agtgcctctt tgataagctg tccaaagaca gactaaagga ctctgctggt   5640
gactgactta taagagcttt gtgggtttt ttttccctaa taatatacat gtttagaaga   5700
attgaaaata atttcgggaa aatgggatta tgggtccttc actaagtgat tttataagca   5760
gaactggctt tccttttctc tagtagttgc tgagcaaatt gttgaagctc catcattgca   5820
tggttggaaa tggagctgtt cttagccact gtgtttgcta gtgcccatgt tagcttatct   5880
gaagatgtga aaccccttgct gataagggag catttaaagt actagattt gcactagagg    5940 gacagcaggc agaaatcctt atttctgccc actttggatg gcacaaaaag ttatctgcag   6000
ttgaaggcag aaagttgaaa tacattgtaa atgaatattt gtatccatgt ttcaaaattg   6060
aaatatatat atatatatat atatatatat atatatatat atagtgtgtg tgtgtgttct   6120
gatagcttta actttctctg catctttata tttggttcca gatcacacct gatgccatgt   6180
acttgtgaga gaggatgcag ttttgttttg gaagctctct cagaacaaac aagacacctg   6240
gattgatcag ttaactaaaa gttttctccc ctattgggtt tgacccacag gtcctgtgaa   6300
ggagcagagg gataaaaaga gtagaggaca tgatacattg tactttacta gttcaagaca   6360
gatgaatgtg gaaagcataa aaactcaatg gaactgactg agatttacca cagggaaggc   6420
ccaaacttgg ggccaaaagc ctacccaagt gattgaccag tggcccccta atgggacctg   6480
agctgttgga agaagagaac tgttccttgg tcttcaccat ccttgtgaga gaagggcagt   6540
ttcctgcatt ggaacctgga gcaagcgctc tatctttcac acaaattccc tcacctgaga   6600
ttgaggtgct cttgttactg ggtgtctgtg tgctgtaatt ctggttttgg atatgttctg   6660
taaagatttt gacaaatgaa aatgtgtttt tctctgttaa aacttgtcag agtactagaa   6720
gttgtatctc tgtaggtgca ggtccatttc tgcccacagg tagggtgttt ttctttgatt   6780
aagagattga cacttctgtt gcctaggacc tcccaactca accatttcta ggtgaaggca   6840
gaaaaatcca cattagttac tcctcttcag acatttcagc tgagataaca aatcttttgg   6900
```

```
aatttttca cccatagaaa gagtggtaga tatttgaatt tagcaggtgg agtttcatag    6960
taaaaacagc ttttgactca gctttgattt atcctcattt gatttggcca gaaagtaggt    7020
aatatgcatt gattggcttc tgattccaat tcagtatagc aaggtgctag gttttttcct    7080
ttccccacct gtctcttagc ctggggaatt aaatgagaag ccttagaatg ggtggccctt    7140
gtgacctgaa acacttccca cataagctac ttaacaagat tgtcatggag ctgcagattc    7200
cattgcccac caaagactag aacacacaca tatccataca ccaaaggaaa gacaattctg    7260
aaatgctgtt tctctggtgg ttccctctct ggctgctgcc tcacagtatg ggaacctgta    7320
ctctgcagag gtgacaggcc agatttgcat tatctcacaa ccttagccct tggtgctaac    7380
tgtcctacag tgaagtgcct gggggggttgt cctatcccat aagccacttg gatgctgaca    7440
gcagccacca tcagaatgac ccacgcaaaa aaagaaaaa aaaaattaaa aagtcccctc    7500
acaacccagt gacacctttc tgctttcctc tagactggaa cattgattag ggagtgcctc    7560
agacatgaca ttcttgtgct gtccttggaa ttaatctggc agcaggaggg agcagactat    7620
gtaaacagag ataaaaatta attttcaata ttgaaggaaa aaagaaataa gaagagagag    7680
agaaagaaag catcacacaa agatttctt aaaagaaaca attttgcttg aaatctcttt    7740
agatggggct catttctcac ggtggcactt ggcctccact gggcagcagg accagctcca    7800
agcgctagtg ttctgttctc tttttgtaat cttggaatct tttgttgctc taaatacaat    7860
taaaaatggc agaaacttgt ttgttggact acatgtgtga ctttgggtct gtctctgcct    7920
ctgctttcag aaatgtcatc cattgtgtaa aatattggct tactggtctg ccagctaaaa    7980
cttggccaca tccctgtta tggctgcagg atcgagttat tgttaacaaa gagacccaag    8040
aaaagctgct aatgtcctct tatcattgtt gttaatttgt taaaacataa agaaatctaa    8100
aatttcaaaa aa    8112

<210> SEQ ID NO 94
<211> LENGTH: 4586
<212> TYPE: DNA
<213> ORGANISM: Homo sapiens

<400> SEQUENCE: 94
gaattccgcc ctcgccgccc gcggcgcccc gagcgctttg tgagcagatg cggagccgag      60
tggagggcgc gagccagatg cggggcgaca gctgacttgc tgagaggagg cggggaggcg     120
cggagcgcgc gtgtggtcct tgcgccgctg acttctccac tggttcctgg gcaccgaaag     180
ataaacctct cataatgaag gccccgctg tgcttcacc tggcatcctc gtgctcctgt     240
ttaccttggt gcagaggagc aatggggagt gtaaagaggc actagcaaag tccgagatga     300
atgtgaatat gaagtatcag cttcccaact tcaccgcgga acacccatc cagaatgtca     360 ttctacatga gcatcacatt ttccttggtg ccactaacta catttatgtt ttaaatgagg     420
aagaccttca gaaggttgct gagtacaaga ctgggcctgt gctggaacac ccagattgtt     480
tcccatgtca ggactgcagc agcaaagcca atttatcagg aggtgtttgg aaagataaca     540
tcaacatggc tctagttgtc gacacctact atgatgatca actcattagc tgtggcagcg     600
tcaacagagg gacctgccag cgacatgtct ttccccacaa tcatactgct gacatacagt     660
cggaggttca ctgcatattc tccccacaga tagaagagcc cagccagtgt cctgactgtg     720
tggtgagcgc cctgggagcc aaagtccttt catctgtaaa ggaccggttc atcaacttct     780
ttgtaggcaa taccataaat tcttcttatt cccagatca tccattgcat tcgatatcag     840
tgagaaggct aaaggaaacg aaagatggtt ttatgttttt gacggaccag tcctacattg     900
```

```
atgttttacc tgagttcaga gattcttacc ccattaagta tgtccatgcc tttgaaagca    960
acaatttat  ttacttcttg acggtccaaa gggaaactct agatgctcag acttttcaca   1020
caagaataat caggttctgt tccataaact ctggattgca ttcctacatg gaaatgcctc   1080
tggagtgtat tctcacagaa aagagaaaaa agagatccac aaagaaggaa gtgtttaata   1140
tacttcaggc tgcgtatgtc agcaagcctg gggcccagct tgctagacaa ataggagcca   1200
gcctgaatga tgacattctt ttcggggtgt tcgcacaaag caagccagat tctgccgaac   1260
caatggatcg atctgccatg tgtgcattcc ctatcaaata tgtcaacgac ttcttcaaca   1320
agatcgtcaa caaaaacaat gtgagatgtc tccagcattt ttacggaccc aatcatgagc   1380
actgctttaa taggacactt ctgagaaatt catcaggctg tgaagcgcgc cgtgatgaat   1440
atcgaacaga gttaccaca gctttgcagc gcgttgactt attcatgggt caattcagcg    1500
aagtcctctt aacatctata tccaccttca ttaaaggaga cctcaccata gctaatcttg   1560
ggacatcaga gggtcgcttc atgcaggttg tggtttctcg atcaggacca tcaacccctc   1620
atgtgaattt tctcctggac tcccatccag tgtctccaga agtgattgtg gagcatacat   1680
taaaccaaaa tggctacaca ctggttatca ctgggaagaa gatcacgaag atcccattga   1740
atggcttggg ctgcagacat ttccagtcct gcagtcaatg cctctctgcc ccaccctttg   1800
ttcagtgtgg ctggtgccac gacaaatgtg tgcgatcgga ggaatgcctg agcgggacat   1860
ggactcaaca gatctgtctg cctgcaatct acaaggtttt cccaaatagt gcacccttg    1920
aaggagggac aaggctgacc atatgtggct gggactttgg atttcggagg aataataaat   1980
ttgatttaaa gaaaactaga gttctccttg gaaatgagag ctgcaccttg actttaagtg   2040
agagcacgat gaatacattg aaatgcacag ttggtcctgc catgaataag catttcaata   2100
tgtccataat tatttcaaat ggccacggga caacacaata cagtacattc tcctatgtgg   2160
atcctgtaat aacaagtatt tcgccgaaat acggtcctat ggctggtggc actttactta   2220
cttaactgg  aaattaccta aacagtggga attctagaca catttcaatt ggtggaaaaa   2280
catgtacttt aaaaagtgtg tcaaacagta ttcttgaatg ttatacccca gcccaaacca   2340
tttcaactga gtttgctgtt aaattgaaaa ttgacttagc caaccgagag acaagcatct   2400
tcagttaccg tgaagatccc attgtctatg aaattcatcc aaccaaatct tttattagtg   2460
gtgggagcac aataacaggt gttggaaaaa acctgaattc agttagtgtc ccgagaatgg   2520
tcataaatgt gcatgaagca ggaaggaact ttacagtggc atgtcaacat cgctctaatt   2580
cagagataat ctgttgtacc actccttccc tgcaacagct gaatctgcaa ctcccctga   2640
aaaccaaagc cttttcatg  ttagatggga tcctttccaa atactttgat ctcatttatg   2700
tacataatcc tgtgtttaag ccttttgaaa agccagtgat gatctcaatg ggcaatgaaa   2760
atgtactgga aattaaggga aatgatattg accctgaagc agttaaaggt gaagtgttaa   2820
aagttggaaa taagagctgt gagaatatac acttacattc tgaagccgtt ttatgcacgg   2880
tccccaatga cctgctgaaa ttgaacagcg agctaaatat agagtggaag caagcaattt   2940
cttcaaccgt ccttggaaaa gtaatagttc aaccagatca gaatttcaca ggattgattg   3000
ctggtgttgt ctcaatatca acagcactgt tattactact tgggttttc  ctgtggctga   3060
aaaagagaaa gcaaattaaa gatctgggca gtgaattagt tcgctacgat gcaagagtac   3120
acactcctca tttggatagg cttgtaagtg cccgaagtgt aagcccaact acagaaatgg   3180
tttcaaatga atctgtagac taccgagcta cttttccaga agatcagttt cctaattcat   3240
```

```
ctcagaacgg ttcatgccga caagtgcagt atcctctgac agacatgtcc cccatcctaa    3300
ctagtgggga ctctgatata tccagtccat tactgcaaaa tactgtccac attgacctca    3360
gtgctctaaa tccagagctg gtccaggcag tgcagcatgt agtgattggg cccagtagcc    3420
tgattgtgca tttcaatgaa gtcataggaa gagggcattt tggttgtgta tatcatggga    3480
ctttgttgga caatgatggc aagaaaattc actgtgctgt gaaatccttg aacagaatca    3540
ctgacatagg agaagtttcc caatttctga ccgagggaat catcatgaaa gattttagtc    3600
atcccaatgt cctctcgctc ctgggaatct gcctgcgaag tgaagggtct ccgctggtgg    3660
tcctaccata catgaaacat ggagatcttc gaaatttcat tcgaaatgag actcataatc    3720
caactgtaaa agatcttatt ggctttggtc ttcaagtagc caaaggcatg aaatatcttg    3780
caagcaaaaa gtttgtccac agagacttgg ctgcaagaaa ctgtatgctg atgaaaaat    3840 tcacagtcaa ggttgctgat tttggtcttg ccagagacat gtatgataaa gaatactata    3900
gtgtacacaa caaaacaggt gcaaagctgc cagtgaagtg gatggctttg gaaagtctgc    3960
aaactcaaaa gtttaccacc aagtcagatg tgtggtcctt tggcgtcgtc ctctgggagc    4020
tgatgacaag aggagcccca ccttatcctg acgtaaacac ctttgatata actgtttact    4080
tgttgcaagg gagaagactc ctacaacccg aatactgccc agacccctta tatgaagtaa    4140
tgctaaaatg ctggcaccct aaagccgaaa tgcgcccatc cttttctgaa ctggtgtccc    4200
ggatatcagc gatcttctct actttcattg gggagcacta tgtccatgtg aacgctactt    4260
atgtgaacgt aaaatgtgtc gctccgtatc cttctctgtt gtcatcagaa gataacgctg    4320
atgatgaggt ggacacacga ccagcctcct tctgggagac atcatagtgc tagtactatg    4380
tcaaagcaac agtccacact ttgtccaatg gttttttcac tgcctgacct ttaaaaggcc    4440
atcgatattc tttgctcctt gccaaattgc actattaata ggacttgtat tgttatttaa    4500
attactggat tctaaggaat ttcttatctg acagagcatc agaaccagag gcttggtccc    4560
acaggccagg gaccaatgcg ctgcag                                         4586
```

<210> SEQ ID NO 95  
<211> LENGTH: 906  
<212> TYPE: DNA  
<213> ORGANISM: Artificial Sequence  
<220> FEATURE:  
<223> OTHER INFORMATION: GFP

<400> SEQUENCE: 95

```
atgggcaagg gcgaggaact gttcactggc gtggtcccaa tcctggtgga actggatggt      60
gatgtgaacg ggcacaagtt ctccgtcagc ggagagggtg aaggtgatgc cacctacgga     120
aagctcaccc tgaagttcat ctgcactacc ggaaagctcc ctgttccgtg gccaaccctc     180
gtcaccactt tcacctacgg tgttcagtgc ttctcccggt acccagatca catgaagcag     240
catgacttct tcaagagcgc catgcccgaa ggctacgtgc agaaaggac tatcttcttc     300 aaggatgacg ggaactacaa gacacgtgcc gaagtcaagt tcgaaggtga tacccctggtg    360 aaccgcatcg agctgaaagg taagtttctg cttctacctt tgatatatat ataataatta     420
tcattaatta gtagtaatat aatatttcaa atatttttt caaataaaa gaatgtagta       480 tatagcaatt gcttttctgt agtttataag tgtgtatatt ttaattata acttttctaa      540 tatatgacca aaatttgttg atgtgcaggt atcgatttca aggaagatgg aaacatcctc     600
ggacacaagc tggagtacaa ctacaactcc cacaacgtat acatcatggc cgacaagcag     660
aagaacggca tcaaggtgaa cttcaagatc aggcacaaca tcgaagatgg aagcgtgcaa     720
```

```
ctggcggacc actaccagca gaacacgccc atcggcgatg ccctgtcct gctgccggac    780 aaccattacc tgtccacgca atctgccctc tccaaggacc ccaacgagaa gagggaccac    840
atggtcctgc tggagttcgt gacggctgct gggatcacgc atggcatgga tgaactctac    900
aagtga                                                              906
```

```
<210> SEQ ID NO 96
<211> LENGTH: 784
<212> TYPE: DNA
<213> ORGANISM: Diabrotica virgifera
<220> FEATURE:
<221> NAME/KEY: misc_feature
<222> LOCATION: (200)..(200)
<223> OTHER INFORMATION: n is a, c, g, or t
<220> FEATURE:
<221> NAME/KEY: misc_feature
<222> LOCATION: (692)..(692)
<223> OTHER INFORMATION: n is a, c, g, or t
<220> FEATURE:
<221> NAME/KEY: misc_feature
<222> LOCATION: (758)..(758)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t

<400> SEQUENCE: 96
cggaatattc caactctgat gtcattatct acgtcggttg cggagaaaga ggtaacgaaa     60
tgtctgaagt attgagagat ttccctgaat tgactgttga aattgacggg cacactgaat    120
ctattatgaa acgtaccgca ttggtcgcca acacatctaa catgcctgta gctgctcgtg    180
aagcttctat ctatactggn attactcttt ctgaatactt ccgtgatatg ggttacaacg    240
tatctatgat ggctgactcg acatcacgtt gggccgaagc tttgagagaa atttcaggtc    300
gtttggctga aatgcctgcc gattccggtt atccggctta cttaggtgcc cgtttggctt    360
ccttctacga acgtgctggt cgcgttaaat gtttaggtaa tccagacaga gaaggatccg    420
tttcaattgt aggagccgta tcacctcctg gtggtgattt ctcagatcct gttaccactg    480
ctactcttgg tattgtacag gtgttctggg gtttggacaa gaaacttgcc caacgtaagc    540
acttcccttc agtagactgg cttggatcat attccaaata tttaagagca ttggacgact    600
tttatgacaa aaacttccaa gagttttattc ctcttagaac caaagttaag gaaattcttc    660
aggaagaaga tgatctagcc gaaattgtgc ancttggtag gtaaagcatc tctggcagaa    720
acggacaaaa tcacccttgg aaattgccag gcttcttnaa gaanaatttc ttgcaacaaa    780
actc                                                                784
```

```
<210> SEQ ID NO 97
<211> LENGTH: 1506
<212> TYPE: DNA
<213> ORGANISM: Diabrotica virgifera

<400> SEQUENCE: 97
atggatgttt ttaaaaactt atctgccgtg ttagcagcag tgtttgttat ttatattgtt     60
tacaaatttt taaaaatacg tagtgtttta agaaaagttt acaagttgcc aggtcctccg    120
aaacttccga ttttggggaa cttcaatgat ttattctact ctgattcagt gcaactattt    180
aaaaattttc gagaatggag tcgaaaatat tcaccacttt attcagtcgt tgtacttgac    240
atacccgtag tagttgtcac tggacctgat gagtttgaaa aaatcgcatc tggatcaaaa    300
```

```
catattacca aaggaatgat ttacggtctt gtagaaccat ggcttggaaa aggtcttctg    360
acaaattcag gttccctgtg caacaaaga aggaagattt tgacacctgc atttcacttc    420
agtattctac aggagttcgt taaagtgttt aataaagaaa ctgctaggtt ggtcgagacc    480
atcaaacaag aaaataagaa atcagcaaca aatataattc cactaatttc tcagaccgct    540
ttaaacacta ttgcagaaac atctttcgga acaacgctcg atttgaccaa aaaagacgac    600
aaaaattatg tctctgcaat tcatgaaatg ggaaaaatct tgatatatag aatggtaagg    660
ccttggttct attctttatt tgtatttat atattatctt ctgttggcgc taaactcaaa    720
caagtcttat caacgctgca tagctttaca gaacgtatta taccagaacg atcaaaagat    780
tttaaacctt tcgaagttaa tacagatggc gaaacaaaga gaaagaaact agcttttcta    840
gatttattgt tgaatgcaaa actctccaag ggcatcatcg atgaccaagg tattaaggat    900
gaagtgaata catttatgtt tgaaggacac gatacaactg ccactggaat atcatggatt    960
ttacgtcaat tggcaacaca tagcgaatat caggatcaaa tttatgaaga aatcataact   1020
gtattaggag atgcacaaaa acagccagac ctgaacgacc taaatgaact aaaggtaatg   1080
gaaagattta tcaaagaaac tttacgtctt ttccctcctg taccatatat agcaaggacg   1140
ttggacgaag acattgagct gaatggatat ttgattccta aggaggcgtc tattgatatc   1200
tggatatatg acattcacag aaacccgaaa cattggccag aacctgagaa atttgatccg   1260
gatcggtttt tacctgaaaa ttgtgttaac agacatccat ttgcttatgt acccttcagt   1320
gctggaccca gaaattgcat tggtcagaga tttgccatgt acgagatgaa ggccattatt   1380
tgtggaatta tgcagaactt ctcagtgaaa ctcgctgata aaaatgaaaa agttgaaata   1440
atgactgatt tggtgctaag aagtgcacac gaaattaatt tgaacttcat acctcgtact   1500
aactaa                                                              1506
```

<210> SEQ ID NO 98
<211> LENGTH: 1285
<212> TYPE: DNA
<213> ORGANISM: Diabrotica virgifera

<400> SEQUENCE: 98

```
gcactgattc gtttatttca cctagaagat tgaaagccga ttctactcca tcatccgcaa     60
cctgattgtt atctctggct ttttgaactt catcagaatc ataagaaaga ataaagtagc    120
tatcttctgt ggccaaacat actaatttac cactatctga ccagtaaact gcttttggtt    180
gtatctcgat tcttctgact aaatcgagag tttcccaatc atagaaagtc aaaccagaaa    240
ccgatttgac tcccaaaagg tatccaccgt atataccttc agctccaaaa tcggacttaa    300
aattcttctt ctcttttgaaa ttcttaaaaa ttctgatagt agatccggat tctctgatgg    360
catattcgct ggaatcttga gcccacacaa attcttgtgc gctaccaaac gctttgtttc    420
ttaaagccat tgctgtgtag attatgtatt ctccatcccc acagacaaca acaaaacggc    480
cattgggatt gtgttgaatt gtctgagggt atatctcgca agcacccata tcttttacag    540
aaactggaag gcgttctcca tctcttattt ccgcaccttc agctaacgcc ttgagatttg    600
cctgttgaag ttcagagtgt ctggcccaaa taattttgcc tccactggca tccatactaa    660
cagctggttc ttctctacca actttaacca aaatgctacc ttcatcataa cccaatgcca    720
cgttattgga tcccttttagg cagaaaatag tccatactct ttcaaagcca taatttaagc    780
tactttctaa cctatgggtg ttggcatgcc acactctgac agtaccatct tcacttccag    840
taagagctac aggaagttct ggatggaaac atgcagcggt tacattttga gcatgtcctt    900
```

```
ccaaagtttg aacacaagtt ttgttttgat aatcccagat ttttactaat ctatcatcag    960
cgcctgagat taaataaggt ttatctccac cgtgataata gtccacacag ttaacgcctt   1020
tctcatgacc ttctagtgtg aaattcgctg tggacgctcc caattgccat actttcaatg   1080
ttctatctag ggatgcactg gcaaatgtgt tgttgtcttt tggatttatg gcgatttgca   1140
taatataatg agtgtgtcct tcgaaaactt gctgacaagc ccatgctttt tcccaattcc   1200
aaagcttgat aagcatatca tcactacttg ttaatatata aggttgtgta gggtgtacga   1260
caatacatct cacataatcc gaatg                                         1285
```

<210> SEQ ID NO 99
<211> LENGTH: 703
<212> TYPE: DNA
<213> ORGANISM: Diabrotica virgifera

<400> SEQUENCE: 99

```
gtgttttggc ctcttgggag tagtagcaaa gacgttccct ataagtttcc ggatggtgtc     60
tcaccaagaa attttgcttc gacggaagaa tactgtctgt cttcactgtt attctctcaa    120
ccaacatcca tgctaacctc ggaaacgaag tacatgacca attgataact agattcgaac    180
attgactttg tggaattcct ttcagcggta ttcaccagtc tctgactttt cttgtgagga    240
tgcttgtctc tctgccttag ctcttagcat cttgtaccta cacttaatgt agtatgtttg    300
ggttttggtc cagatacggt gaattctcaa tagccatcga ctttacttta gtcccggtgg    360
atgcttcagc aatccttacc aattaacatg cacgacccaa attctagaat tttcagggta    420
tcttttggac tcttggcaaa tcttaataac atctaattaa tcttgtttct taaagacaat    480
ttgaatgaaa acgaatatca aagtcttcct ccaagatgtg gcatcgtact ttgaccttta    540
acacataaat cctttgcata acagaaaatt actaaataca cctactccct ttcttattta    600
accgatccag gatgtgatca tacatttcca attccatcat gtgcagagtt tgttcataga    660
taagcaggat agtattttg tgaaatggta agcccaatt tgt                        703
```

<210> SEQ ID NO 100
<211> LENGTH: 663
<212> TYPE: DNA
<213> ORGANISM: Diabrotica virgifera

<400> SEQUENCE: 100

```
atgagctttt ttggaaaatt gttcgggggg aaaaaggaag agatagcccc tagtcctggg     60
gaggctattc aaaaactcag agagactgaa gaaatgttaa taaaaaaaca ggatttttta    120
gaaaagaaga tagaagaatt taccatggta gcaaagaaaa atgcgtcgaa aaataaaaga    180
gttgcactcc aagcccctcaa aaagaagaaa cgattggaaa agacccaact acaaatagat    240
ggaacccctta caactattga aatgcagagg gaagccctcg aaggagctag cacaaatact    300
gctgtattag attctatgaa aaatgctgca gatgccctta agaaagctca taagaatttg    360
aatgtagatg atgttcacga tatcatggat gacatagccg aacaacacga catagccaac    420
gaaatcacaa acgctattag caatcctgtc ggattcaccg acgatctgga tgacgatgaa    480
ttagaaaaag aattagaaga gctcgaacaa gaaggattgg aagaagacct gctccaagtg    540
ccaggtccaa ctcaactgcc ggctgtgcct gctgatgcag ttgctactaa accaatcaaa    600
ccagcagcta aaaagttgaa agatgatgac gatatgaaag aattggaagc ctgggcctcg    660
taa                                                                 663
```

<210> SEQ ID NO 101
<211> LENGTH: 1799
<212> TYPE: DNA
<213> ORGANISM: Diabrotica virgifera

<400> SEQUENCE: 101

```
acacacgcta taatttgatc tttgatcggt cacaatgttg tagtgttttt agtttattgt      60
gcctcgaaga dacaaaatct aaccatggct catgtggtgc aactagcgga aggaaaaatt     120
tctggaggca ctaggacaga tctcaatggg gataagtttc attcgttttt atgtatccca     180
tacggaaaag ctccagtagg cgacctacgg tttaaggcgc cattacctgt tgaaccatgg     240
gaagggtaa aacaagttat cacagaagac aaaacgccat tccagaagaa cattgttctg     300
aaggaatata ctggagaaga agattgcttg tctcttcatg tatttacaaa gaaacttccc     360
catgaagaat ccaaactgaa acctgtgatg gtgtacattc atggaggagg ttttataatg     420
ggatctcacg aaactacgat gtatggtcca gaataccta tgactgaaga catagttctc     480
gtaagcatca cttaccgagt tggtctactg ggttttctta gtatagaaga cgaatcactg     540
gacgttcctg gaaatgcagg tctaaaagat caagtactgg ctttaaagtg ggtccagcga     600
aacataagaa atttcaatgg agatcccaat aacattacca tatttggaga agtgcggga     660
ggggcatctg ttgaattttt gctgttatct ccttcagcca aaggtttatt tcataaagcc     720
atacttcaga gcgggtcgac tttaaatcca tggactctta aaaactcccc agcaactgag     780
tttgctgagt ttaccaaact acataacttg cctgatattg acattttgaa aagcttgagg     840
cgtatgactg ttagggagct gtacgatcaa caaaatcaat atattaagtc taagaagcta     900
tttgtagatt tcggtctaat aaccccagtg atagaaaaac ccaacccaac agcatttttg     960
acagagaaac ctatcgacat catccagtca gggaaataca acaatgtgcc agtgataatg    1020
ggttacaccg acagtgaagg tcttcttcta gacttcttgt cggcacttgg aatgaacggg    1080
gcaaagagg gagaagatat acctattgag cagatactac catacgagac aaatttaaca    1140
gatgcacaac aagtcaaacg attagttgaa aagttaagaa atttttatcg tccagaagct    1200
gatccggttg gacgaattaa tttatctacg gatgccttgt ttgcggctgg aataatcact    1260
tctgcaaaaa atcaagcgaa agtgtcaaag aaccctgtat attttttatag attttcattg    1320
gacgcaggcc ttaacatgct gaagaaaatg gtgaatgata cacgtccagg agcttgtcac    1380
ggggatgaac tgggatacct atttaaaaac cttttgacaa cagacattgg agatgaagat    1440
aaaacttata tacatcgaat ggtaacacta tggacaaact ttgccaaata tggaaatcca    1500
acaccaccag gaaataatct aaacattgaa tggaagccga tacagaatgg tcagttgaat    1560
ttcttagata ttggaaaaca actaaagatg gatgtgaatc cagacgctga caggatgaaa    1620
atttggaatg agctttacca gtgtaatcca ctgacagcta atattaaat ttgtttgcaa    1680
caactctcag aaatacatgt tattatattt ttatattata aaaaatattt atatcatatt    1740
ttaagactat acgaataaaa ctgattactt tattttaaaa taaagttact acacaaaaa    1799
```

<210> SEQ ID NO 102
<211> LENGTH: 287
<212> TYPE: DNA
<213> ORGANISM: Diabrotica virgifera

<400> SEQUENCE: 102

```
aacggttatt tggaaggcct gtgtcgtggc tttaaatgtg ggatcctgaa acaatccgat      60
tatttgaatt tggtccagtg tgaaactctt gaagatttaa aactgcactt gcaaggcact     120
```

```
gactatggaa cttttttggc caatgaacct tcacctttgt cagtatccgt catcgattca    180
agacttcgag aaaaactcgt gattgagttc cagcacatgc gtaaccaagc agtagagcct    240
ctctcgacat ttatggactt cattacctac agttacatga tcgacaa                 287
```

<210> SEQ ID NO 103
<211> LENGTH: 899
<212> TYPE: DNA
<213> ORGANISM: Diabrotica virgifera
<220> FEATURE:
<221> NAME/KEY: misc_feature
<222> LOCATION: (805)..(805)
<223> OTHER INFORMATION: n is a, c, g, or t

<400> SEQUENCE: 103

```
acaataaatt ttcatcggcg aagattttct ccacaagaaa aaaataatct ttttcacatc     60
acatcatcaa acatcaaatc acgaatatca ttcttcgaga aaaaaaatca aggtagtatc    120
aactcgaaac ctcaataatt cttctcaagg atctttcaaa aaatattctc gcttcgacaa    180
ggatcacaat tagggtaaca acaaactcta actcgtttaa aatactctca aaaaaggaa    240 tcggtttatt atcatcatca ttcgtatcat acatcagtag tttaaaaggt ttttcgaaga    300
tctcgtctaa gcaaccaaca atcgttttac aatactatat aaaatacagg gaatacacag    360
tatccaaaaa atacttaatc agtgaatttt ctggttgacg ttgcgtccga acagagcatt    420
acggatctgg ggaatcaatt gttgtgagat gagctcaaga cgggcttcca gagtattgtt    480
gattttgatc ttgtttctca aggccaacag ttcgattcct ccggtggttt cttgagaaag    540
gtggctctcg tcgtcgattt ttagatttac gtctttaccg ttatgtcct tgtacttttg     600 ggagacgtta ggcatgatag attttaccaa ttctctgtcc tgagggcgta ctctaatggt    660
gatgtccttt tcgaagagct gatagagccc ttggaggatg agactttcca ggatttgtgt    720
atatttgcct gaatctctgg ttacctcacc aagacgtttg cgagcatctt ccaaaacggc    780
acgtacatgg tcttcccctta ctttncatac ccttcatctt gcctggttca acatgttttg    840
atgattggat ttttttttctg gagttctact tgcttctctt ttttctcgta gtactccat    899
```

<210> SEQ ID NO 104
<211> LENGTH: 1544
<212> TYPE: DNA
<213> ORGANISM: Artificial Sequence
<220> FEATURE:
<223> OTHER INFORMATION: Amaranthus palmeri PDS

<400> SEQUENCE: 104

```
tcaatttcat ctattggaag tgattttttg ggtcattctg tgagaaattt cagtgttagt     60
aaagtttatg gagcaaagca agaaatggg cactgccctt taaaggttgt ttgtatagat    120
tatcctaggc cagagcttga agtacatcc aatttcttgg aagccgccta cttatcttct    180
acttttcgga attcgcctcg tcctcagaag ccattagaag ttgtaattgc tggagcaggt    240
ttggctggtc tatccacggc aaagtattta gctgatgcag gtcacaaacc catattgttg    300
gaagcacgag atgttttagg aggaaaggtt gcagcgtgga aggatgagga tggtgactgg    360
tatgagactg gctacatat attctttggg gcatatccaa atgtccaaaa tctatttgga    420
gaacttggta taaatgaccg actgcaatgg aaggagcact ctatgatttt tgcaatgccc    480
agcaagcccg gtgaattcag tcgctttgat tttcccgaaa tcctgcctgc accattaaat    540
ggcatatggg caatcctaag aaataatgaa atgctaacct ggccagaaaa aatcaagttt    600
```

| | | |
|---|---|---|
| gccattggct tgttgcctgc tatggcaggc ggacagtcat atgttgaagc acaagatggt | 660 | |
| ttgagtgtcc aagagtggat gagaaaacaa ggagtacccg atcgtgtaac tgatgatgtg | 720 | |
| tttattgcca tgtcaaaggc actgaacttc ataaatcccg atgaactttc aatgcagtgc | 780 | |
| atcttgattg ctctgaaccg attcctgcag gagaaacatg gttctaagat ggccttccta | 840 | |
| gacggaaacc ctccagagag gctgtgcatg cctattgtta aacacatcga gtcactaggt | 900 | |
| ggtgaagtta aacttaactc tcgtatacag atgcctatgt ttttgccacc ccagttgaca | 960 | |
| tcttgaagct gttactacct gatacttgga aggaaatctc atacttcaag aaacttgaga | 1020 | |
| aattagtggg cgttcctgtg attaatgttc acatatggtt tgacagaaaa ttaaagaata | 1080 | |
| catatgacca tctactcttc agcaggagtc ctcttttgag tgtctatgct gatatgtcgg | 1140 | |
| agacatgcaa ggaatataag gatccaaata gatccatgct ggaattggtt tttgcacccg | 1200 | |
| cggaggaatg gatttcacga agcgacactg atattataga ggcaacaatg aaagagcttg | 1260 | |
| ccaagctttt cccggatgaa atcgctgccg atggaagcaa ggccaagatc ctcaaatatc | 1320 | |
| atgtcgtcaa aactccaagg tcggtttata agactgtacc ggattgtgaa ccttgtcggc | 1380 | |
| cgctgcaaag atcaccaata gagggtttct atttagctgg tgattacaca aaacaaaaat | 1440 | |
| atttggcttc tatggaaggt gctgtcttat ctgggaagct tgtgcacag gctatcgtac | 1500 | |
| aggattatga tctgctgagt tctcgagcac aaagagaatt ggcg | 1544 | |

<210> SEQ ID NO 105
<211> LENGTH: 1557
<212> TYPE: DNA
<213> ORGANISM: Artificial Sequence
<220> FEATURE:
<223> OTHER INFORMATION: Amaranthus palmeri EPSPS

<400> SEQUENCE: 105

| | | |
|---|---|---|
| atggctcaag ctactaccat caacaatggt gtccatactg gtcaattgca ccatacttta | 60 | |
| cccaaaaccc agttacccaa atcttcaaaa actcttaatt ttggatcaaa cttgagaatt | 120 | |
| tctccaaagt tcatgtcttt aaccaataaa agagttggtg ggcaatcatc aattgttccc | 180 | |
| aagattcaag cttctgttgc tgctgcagct gagaaacctt catctgtccc agaaattgtg | 240 | |
| ttacaaccca tcaaagagat ctctggtact gttcaattgc ctgggtcaaa gtctttatcc | 300 | |
| aatcgaatcc ttcttttagc tgctttgtct gagggcacaa cagtggtcga caacttgctg | 360 | |
| tatagtgatg atattcttta tgttggac gctctcagaa ctcttggttt aaaagtggag | 420 | |
| gatgatagta cagccaaaag ggcagtcgta gagggttgtg gtggtctgtt tcctgttggt | 480 | |
| aaagatggaa aggaagagat tcaactttc cttggtaatg caggaacagc gatgcgccca | 540 | |
| ttgacagctg cggttgccgt tgctggagga aattcaagtt atgtgcttga tggagtacca | 600 | |
| agaatgaggg agcgccccat tggggatctg gtagcaggtc taaagcaact tggttcagat | 660 | |
| gtagattgtt ttcttggcac aaattgccct cctgttcggg tcaatgctaa aggaggcctt | 720 | |
| ccaggggca aggtcaagct ctctggatcg gttagtagcc aatatttaac tgcacttctc | 780 | |
| atggctactc ctttgggtct tggagacgtg agattgaga tagttgataa attgatttct | 840 | |
| gtaccgtatg ttgaaatgac aataaagttg atggaacgct tggagtatc cgtagaacat | 900 | |
| agtgatagtt gggacaggtt ctacattcga ggtggtcaga aatacaaatc tcctggaaag | 960 | |
| gcatatgttg agggtgatgc ttcaagtgct agctacttcc tagccggagc cgccgtcact | 1020 | |
| ggtgggactg tcactgtcaa gggttgtgga acaagcagtt tacagggtga tgtaaaattt | 1080 | |
| gccgaagttc ttgagaagat gggttgcaag gtcacctgga cagagaatag tgtaactgtt | 1140 | |

```
actggaccac ccagggattc atctggaaag aaacatctgc gtgctatcga cgtcaacatg    1200
aacaaaatgc cagatgttgc tatgactctt gcagttgttg ccttgtatgc agatgggccc    1260
accgccatca gagatgtggc tagctggaga gtgaaggaaa ccgaacggat gattgccatt    1320
tgcacagaac tgagaaagct tggggcaaca gttgaggaag gatctgatta ctgtgtgatc    1380
actccgcctg aaaagctaaa ccccaccgcc attgaaactt atgacgatca ccgaatggcc    1440
atggcattct ctcttgctgc ctgtgcagat gttcccgtca ctatccttga tccgggatgc    1500
acccgtaaaa ccttcccgga ctactttgat gttttagaaa agttcgccaa gcattga      1557

<210> SEQ ID NO 106
<211> LENGTH: 1083
<212> TYPE: DNA
<213> ORGANISM: Artificial Sequence
<220> FEATURE:
<223> OTHER INFORMATION: Amaranthus palmeri HPPD

<400> SEQUENCE: 106
cgtcgaagta gaagacgcgg aagctgcttt taacatcagc gtttcgcatg gggctattcc      60
ctgtgtttct cctattcaat tggaaaacgg tgtcgtttta tctgaggttc atttatatgg     120
ggatgttgtg cttcggtatg taagctacgg aaatgaatgt ggggatgtgt tttttcttcc     180
tgggtttgag gaaatgccgg aggaatcatc gtttagagga cttgattttg gcattcgaag     240
gttggatcat gctgtaggga atgtccctga gttggctcct gcaattgctt atttgaagaa     300
gtttactggg tttcatgagt ttgctgagtt tacagctgaa gatgttggga cgagtgaaag     360
tggattgaat tcagccgtat tggcaaacaa tgatgaaatg gtgttgtttc cgatgaatga     420
acctgtgtat gggacaaaaa ggaagagcca aattcaaact tatttggagc ataatgaagg     480
ggctggtgta cagcatttgg ctttgatgag tgaagacata ttttggactt aagggagat     540 gaggaagaga agtgttcttg gtgggtttga gtttatgccg tcgccgcctc cgacttatta     600
ccggaatttg aggaacagag ctgctgatgt attgagtgag gagcagatga aggagtgtga     660
agagttgggg attttggtgg ataaagatga tcagggcact ttgcttcaaa tcttcaccaa     720
acctattgga gacaggtaaa ttttaatctt gctttcaatt gcttttgctt gatggattga     780
ctagcaaatt tgatcgcatt ttgttgctta tatgacttga tgatacttcc tctgtttcga     840
aatactcgct acattcgcta catttgtttt tgtgcactat tcatcgttca agcttatttt     900
acatattgcg actaatgtgt aactaaaaat atagtcaagt gggatcttgt ttgaatcgtc     960
taatggcata ctttcatcat attaaatttt tataattttt agattagtgt agtttaagat    1020
attaatgctc aaaattgtgc attggattgc gtaaaaagt gaaatgtagc aagtattatg    1080
aaa                                                                  1083
```